US012624107B2

(12) United States Patent
Cogswell et al.

(10) Patent No.: US 12,624,107 B2
(45) Date of Patent: *May 12, 2026

(54) CANCER IMMUNOTHERAPY BY DISRUPTING PD-1/PD-L1 SIGNALING

(71) Applicant: Bristol-Myers Squibb Company, Princeton, NJ (US)

(72) Inventors: John P. Cogswell, Yardley, PA (US); Stacie M. Goldberg, Potomac, MD (US); Ashok K Gupta, Clarksburg, MD (US); Maria Jure-Kunkel, Plainsboro, NJ (US); Xi-Tao Wang, Wellesley, MA (US); Jon M. Wigginton, Collegeville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/193,595

(22) Filed: Apr. 29, 2025

(65) Prior Publication Data

US 2025/0257136 A1 Aug. 14, 2025

Related U.S. Application Data

(60) Continuation of application No. 18/662,447, filed on May 13, 2024, which is a continuation of application No. 18/052,099, filed on Nov. 2, 2022, now abandoned, which is a continuation of application No. 16/827,580, filed on Mar. 23, 2020, now abandoned, which is a continuation of application No. 16/231,211, filed on Dec. 21, 2018, now Pat. No. 10,604,575, which is a division of application No. 16/006,365, filed on Jun. 12, 2018, now Pat. No. 10,316,090, which is a continuation of application No. 14/950,748, filed on Nov. 24, 2015, now Pat. No. 10,072,082, which is a division of application No. 13/892,671, filed on May 13, 2013, now Pat. No. 9,212,224.

(60) Provisional application No. 61/790,747, filed on Mar. 15, 2013, provisional application No. 61/647,442, filed on May 15, 2012.

(51) Int. Cl.
| | |
|---|---|
| *C07K 16/28* | (2006.01) |
| *A61K 39/395* | (2006.01) |
| *A61P 35/00* | (2006.01) |
| *C07K 16/18* | (2006.01) |
| *G01N 33/575* | (2026.01) |
| *A61K 39/00* | (2006.01) |

(52) U.S. Cl.
CPC ...... *C07K 16/2818* (2013.01); *A61K 39/3955* (2013.01); *C07K 16/18* (2013.01); *C07K 16/2803* (2013.01); *C07K 16/2827* (2013.01); *G01N 33/5759* (2026.01); *A61K 2039/505* (2013.01); *A61K 2039/507* (2013.01); *C07K*

*2317/76* (2013.01); *G01N 2333/70596* (2013.01); *G01N 2800/52* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,952,199 | A | 9/1999 | Davis-Smyth et al. |
| 5,977,318 | A | 11/1999 | Linsley et al. |
| 6,051,227 | A | 4/2000 | Allison et al. |
| 6,682,736 | B1 | 1/2004 | Hanson et al. |
| 6,803,192 | B1 | 10/2004 | Chen |
| 6,808,710 | B1 | 10/2004 | Wood et al. |
| 6,984,720 | B1 | 1/2006 | Korman et al. |
| 7,034,121 | B2 | 4/2006 | Carreno et al. |
| 7,169,901 | B2 | 1/2007 | Baca et al. |
| 7,297,334 | B2 | 11/2007 | Baca et al. |
| 7,423,125 | B2 | 9/2008 | Alitalo et al. |

(Continued)

FOREIGN PATENT DOCUMENTS

| | | |
|---|---|---|
| CN | 101215329 A | 7/2008 |
| CN | 102833441 A | 12/2012 |

(Continued)

OTHER PUBLICATIONS

Brahmer et al. (2010) J Clin Oncol 28: 3167-3175.*

(Continued)

*Primary Examiner* — Ilia I Ouspenski
(74) *Attorney, Agent, or Firm* — Sterne, Kessler, Goldstein & Fox P.L.L.C.

(57) ABSTRACT

The disclosure provides a method for immunotherapy of a subject afflicted with cancer, comprises administering to the subject a composition comprising a therapeutically effective amount of an antibody that inhibits signaling from the PD-1/PD-L1 signaling pathway. This disclosure also provides a method for immunotherapy of a subject afflicted with cancer comprising selecting a subject that is a suitable candidate for immunotherapy based on an assessment that the proportion of cells in a test tissue sample from the subject that express PD-L1 on the cell surface exceeds a predetermined threshold level, and administering a therapeutically effective amount of an anti-PD-1 antibody to the selected subject. The invention additionally provides rabbit mAbs that bind specifically to a cell surface-expressed PD-L1 antigen in a FFPE tissue sample, and an automated IHC method for assessing cell surface expression in FFPE tissues using the provided anti-PD-L1 Abs.

6 Claims, 24 Drawing Sheets

Specification includes a Sequence Listing.

(56)  References Cited

U.S. PATENT DOCUMENTS

| | | | |
|---|---|---|---|
| 7,488,802 | B2 | 2/2009 | Collins et al. |
| 7,498,414 | B2 | 3/2009 | Zhu |
| 7,595,048 | B2 | 9/2009 | Honjo et al. |
| 7,605,238 | B2 | 10/2009 | Korman et al. |
| 7,635,757 | B2 | 12/2009 | Freeman et al. |
| 7,892,540 | B2 | 2/2011 | Chen |
| 7,943,743 | B2 | 5/2011 | Korman et al. |
| 7,972,596 | B2 | 7/2011 | Wu et al. |
| 8,008,449 | B2 | 8/2011 | Korman et al. |
| 8,034,905 | B2 | 10/2011 | Kavile et al. |
| 8,168,179 | B2 | 5/2012 | Honjo et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 8,383,796 | B2 | 2/2013 | Korman et al. |
| 8,609,089 | B2 | 12/2013 | Langermann et al. |
| 8,686,119 | B2 | 4/2014 | Rotem-Yehudar et al. |
| 8,728,474 | B2 | 5/2014 | Honjo et al. |
| 8,779,105 | B2 | 7/2014 | Korman et al. |
| 8,779,108 | B2 | 7/2014 | Queva et al. |
| 8,900,587 | B2 | 12/2014 | Carven et al. |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,102,725 | B2 | 8/2015 | Korman et al. |
| 9,212,224 | B2 | 12/2015 | Cogswell et al. |
| 9,273,135 | B2 | 3/2016 | Korman et al. |
| 9,358,289 | B2 | 6/2016 | Korman et al. |
| 9,387,247 | B2 | 7/2016 | Korman et al. |
| 9,393,301 | B2 | 7/2016 | Honjo et al. |
| 9,402,899 | B2 | 8/2016 | Honjo et al. |
| 9,439,962 | B2 | 9/2016 | Honjo et al. |
| 9,492,539 | B2 | 11/2016 | Korman et al. |
| 9,492,540 | B2 | 11/2016 | Korman et al. |
| 9,683,048 | B2 | 6/2017 | Freeman et al. |
| 9,765,147 | B2 | 9/2017 | Wong et al. |
| 9,856,320 | B2 * | 1/2018 | Cogswell ........... C07K 16/2827 |
| 9,907,849 | B2 | 3/2018 | Petit et al. |
| 10,072,082 | B2 | 9/2018 | Cogswell et al. |
| 10,081,681 | B2 | 9/2018 | Korman et al. |
| 10,138,299 | B2 | 11/2018 | Cogswell et al. |
| 10,174,113 | B2 | 1/2019 | Yang |
| 10,221,244 | B2 | 3/2019 | Wong et al. |
| 10,266,594 | B1 | 4/2019 | Cogswell et al. |
| 10,266,595 | B2 | 4/2019 | Cogswell et al. |
| 10,266,596 | B1 | 4/2019 | Cogswell et al. |
| 10,308,714 | B2 | 6/2019 | Cogswell et al. |
| 10,316,090 | B2 | 6/2019 | Cogswell et al. |
| 10,316,091 | B2 | 6/2019 | Cogswell et al. |
| 10,323,092 | B2 | 6/2019 | Cogswell et al. |
| 10,323,093 | B2 | 6/2019 | Cogswell et al. |
| 10,370,446 | B2 | 8/2019 | Freeman et al. |
| 10,392,442 | B2 | 8/2019 | Coric et al. |
| 10,441,655 | B2 | 10/2019 | Korman et al. |
| 10,544,224 | B2 | 1/2020 | Manekas et al. |
| 10,577,423 | B2 | 3/2020 | Cogswell et al. |
| 10,584,170 | B2 | 3/2020 | Cogswell et al. |
| 10,604,575 | B2 | 3/2020 | Cogswell et al. |
| 10,618,967 | B2 | 4/2020 | Wong et al. |
| 10,668,152 | B2 | 6/2020 | Coric et al. |
| 11,078,278 | B2 | 8/2021 | Simon et al. |
| 11,078,279 | B2 | 8/2021 | Wigginton et al. |
| 11,103,579 | B2 | 8/2021 | Barnhart et al. |
| 11,174,315 | B2 | 11/2021 | Vasselli et al. |
| 11,207,391 | B2 | 12/2021 | Engelhardt et al. |
| 11,332,529 | B2 * | 5/2022 | Axelson ............. C07K 16/2818 |
| 11,351,163 | B2 | 6/2022 | Basciano et al. |
| 11,566,073 | B2 | 1/2023 | Edwards et al. |
| 11,767,361 | B2 * | 9/2023 | Tschaika ............ C07K 16/2827 |
| | | | 424/142.1 |
| 12,479,917 | B2 | 11/2025 | Maier et al. |
| 12,528,865 | B2 | 1/2026 | Nathan |
| 2002/0102651 | A1 | 8/2002 | Freeman |
| 2003/0039653 | A1 | 2/2003 | Chen |
| 2006/0083744 | A1 | 4/2006 | Chen et al. |
| 2006/0110383 | A1 | 5/2006 | Honjo et al. |
| 2009/0055944 | A1 | 2/2009 | Korman et al. |
| 2009/0074787 | A1 | 3/2009 | Gomez-Navarro et al. |
| 2009/0215812 | A1 | 8/2009 | Bedrosian |
| 2009/0217401 | A1 | 8/2009 | Korman et al. |
| 2009/0297518 | A1 | 12/2009 | Honjo et al. |
| 2009/0304711 | A1 | 12/2009 | Pardoll et al. |
| 2009/0317368 | A1 | 12/2009 | Chen |
| 2010/0015642 | A1 | 1/2010 | Kwon et al. |
| 2010/0151447 | A1 | 6/2010 | Ely |
| 2010/0203056 | A1 | 8/2010 | Irving et al. |
| 2011/0008369 | A1 | 1/2011 | Finnefrock et al. |
| 2011/0081341 | A1 | 4/2011 | Honjo et al. |
| 2011/0206701 | A1 | 8/2011 | Afar |
| 2011/0244546 | A1 | 10/2011 | Hansen et al. |
| 2011/0250201 | A1 | 10/2011 | Smith |
| 2011/0269948 | A1 | 11/2011 | Sanjuan |
| 2012/0263677 | A1 | 10/2012 | Eagle et al. |
| 2013/0017199 | A1 | 1/2013 | Langermann |
| 2013/0022629 | A1 | 1/2013 | Sharpe et al. |
| 2013/0133091 | A1 | 5/2013 | Korman et al. |
| 2013/0309250 | A1 | 11/2013 | Cogswell et al. |
| 2014/0212422 | A1 | 7/2014 | Korman et al. |
| 2014/0294852 | A1 | 10/2014 | Korman et al. |
| 2014/0314714 | A1 | 10/2014 | Honjo et al. |
| 2014/0328833 | A1 | 11/2014 | Korman et al. |
| 2014/0341917 | A1 | 11/2014 | Nastri et al. |
| 2014/0348743 | A1 | 11/2014 | Korman et al. |
| 2014/0356353 | A1 | 12/2014 | Queva et al. |
| 2015/0079109 | A1 | 3/2015 | Li et al. |
| 2015/0093380 | A1 | 4/2015 | Honjo et al. |
| 2015/0125463 | A1 | 5/2015 | Cogswell et al. |
| 2015/0165025 | A1 | 6/2015 | Korman et al. |
| 2015/0197572 | A1 | 7/2015 | Honjo et al. |
| 2015/0290316 | A1 | 10/2015 | Graziano et al. |
| 2016/0022814 | A1 | 1/2016 | Petit et al. |
| 2016/0031990 | A1 | 2/2016 | Steele et al. |
| 2016/0075782 | A1 | 3/2016 | Korman et al. |
| 2016/0090417 | A1 | 3/2016 | Cogswell et al. |
| 2016/0158355 | A1 | 6/2016 | Honjo et al. |
| 2016/0158356 | A1 | 6/2016 | Honjo et al. |
| 2016/0222116 | A1 | 8/2016 | Korman et al. |
| 2016/0340428 | A1 | 11/2016 | Yang |
| 2016/0362489 | A1 | 12/2016 | Yang |
| 2016/0362495 | A1 | 12/2016 | Korman et al. |
| 2017/0028040 | A1 | 2/2017 | Lan et al. |
| 2017/0051060 | A1 | 2/2017 | Honjo et al. |
| 2017/0088615 | A1 | 3/2017 | Korman et al. |
| 2017/0088626 | A1 | 3/2017 | Jure-Kunkel et al. |
| 2017/0158776 | A1 | 6/2017 | Feltquate et al. |
| 2017/0174774 | A1 | 6/2017 | Coric et al. |
| 2017/0247455 | A1 | 8/2017 | Jure-Kunkel et al. |
| 2018/0094067 | A1 | 4/2018 | Wong |
| 2018/0099045 | A1 | 4/2018 | Graziano et al. |
| 2018/0133313 | A1 | 5/2018 | Coric et al. |
| 2018/0155429 | A1 | 6/2018 | Finckenstein |
| 2018/0179282 | A1 | 6/2018 | Cardarelli et al. |
| 2018/0237534 | A1 | 8/2018 | Cai et al. |
| 2018/0273624 | A1 | 9/2018 | Cogswell et al. |
| 2018/0282413 | A1 | 10/2018 | Cogswell et al. |
| 2018/0282414 | A1 | 10/2018 | Cogswell et al. |
| 2018/0312590 | A1 | 11/2018 | Cogswell et al. |
| 2018/0319887 | A1 | 11/2018 | Cogswell et al. |
| 2018/0319892 | A1 | 11/2018 | Feltquate et al. |
| 2018/0371092 | A1 | 12/2018 | Nathan |
| 2019/0092863 | A1 | 3/2019 | Cogswell et al. |
| 2019/0100589 | A1 | 4/2019 | Cogswell et al. |
| 2019/0100590 | A1 | 4/2019 | Cogswell et al. |
| 2019/0112376 | A1 | 4/2019 | Cogswell et al. |
| 2019/0112377 | A1 | 4/2019 | Cogswell et al. |
| 2019/0135920 | A1 | 5/2019 | Cogswell et al. |
| 2019/0153099 | A1 | 5/2019 | Cogswell et al. |
| 2019/0194328 | A1 | 6/2019 | Yang |
| 2020/0010549 | A1 | 1/2020 | Yang |
| 2020/0062846 | A1 | 2/2020 | Honjo et al. |
| 2020/0109204 | A1 | 4/2020 | Edwards et al. |
| 2020/0138945 | A1 | 5/2020 | Korman et al. |
| 2020/0190198 | A1 | 6/2020 | Manekas et al. |
| 2020/0308282 | A1 | 10/2020 | Cogswell et al. |

(56) References Cited

U.S. PATENT DOCUMENTS

| | | | |
|---|---|---|---|
| 2020/0325226 A1 | 10/2020 | Edwards et al. | |
| 2021/0009697 A1 | 1/2021 | Lewis et al. | |
| 2021/0030739 A1 | 2/2021 | Basciano et al. | |
| 2021/0054063 A1 | 2/2021 | Carleton et al. | |
| 2021/0101980 A1 | 4/2021 | Bhagavatheeswaran et al. | |
| 2021/0147570 A1 | 5/2021 | Altura et al. | |
| 2021/0206854 A1 | 7/2021 | Nathan | |
| 2021/0380693 A1 | 12/2021 | Maier et al. | |
| 2022/0017619 A1 | 1/2022 | Nathan | |
| 2022/0041733 A1 | 2/2022 | Lei et al. | |
| 2022/0195046 A1 | 6/2022 | Lei et al. | |
| 2022/0281974 A1 | 9/2022 | Yang | |
| 2022/0356254 A1 | 11/2022 | Axelson | |
| 2024/0002512 A1 | 1/2024 | Cogswell et al. | |
| 2024/0034793 A1 | 2/2024 | Cogswell et al. | |
| 2024/0052035 A1* | 2/2024 | Tschaika | C07K 16/2818 |
| 2024/0190963 A1* | 6/2024 | Bhagavatheeswaran | A61P 35/00 |
| 2024/0417471 A1 | 12/2024 | Cogswell et al. | |
| 2025/0011466 A1* | 1/2025 | Feltquate | A61P 35/00 |
| 2025/0026831 A1* | 1/2025 | Axelson | C07K 16/2878 |
| 2025/0051448 A1 | 2/2025 | Srivastava | |
| 2025/0263486 A1 | 8/2025 | Cogswell et al. | |
| 2025/0270322 A1 | 8/2025 | Cogswell et al. | |
| 2026/0000757 A1 | 1/2026 | Abaskharoun et al. | |

FOREIGN PATENT DOCUMENTS

| | | |
|---|---|---|
| CN | 110505882 A | 11/2019 |
| EP | 3322731 A1 | 5/2018 |
| EP | 3464373 B1 | 10/2021 |
| WO | WO-0037504 A2 | 6/2000 |
| WO | WO-0044777 A1 | 8/2000 |
| WO | WO-0114424 A2 | 3/2001 |
| WO | WO-0114556 A1 | 3/2001 |
| WO | WO-0114557 A1 | 3/2001 |
| WO | WO-0121631 A2 | 3/2001 |
| WO | WO-0139722 A2 | 6/2001 |
| WO | WO-02078731 A1 | 10/2002 |
| WO | WO-02079499 A1 | 10/2002 |
| WO | WO-02086083 A2 | 10/2002 |
| WO | WO-03042402 A2 | 5/2003 |
| WO | WO-03072822 A2 | 9/2003 |
| WO | WO-2004004771 A1 | 1/2004 |
| WO | WO-2004056875 A1 | 7/2004 |
| WO | WO-2004072286 A1 | 8/2004 |
| WO | WO-2005021743 A1 | 3/2005 |
| WO | WO-2006042237 A2 | 4/2006 |
| WO | WO-2006121168 A1 | 11/2006 |
| WO | WO-2006133396 A2 | 12/2006 |
| WO | WO-2007005874 A2 | 1/2007 |
| WO | WO-2007113648 A2 | 10/2007 |
| WO | WO-2010019570 A2 | 2/2010 |
| WO | WO-2010036959 A2 | 4/2010 |
| WO | WO-2011066389 A1 | 6/2011 |
| WO | WO-2012006589 A2 | 1/2012 |
| WO | WO-2012122444 A1 | 9/2012 |
| WO | WO-2012145493 A1 | 10/2012 |
| WO | WO-2013004618 A1 | 1/2013 |
| WO | WO-2013014668 A1 | 1/2013 |
| WO | WO-2013173223 A1 | 11/2013 |
| WO | WO-2014179664 A2 | 11/2014 |
| WO | WO-2014194302 A2 | 12/2014 |
| WO | WO-2015042246 A1 | 3/2015 |
| WO | WO-2015085847 A1 | 6/2015 |
| WO | WO-2015112800 A1 | 7/2015 |
| WO | WO-2015112900 A1 | 7/2015 |
| WO | WO-2015116868 A2 | 8/2015 |
| WO | WO-2015181331 A1 | 12/2015 |
| WO | WO-2016029073 A2 | 2/2016 |
| WO | WO-2016077553 A1 | 5/2016 |
| WO | WO-2016149201 A2 | 9/2016 |
| WO | WO-2016176503 A1 | 11/2016 |
| WO | WO-2016176504 A1 | 11/2016 |
| WO | WO-2016197067 A1 | 12/2016 |
| WO | WO-2017011666 A1 | 1/2017 |
| WO | WO-2017210637 A1 | 12/2017 |

OTHER PUBLICATIONS

Cartwright T.H. (2012) Clinical Colorectal Cancer, vol. 11, No. 3, 155-166.*

Maughan et al. (2011) The Lancet 377(9783): 2103-2114.*

Androsky, D.J. et al., "Programmed Death Ligand 1 is Expressed by Non-Hodgkin Lymphomas and Inhibits the Activity of Tumor-Associated T Cells", Clinical Cancer Research, vol. 17, No. 13, pp. 4232-4244 (Jul. 2011).

Blank, C. et al., "Interaction of PO-L 1 on tumor cells with PD-1 on tumor specific T cells as a mechanism of immune evasion: implications for tumor immunotherapy", Cancer Immunol. Immunother., vol. 54, pp. 307-314 (Apr. 2005).

Blank, C. et al., "PD-L1/B7H-1 Inhibits the Effector Phase of Tumor Rejection by T Cell Receptor (TCR) Transgenic CDS+ T Cells", Cancer Research, vol. 64, pp. 1140-1145 (Feb. 2004).

Brahmer, J.R. et al., "Safety and Activity of Anti-PD-L1 Antibody in Patients with Advanced Cancer", The New England Journal of Medicine, vol. 366, No. 26, pp. 2455-2465 (Jun. 2012).

Brown, J.A. et al., "Blockade of Programmed Death-1 Ligands on Dendritic Cells Enhances T Cell Activation and Cytokine Production", The Journal of Immunology, vol. 170, pp. 1257-1266 (Feb. 2003).

Carter, L.L. et al., "PD-1:PD-L inhibitory pathway affects both CD4+ and CDS+ T cells and is overcome by IL-2", Eur. J. Immunol., vol. 32, pp. 634-643 (Mar. 2002).

Dasanu, C.A. et al., "Immune alterations and emerging immunotherapeutic approaches in lung cancer", Expert Opin. Bioi. Ther., vol. 12, No. 7, pp. 923-937 (Jul. 2012).

Dodson, L.F. et al., "Potential targets for pancreatic cancer immunotherapeutics", Immunotherapy, vol. 3, No. 4, pp. 517-537 (Apr. 2011).

Dong, H. et al., "B7-H1 pathway and its role in the evasion of tumor immunity", J. Mol. Med., vol. S1, pp. 2S1-2S7 (May 2003).

Dong, H. et al., "Tumor-associated B7-H1 promotes T-cell apoptosis: A potential mechanism of immune evasion", Nature Medicine, vol. S, No. S, pp. 793-800 (Aug. 2002).

Flies, D. B. et al., "Blockade of the B7-H1/PD-1 Pathway for Cancer Immunotherapy", Yale Journal of Biology and Medicine, vol. S4, pp. 409-421 (Dec. 2011).

Freeman, G.J. et al., "Engagement of the PD-1 Immunoinhibitory Receptor by a Novel B7 Family Member Leads to Negative Regulation of Lymphocyte Activation", J. Exp. Med., vol. 192, No. 7, pp. 1027-1034 (Oct. 2000).

Gadiot, J. et al., "Overall Survival and PO-L 1 Expression in Metastasized Malignant Melanoma", Cancer, vol. 117, pp. 2192-2201 (May 2011).

Gajewski, T.F. et al., "Gene Signature in Melanoma Associated with Clinical Activity: A Potential Clue to Unlock Cancer Immunotherapy", The Cancer Journal, vol. 16, No. 4, pp. 399-403 (Jul. 2010).

Garbe, C. et al., "Diagnosis and treatment of melanoma. European consensus-based interdisciplinary guideline—Update 2012", European Journal of Cancer, vol. 48, pp. 2375-2390 (Oct. 2012).

Hamanishi, J. et al., "Programmed cell death 1 ligand 1 and tumor-infiltrating cos+ T lymphocytes are prognostic factors of human ovarian cancer", Proc. Natl. Acad. Sci., vol. 104, No. 9, pp. 3360-3365 (Feb. 2007).

Hamid, O. et al., "Anti-programmed death-1 and anti-programmed deathligand 1 antibodies in cancer therapy", Expert Opin. Bioi. Ther., vol. 13, No. 6, pp. 847-861 (Jun. 2013).

He, Y.-F. et al., "Blocking Programmed Death-1 Ligand-PD-1 Interactions by Local Gene Therapy Results in Enhancement of Antitumor Effect of Secondary Lymphoid Tissue Chemokine", The Journal of Immunology, vol. 173, pp. 4919-4928 (Oct. 2004).

Hino, R. et al., "Tumor Cell Expression of Programmed Cell Death-1 Ligand 1 is a Prognostic Factor for Malignant Melanoma", Cancer, vol. 116, pp. 1757-1766 (Apr. 2010).

(56) References Cited

OTHER PUBLICATIONS

Hirano, F. et al., "Blockade of B7-H1 and PD-1 by Monoclonal Antibodies Potentiates Cancer Therapeutic Immunity", Cancer Res., vol. 65, No. 3, pp. 1 089-1 096 (Feb. 2005).

Holt, G. E. et al., "Immune Modulation as a Therapeutic Strategy for Non-Small-Cell Lung Cancer", Clinical Lung Cancer, vol. 9, Suppl. 1, pp. S13-S19 (Feb. 2008).

Holt, G. E. et al., "Immunotherapy as a strategy for the treatment of nonsmall-cell lung cancer", Therapy, vol. 8, No. 1, pp. 43-54 (Jun. 2011).

Lwai, Y. et al., "Involvement of PO-L 1 on tumor cells in the escape from host immune system and tumor immunotherapy by PO-L 1 blockade", Proc. Natl. Acad. Sci., vol. 99, No. 19, pp. 12293-12297 (Sep. 2002).

Lwai, Y. et al., "PD-1 blockade inhibits hematogenous spread of poorly immunogenic tumor cells by enhanced recruitment of effector T cells", International Immunology, vol. 17, No. 2, pp. 133-144 (Feb. 2004).

Kim, P.S. et al., "Features of responding T cells in cancer and chronic infection", Current Opinion in Immunology, vol. 22, pp. 223-230 (Apr. 2010).

Konishi, J. et al., "B7-H1 Expression on Non-Small Cell Lung Cancer Cells and Its Relationship with Tumor-Infiltrating Lymphocytes and Their PD-1 Expression", Clinical Cancer Research, vol. 10, pp. 5094-5100 (Aug. 2004).

Lipson, E.J. et al., "Durable Cancer Regression Off-Treatment and Effective Reinduction Therapy with an Anti-PD-1 Antibody", Clinical Cancer Research, vol. 19, No. 2, pp. 462-468 (Nov. 2012).

Mellman, I. et al., "Cancer immunotherapy comes of age", Nature, vol. 480, pp. 480-489 (Dec. 2011).

Pardoll, D.M., "The blockade of immune checkpoints in cancer immunotherapy", Nature Reviews: Cancer, vol. 12, pp. 252-264 (Mar. 2012).

Parry, R.V. et al., "CTLA-4 and PD-1 Receptors Inhibit T-Cell Activation by Distinct Mechanisms", Molecular and Cellular Biology, vol. 25, No. 21, pp. 9543-9553 (Nov. 2005).

Schreiber, R.D. et al., "Cancer Immunoediting: Integrating Immunity's Roles in Cancer Suppression and Promotion", Science, vol. 331, pp. 1565-1570 (Mar. 2011).

Sharma, P. et al., "Novel cancer immunotherapy agents with survival benefit: recent successes and next steps", Nature Reviews: Cancer, vol. 11, pp. 805-812 (Oct. 2011).

Shepherd, F.A. et al., "Immunotherapy for Non-small Cell Lung Cancer: Novel Approaches to Improve Patient Outcome", Journal of Thoracic Oncology, vol. 6, No. 10, pp. 1763-1773 (Oct. 2011).

Sompuram, S.R. et al., "Antibodies Immunoreactive with Formalin-Fixed Tissue Antigens Recognize Linear Protein Epitopes", Am. J. Clin. Pathol., vol. 125, pp. 82-90 (Jan. 2006).

Taube, J.M. et al., "Colocalization of Inflammatory Response with B7-H1 Expression in Human Melanocytic Lesions Supports an Adaptive Resistance Mechanism of Immune Escape", Science Translational Medicine, vol. 4, No. 127, 127ra37 (Mar. 2012), and Supplementary Materials, http:l/stm.sciencemag.org/content/suppl/2012/03/26/4.127 .127ra37 .DC 1. Html.

Topalian, S.L. et al., "Cancer Immunotherapy Comes of Age", Journal of Clinical Oncology, vol. 29, No. 36, pp. 4828-4836 (Oct. 2011).

Topalian, S.L. et al., "Safety, Activity, and Immune Correlates of Anti-PD-1 Antibody in Cancer", The New England Journal of Medicine, vol. 366, No. 26, pp. 2443-2454 (Jun. 2012).

Topalian, S.L. et al. "Targeting the PD-1/B7-H1 (PD-L1) pathway to activate anti-tumor immunity", Current Opinion in Immunology, vol. 24, pp. 207-212 (Apr. 2012).

Wolchok, J.D. et al., "Ipilimumab monotherapy in patients with pretreated advanced melanoma: a randomised, double-blind, multicentre, phase 2, dose-ranging study", Lancet Oncol., vol. 11, pp. 155-164 (Feb. 2010).

Wong, R.M. et al., "Programmed death-1 blockade enhances expansion and functional capacity of human melanoma antigen-specific CTLs", International Immunology, vol. 19, No. 10, pp. 1223-1234 (Oct. 2007).

Zou, W. et al., "Inhibitory 87-family molecules in the tumour microenvironment", Nature Reviews: Immunology, vol. 8, pp. 467-477 (Jun. 2008).

International Preliminary Report on Patentability and Written Opinion for International Application No. PCT/US2013/040764, The International Bureau of WIPO, Geneva, Switzerland, issued on Nov. 18, 2014, 10 pages.

International Search Report for International Application No. PCT/US2013/040764, European Patent Office, Netherlands, mailed on Oct. 31, 2013, 8 pages.

Ascierto, P.A., et al., "Clinical experiences with anti-CD137 and anti-PD1 therapeutic antibodies," Semin Oncol 37(5):508-516, Elsevier Inc., United States (Oct. 2010).

National Institutes of Health Clinical Center, Clinical Trial Identifier NCT01024231 entitled "Dose-escalation Study of Combination BMS-936558 (MDX-1106) and Ipilimumab in Subjects With Unresectable Stage III or Stage IV Malignant Melanoma," ClinicalTrials.gov, available at https://clinicaltrials.gov/ct2/show/NCT01024231?term=NCT01024231&rank=1, last accessed on Jun. 30, 2017, 7 pages (same clinical trial accessed on Apr. 27, 2017 in related U.S. Appl. No. 14/400,667, filed Nov. 12, 2014).

Curran, M.A., et al., "PD-1 and CTLA-4 combination blockade expands infiltrating T cells and reduces regulatory T and myeloid cells within B16 melanoma tumors," Proc Natl Acad Sci USA 107(9):4275-4280, National Academy of Sciences, United States (Mar. 2010).

May Jr., K.F., et al., "Prostate Cancer Immunotherapy," Clinical Cancer Research 17(16):5233-5238, American Association of Cancer Research, United States (Aug. 2011).

Natarajan, N., et al., "Novel immunotherapeutic agents and small molecule antagonists of signaling kinases for the treatment of metastatic melanoma," Drugs 71(10):1233-1250, Springer International, New Zealand (Jul. 2011).

Office Action mailed Nov. 9, 2017 in U.S. Appl. No. 14/950,748, inventor Cogswell, J.P., et al., filed Nov. 24, 2015, 11 pages.

Postow, M.A., et al., "Targeting Immune Checkpoints: Releasing the Restraints on Anti-tumor Immunity for Patients With Melanoma," Cancer Journal 18(2):153-159, Lippincott Williams & Wilkins, United States (Mar. 2012).

Sznol, M., "Advances in the treatment of metastatic melanoma: new immunomodulatory agents," Semin Oncol. 39(2):192-203, Elsevier Inc., United States (Apr. 2012).

Wolchok, J.D., "Immunobiology of immune checkpoints," Pigment Cell Research 24:1005, John Wiley & Sons A/S, United States (Dec. 2011).

National Institutes of Health, "Dose-escalation Study of Combination BMS-936558 (MDX-1106) and Ipilimumab in Subjects With Unresectable Stage III or Stage IV Malignant Melanoma," ClinicalTrials. gov Identifier NCT01024231, accessed at https://web.archive.org/web/20111023232455/https://clinicaltrials.gov/ct2/show/NCT01024231, accessed on Sep. 22, 2017, 3 pages.

Shibayama, S. and Yoshida, T., "Development of ONO-4538, fully human anti-PD-1 antibody for malignant tumors," Medical Science Digest 36(12):1120-1123, New Science Co., Japan (2010).

Wang, G. et al., "A Therapeutic strategy of targeting PD1/PDL signal pathway," Chinese Bulletin of Life Sciences 23:86-89, (2011).

Gao, Q., et al., "Overexpression of PD-L1 Significantly Associates with Tumor Aggressiveness and Postoperative Recurrence in Human Hepatocellular Carcinoma," Clinical Cancer Research 15(3);971-979, American Association for Cancer Research, United States (Feb. 2009).

Ghebeh, H., et al., "The B7-H1 (PD-L1) T Lymphocyte-Inhibitory molecule Is Expressed in Breast cancer Patients with Infiltrating Ductal Carcinoma: Correlation with Important high-Risk Prognostic Factors," Neoplasia 8(3):190-198, Elsevier, Netherlands (Mar. 2006).

(56)  References Cited

OTHER PUBLICATIONS

Roth, T., et al., "B7-H3 Ligand Expression by Prostate Cancer: A Novel Marker of Prognosis and Potential Target for Therapy," Cancer Res 67(16):7893-7900, American Association for Cancer, United States (Aug. 2007).

National Institutes of Health Clinical Center, Clinical Trial Identifier NCT01024231 entitled "Dose-escalation Study of Combination BMS-936558 (MDX-1106) and Ipilimumab in Subjects With Unresectable Stage III or Stage IV Malignant Melanoma," ClinicalTrials.gov, available at https://clinicaltrials.gov/archive/NCT01024231/2012_04_30, last accessed on Jul. 18, 2017, 4 pages (same clinical trial accessed on Apr. 27, 2017 in same application).

Study NCT01024231, "Dose-Escalation Study of Combination BMS-936558 (MDX-1106) and Ipilimumab in Subjects with Unrespectable Stage III or Stage IV Malignant Melanoma," Apr. 18, 2012, 3 pages.

Simeone, E., et al., "Immunotreatment of metastatic melanoma: the experience with anti-CTLA-4," *Journal of Immunotoxicology* 9(3):241-247, Taylor & Francis, United Kingdom (Jul. 2012).

Wolchok, J.D., et a., " Nivolumab Plus Ipilimumab in Advanced Melanoma," *New England Journal of Medicine* 369(2):122-133, Massachusetts Medical Society, United States (Jul. 2012).

Phase 3 study of Nivolumab, or Nivolumab Plus Ipilimumab Versus Ipilimumab alone in Previously Untreated Advanced Melanoma (Checkmate 067), last updated Dec. 18, 2017.

Kuenen, B., et al., "A Phase 1 Pharmacologic Study of Necitumumab (IMC-11F8), a Fully Human IgG1 Monoclonal Antibody Directed Against EGFR in Patients with Advanced Solid Malignancies," Clinical Cancer Research 16:1915-1923, American Association for Cancer Research, United States (Mar. 2010).

Seiwert, T.Y., et al., "Safety and clinical activity of pembrolizumab for treatment of recurrent or metastatic squamous cell carcinoma of the head and neck (Keynote 0-12): an open-label, multicenter, phase 1b trial." Lancet Oncology 17:956-965, Elsevier, Netherlands (Jul. 2016).

Wang, D., et al., "Fixed Dosing Versus Body Size-based Dosing of Monoclonal Antibodies in Adult Clinical Trials," J. Clin Pharmacol 49:1012-1024, John Wiley & Sons, United States (Sep. 2009).

American Cancer Society, "What is Non-Small Cell Lung Cancer?," retrieved from https://www.cancer.org/cancer/non-small-cell-lung-cancer/about/what-is-non-small-cell-lung-cancer.html, retrieved on Aug. 6, 2018. 5 pages.

Auperin, A., et al., "Meta-Analysis of Concomitant versus Sequential Radiochemotherapy in Locally Advanced Non-Small-Cell Lung Cancer," Journal of Clinical Oncology 28(13):2181-2190, American Society of Clinical Oncology Journal, United States (May 2010).

Clark, P., et al., "Bladder Cancer," Journal of the National Comprehensive Cancer Network 11(4):446-475, Harborside Press, United States (Apr. 2013).

Leighl, N.B., "Treatment paradigms for Patients with metastatic non-small-cell lung cancer: first-, second-, and third-line," Curr Oncol, 19:S52-S58, Multimed Inc., Canada (Jun. 2012).

Office Action mailed Aug. 15, 2018, in U.S. Appl. No. 16/024,340, inventors Cogswell, et al., filed Jun. 29, 2018, 7 pages.

Office Action mailed Oct. 18, 2018 in U.S. Appl. No. 16/024,340, inventors Cogswell, et al., filed Jun. 29, 2018, 5 pages.

Office Action mailed Aug. 10, 2018, in U.S. Appl. No. 16/006,493, inventors Cogswell, et al., filed Jun. 12, 2018, 9 pages.

Office Action mailed Aug. 15, 2018, in U.S. Appl. No. 16/024,333, inventors Cogswell, et al., filed Jun. 29, 2018, 10 pages.

Office Action mailed Aug. 10, 2018, in U.S. Appl. No. 16/006,365, inventors Cogswell, et al., filed Jun. 12, 2018, 10 pages.

Office Action mailed Dec. 14, 2018, in U.S. Appl. No. 16/006,365, inventors Cogswell, et al., filed Jun. 12, 2018, 9 pages.

Atmar, J., et al., "Review of the safety and feasibility of rapid infusion rituximab," Journal of Oncology Practice 6(2):91-93, American Society of Clinical Oncology, United States (Mar. 2009).

Hawker, K., et al., "Safe Administration and Monitoring of Monoclonal Antibodies in Treatment of Multiple Sclerosis," International Journal of MS Care 9(2):1-23, Bentham Science Publishers, United States (2007).

Lenz, H-J., et al., "Management and Preparedness for Infusion and Hypersensitivity reactions," The Oncologist 12:601-609, AlphaMed Press, United States (May 2007).

Reiss, K.A., et al., "Harnessing the power of the immune system via blockade of PD-1 and PD-L1: a promising new anticancer strategy," Immunotherapy 6(4):459-475, Future Medicine, United Kingdom (2014).

Vogel, W.H., "Infusion reactions: diagnosis, assessment, and management," Clin J. Oncol Nurs 14(2):E10-E21, Oncology Nursing Society, United States (Apr. 2010).

Office Action mailed Jan. 8, 2019, in U.S. Appl. No. 16/213,954, inventors Cogswell, et al., filed Dec. 7, 2018, 8 pages.

Office Action mailed Jan. 8, 2019, in U.S. Appl. No. 16/213,960, inventors Cogswell, et al., filed Dec. 7, 2018, 8 pages.

Office Action mailed Jan. 8, 2019, in U.S. Appl. No. 16/213,965, inventors Cogswell, et al., filed Dec. 7, 2018, 8 pages.

Patrylak, P.P., et al., "Results of the Southwest Oncology Group phase II evaluation (study S0031) of ZD1839 for advanced transitional cell carcinoma of the urothelium," BJU 105:317-21, Southwest Oncology Group (Nov. 2009).

Roupret, M., et al., "European Guidelines for the Diagnosis and Management of Upper Urinary Tract Urothelial Cell Carcinomas: 2011 Update," European Urology 59:584-94, European Association of Urology (Apr. 2011).

Joung, J.Y., et al., "Paclitaxel and cisplatin chemotherapy for metastatic urothelial carcinoma after failure of two courses of platinum-based regimens," Int'l J. Urology 18:350-57, The Japanese Urological Association (May 2011).

Office Action mailed Jan. 18, 2019, in U.S. Appl. No. 16/230,657, inventors Cogswell, et al., filed Dec. 21, 2018, 13 pages.

Office Action mailed Mar. 15, 2019, in U.S. Appl. No. 16/006,493, inventor Cogswell J.P., et al., filed Jun. 12, 2018, 10 pages.

Office Action mailed Mar. 18, 2019, in U.S. Appl. No. 16/024,333, inventor Cogswell J.P., et al., filed Jun. 29, 2018, 10 pages.

Office Action mailed Mar. 18, 2019, in U.S. Appl. No. 16/024,340, inventor Cogswell J.P., et al., filed Jun. 29, 2018, 10 pages.

Office Action mailed Jun. 28, 2019, in U.S. Appl. No. 16/248,222, inventor Cogswell, John P., et al., filed Jan. 15, 2019, 9 pages.

Office Action mailed Jun. 28, 2019, in U.S. Appl. No. 16/248,215, inventor Cogswell, John P., et al., filed Jan. 15, 2019, 9 pages.

National Institutes of Health Clinical Center, Clinical Trial Identifier NCT01024231 entitled "Dose-escalation Study of Combination BMS-936558 (MDX-1106) and Ipilimumab in Subjects With Unrespectable Stage III or Stage IV Malignant Melanoma," (Dec. 1, 2009), 7 pages.

National Institutes of Health Clinical Center, Clinical Trial Identifier NCT01024231 entitled "Dose-escalation Study of Combination BMS-936558 (MDX-1106) and Ipilimumab in Subjects With Unrespectable Stage III or Stage IV Malignant Melanoma," (Apr. 30, 2012), 8 pages.

Abdiche, Y.N., et al., "Assessing Kinetic and Epitopic Diversity Across Orthogonal Monoclonal Antibody Generation Platforms," mAbs 8(2):264-277, Taylor & Francis, United States (Dec. 2015).

Boyd, S.D., et al., "Deep Sequencing and Human Antibody Repertoire Analysis," Current Opinion in Immunology 40:103-109, Elsevier, United Kingdom (Jun. 2016).

Conroy, P.J., et al., "Antibodies: From Novel Repertoires to Defining and Refining the Structure of Biologically Important Targets," Methods (San Diego, Calif.) 116:12-22, Academic Press, United States (Mar. 2017).

Ferrara, F., et al., "Recombinant Renewable Polyclonal Antibodies," MAbs 7(1):32-41, Taylor & Francis, United Kingdom (Jan. 2015).

Kanyavuz, A., et al., "Breaking the Law: Unconventional Strategies for Antibody Diversification," Nature Reviews. Immunology 19(6):355-368, Nature Publishing Group, United Kingdom (Jun. 2019).

Khan, L., et al., "Cross-neutralizing Anti-HIV-1 Human Single Chain Variable Fragments (ScFvs) Against CD4 Binding Site and

(56) References Cited

OTHER PUBLICATIONS

N332 Glycan Identified From a Recombinant Phage Library," Scientific Reports 7:45163:1-12, Nature Publishing Group, United Kingdom (Mar. 2017).

Konitzer, J.D., et al., "Generation of a Highly Diverse Panel of Antagonistic Chicken Monoclonal Antibodies Against the GIP Receptor," mAbs 9(3):536-549, Taylor & Francis, United States (Apr. 2017).

Lee, J., et al., "Molecular-Level Analysis of the Serum Antibody Repertoire In Young Adults Before and After Seasonal Influenza Vaccination," Nature Medicine 22(12):1456-1464, Nature Publishing Company, United States (Dec. 2016).

Parola, C., et al., "Integrating High-throughput Screening and Sequencing for Monoclonal Antibody Discovery and Engineering," Immunology 153(1):31-41, Blackwell Scientific Publications, United Kingdom (Jan. 2018).

Sheehan, J., and Marasco, W.A., "Phage and Yeast Display," Microbiology Spectrum 3(1):AID-0028-2014 1-17, ASM Press, United States (Feb. 2015).

Van Regenmortel, M.H.V., Development of a Preventive HIV Vaccine Requires Solving Inverse Problems Which is Unattainable by Rational Vaccine Design, Frontiers in Immunology 8:2009, Frontiers Research Foundation, Switzerland (Jan. 2018).

Zhou, T., et al., "Structural Repertoire of HIV-1-Neutralizing Antibodies Targeting the CD4 Supersite in 14 Donors," Cell 161(6):1280-1292, Cell Press, United States (Jun. 2015).

Baitsch, L., et al., "Extended Co-expression of Inhibitory Receptors by Human Cd8 T-cells Depending on Differentiation, Antigen-specificity and Anatomical Localization," PLoS One, 7(2):e30852, Public Library of Science, United States (Feb. 2012).

Barbas, S.M., et al., "Human Autoantibody Recognition of DNA," Proceedings of the National Academy of Sciences USA 92(7):2529-2533, National Academy of Sciences, United States (Mar. 1995).

Barbas, S.M., et al., "Recognition of DNA by Synthetic Antibodies," Journal of the American Chemical Society 116(5):2161-2162, American Chemical Society, United States (Mar. 1994).

Beck, K.M., et al., "Enterocolitis in Patients With Cancer After Antibody Blockade of Cytotoxic T-lymphocyte-associated Antigen 4," Journal of Clinical Oncology 24(15):2283-2289, American Society of Clinical Oncology, United States (May 2006).

Beiboer, S.H., et al., "Guided Selection of a Pan Carcinoma Specific Antibody Reveals Similar Binding Characteristics yet Structural Divergence between the Original Murine Antibody and its Human Equivalent," Journal of Molecular Biology 296(3):833-849, Elsevier, United Kingdom (Feb. 2000).

Berezov, A., et al., "Biacore Analysis of Rationally Designed Anit-HER2 Exocyclic Mimetics of Antibodies," BIA Journal 8(1):4 pages, British Infection Association, United Kingdom (Jan. 2001).

Bordeaux, J., et al., "Antibody Validation," BioTechniques 48(3):197-209, Future Science, United Kingdom (Mar. 2010).

Bourgeois, C., et al., "Prophylactic Administration of a Complementarity-determining Region Derived from a Neutralizing Monoclonal Antibody is Effective Against Respiratory Syncytial Virus Infection in BALB/c Mice," Journal of Virology 72(1):807-810, American Society For Microbiology, United States (Jan. 1998).

Butte, M.J., et al., "Interaction of Human PD-L1 and B7-1," Molecular Immunology 45(13):3567-3572, Pergamon Press, United Kingdom (Aug. 2008).

Butte, M.J., et al., "Programmed Death-1 Ligand 1 Interacts Specifically with the B7-1 Costimulatory Molecule to Inhibit T Cell Responses," Immunity 27(1):111-122, Cell Press, United States (Jul. 2007).

Cheang, M.C.U., et al., "Immunohistochemical Detection Using the New Rabbit Monoclonal Antibody Sp1 of Estrogen Receptor in Breast Cancer is Superior to Mouse Monoclonal Antibody 1d5 in Predicting Survival," Journal of Clinical Oncology 24(36):5637-5644, American Society of Clinical Oncology, United States (Dec. 2006).

Clinical Trials.gov, "An Immuno-therapy Study to Evaluate the Effectiveness, Safety and Tolerability of Nivolumab or Nivolumab in Combination With Other Agents in Patients With Advanced Liver Cancer (CheckMate040)," NCT01658878, accessed at https://clinicaltrials.gov/study/NCT01658878, Dec. 14, 2023, 14 pages.

Clinical Trials.gov, "Study of Nivolumab (BMS-936558) Compared With Dacarbazine in Untreated, Unresectable, or Metastatic Melanoma (CheckMate 066)," NCT01721772, (2012), accessed at https://clinicaltrials.gov/ct2/show/NCT01721772?term=480+mg+nivolumab&strde-07%, last accessed Jan. 22, 2019, 9 pages.

Clinical Trials.gov, "A Study of an Anti-KIR Antibody Lirilumab in Combination With an Anti-PD1 Antibody Nivolumab and Nivolumab Plus an Anti-CTLA-4 Ipilimumab Antibody in Patients With Advanced Solid Tumors," NCT01714739, accessed at ://clinicaltrials.gov/study/NCT01714739?cond=NCT01714739&rank=1, accessed on May 6, 2025, 31 pages.

Clinical Trials.gov, "Multiple Class I Peptides & Montanide ISA 51 VG w Escalating Doses of Anti-PD-1 ab BMS936558," NCT01176461, accessed at https://clinicaltrials.gov/study/NCT01176461?cond=NCT01176461&rank=1, accessed on May 6, 2025, 13 pages.

Clinical Trials.gov, "Nivolumab (BMS-936558; MDX-1106) in Combination With Sunitinib, Pazopanib, or Ipilimumab in Subjects With Metastatic Renal Cell Carcinoma (RCC) (CheckMate 016)," NCT01472081, accessed at https://clinicaltrials.gov/study/NCT01472081, accessed on May 5, 2025, 18 pages.

Clinical Trials.gov, "Vaccine Combining Multiple Class I Peptides and Montanide ISA 51VG With Escalating Doses of Anti-PD-1 Antibody Nivolumab or Ipilimumab With Nivolumab For Patients With Resected Stages IIIC/? IV Melanoma," NCT01176474, accessed at https://clinicaltrials.gov/study/NCT01176474?cond=NCT01176474&rank=1, accessed on May 6, 2025, 14 pages.

ClinicalTrials.gov, "An Investigational Immuno-Therapy Study to Determine the Safety and Effectiveness of Nivolumab and Daratumumab in Patients With Multiple Myeloma," NCT01592370, accessed at https://clinicaltrials.gov/study/NCT01592370?term=NCT01592370&limit=10&rank=1, accessed on Aug. 29, 2024.

ClinicalTrials.gov, "A Study to Compare BMS-936558 to the Physician's Choice of Either Dacarbazine or Carboplatin and Paclitaxel in Advanced Melanoma Patients That Have Progressed Following Anti-CTLA-4 Therapy (CheckMate 037)," NCT01721746, accessed at https://clinicaltrials.gov/ct2/show/NCT01721746, Nov. 6, 2012, 14 pages.

ClinicalTrials.gov, "Study of BMS-936558 (Nivolumab) Compared to Docetaxel in Previously Treated Advanced or Metastatic Squamous Cell Non-small Cell Lung Cancer (NSCLC) (CheckMate 017)," NCT01642004, accessed at https://www.clinicaltrials.gov/ct2/show/NCT01642004, Jul. 17, 2012, 11 pages.

ClinicalTrials.gov, "Study of BMS-936558 (Nivolumab) Compared to Docetaxel in Previously Treated Metastatic Non-squamous NSCLC Checkmate057," NCT01673867, accessed at https://www.clinicaltrials.gov/ct2/show/NCT01673867, Aug. 28, 2012, 29 pages.

ClinicalTrials.gov, "Study of Nivolumab (BMS-936558) vs. Everolimus in Pre-Treated Advanced or Metastatic Clear-cell Renal Cell Carcinoma (CheckMate 025)," NCT01668784, accessed at https://www.clinicaltrials.gov/ct2/show/NCT01668784, Aug. 20, 2012, 10 pages.

Colman, P.M., "Effects of Amino Acid Sequence Changes on Antibody-antigen Interactions," Research in Immunology 145(1):33-36, Elsevier, Netherlands (Jan. 1994).

Condeelis, J., and Weissleder, R., "In Vivo Imaging in Cancer," Cold Spring Harbor Perspectives in Biology 2(12):a003848, pp. 1-24, Cold Spring Harbor Laboratory Press, United States (Dec. 2010).

Ditzel, H.J., et al., "Determinants of Polyreactivity in a Large Panel of Recombinant Human Antibodies from HIV-1 Infection," Journal of Immunology 157(2):739-749, American Association of Immunologists, United States (Jul. 1996).

Dong, H., et al., "B7-H1 Determines Accumulation and Deletion of Intrahepatic CD8(+) T Lymphocytes," Immunity 20(3):327-336, Cell Press, United States (Mar. 2004).

Fife, B.T., et al., "Interactions Between Pd-1 and Pd-11 Promote Tolerance by Blocking the Tcr-induced Stop Signal," Nature Immunology 10(11):1185-1192, Nature America Inc., United States (Nov. 2009).

Final Office Action mailed Jun. 14, 2019, in U.S. Appl. No. 16/231,211, Cogswell, J. P., et al., filed Dec. 21, 2018, 7 pages.

(56) References Cited

OTHER PUBLICATIONS

Fischer, T., et al., "Reassessment of CXCR4 Chemokine Receptor Expression in Human Normal and Neoplastic Tissues Using the Novel Rabbit Monoclonal Antibody UMB-2," PLoS One 3(12):e4069, Public Library of Science, United States (Dec. 2008).

Flaherty, K.T., et al., "Inhibition of Mutated, Activated Braf in Metastatic Melanoma," The New England Journal of Medicine 363(9):809-819, Massachusetts Medical Society, United States (Aug. 2010).

Garber, K., "Beyond Ipilimumab: New Approaches Target the Immunological Synapse," Journal of the National Cancer Institute 103(14):1079-1082, Oxford University Press, United States (Jul. 2011).

GenBank, "Human hPD-1 (hPD-1) mRNA, Complete Cds," Accession No. U64863, accessed at https://www.ncbi.nlm.nih.gov/nuccore/U64863, accessed on Nov. 3, 2020, 2 pages.

GenBank, "RecName: Full=Programmed cell death 1 ligand 1; Short—PD-L1; Short—PDCD1 ligand 1; Short=Programmed death ligand 1; AltName: Full=B7 homolog 1; Short=B7-H1;AltName: CD_antigen=CD274; Flags: Precursor," Accession No. Q9NZQ7.1, accessed at https://www.ncbi.nlm.nih.gov/protein/Q9NZQ7, accessed on Nov. 2, 2016, 11 pages.

Gridelli, C., et al., "Second-line Treatment of Advanced Non-small Cell Lung Cancer," Journal of Thoracic Oncology 3(4):430-440, Elsevier, United States (Apr. 2008).

Hanna, N., et al., "Randomized Phase III Trial of Pemetrexed Versus Docetaxel in Patients with Non-small-cell Lung Cancer Previously Treated with Chemotherapy," Journal of Clinical Oncology 22(9):1589-1597, American Society of Clinical Oncology, United States (May 2004).

Hodi, F.S., et al., "Improved Survival with Ipilimumab in Patients with Metastatic Melanoma," The New England Journal of Medicine 363(8):711-723, Massachusetts Medical Society, United States (Aug. 2010).

Holliger, P., and Hudson, P.J., "Engineered Antibody Fragments and the Rise of Single Domains," Nature Biotechnology 23(9):1126-1136, Nature America Publishing, United States (Sep. 2005).

Hutson, T., et al., "LBA22_PR—Temsirolimus vs Sorafenib As Second Line Therapy in Metastatic Renal Cell Carcinoma: Results from the Intorsect Trial," Annals of Oncology 23(Suppl 9): ixe14, Abstract LBA22 PR, Elsevier, Netherlands (Sep. 2012).

Igarashi, K., et al., "Specific Binding of a Synthetic Peptide Derived from an Antibody Complementarity Determining Region to Phosphatidylserine," Journal of Biochemistry 117(2):452-457, Oxford University Press, England (Feb. 1995).

Klimka, A., et al., "Human Anti-CD30 Recombinant Antibodies by Guided Phage Antibody Selection Using Cell Panning," British Journal of Cancer 83(2):252-260, Nature Publishing Group, United Kingdom (Jul. 2000).

Latchman, Y., et al., "PD-L2 is a Second Ligand for PD-1 and Inhibits T Cell Activation," Nature Immunology 2(3):261-268, Nature Publishing Group, United Kingdom (Mar. 2001).

Lebbe, C., et al., "1116PD—Five-Year Survival Rates for Patients (PTS) with Metastatic Melanoma (MM) Treated with Ipilimumab (IPI) in Phase II Trials," Annals of Oncology 23(Suppl 9):ix363, Abstract 116PD, Elsevier, Netherlands (Sep. 2012).

Lederman, S., et al., "A Single Amino Acid Substitution in a Common African Allele of the CD4 Molecule Ablates Binding of the Monoclonal Antibody, OKT4," Molecular Immunology 28(11):1171-1181, Pergamon Press, United Kingdom (Nov. 1991).

Levi, M., et al., "A Complementarity-determining Region Synthetic Peptide acts as a Miniantibody and Neutralizes Human Immunodeficiency Virus Type 1 in Vitro," Proceedings of the National Academy of Sciences, USA 90(10):4374-4378, National Academy of Sciences, United States (May 1993).

Mccabe, K.E., and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).

Mcdermott, D.F., et al., "Interleukin-2 Therapy of Metastatic Renal Cell Carcinoma—predictors of Response," Seminars in Oncology 33(5):583-587, Saunders, United States (Oct. 2006).

Mcdermott, D.F., and Atkins, M.B., "PD-1 as a potential target in cancer therapy," Cancer Medicine 2(5):662-673, Wiley, United States (Oct. 2013).

Miller, V.A., et al., "Optimizing Therapy in Previously Treated Non-Small Cell Lung Cancer," Seminars in Oncology 33(1):S25-S31, Elsevier, Netherlands (Feb. 2006).

Motzer, R.J., et al., "Efficacy of Everolimus in Advanced Renal Cell Carcinoma: A Double-blind, Randomised, Placebo-controlled Phase III Trial," Lancet 372(9637):449-456, Elsevier, Netherlands (Aug. 2008).

Motzer, R.J., et al., "Phase 3 Trial of Everolimus for Metastatic Renal Cell Carcinoma: Final Results and Analysis of Prognostic Factors," Cancer 116(18):4256-4265, Wiley, United States (Sep. 2010).

Mu, C-Y., et al., "High Expression of PD-L1 in Lung Cancer May Contribute to Poor Prognosis and Tumor Cells Immune Escape Through Suppressing Tumor Infiltrating Dendritic Cells Maturation," Medical Oncology 28:682-688, Springer Nature, Germany (Sep. 2011).

Mulders, P., "Vascular Endothelial Growth Factor and mTOR Pathways in Renal Cell Carcinoma: Differences and Synergies of Two Targeted Mechanisms," BJU International 104(11):1585-1589, Blackwell Science, England (Dec. 2009).

Nishimura, H., et al., "Development of Lupus-like Autoimmune Diseases by Disruption of the PD-1 Gene Encoding an ITIM Motif-carrying Immunoreceptor," Immunity 11(2):141-151, Cell Press, United States (Aug. 1999).

Office Action dated Sep. 26, 2019, in U.S. Appl. No. 16/231,211, inventor Cogswell, J., et al., filed Dec. 21, 2018, 3 pages.

Office Action mailed Jan. 23, 2015, in U.S. Appl. No. 13/892,671, inventor Cogswell, J.P., et al., filed May 13, 2013, 7 pages.

Office Action mailed Aug. 7, 2018, in U.S. Appl. No. 16/006,473, Cogswell, J. P., et al., filed Jun. 12, 2018, 7 pages.

Office Action mailed Jan. 22, 2019, in U.S. Appl. No. 16/231,211, Cogswell, J. P., et al., filed Dec. 21, 2018, 14 pages.

Office Action mailed May 2, 2017, in U.S. Appl. No. 14/400,667, Cogswell, J. P., et al., filed Nov. 12, 2014, 8 pages.

Olafsen, T., et al., "Antibody Vectors for Imaging," Seminars in Nuclear Medicine 40(3):167-81, Saunders, United States (May 2010).

Park, J-J, et al., "B7-H1/CD80 Interaction is Required for the Induction and Maintenance of Peripheral T-cell Tolerance," Blood 116(8):1291-1298, Elsevier, Netherlands (Aug. 2010).

Patel, S.P., and Woodman, S.E., "Profile of Ipilimumab and Its Role in the Treatment of Metastatic Melanoma," Drug Design, Development and Therapy 5:489-495, Dove Press Limited, New Zealand (Dec. 2011).

Paterson, A.M., et al., "The Programmed Death-1 Ligand 1:B7-1 Pathway Restrains Diabetogenic Effector T Cells in Vivo," Journal of Immunology 187(3):1097-1105, American Association of Immunologists, United States (Aug. 2011).

Phan, G.Q., et al., "Cancer Regression and Autoimmunity Induced by Cytotoxic T Lymphocyte-associated Antigen 4 Blockade in Patients With Metastatic Melanoma," Proceedings of the National Academy of Sciences of the United States of America 100(14):8372-8377, National Academy of Sciences, United States (Jun. 2003).

Polymenis, M. and Stollar, B.D., "Critical Binding Site Amino Acids of Anti-Z-DNA Single Chain Fv Molecules. Role of Heavy and Light Chain CDR3 and Relationship to Autoantibody Activity," Journal of Immunology 152(11):5318-5329, American Association of Immunologists, United States (Jun. 1994).

Rader, C., et al., "A Phage Display Approach for Rapid Antibody Humanization: Designed Combinatorial V Gene Libraries," Proceedings of the National Academy of Sciences USA 95(15):8910-8915, National Academy of Sciences, United States (Jul. 1998).

Ribas, A., et al., "Antitumor Activity in Melanoma and Anti-self Responses in a Phase I Trial With the Anti-cytotoxic T Lymphocyte-associated Antigen 4 Monoclonal Antibody Cp-675,206," Journal of Clinical Oncology 23(35):8968-8977, American Society of Clinical Oncology, United States (Dec. 2005).

(56) References Cited

OTHER PUBLICATIONS

Robert, C., et al., "Ipilimumab Plus Dacarbazine for Previously Untreated Metastatic Melanoma," The New England Journal of Medicine 364:2517-2526, Massachusetts Medical Society, Boston (Jun. 2011).

Rossi, S., et al., "Rabbit Monoclonal Antibodies: a Comparative Study Between a Novel Category of Immunoreagents and the Corresponding Mouse Monoclonal Antibodies," American Journal of Clinical Pathology 124(2):295-302, Oxford University Press, United Kingdom (Aug. 2005).

Scagliotti, G., et al., "Treatment-by-histology Interaction Analyses in Three Phase III Trials Show Superiority of Pemetrexed in Nonsquamous Non-small Cell Lung Cancer," Journal of Thoracic Oncology 6(1):64-70, Elsevier, Netherlands (Jan. 2011).

Shepherd, F.A., et al., "Erlotinib in Previously Treated Non-small-cell Lung Cancer," The New England Journal of Medicine 353(2):123-132, Massachusetts Medical Society, United States (Jul. 2005).

Shepherd, F.A., et al., "Prospective Randomized Trial of Docetaxel Versus Best Supportive Care in Patients With Non-Small-Cell Lung Cancer Previously Treated With Platinum-Based Chemotherapy," Journal of Clinical Oncology 18:2095-2103, American Society of Clinical Oncology, Alexandria (May 2000).

Sjoblom, T., et al., "The Consensus Coding Sequences of Human Breast and Colorectal Cancers," Science 314(5797):268-274, American Association for the Advancement of Science, United States (Oct. 2006).

Sosman, J.A., et al., "Survival in BRAF V600-mutant Advanced Melanoma Treated With Vemurafenib," The New England Journal of Medicine 366(8):707-714, Massachusetts Medical Society, United States (Feb. 2012).

Sullivan, R.J., and Flaherty, K.T., "BRAF in Melanoma: Pathogenesis, Diagnosis, Inhibition, and Resistance," Journal of Skin Cancer 2011:423239, pp. 1-8, Wiley, United States (Nov. 2011).

Thompson, R.H., et al., "Tumor B7-H1 is Associated With Poor Prognosis in Renal Cell Carcinoma Patients With Long-term Follow-up," Cancer Research 66(7):3381-3385, American Association for Cancer Research, United States (Apr. 2006).

Tivol, E.A., et al., "Loss of CTLA-4 Leads to Massive Lymphoproliferation and Fatal Multiorgan Tissue Destruction, Revealing a Critical Negative Regulatory Role of CTLA-4," Immunity 3(5):541-547, Cell Press, United States (Nov. 1995).

Weber, U.S., et al., "Safety, Efficacy, and Biomarkers of Nivolumab With Vaccine in Ipilimumab-Refractory or -Naïve Melanoma," J Clin Oncol 31(34):4311-4318 American Society of Clinical Oncology, United States (Dec. 2013).

Wolchok, J.D., et al., "Guidelines for the Evaluation of Immune Therapy Activity in Solid Tumors: Immune-related Response Criteria," Clinical Cancer Research 15(23):7412-7420, The Association, United States (Dec. 2009).

Xu, J.L. and Davis, M.M., "Diversity in the CDR3 Region of V(H) is Sufficient for Most Antibody Specificities," Immunity 13(1):37-45, Cell Press, United States (Jul. 2000).

Xu, L.-H., et al., "Preparation and Identification of Human Soluble sPD-L1 and Its Antibodies," Chinese Journal of Biotechnology 23(1):106-111, China (Jan. 2007).

Yang, J., et al., "The Novel Costimulatory Programmed Death Ligand 1/B7.1 Pathway Is Functional in Inhibiting Alloimmune Responses in Vivo," Journal of Immunology 187(3):1113-1119, American Association of Immunologists, United States (Aug. 2011).

Zhao, X., et al., "Model-based Evaluation of Tire Efficacy and Safety of Nivolumab Once Every 4 Weeks Across Multiple Tumor Types," Annals of Oncology 31(2):302-309, Elsevier, Netherlands (Feb. 2020).

Co-pending U.S. Appl. No. 12/248,215, filed Jan. 15, 2019. (Not yet Published).

Co-pending U.S. Appl. No. 19/199,098, filed May 5, 2025. (Not yet Published).

Finn, R.S., "Current and Future Treatment Strategies for Patients With Advanced Hepatocellular Carcinoma: Role of mTOR Inhibition," Liver Cancer 1(3-4):247-256, S.Karger, Switzerland (Nov. 2012).

Office Action mailed Feb. 2, 2023, in U.S. Appl. No. 16/827,580, inventor Cogswell, J.P., et al., filed Mar. 23, 2020, 13 pages.

Office Action mailed Oct. 24, 2023, in U.S. Appl. No. 18/052,076, inventor Cogswell, J.P., et al., filed Nov. 2, 2022, 14 pages.

Office Action mailed Feb. 13, 2024, in U.S. Appl. No. 18/052,099, inventor Cogswell, J.P., et al., filed Nov. 2, 2022, 14 pages.

Office Action mailed Jun. 16, 2025, in U.S. Appl. No. 19/193,629, inventor Cogswell, J.P., et al., filed Apr. 29, 2025, 8 pages.

Office Action mailed Jun. 17, 2025, in U.S. Appl. No. 19/193,652, inventor Cogswell, J.P., et al., filed Apr. 29, 2025, 7 pages.

Affidavit of Nathaniel E. Frank-White, Sep. 26, 2024, 40 pages.

Amended claims with annotations filed after European Search Report, European Patent Application No. 22196038.8, dated Oct. 18, 2023, 2 pages.

Amended Claims, European Patent Application No. 17189595.6, dated Oct. 18, 2018, 6 pages.

Amgen Inc., "Amgen Reports First Quarter 2025 Financial Results," Press Release, dated May 1, 2025, accessed at https://www.amgen.com/newsroom/press-releases/2025/05/amgen-reports-first-quarter-2025-financial-results, accessed on Jun. 6, 2025, 42 pages.

Amgen Inc., "Amgen Reports Fourth Quarter and Full Year 2024 Financial Results," Press Release, dated Feb. 4, 2025, accessed at https://www.amgen.com/newsroom/press-releases/2025/02/amgen-reports-fourth-quarter-and-full-year-2024-financial-results, accessed on Jun. 10, 2025, 42 pages.

Amgen, Inc., "Amgen Biosimilars," accessed at https://www.amgen.com/science/biosimilars, accessed on Jun. 9, 2025, 4 pages.

Amgen, Inc., "Amgen Pipeline," accessed at https://www.amgenpipeline.com/, accessed on Jun. 6, 2025, 3 pages.

Annex to Communication, European Patent Application No. 17189595.6, dated Oct. 7, 2019, 2 pages.

Annex to the Communication, European Patent Application No. 17189595.6, dated Apr. 11, 2022, 4 pages.

Antonia, S.J., et al., "Phase I/II Study of Nivolumab With or Without Ipilimumab for Treatment of Recurrent Small Cell Lung Cancer (SCLC): CA209-032," Journal of Clinical Oncology 33(15 Suppl): Abstract 7503, American Society of Clinical Oncology, United States (May 2015), 3 pages.

Antony, Paul Andrew, M.D., Curriculum Vitae, 11 pages.

Association for Accessible Medicines, "The U.S. Generic & Biosimilar Medicines Savings Report," pp. 1-41, Association for Accessible Medicines, United States (Sep. 2024).

Bai, S., et al., "A Guide to Rational Dosing of Monoclonal Antibodies," Clinical Pharmacokinetics 51(2):119-135, Adis, Springer Science+Business Media, Switzerland (Feb. 2012).

Barbee, M.S., et al., "Current Status and Future Directions of the Immune Checkpoint Inhibitors Ipilimumab, Pembrolizumab, and Nivolumab in Oncology," The Annals of Pharmacotherapy 49(8):907-937, Sage, United States (Aug. 2015).

Bi, T., et al., "Model-informed Drug Development Approach Supporting Approval of the 4-week (Q4W) Dosing Schedule for Nivolumab (Opdivo) Across Multiple Indications: A Regulatory Perspective," Annals of Oncology 30(4):644-651, Elsevier, Netherlands (Apr. 2019).

Biologics HQ, "Biosimilar-Related IPR Petitions," accessed at https://biologicshq.com/stats_entry/biosimilar-related-ipr-petitions/, accessed on Jun. 20, 2025, 1 page.

Biologics HQ, "Biosimilar-Related IPRs by Reference Product," accessed at https://biologicshq.com/stats_entry/biosimilar-related-iprs-by-referenceproduct/, accessed on Jun. 20, 2025, 1 page.

Biologics HQ, "Patents Subject to Biosimilar-Related IPRs and Litigations," accessed at https://biologicshq.com/stats_entry/biosimilar-patents-subject-to-iprand-us-litigation/, accessed on Jun. 20, 2025, 1 page.

Biosimilars Council White Paper, "Breaking Through on Biosimilars: Delivering More-Affordable, Innovative Medicines to America's Patients," The Biosimilars Council, accessed at https://biosimilarscouncil.org/wpcontent/uploads/2019/04/Breaking-Through-on-Biosimilars-

(56)         References Cited

OTHER PUBLICATIONS

Biosimilars- Council-White-Paper.pdf, 24 pages, Association for Accessible Medicines, United States (Apr. 2019).

Biosimilars Forum, "Biosimilars Forum Applauds the Trump Administration for Drug Pricing Executive Order," accessed at https://biosimilarsforum.org/2025/04/16/biosimilars-forum-applauds-the-trump-administration-for-drug-pricing-executive-order/, accessed on Jun. 20, 2025, 1 page.

Brahmer, J., et al., "Phase I study of single-agent anti-programmed death-1 (MDX-1106) in refractory solid tumors: safety, clinical activity, pharmacodynamics, and immunologic correlates," J Clin Oncol 28:3167-3175, American Society of Clinical Oncology, United States (Jul. 2010).

Bristol-Myers Squibb Company, "Annual Report Pursuant to Section 13 or 15(d) of the Securities Exchange Act of 1934 for the fiscal year ended Dec. 31, 2024," Form 10-K, Feb. 2025, United States Securities and Exchange Commission, Washington, D.C., 155 pages.

Bristol-Myers Squibb, "Bristol-Myers Squibb Completes Acquisition of Medarex, Inc.," Press Release, dated Sep. 1, 2009, accessed at https://news.bms.com/news/details/2009/Bristol-Myers-Squibb-to-Acquire-Medarex/default.aspx, 2 pages.

Bristol-Myers Squibb, "Bristol-Myers Squibb Receives Accelerated Approval of Opdivo (nivolumab) from the U.S. Food and Drug Administration," Press Release, dated Dec. 22, 2014, accessed at https://news.bms.com/news/details/2014/Bristol-Myers-Squibb-Receives-Accelerated-Approval-of-Opdivo-nivolumab-from-the-US-Food-and-Drug-Administration/default.aspx, accessed on Jun. 8, 2025, 5 pages.

Bristol-Myers Squibb, "FDA Approves Yervoy™ (ipilimumab) for the Treatment of Patients with Newly Diagnosed or Previously-Treated Unresectable or Metastatic Melanoma, the Deadliest Form of Skin Cancer," Press Release, dated Mar. 25, 2011, accessed at https://news.bms.com/news/details/2011/FDAApproves-YERVOY-ipilimumab-for-the-Treatment-of-Patients-with-Newly-Diagnosed-or-Previously-Treated-Unresectable-or-Metastatic-Melanoma-the-Deadliest-Form-of-Skin-Cancer/default.aspx, accessed on Jun. 8, 2025, 6 pages.

Brittain, B., "Bristol Myers sues AstraZeneca over cancer-treatment patents," Reuters.com, accessed at https://www.reuters.com/legal/transactional/bristol-myers-sues-astrazeneca-over-cancer-treatment-patents-2022-03-18/, published Mar. 18, 2022, 2 pages.

Callahan, M.K. and Wolchok, J.D., "At the Bedside: CTLA-4- and PD-1-Blocking Antibodies in Cancer Immunotherapy," Journal of Leukocyte Biology 94(1):41-53, Oxford University Press, United Kingdom (Jul. 2013).

Callahan, M.K., et al., "Peripheral and Tumor Immune Correlates in Patients With Advanced Melanoma Treated With Combination Nivolumab (Anti-PD-1, BMS-936558, ONO-4538) and Ipilimumab," 31(15 Suppl): Abstract 3003, American Society of Clinical Oncology, United States (May 2013), 3 pages.

Complaint, Bristol-Myers Squibb Co. and E.R. *Squibb & Sons, L.L.C.,* Plaintiffs v. *Astrazeneca Pharmaceuticals LP and Astrazeneca UK Ltd.,* Defendants, Case No. 1:22-cv-00346-UNA, Mar. 17, 2022, 85 pages.

Decision Denying Institution of Inter Partes Review in IPR2025-00601 and IPR2025-00602 and Referring the Petition in IPR2025-00603 to the Board, filed in IPR2025-00601, *Amgen Inc.,* Petitioner v. *Bristol-Myers Squibb Company,* Patent Owner, Jul. 24, 2025, 5 pages.

Declaration of Paul Andrew Antony, M.D., Feb. 28, 2025, 123 pages.

Declaration of Peter P. Lee, M.D., Jul. 10, 2025, 41 pages.

Declaration of Prescott Lassman, Feb. 24, 2025, 26 pages.

Declaration of Sylvia D. Hall-Ellis, Ph.D., Feb. 28, 2025, 391 pages.

Dillard, T., et al., "Anti-CTLA-4 antibody therapy associated autoimmune hypophysitis: serious immune related adverse events across a spectrum of cancer subtypes," Pituitary 13(1):29-38, Kluwer Academic Publishers, United States (Jul. 2009), 13 pages.

Email from Director_PTABDecision_Review@uspto.gov, Subject: "IPR2025-00601 and -00602 Director Review Requests," dated Aug. 26, 2025, 1 page.

Email from Trials@uspto.gov, Subject: "Re: IPR2025-00601: Deposit Account Withdrawal Authorization," dated Aug. 26, 2025, 2 pages.

FDA Approval Label and Prescribing Information, Keytruda, Revised Jun. 2025, 180 pages.

FDA Approval Label and Prescribing Information, Opdivo, Revised Dec. 2014, 20 pages.

FDA Approved Label and Prescribing Information, Opdivo, Revised May 2025, 181 pages.

FDA Approved label and prescribing information, Yervoy, Revised Mar. 2011, 20 pages.

FDA Approved Label And Prescribing Information, Yervoy, Revised May 2025, 81 pages.

Feng, Y., et al., "Model-based Clinical Pharmacology Profiling of Ipilimumab in Patients with Advanced Melanoma," British Journal of Clinical Pharmacology 78(1):106-117, Wiley-Blackwell, United Kingdom (Jul. 2014).

Fife, B.T., and Bluestone, J.A., "Control of Peripheral T-cell Tolerance and Autoimmunity via the CTLA-4 and PD-1 Pathways," Immunological Reviews 224:166-182, Munksgaard, United Kingdom (Aug. 2008), 20 pages.

Giacomo, A.M.D., et al., "The emerging toxicity profiles of anti-CTLA-4 antibodies across clinical indications," Seminars in Oncology, 37(5):499-507, W.B. Saunders, United States (Oct. 2010), 12 pages.

Hammers, H.J., et al., "Expanded Cohort Results From Checkmate 016: A Phase I Study of Nivolumab in Combination With Ipilimumab in Metastatic Renal Cell Carcinoma (Mrcc)," Journal of Clinical Oncology 33(15 Suppl Pt1): Abstract 4516, American Society of Clinical Oncology, United States (May-Jun. 2015), 9 pages.

Hodi, F.S., et al., "Biologic activity of cytotoxic T lymphocyte-associated antigen 4 antibody blockade in previously vaccinated metastatic melanoma and ovarian carcinoma patients," Proceedings of the National Academy of Sciences of the United States of America 100(8):4712-4717, National Academy of Sciences, United States (Apr. 2003), 14 pages.

Humphrey, R.W., et al., "Opportunities and challenges in the development of experimental drug combinations for cancer," Journal of the National Cancer Institute 103(16):1222-1226, Oxford University Press, United States (Aug. 2011), 8 pages.

Iqvia, "Biosimilars in the United States 2023-2027," accessed at https://www.iqvia.com/insights/the-iqvia-institute/reports-andpublications/ reports/biosimilars-in-the-united-states-2023-2027, accessed on Jun. 20, 2025, 2 pages.

Korman, A., et al., "Activity of Anti-PD-1 in Murine Tumor Models: Role of Host PD-L1 and Synergistic Effect of Anti-PD-1 and Anti-CTLA-4." Journal of Immunology 178(Suppl 1):S82, American Association of Immunologists, United States (Apr. 2007).

Larkin, J., et al., "Combined Nivolumab and Ipilimumab or Monotherapy in Untreated Melanoma," The New England Journal of Medicine 373(1):23-34, Massachusetts Medical Society, United States (Jul. 2015).

Lassman, Scott M., J.D., Curriculum Vitae, 4 pages.

Lee, Peter P., M.D., Curriculum Vitae, 21 pages.

Letter accompanying amendments, European Patent Application No. 22196038.8, dated Oct. 18, 2023, 3 pages.

Lipson, E.J., et al., "Ipilimumab: An Anti-CTLA-4 Antibody for Metastatic Melanoma," Clinical Cancer Research 17(22):6958-6962, American Association for Cancer Research, United States (Nov. 2011).

Mansh, M., "Ipilimumab and Cancer Immunotherapy: A New Hope for Advanced Stage Melanoma," The Yale Journal of Biology and Medicine 84(4):381-389, Yale Journal of Biology and Medicine, United States (Dec. 2011).

Mathijssen, R.H., et al., "Flat-Fixed Dosing Versus Body Surface Area Based Dosing of Anticancer Drugs In Adults: Does It Make a Difference?," Oncologist, 12(8):913-923, AlphaMed Press, United States (Aug. 2007).

(56)　　　　References Cited

OTHER PUBLICATIONS

Mould, D.R., and Green, B., "Pharmacokinetics and Pharmacodynamics of Monoclonal Antibodies: Concepts and Lessons for Drug Development," BioDrugs 24(1):23-39, Adis, Springer International, New Zealand (Feb. 2010).
National Cancer Institute, "complete response," in Dictionary of Cancer Terms, accessed at https://www.cancer.gov/publications/dictionaries/cancer-terms/def/complete-response, accessed on Jul. 9, 2025, 1 page.
National Cancer Institute, Definition of "partial response," in Dictionary of Cancer Terms, accessed at https://www.cancer.gov/publications/dictionaries/cancer-terms/def/partial-response, accessed on Jul. 9, 2025, 1 page.
National Library of Medicine, National Center for Biotechnology Information, "Trends and Charts on Registered Studies," ClinicalTrials.gov, accessed at https://clinicaltrials.gov/about-site/trends-charts, accessed on Oct. 8, 2024, 8 pages.
NCT00094653 Version 1, Brief Title: "MDX-010 Antibody, MDX-1379 Melanoma Vaccine, or MDX-010/MDX-1379 Combination Treatment for Patients with Melanoma" (Last Update Posted to clinicaltrials.gov: Jun. 24, 2005).
NCT00323882, Version 1, "Study of MDX-010 in Patients With Metastatic Hormone-Refractory Prostate Cancer," accessed at https://clinicaltrials.gov/study/NCT00323882?cond=NCT00323882&rank=1, accessed on Oct. 4, 2024, 5 pages.
NCT00441337 Version 1, Brief Title: "Safety and PK Study of MDX-1106 in Patients With Selected Refractory or Relapsed Malignancies" (Last Update Posted to clinicaltrials.gov: Feb. 28, 2007).
NCT00729950 Version 1, Brief Title: "Study of MDX-010 in Subjects With Unresectable Stage III or Stage IV Malignant Melanoma" (Last Update Posted to clinicaltrials.gov: Aug. 8, 2008).
NCT00730639 Version 1, Brief Title: "A Phase 1b Study of MDX-1106 in Subjects With Advanced or Recurrent Malignancies" (Last Update Posted to clinicaltrials.gov: Aug. 8, 2008).
NCT00730639, "A Phase 1 Study of Nivolumab (BMS-936558) in Subjects With Advanced or Recurrent Malignancies (MDX1106-03)," (Last Update Posted Dec. 3, 2021), 15 pages.
NCT01024231 Version 3, Brief Title: "Dose-escalation Study of Combination BMS-936558 (MDX-1106) and Ipilimumab in Subjects With Unresectable Stage III or Stage IV Malignant Melanoma" (Last Update Posted to clinicaltrials.gov: Jan. 5, 2010).
NCT01024231 Version 58, Brief Title: "Dose-escalation Study of Combination BMS-936558 (MDX-1106) and Ipilimumab in Subjects With Unresectable Stage III or Stage IV Malignant Melanoma" (Last Update Posted to clinicaltrials.gov: May 1, 2012).
NCT01024231, "Dose-escalation Study of Combination BMS-936558 (MDX-1106) and Ipilimumab in Subjects With Unresectable Stage III or Stage IV Malignant Melanoma," (Last Update Posted Mar. 22, 2021), 10 pages.
NCT01844505 Version 1, Brief Title: "Phase 3 Study of Nivolumab or Nivolumab Plus Ipilimumab Versus Ipilimumab Alone in Previously Untreated Advanced Melanoma" (Last Update Posted to clinicaltrials.gov: May 1, 2013).
NCT01968109 Version 1, Brief Title: "Safety Study of Anti-LAG-3 With and Without Anti-PD-1 in the Treatment of Solid Tumors" (Last Update Posted to clinicaltrials.gov: Oct. 23, 2013).
NCT02713867 Version 2, Brief Title: "A Dose Frequency Optimization, Trial of Nivolumab 240 mg Every 2 Weeks vs Nivolumab 480 mg Every 4 Weeks in Subjects With Advanced or Metastatic Non-small Cell Lung Cancer Who Received 4 Months of Nivolumab at 3 mg/ kg or 240 mg Every 2 Weeks" (Last Update Posted to clinicaltrials. gov: Mar. 22, 2016).
NCT05907122, Brief Title: "A Study to Evaluate Similarity of ABP 206 Compared With OPDIVO® (Nivolumab) in Subjects With Resected Melanoma" (Last Update Posted Nov. 27, 2024), 24 pages.
Notice of Filing Date Accorded to Petition and Time for Filing Patent Owner Preliminary Response, filed in IPR2025-00601, *Amgen Inc.,* Petitioner v. *Bristol-Myers Squibb Company,* Patent Owner, Apr. 10, 2025, 10 pages.

Notice of Final Determination, U.S. Pat. No. 8,008,449, United States Patent and Trademark Office, United States, mailed Mar. 14, 2018, 3 pages.
Notice of Withdrawal, European Patent Application No. 17189595.6, dated Sep. 20, 2022, 1 page.
Okazaki, T., and Honjo, T., "PD-1 and PD-1 Ligands: from Discovery to Clinical Application," International Immunology 19(7):813-824, Oxford University Press, United Kingdom (Jul. 2007).
Patent Owner's Authorized Response to Director Review Request, filed in IPR2025-00601, *Amgen Inc.,* Petitioner v. *Bristol-Myers Squibb Company,* Patent Owner, Sep. 3, 2025, 19 pages.
Patent Owner's Mandatory Notices Pursuant to 37 C.F.R. § 42.8, filed in IPR2025-00601, *Amgen Inc.,* Petitioner v. *Bristol-Myers Squibb Company,* Patent Owner, Mar. 21, 2025, 5 pages.
Patent Owner's Power of Attorney, filed in IPR2025-00601, *Amgen Inc.,* Petitioner v. *Bristol-Myers Squibb Company,* Patent Owner, Mar. 21, 2025, 4 pages.
Patent Owner's Preliminary Response, filed in IPR2025-00601, *Amgen Inc.,* Petitioner v. *Bristol-Myers Squibb Company,* Patent Owner, Jul. 10, 2025, 55 pages.
Patent Owner's Request for Discretionary Denial, filed in IPR2025-00601, *Amgen Inc.,* Petitioner v. *Bristol-Myers Squibb Company,* Patent Owner, Jun. 10, 2025, 51 pages.
Patent Term Extension certificate for U.S. Pat. No. 8,008,449, United States Patent and Trademark Office, United States, mailed Sep. 11, 2018, 2 pages.
Petition for Inter Partes Review Under 35 U.S.C. §§ 311-319 And 37 C.F.R. § 42.1 et seq, filed in IPR2025-00601, *Amgen Inc.,* Petitioner v. *Bristol-Myers Squibb Company,* Patent Owner, Feb. 28, 2025, 90 pages.
Petitioner's Opposition to Patent Owner's Discretionary Denial Brief, filed in IPR2025-00601, *Amgen Inc.,* Petitioner v. *Bristol-Myers Squibb Company,* Jul. 10, 2025, 78 pages.
Petitioner's Request for Director Review of Decision Denying Institution of Inter Partes Review, filed in IPR2025-00601, *Amgen Inc.,* Petitioner v. *Bristol-Myers Squibb Company,* Patent Owner, Aug. 25, 2025, 19 pages.
Philips, G.K., and Atkins, M., "Therapeutic Uses of Anti-PD-1 and Anti-PD-L1 Antibodies," International Immunology 27(1):39-46, The Japanese Society for Immunology, Japan (Oct. 16, 2014).
Postow, M.A., et al., "Nivolumab and Ipilimumab Versus Ipilimumab in Untreated Melanoma," The New England Journal of Medicine 372(21):2006-2017, Massachusetts Medical Society, United States (May 2015).
Power of Attorney Pursuant to 37 C.F.R. § 42.10(B), filed in IPR2025-00601, *Amgen Inc.,* Petitioner v. *Bristol-Myers Squibb Company,* Patent Owner, Feb. 28, 2025, 3 pages.
Prosecution History of U.S. Pat. No. 9,856,320, filed on Nov. 12, 2014, 780 pages.
Raedler, L.A., "Opdivo (Nivolumab): Second PD-1 Inhibitor Receives FDA Approval for Unresectable or Metastatic Melanoma," American Health & Drug Benefits 8(Spec Feature):180-183, Amplity Medical Communications, United States (Mar. 2015).
Reply to Examining Division Communication, European Patent Application No. 17189595.6, dated Apr. 16, 2020, 2 pages.
Schwartz, R.S., Ph.D. "Potential Impact of the Affordable Prescriptions for Patients Act Patent Limit on BPCIA Litigations," Venable LLP, dated Apr. 2, 2025, accessed at https://biologicshq.com/potential-impact-of-the-affordable-prescriptions-for-patients-act-patent-limit-on-bpcia-litigations/, 5 pages.
Sznol, M., et al., "Safety and Antitumor Activity of Biweekly MDX-1106 (Anti-PD-1 BMS-936558/ONO4538) in Patients with Advanced Refractory Malignancies," Journal of Clinical Oncology, 28(15 Suppl): Abstract 2506, American Society of Clinical Oncology, United States (May 2010).
Tourneau, C.L., et al., "Dose Escalation Methods in Phase I Cancer Clinical Trials," Journal of the National Cancer Institute 101(10):708-720, Oxford University Press, United States (May 2009).
Tse, T., et al., "Reporting "Basic Results" in Clinicaltrials.gov," Chest 136(1):295-303, Elsevier, United States (Jul. 2009).
U.S. Food and Drug Administration, "Commemorating the 15th Anniversary of the Biologics Price Competition and Innovation Act," accessed at https://www.fda.gov/drugs/cder-conversations/

(56) References Cited

OTHER PUBLICATIONS commemorating-15thanniversary-biologics-price-competition-and-innovation-act, accessed on Jun. 20, 2025, 1 page.

U.S. Food and Drug Administration, "Step 3: Clinical Research," accessed at https://www.fda.gov/patients/drug-development-process/step-3-clinical-research, accessed on Jul. 9, 2025, 7 pages.

U.S. National Library of Medicine, National Center for Biotechnology Information, "About ClinicalTrials.gov," ClinicalTrials.gov, accessed at https://clinicaltrials.gov/about-site/about-ctg, accessed on Oct. 8, 2024, 8 pages.

U.S. National Library of Medicine, National Center for Biotechnology Information, "Clinical Trial Reporting Requirements," ClinicalTrials.gov, accessed at https://clinicaltrials.gov/policy/reporting-requirements, accessed on Sep. 10, 2024, 4 pages.

U.S. National Library of Medicine, National Institutes of Health, "ClinicalTrials.gov Glossary Terms," ClinicalTrials.gov, accessed at https://clinicaltrials.gov/study-basics/glossary, last updated Jul. 1, 2024, 21 pages.

U.S. National Library of Medicine, National Institutes of Health, "Press Release: National Institutes of Health Launches 'ClinicalTrials.gov,'" ClinicalTrials.gov, accessed at https://www.nlm.nih.gov/archive/20040831/news/press_releases/clntrlpr00.html, accessed on Feb. 29, 2000, 6 pages.

U.S. National Library of Medicine, National Institutes of Health, ClinicalTrials.gov, "How to Edit Your Study Record," ClinicalTrials.gov, accessed at https://clinicaltrials.gov/submit-studies/prs-help/how-edit-record, accessed on Sep. 10, 2024, 1 page.

Umscheid, C.A., et al., "Key concepts of clinical trials: a narrative review," Postgraduate Medicine, 123(5):194-204, Informa Healthcare, United Kingdom (Sep. 2011).

Weber, J., "Review: Anti-CTLA-4 Antibody Ipilimumab: Case Studies of Clinical Response and Immune-Related Adverse Events," The Oncologist 12(7): 864-872, Oxford University Press, United Kingdom (Jul. 2007).

Robert, C., Wolchok, J.D., et al., "Ipilimumab plus Dacarbazine for Previously Untreated Metastatic Melanoma," The New England Journal of Medicine 346(26):2517-1526, Massachusetts Medical Society, United States (Jun. 2011).

Wolchok, J.D., et al., "Nivolumab plus Ipilimumab in Advanced Melanoma" The New England Journal of Medicine, Supplementary Appendix, 369(2): 27 pages (Jul. 2013).

Zalevsky, J., et al., "Enhanced Antibody Half-life Improves in Vivo Activity," Nature Biotechnology 28(2):157-159, Nature America Publishing, United States (Feb. 2010).

Office Action mailed Jan. 21, 2026, in U.S. Appl. No. 19/193,629, inventor Cogswell, J.P., et al., filed Apr. 29, 2025, 8 pages.

Tarhini, A., et al., "Releasing the brake on the immune system: ipilimumab in melanoma and other tumors," Cancer Biotherapy and Radiopharmaceuticals, 25(6):601-613, Mary Ann Liebert, United States (Dec. 2010).

Tomasini, P., et al., "Ipilimumab: its Potential in Non-small Cell Lung Cancer," Therapeutic Advances in Medical Oncology 4(2):43-50, Sage, United Kingdom (Mar. 2012).

Order Denying Director Review of Institution Decision, filed in IPR2025-00601, Amgen Inc., Petitioner v. Bristol-Myers Squibb Company, Patent Owner, Oct. 20, 2025, 3 pages.

Notice of Allowance mailed Oct. 3, 2025, in U.S. Appl. No. 19/193,629, inventor Cogswell, J.P., et al., filed Apr. 29, 2025, 7 pages.

Notice of Allowance mailed Oct. 28, 2025, in U.S. Appl. No. 19/193,652, inventor Cogswell, J.P., et al., filed Apr. 29, 2025, 7 pages.

Advisory Action mailed Aug. 3, 2018, in U.S. Appl. No. 15/141,772, Yang, A., et al., filed Apr. 28, 2016, 3 pages.

Affidavit of Nathaniel E. Frank-White (Internet Archive), dated Sep. 26, 2024, filed in Petition for Inter Partes Review of U.S Pat. No. 10,174.113, Case No. IPR2025-00602, Feb. 28, 2025, 40 pages.

Affidavit of Nathaniel E. Frank-White with Exhibit A attaching online versions of Le (EX1008) dated Jun. 2, 2015 and Larkin (EX1011) dated Jun. 3, 2015, 17 pages.

Alberts, B., et al., "How Genes and Genomes Evolve," in Essential Cell Biology, Second Edition, pp. 293-295, Taylor & Francis, United States (Sep. 2003).

Amgen Inc., Petitioner v. Bristol-Myers Squibb Company, Patent Owner in IPR2025-00601, IPR2025-00602, IPR2025-00603 on Jul. 24, 2025, 5 pages.

Amgen Inc., vs. Bristol-Myers Squibb Company, Authorized Sur-reply in Response to Patent Owner's Supplemental Pre-institution Brief, IPR2025-00603, U.S. Pat. No. 11,332,529, dated Sep. 12, 2025, 7 pages.

Amgen Inc., vs. Bristol-Myers Squibb Company, Before Jeffrey N. Fredman, Grace Karaffa Obermann, and Sheridan K. Snedden, Administrative Patent Judges., IPR2025-00603, U.S. Pat. No. 11,332,529 B2, dated Oct. 1, 2025, 9 pages.

Patent Owner's Supplemental Pre-Institution Brief, filed in IPR2025-00603, Amgen Inc., Petitioner v. Bristol-Myers Squibb Company, Patent Owner, Aug. 21, 2025, 10 pages.

Amgen Inc., vs. Bristol-Myers Squibb Company, Patent Owner's Updated Exhibit List, IPR2025-00603, U.S. Pat. No. 11,332,529 B2, dated Aug. 21, 2025, 4 pages.

Petitioner's Response to Patent Owner's Supplemental Pre-Institution Brief, filed in IPR2025-00603, Amgen Inc., Petitioner v. Bristol-Myers Squibb Company, Patent Owner, Aug. 25, 2025, 9 pages.

Amgen Inc., vs. Bristol-Myers Squibb Company, Reply to Petitioner's Response to Patent Owner's Supplemental Pre-institution Brief, IPR2025-00603, U.S. Pat. No. 11,332,529, dated Sep. 5, 2025, 7 pages.

Ang, K.K., et al., "Human Papillomavirus and Survival of Patients with Oropharyngeal Cancer" N Engl J Med 363(1):24-35, Massachusetts Medical Society, United States (Jul. 2010).

Anonymous: "An Investigational Immuno-therapy Study of Nivolumab and Nivolumab in Combination With Other Anti-cancer Drugs, in Colon Cancer That Has Come Back or Has Spread—Full Text View—Clinical Trials.gov," Dec. 18, 2013 (Dec. 18, 2013). XP055390376. Retrieved from the Internet: URL:https://clinicaltrials.gov/ct2/show/NCT02060188 [retrieved on Jul. 12, 2017].

Anonymous: "A Study of Nivolumab and Nivolumab Plus Ipilimumab in Recurrent and Metastatic Colon Cancer (CheckMate 142)," Retrieved from the Internet: URL: https://clinicaltrials.gov/ct2/history/NCT02060188?V_17=View#StudyPageTop [retrieved on Aug. 30, 2021], 9 pages.

Anonymous: "A Study of Nivolumab and Nivolumab Plus Ipilimumab in Recurrent and Metastatic Colon Cancer (CheckMate 142)," Retrieved from the Internet: URL: https://clinicaltrials.gov/ct2/history/NCT02060188?V_49=View#StudyPageTop [retrieved on Aug. 6, 2021], 22 pages.

Anonymous: "An Investigational Immuno-therapy Study of Nivolumab. and Nivolumab in Combination With Other Anti-cancer Drugs, in Colon Cancer That Has Come Back or Has Spread—Full Text View—Clinical Trials.gov". Retrieved from the Internet: URL: https://clinicaltrials.gov/ct2/history/NCT02060188?V_50=View#StudyPageTop [retrieved on Jun. 23, 2021], 9 pages.

Anonymous: "Phase 2 Study of MK-3475 in Patients With Micro satellite Unstable (MSI) Tumors—Full Text View Clinical Trials.gov" Jun. 10, 2013 (Jun. 10, 2013). XP055390377.Retrieved from the Internet: URL:https://clinicaltrials.gov/ct2/show/NCT01876511 [retrieved on Apr. 11, 2019].

Anonymous: "Phase 2 Study of MK-3475 in Patients With Micro satellite Unstable (MSI) Tumors—Full Text View Clinical Trials.gov" Sep. 24, 2013 (Sep. 24, 2013). Retrieved from the Internet: URL:https://clinicaltrials.gov/ct2/show/NCT01876511 [retrieved on Aug. 30, 2021], 4 pages.

Ansell, S., et al., "Nivolumab in Patients (Pts) With Relapsed or Refractory Classical Hodgkin Lymphoma (R/R cHL): Clinical Outcomes From Extended Follow-up of a Phase 1 Study (CA209-039)," Blood 126(23):583, American Society of Hematology, United States (Dec. 3, 2015).

Ansell, S.M., et al., "PD-1 Blockade With Nivolumab in Relapsed or Refractory Hodgkin's Lymphoma," The New England Journal of Medicine 372(4):311-319, Massachusetts Medical Society, United States (Jan. 2015).

(56) References Cited

OTHER PUBLICATIONS

Antonia, S., et al., "Checkmate 032: Nivolumab (N) alone or in combination with ipilimumab (I) for the treatment of recurrent small cell lung cancer (SCLC)," Journal of Clinical Oncology, 34(Suppl 15): Abstract 100, American Society of Clinical Oncology (May 2016), 3 pages.

Antonia, S., et al., "Nivolumab (anti-PD-1; BMS-936558, ONO-4538) and ipilimumab in first-line non-small cell lung cancer (NSCLC): interim phase 1 results," Meeting Abstract, 2014 ASCO Annual Meeting Proceedings, Journal of Clinical Oncology 32(15 Suppl):Abstract 8023, American Society of Clinical Oncology, United States (May 2014).

Antonia, S.J., et al., "Phase I/II study (CheckMate 032) of nivolumab with or without ipilimumab for treatment of recurrent small cell lung cancer (SCLC)," Poster Presentation, 2015 ASCO Annual Meeting Proceedings, May 29-Jun. 2, 2015, American Society of Clinical Oncology, United States, 17 pages.

Monjazeb, Arta Monir, M.D., Ph.D. Curriculum Vitae, Feb. 2025, 32 pages.

Ascierto, P.A., et al., "Biomarkers for Immunostimulatory Monoclonal Antibodies in Combination Strategies for Melanoma and Other Tumor Types," Clinical Cancer Research 19(5):1009-1020, American Association for Cancer Research, United States (Mar. 2013).

Ascierto, P.A., et al., "The Additional Facet of Immunoscore: Immunoprofiling as a Possible Predictive Tool for Cancer Treatment," Journal of Translational Medicine 11:54, BioMed Central Ltd., United Kingdom, 4 pages (Mar. 2013).

ASCO Meeting Library Digital Program from 2015 ASCO Annual Meeting, "Oral Abstract Presentation: Head and Neck Cancer on Jun. 1, 2015," accessed at https://meetinglibrary.asco.org/browse-meetings/2015%20ASCO%20Annual%20Meeting/SEIWERT?page=1, 5 pages.

Assignment of all of the rights, title and interest in U.S. Appl. No. 15/210,612 and International Patent Application No. PCT/US2016/042297, each filed on Jul. 14, 2016, of the inventors Demetrios Manekas, Joseph Grosso and Jeffrey A. Anderson to Bristol-Myers Squibb Company, which assignment was executed by the inventors on Nov. 14, 2016, Oct. 10, 2016 and Nov. 7, 2016, respectively.

Bacher, J.W., et al., "Development of a Fluorescent Multiplex Assay for Detection of MSI-High Tumors," Disease Markers 20(4-5):237-250, IOS Press, United States (Oct. 2004).

Badoual, C., et al., "PD-1-expressing tumor-infiltrating T cells are a favorable prognostic biomarker in HPV-associated head and neck cancer," Cancer Res. 73(1):128-138, American Association for Cancer Research, United States (Jan. 2013).

Bamford, J., and Webster, R., "The SCCHN drug market," Nat. Rev. Drug Discov 16(4):235-236, Nature Publishing Group, Germany (Apr. 2017).

Banerjee, R., et al., "Adaptive Immune Neuroprotection in G93A-SOD1 Amyotrophic Lateral Sclerosis Mice," PLoS One 3(7):e2740, PLOS, United States (Jul. 2008).

Barber, D., et al., "Restoring function in exhausted CD8 T cells during chronic viral infection," Nature 439(7077):682-687, Nature Publishing Group, United Kingdom (Feb. 2006).

Barraclough, H., et al., "Biostatistics primer: what a clinician ought to know: hazard ratios," J Thorac Oncol 6:978-982, Elsevier, Netherlands (Jun. 2011).

Baruah, P., et al., "Impact of human papilloma virus (HPV) on stromal cells and programmed death receptor/ligand pathway in head and neck squamous cell carcinoma (HNSCC) tumour microenvironment,", Dec. 1-4, 2014, Brighton, UK, Immunology (Abstracts of the British Society for Immunology Annual Congress) 143(Suppl 2):62-186, Abstract 568, p. 168, Dec. 1-4, 2014, United Kingdom (Dec. 2014).

Belizzi, A.M., and Frankel, W.L., "Colorectal Cancer Due to Deficiency in DNA Mismatch Repair Function: a review," Advances in Anatomic Pathology 16(6):405-417, Lippincott Williams & Wilkins, United States (Nov. 2009).

Berglund, L., et al. "The epitope space of the human proteome." Protein Science 17(4):606-613, Cold Spring Harbor Laboratory Press, United States (Apr. 2008).

Boland, C.R., et al., "A National Cancer Institute Workshop on Microsatellite Instability for Cancer Detection and Familial Predisposition: Development of International Criteria for the Determination of Microsatellite Instability in Colorectal Cancer," Cancer Research 58(22):5248-5257, American Association for Cancer Research, United States (Nov. 1998).

Boland, C.R., et al., "Microsatellite Instability In Colorectal Cancer," Gastroenterology 138(6):2073-2087, Elsevier, Netherlands (Jun. 2010).

Boland, C.R., "Roles of the DNA Mismatch Repair Genes in Colorectal Tumorigenesis," International Journal of Cancer 69(1):47-49, Wiley, United States (Feb. 1996).

Boutros, C., et al., "Safety Profiles of Anti-CTLA-4 And Anti-PD-1 Antibodies Alone And In Combination," Nature Reviews Clinical Oncology 13(8):473-486, Springer, Germany (Aug. 2016).

Bowyer, S., et al., "Efficacy and Toxicity of Treatment with the Anti-CTLA-4 Antibody Ipilimumab in Patients with Metastatic Melanoma after Prior Anti-PD-1 Therapy," British Journal of Cancer 114(10):1084-1089, Nature Publishing Group, United Kingdom (May 2016).

Bristol-Myers Squibb Company Form 10-K (Exhibit No. 1073 filed in IPR2025-00603), (Dec. 31, 2024), 155 pages.

Broderick, J.M., "Nivolumab/Ipilimumab Combo More Effective than Monotherapy in Mcrc" Targeted Oncology, published Jun. 14, 2016, accessed at https://www.targetedonc.com/view/nivolumabipilimumab-combo-more-effective-than-monotherapy-in-mcrc, 7 pages.

Brown, C.A., et al. "Role of Protein Biomarkers in the Detection of High-Grade Disease in Cervical Cancer Screening Programs," J Oncol 2012:289315, Hindawi Publishing, United Arab Emirates (Feb. 2012).

Buchbinder, E., et al., "CTLA-4 and PD-1 Pathways: Similarities, Differences, and Implications of Their Inhibition," American Journal of Clinical Oncology 39(1):98-106, Lippincott Williams & Wilkins, United States (Feb. 2016).

Buecher, B., et al., "Role of Microsatellite Instability in the Management of Colorectal Cancers," Digestive and Liver Disease 45(6):441-449, Elsevier, Netherlands (Jun. 2013).

Burd, E.M., "Human Papillomavirus and Cervical Cancer," Clinical Microbiology Reviews 16(1):1-17, American Society for Microbiology, United States (Jan. 2003).

Burtness, B., "Moving Forward in the Management of Squamous Cell Carcinoma of the Head and Neck: Promising Immuno-Oncology Approaches," Am J Hematol Oncol 11(11):28-31, Wiley-Liss, United States (Nov. 2015).

Cancer.net, "The Genetics of Cancer," published Aug. 2015, accessed at https://web.archive.org/web/20160523004649/https://cancer.net, 3 pages.

"Cervista™M HPV HR," Third Wave Technologies, accessed at https://www.accessdata.fda.gov/cdrh_docs/pdf8/p080014c.pdf, 2008, 46 pages.

Chen, Z.W., et al., "Equivocal p16 immunostaining in squamous cell carcinoma of the head and neck: staining patterns are suggestive of HPV status," Head Neck Pathol 6(4):422-429, Humana Press, United States (Dec. 2012).

Chow, L., et al., "A Phase 1b Study of Pembrolizumab (MK-3475) in Patients with Human Papillomavirus (HPV)-Positive and HPV-Negative Head and Neck Cancer," Poster Presented at the European Society for Medical Oncology 2014 Congress (Sep. 26-30, 2014).

Chow, L.Q., et al., "A phase 1B study of Pembrolizumab (MK-3467) in patients with Human Papillomavirus (HPV)-positive and HPV-negative Head and Neck Cancer," Annal. Oncol. (European Society for Medical Oncology 2014 Congress Poster Abstracts) S5: Abstract LBA31, pp. v1-v14, Sep. 26-30, Madrid, Spain (Oct. 2014).

Clinical Trials.gov, NCT01673867, "History of Changes for Study: NCT01673867: Study of BMS-936558 (Nivolumab) Compared to Docetaxel in Previously Treated Metastatic Non-Sequamous NSCLC," accessed at https://clinicaltrials.gov/ct2/history/NCT01673867?V_55=View, last accessed Jun. 11, 2019, 50 pages.

(56) References Cited

OTHER PUBLICATIONS

Clinical Trials.gov, NCT01693562, "A Phase 1/2 Study to Evaluate MEDI4736," accessed at https://clinicaltrials.gov/ct2/show/ NCT01693562, Sep. 26, 2012, 26 pages.

Clinical Trials.gov, NCT01721772, "History of Changes for Study:NCT01721772: Study of Nivolumab (BMS-936558) Compared with Dacarbazine in Untreated, Unrespectable, or Metastatic Melanoma," accessed at https://clinicaltrials.gov/ct2/history/ NCT01721772?V_42-View, last accessed Jun. 11, 2019, 41 pages.

Clinical Trials.gov, NCT01772004 "Avelumab in Metastatic or Locally Advanced Solid Tumors (JAVELIN Solid Tumor)" accessed at https://clinicaltrials.gov/ct2/show/NCT01772004, Dec. 20, 2021, 26 pages.

Clinical Trials.gov, NCT01848834, "Study of Pembrolizumab (MK-3475) in Participants With Advanced Solid Tumors (MK-3475-012/ KEYNOTE-012)," accessed at https://clinicaltrials.gov/ct2/show/ NCT01848834?term=NCT01848834&draw=2&rank=1, Jun. 28, 2021, 12 pages.

Clinical Trials.gov, NCT02105636, "Trial of Nivolumab vs Therapy of Investigator's Choice in Recurrent or Metastatic Head and Neck Carcinoma," accessed at https://clinicaltrials.gov/ct2/show/ NCT02105636?term=nct02105636&draw=2&rank=1, last accessed Jan. 22, 2019, 9 pages.

Clinical Trials.gov, NCT02255097, "Study of MK-3475 (Pembrolizumab) in Recurrent or Metastatic Head and Neck Squamous Cell Carcinoma After Treatment With Platinum-based and Cetuximab Therapy (MK-3475-055/KEYNOTE-055)," accessed at https:// clinicaltrials.gov/ct2/show/NCT02255097, Jun. 28, 2022, 8 pages.

Clinical Trials.gov, NCT02291055, "Phase 1-2 Study of ADXS11-001 or MEDI4736 Alone or Combo In Cervical or HPV+ Head & Neck Cancer," accessed at https://clinicaltrials.gov/ct2/show/ NCT02291055, Nov. 14, 2014, 7 pages.

Clinical Trials.gov, NCT02426892, "Nivolumab and HPV-16 Vaccination in Patients With HPV-16 Positive Incurable Solid Tumors," accessed at https://clinicaltrials.gov/ct2/show/NCT02426892, Apr. 27, 2015, 8 pages.

Clinical Trials.gov, NCT02764593, "Safety Testing of Adding Nivolumab to chemotherapy in Patients with Intermediated and High-Risk Local-Regionally Advanced Head and Neck Cancer," accessed at https://clinicaltrials.gov/ct2/show/NCT02764593, last accessed Sep. 13, 2018, 9 pages.

clinicaltrials.gov, "Glossary of Common Site Terms," U.S. National Library of Medicine, National Institutes of Health, Retrieved from URL: https://clinicaltrials.gov/ct2/about-studies/glossary, Retrieved on Aug. 9, 2024, 21 pages.

Cohen, E.E.W., et al., "Biomarker analysis in recurrent and/or metastatic head and neck squamous cell carcinoma (R/M HNSCC) patients (pts) treated with second-line afatinib versus methotrexate (MTX): LUX-Head & Neck 1 (LUX-H&N1).," J Clin Oncol 33(15S): Abstract 6023, American Society of Clinical Oncology, United States (May 2015).

Consolidated List of Cited Opposition Documents, European Patent No. EP3464373 B1, dated Jul. 27, 2022, 6 pages.

Corada, M., et al. "Monoclonal antibodies directed to different regions of vascular endothelial cadherin extracellular domain affect adhesion and clustering of the protein and modulate endothelial permeability," Blood, The Journal of the American Society of Hematology 97(6): 1679-1684, The American Society of Hematology, United States (Mar. 2001).

De Angelis, G.L., et al., "Microsatellite Instability in Colorectal Cancer," Biomedical Journal: Athenaeum of Parma 89(9-S):97-101, Mattioli, Italy (Dec. 2018).

De La Chapelle, A., and Hampel, H., "Clinical Relevance of Microsatellite Instability in Colorectal Cancer," Journal of Clinical Oncology: official journal of the American Society of Clinical Oncology 28(20):3380-3387, American Society of Clinical Oncology, United States (Jul. 2010).

De Lartigue, J., "Rising to the therapeutic challenge of head and neck cancer," Journal of Community and Supportive Oncology 13:73-80, Frontline Medical Communications Inc., United States (February 2015).

Decision Denying Institution of Inter Partes Review in IPR2025-00601 and IPR2025-00602 and Referring the Petition in IPR2025-00603 to the Board, Jul. 24, 2025, 5 pages.

Declaration of Dr. Arta M. Monjazeb, Feb. 28, 2025, 132 pages.

Declaration of Dr. Brent Hanks M.D., Ph.D., filed in Petition for Inter Partes Review of U.S. Pat. No. 10,174,113, Case No. IPR2025-00602, Feb. 28, 2025, 155 pages.

Declaration of Dr. Dhaval K. Shah, Ph.D., filed in Petition for Inter Partes Review of U.S. Pat. No. 10,174,113, Case No. IPR2025-00602, Feb. 28, 2025, 82 pages.

Declaration of Prescott Lassman, Feb. 24, 2025, 30 pages.

Declaration of Prescott Lassman, filed in Petition for Inter Partes Review of U.S. Pat. No. 10,174,113, Case No. IPR2025-00602, Feb. 28, 2025, 37 pages.

Declaration of Sylvia D. Hall-Ellis, Ph.D, Feb. 28, 2025, 552 pages.

Declaration of Sylvia, D. Hall-Ellis, Ph.D., filed in Petition for Inter Partes Review of U.S. Pat. No. 10,174,113, Case No. IPR2025-00602, Feb. 28, 2025, 370 pages.

Demetri, G.D., et al., "Efficacy and Safety of Trabectedin in Patients With Advanced or Metastatic Liposarcoma or Leiomyosarcoma After Failure of Prior Anthracyclines and Ifosfamide: Results of a Randomized Phase II Study of Two Different Schedules," Journal of Clinical Oncology 27(25):4188-4196, American Society of Clinical Oncology, United States (Sep. 2009).

Dietmaier, W., [Microsatellite instability. A new predictive marker (?)] Pathologe 31 (Suppl 2):268-273, Springer, Germany (Sep. 2010).

Dirks, N.L. and Meibolm, B., "Population Pharmacokinetics of Therapeutic Monoclonal Antibodies," Clinical Pharmacokinetics 49(10):633-659, Springer Nature, Germany (Oct. 2010), 30 pages.

Drake, "Safety, Durable Clinical Benefit, and Remission Resulting from Nivolumanb (Anti-PD-1; BMS-936558; ONO-4538) in a Phase 1 Trial In Patients With Previously Treated Metastatic Renal Cell Carcinoma (mRCC); Long-Term Patient Follow-Up, Abstracts of the 12th International Kidney Cancer Symposium. Oct. 25-26, 2013. Chicago, Illinois, USA," BJU International 112 (Suppl 3):1-17, Blackwell Science, England (Nov. 2013).

Dudley, J.C., et al., "Microsatellite Instability as a Biomarker for PD-1 Blockade," Clinical Cancer Research 22(4):813-820, The Association, United States (Feb. 2016).

Duraiswamy, J., et al., "Dual Blockade of PD-1 and CTLA-4 Combined With Tumor Vaccine Effectively Restores T-cell Rejection Function in Tumors," Cancer Research 73(12):3591-3603, American Association for Cancer Research, United States (Jun. 2013).

Durie, N., et al., "Retrospective review of colorectal cancer specimens in individuals younger than age 50 for microsatellite instability testing and DNA mismatch repair enzyme expression," Journal of Clinical Oncology 29(4):392-392, American Society of Clinical Oncology, United States (Feb. 2011).

Eisenhauer, E.A., et al., "New Response Evaluation Criteria in Solid Tumours: Revised RECIST Guideline (Version 1.1)," European Journal of Cancer 45(2):228-247, Elsevier Ltd., United Kingdom (Jan. 2009).

Eroglu, Z., et al., "Checkpoint Inhibition of PD-1: The Promise of Pembrolizumab (MK-3475) and Beyond," Personalized Medicine in Oncology: 13 pages, The Lynx Group, United States (2014).

ESMO, "ESMO 2014 Congress Scientific Meeting Report—Head and Neck Cancer Extract," Madrid, Spain, accessed at https:// oncologypro.esmo.org/content/download/57268/1055948/1/ESMO-2014-Scientific-Report-Head-Neck-Cancer.pdf, Sep. 26-30, 2014, 7 pages.

ESMO, "ESMO 2014 Programme Overview," Sep. 28, 2014, accessed at https://www.esmo.org/content/download/20380/340098/1/ESMO-2014-Programme-Overview.pdf, 6 pages.

ESMO Press Release on Sep. 30, 2014, "Pembrolizumab Shows Promise In Several Solid Tumours," accessed at https://www.esmo. org/meetings/past-meetings/esmo-2014-congress/News-Articles/ pembrolizumab-shows-promise-in-several-solid-tumours, 5 pages.

(56) References Cited

OTHER PUBLICATIONS

"Executive Summary of Immunotherapy in Head & Neck Cancer Clinical Trials Planning Meeting," Head & Neck Cancer Steering Committee, National Cancer Institute, Maryland, United States, Nov. 9-10, 2014, accessed at https://www.cancer.gov/about-nci/organization/ccct/steering-committees/nctn/head-neck/hnscimmunotherapyctpmexecsum.pdf, 5 pages.

Farashi-Bonab, S., et al., "Improving of Antitumor Immunity and Therapeutic Efficacy of Cancer Vaccines and Adoptive Immunotherapies Using Monoclonal Antibodies," MOJ Immunology 2(5):00062, MedCrave Group, United States (Oct. 2015).

FDA, "Opdivo (Nivolumab) Injection, for Intravenous Use," (2014), 27 pages.

FDA, "Yervoy," FDA Approval Label and Prescribing Information, Mar. 2011, 20 pages.

FDA, "Opdivo," FDA Approval Label and Prescribing Information, Dec. 2014, 20 pages.

Feldman, R., et al., "Pdl and Pdl1 in Hpv + and Hpv −/Tp53 Mutated Head and Neck Squamous Cell Carcinomas," Annals Oncol 25(Supplement 4):iv340-iv356, Abstract 1019P, Elsevier, Netherlands (Sep. 2014).

Ferris, R.L., et al., "Safety evaluation of nivolumab (Nivo) concomitant with cetuximab-radiotherapy for intermediate (IR) and high-risk (HR) local-regionally advanced head and neck squamous cell carcinoma (HNSCC): RTOG 3504," Presented Friday, Jun. 1, 2018, retrieved from: meetinglibrary.asco.org/record/160234/abstract, Sep. 10, 2018, 2 pages.

Ferris, R.L., et al., "Nivolumab for Recurrent Squamous-Cell Carcinoma of the Head and Neck," N Engl J Med 375:1856, Massachusetts Medical Society, United States (Nov. 2016).

Ferris, R.L., et al., "Nivolumab vs investigator's choice in recurrent or metastatic squamous cell carcinoma of the head and neck: 2-year long-term survival update of CheckMate 141 with analyses by tumor PD-L1 expression," Oral Oncol 81:45-51, Elsevier, Netherlands (Jun. 2018).

Ferris, R.L., et al., "Two-Year Update From CheckMate 141: Outcomes with Nivolumab (Nivo) vs Investigator's Choice (IC) in Recurrent or Metastatic (R/M) Squamous Cell Carcinoma of the Head and Neck (SCCHN) in the Overall Population and PD-L1 Subgroups," Radiation Oncology 100(5):1317, BioMed Central, United Kingdom (2018).

Ferris, R.L., "Nivolumab confers significant OS benefit in recurrent or metastatic head and neck squamous cell carcinoma," HemONC today, retrieved from: https://www.healio.com/news/hematology-oncology/20180416/nivolumab-confers-significant-os-benefit-in-recurrent-or-metastatic-head-and-neck-squamous-cell-carc#, presented at American Association for Cancer Research Annual meeting (Apr. 2018).

Field, N., and Lechner, M., "Exploring the implications of HPV infection for head and neck cancer," Sex Transm Infect 91(4):229-230, BMJ, United Kingdom (Jun. 2015).

Office Action mailed Jun. 13, 2018, in U.S. Appl. No. 15/210,612, Manekas, D. et al., filed Jul. 14, 2016, 16 pages.

Office Action mailed Jun. 22, 2018, in U.S. Appl. No. 15/141,769, Yang, A., et al., filed Apr. 28, 2016, 7 pages.

Office Action mailed May 2, 2018, in U.S. Appl. No. 15/311,409, Feltquate, D. et al., filed Nov. 15, 2016, 13 pages.

Food and Drug Administration Label, "Keytruda," 91 pages (2020).

Food and Drug Administration Label, "Libtayo," 17 pages (2020).

Food and Drug Administration Label, "Opdivo," 110 pages (2021).

Food and Drug Administration Label, "Opdivo," 27 pages (2015).

Fury, M., et al., "Clinical Activity and Safety of MEDI4736, an Anti-PD-L1 Antibody, in Patients with Head and Neck Cancer," Annals of Oncology 25(4):iv341, Abstract 988PD, Oxford University Press, England, 2 pages (Sep. 1, 2014).

Gangadhar, T.C., et al., "Clinical applications of PD-1-based therapy: a focus on pembrolizumab (MK-3475) in the management of melanoma and other tumor types," Onco Targets Ther 8:929-937, Dove Medical Press, United Kingdom (Apr. 2015).

Gatalica, Z., et al., "High Microsatellite Instability (Msi-h) Colorectal Carcinoma: A Brief Review of Predictive Biomarkers in the Era of Personalized Medicine," Familial Cancer 15(3):405-412, Springer Link, United States (Feb. 2016).

Gatalica, Z., et al., "Programmed Cell Death 1 (PD-1) And Its Ligand (PD-L1) In Common Cancers And Their Correlation With Molecular Cancer Type," Cancer Epidemiol Biomarkers Prevention 23(12):2965-2970, American Association of Cancer Research, United States (Dec. 2014).

GenBank, "cytotoxic T-lymphocyte-associated protein 4 [Homo sapiens]," Accession No. AAB59385.1, Nov. 1, 1994, accessed at https://www.ncbi.nlm.nih.gov/protein/AAB59385, accessed on Dec. 6, 2016, 3 pages.

Gettinger, S.N., et al., "Overall Survival and Long-Term Safety of Nivolumab (Anti-Programmed Death 1 Antibody, BMS-936558, ONO-4538) in Patients with Previously Treated Advanced Non-Small-Cell Lung Cancer," Journal of Clinical Oncology 33(18):2004-2012, American Society of Clinical Oncology, United States (Jun. 2015).

Giardello, F.M., et al., "AGA Technical Review on Hereditary Colorectal Cancer and Genetic Testing," Gastroenterology 121(1):198-213, Elsevier, Netherlands (Jul. 2001).

Gildener-Leapman, N., et al., "Promising systemic immunotherapies in head and neck squamous cell carcinoma." Oral Oncology 49(12):1089-1096, Elsevier, Netherlands (Dec. 2013).

Goodman, A., "Clinically Meaningful Preliminary Results With Pembrolizumab in Recurrent Head and Neck Cancer," ASCOPost.com, Jun. 10, 2015, accessed at https://ascopost.com/issues/june-10-2015/clinically-meaningful-preliminary-results-with-pembrolizumab-in-recurrent-head-and-neck-cancer/, 5 pages.

Graham, S.V., "The human papillomavirus replication cycle, and its links to cancer progression: a comprehensive review," Clin Sci (Lond) 131(17):2201-2221, Portland Press, United Kingdom (Aug. 2017).

Green, L., "Keytruda Doubles Efficacy of Only Targeted Therapy for Head and Neck Cancer," Cancer Updates, pp. 1-6, (May 2015), accessed at https://www.curetoday.com/articles/keytruda-doubles-efficacy-of-only-targeted-therapy-for-head- and-neck-cancer, accessed on Dec. 12, 2017.

Guler, E., et al., "A review of the fixed douse use of new oral anticoagulants in obese patients: Is it really enough?" Anatol J Cardiol 15:1020-1029, Turkish Society of Cardiology, Turkey (Dec. 2015).

Hamid, O., et al., "Safety and Tumor Responses with Lambrolizumab (Anti-PD-1) in Melanoma," The New England Journal of Medicine 369(2):134-144, Massachusetts Medical Society, United States (Jul. 2013).

Hammers, H., et al., "Phase I Study of Nivolumab in Combination with Ipilimumab in Metastatic Renal Cell Carcinoma (Mrcc)," Annals of Oncology 25(Supplement 4):iv361, Elsevier, Netherlands (Sep. 2014).

Hammers, H.J., et al., "Checkmate 214: A Phase III. Randomized, Openlabel Study of Nivolumab Combined With Ipilimumab Versus Sunitinib Monotherapy in Patients With Previously Untreated Metastatic Renal Cell Carcinoma," Meeting Abstract. 2015 ASCO Annual Meeting Proceedings, Journal of Clinical Oncology 33(15):Abstract TPS4578, 2015 ASCO Annual Meeting Proceedings, American Society of Clinical Oncology, United States (May 2015).

Hayes, D.N., et al., "Genetic Landscape of Human Papillomavirus-Associated Head and Neck Cancer and Comparison to Tobacco-Related Tumors," Journal of Clinical Oncology 33(29):3227-3234, American Society of Clinical Oncology, United States (Oct. 2015).

Hellman, K., et al. "Human papillomavirus, p161NK4A, and Ki-67 in relation to clinicopatho logical variables and survival in primary carcinoma of the vagina" Br J Cancer 110(6): 1561-1570, Nature Portfolio, Germany (Feb. 2014).

Hellmann, M.D., et al., "Checkmate 012: Safety and efficacy of first-line (1L) nivolumab (nivo;N) and ipilimumab (ipi;I) in advanced (adv) NSCLC," Journal of Clinical Oncology 34(Suppl 15):Abstract 3001, American Society of Clinical Oncology, United States (May 2016).

Herbst, R.S., et al., "A Study of MPDL3280A, an Engineered PD-L1 Antibody in Patients with Locally Advanced or Metastatic

(56)            References Cited

OTHER PUBLICATIONS

Tumors," Journal of Clinical Oncology 31(Suppl):3000, American Society of Clinical Oncology, United States (May 2013), 2 pages.

Herbst, R.S., et al., "Predictive Correlates of Response to the Anti-PD-L1 Antibody MPDL3280A in Cancer Patients," Nature 515(7528):563-567, Nature Publishing Group, United Kingdom (Nov. 27, 2014).

History of Changes for Study NCT01928394, ClinicalTrials.gov, accessed at https://clinicaltrials.gov/ct2/history/NCT01928394, database entry dated May 25, 2016, 12 pages.

History of Changes for Study NCT02060188, ClinicalTrials.gov, accessed at https://clinicaltrials.gov/history/NCT02060188, database entry dated Jun. 1, 2017, 12 pages.

History of Changes for Study NCT02231749, ClinicalTrials.gov, accessed at https://clinicaltrials.gov/ct2/history/NCT02231749, database entry dated May 25, 2016, 17 pages.

Hoffman, J., et al., "Nivolumab ± Ipilimumab Demonstrates Encouraging Activity, Survival in mCRC," Cancer Therapy Advisor, ASCO 2016, published Jun. 5, 2016, https://www.cancertherapy advisor. com/home/news/conference-coverage/american-society-of-clinical-oncologv-asco/asco-2016/nivolumab-%C2%BI-ipilimumab-demonstrates-encouraging-activity-survival-in-mcrc/, 5 pages.

Hoffman, J., "No Survival Benefit from Lymph Node Dissection in Biopsy-Positive Melanoma," CancerTherapyAdvisor.com, May 30, 2015, accessed at https://www.cancertherapyadvisor.com/home/news/conference-coverage/american-society-of-clinical-oncology-asco/asco-2015/no-survival-benefit-from-lymph-node-dissection-in-biopsy-positive-melanoma/, 5 pages.

Hong, A.M., et al., "Use of cyclin D1 in conjunction with human papillomavirus status to predict outcome in oropharyngeal cancer," Int J Cancer 128:1532-1545, Wiley, United States (Apr. 2011).

Hughes, D., "Pembrolizumab Immunotherapy Effective in Recurrent, Metastatic Head and Neck Cancer," CancerTherapyAdvisor. com, accessed at https://www.cancertherapyadvisor.com/home/news/conference-coverage/american-society-of-clinical-oncology-asco/asco-2015/pembrolizumab-immunotherapy-effective-in-recurrent-metastatic-head-and-neck-cancer/, Jun. 2, 2015, 5 pages.

IARC Working Group, "Human Papillomaviruses," in *IARC Monographs on the Evaluation of Carcinogenic Risks to Humans*, vol. 90, World Health Organization International Agency for Research on Cancer, Lyon, France (2007).

Ibrahim, R., et al., "PD-L1 Blockade for Cancer Treatment: MEDI4736," Seminars in Oncology 42(3):474-483, Elsevier, United States (Feb. 25, 2015).

International Preliminary Report on Patentability for International Application No. PCT/US2016/029877, European Patent Office, Netherlands, mailed on Oct. 31, 2017, 8 pages.

International Preliminary Report on Patentability for International Application No. PCT/US2016/042297, European Patent Office, Netherlands, mailed on Jan. 25, 2018, 11 pages.

International Search Report and Written Opinion for International Application No. PCT/US2016/029877, European Patent Office, Rijswijk, mailed on Jul. 13, 2016, 16 pages.

International Search Report and Written Opinion for International Application No. PCT/US2016/029878, European Patent Office, Netherlands, mailed on Jul. 13, 2016, 12 pages.

International Search Report and Written Opinion for International Application No. PCT/US2016/042297, European Patent Office, Netherlands, mailed on Dec. 23, 2016, 18 pages.

International Search report and Written Opinion for International Application No. PCT/US2017/035822, mailed on Aug. 1, 2017, 14 pages.

Jaafar, L., "Elucidating the Role of Human Mismatch Repair Factor Hmlh3," Cancer Biology & Therapy 8(14):1421-1423, Taylor & Francis, United Kingdom (Jul. 2009).

Jass, J.R., "Towards a Molecular Classification of Colorectal Cancer," International Journal of Colorectal Disease 14(4-5):194-200, Springer, Germany (Nov. 1999).

Johnson, D.B., et al., "Severe Cutaneous and Neurologic Toxicity in Melanoma Patients during Vemurafenib Administration Following Anti-PD-1 Therapy," Cancer Immunology Research 1(6):373-377, American Association for Cancer Research, United States (Dec. 2013).

Johnson, D. B., et al., "Immune Checkpoint Inhibitors in NSCLC," Current Treatment Option in Oncology 15(4):658-669, SpringerLink, United States (Dec. 2014).

Jordan, R.C et al., "Validation of methods for oropharyngeal cancer HPV status determination in US cooperative group trials," Am J Surg Pathol 36(7):945-954, Lippincott Williams & Wilkins, United States (Jul. 2012).

Karahan, B., et al., "Relationship Between MLH-1, MSH-2, PMS-2,MSH-6 Expression and Clinicopathological Features in Colorectal Cancer," International Journal of Clinical and Experimental Pathology 8(4):4044-4053, e-Century Publishing Corporation, United States (Apr. 2015).

Keck, M.K., et al., "Integrative Analysis of Head and Neck Cancer Identifies Two Biologically Distinct HPV and Three Non-HPV Subtypes," Clinical Cancer Research 21(4):870-881, The Association, United States (Feb. 2015).

Kellogg, A., Case No. IPR2025-00603—Request for authorization to file a response, dated Aug. 28, 2025, 2 pages.

Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).

Kim, K.Y., et al., "Current status of clinical testing for human papillomavirus in oropharyngeal squamous cell carcinoma," J Pathol Clin Res 4(4):213-226, Wiley, United States (Oct. 2018).

Kofler, B., et al., "New treatment strategies for HPV-positive head and neck cancer," Eur Arch Otorhinolaryngol 271:1861-1867, SpringerLink, Germany (Jul. 2014).

Kroemer, G., et al., "Colorectal Cancer: the First Neoplasia Found to Be Under Immunosurveillance and the Last One to Respond to Immunotherapy?" Oncoimmunology 4(7):e1058597. Taylor & Francis, United States (Jun. 2015).

Kulkarni-Kale, U. et al., "CEP: a conformational epitope prediction server." Nucleic acids research 33(suppl 2):W168-W171, Oxford University Press, United Kingdom (Jul. 2005).

Le, D., et al., "Phase 2 study of programmed death-1 antibody (anti-PD-1, MK-3475) in patients with microsatellite unstable (MSI) tumors," Journal of Clinical Oncology, 32(15): 4 pages, American Society of Clinical Oncology Journal, United States (May 2014).

Le, D.T., et al., "PD-1 Blockade in Tumors with Mismatch-Repair Deficiency," The New England Journal of Medicine 372(26):2509-2520, Massachusetts Medical Society, United States (Jun. 2015).

Le, D.T., et al., "Supplementary Appendix to PD-1 Blockade in Tumors with Mismatch-Repair Deficiency," The New England Journal of Medicine 372(26): Supplementary Appendix pp. 1-25, Massachusetts Medical Society, United States (Jun. 2015).

Lee, S.M. and Chow, L.Q., "A New Addition to the PD-1 Checkpoint Inhibitors for Non-small Cell Lung Cancer—the Anti-PDL1 Antibody-MEDI4736," Translational Lung Cancer Research 3(6):408-410, Translational Lung Cancer Research, China (Nov. 2014).

Lewis, J. S., et al., "Human Papillomavirus Testing in Head and Neck Carcinomas," Arch Pathol Lab Med 142(5):559-597, College of American Pathologists, United States (Dec. 2017).

Li, S.K.H., and Martin, A., "Mismatch Repair and Colon Cancer: Mechanisms and Therapies Explored," Trends in Molecular Medicine 22(4):274-289, Elsevier Science Ltd, United Kingdom (Apr. 2016).

Lindor, N.M., et al., "Immunohistochemistry Versus Microsatellite Instability Testing in Phenotyping Colorectal Tumors," Journal of Clinical Oncology 20(4):1043-1048, American Society of Clinical Oncology, United States (Feb. 2002).

Llosa, N.J., et al., "Immune checkpoints expression in MSI versus MSS colorectal cancers and their potential therapeutic implications," Journal of Clinical Oncology 32(15): 3620-3620, American Society of Clinical Oncology Journal, United States (May 2014).

Llosa, N.J., et al., "The Vigorous Immune Microenvironment of Microsatellite Instable Colon Cancer Is Balanced by Multiple

(56)                References Cited

OTHER PUBLICATIONS

Counter-inhibitory Checkpoints," Cancer Discovery 5(1):43-51, American Association for Cancer Research, United States (Jan. 2015).

Lobo, E.D., "Antibody Pharmacokinetics and Pharmacodynamics," Journal of Pharmaceutical Sciences 93(11):2645-2668, (Nov. 2004), 29 Pages.

Long, G.V., et al. "Assessment of nivolumab exposure and clinical safety of 480 mg every 4 weeks flat-dosing schedule in patients with cancer," Annals of Oncology 29(11):2208-2213, Elsevier, Netherlands (Nov. 2018).

Loughrey, M.B., et al., "Incorporation Of Somatic BRAF Mutation Testing Into An Algorithm For The Investigation Of Hereditary Non-polyposis Colorectal Cancer," Familial Cancer 6(3):301-310, Springer, Germany (2007).

Lyford-Pike, S., et al.," Evidence for a role of the PD-1:PD-L1 pathway in immune resistance of HPV-associated head and neck squamous cell carcinoma," Cancer Res 73(6):1733-1741, American Association for Cancer Research, United States (Mar. 2013).

Machiels, J.P., et al., "Squamous cell carcinoma of the oral cavity, larynx, oropharynx and hypopharynx: EHNS-ESMO-ESTRO Clinical Practice Guidelines for diagnosis, treatment and follow-up," Ann Oncol 31(11):1462-1475, Elsevier, Netherlands (Nov. 2020).

Mahoney, K.M., et al., "The Next Immune-Checkpoint Inhibitors: PD-1/PD-L1 Blockade in Melanoma," Clinical Therapeutics 37(4):764-782, Elsevier HS Journals, United States (Mar. 2015).

Marzuka, A., et al., "Melanoma Treatments: Advances and Mechanisms," Journal of Cellular Physiology 230(11):2626-2633, Wiley Periodicals, United States (Jul. 2015).

Merck, "First Presentation of Early Data for Pembrolizumab (MK-3475), Merck's Investigational Anti-PD-1 Antibody, in Advanced Head and Neck Cancer at ASCO 2014," Business Wire.com, Jun. 1, 2014, accessed at https://www.businesswire.com/news/home/20140601005057/en/First-Presentation-of-Early-Data-for-Pembrolizumab-MK-3475-Merck%E2%80%99s-Investigational-Anti-PD-1-Antibody-in-Advanced-Head-and-Neck-Cancer-at-ASCO-2014, 5 pages.

Merriam-Webster, "colorectal," in Collegiate Dictionary, accessed at https://www.merriam-webster.com/dictionary/colorectal, accessed on Aug. 9, 2024, 3 pages.

Merriam-Webster Dictionary, Definition of Colorectal, accessed at https://www.merriam-webster.com/dictionary/colorectal, May 22, 2016, 1 page.

Merriam-Webster, "monotherapy," in Medical Dictionary, accessed at https://www.merriam-webster.com/medical/monotherapy, accessed on Aug. 9, 2024, 2 pages.

Misiukiewicz, K., et al., "The role of HPV status in recurrent/metastatic squamous cell carcinoma of the head and neck," Clin Adv Hematol Oncol 12(12):812-819, Millennium Medical Publishing, Inc., United States (Dec. 2014).

Miyoshi, S., and Yoshino, T., "Cancer Treatments Based on Genetic Analyses: Colorectal Cancer," Journal of Molecular Targeted Therapy for Cancer 14(1):13-20, Japan (Mar. 2016).

Monjazeb, A.M., et al., "A Randomized Trial of Combined PD-L1 and CTLA-4 Inhibition With Targeted Low-dose or Hypofractionated Radiation for Patients With Metastatic Colorectal Cancer," Clinical Cancer Research 27(9):2470-2480, American Association for Cancer Research, United States (May 2021).

Motzer, R., et al., "Nivolumab for Metastatic Renal Cell Carcinoma: Results of a Randomized Phase II Trial," J Clin Oncol 33(13):1430-1437, American Society of Clinical Oncology, United States (May 2015).

Naing, A., et al., "A First-in-human Phase I Study of the Anti-PD-1 Antibody PDR001 in Patients with Advanced Solid Tumors," Journal of Clinical Oncology 34(15):Abstract 3060, American Society of Clinical Oncology, United States (May 2016).

Naing, A., et al., "Anti-PD-1 monoclonal antibody MEDI0680 in a phase I study of patients with advanced solid malignancies," Journal of Immunotherapy of Cancer 7:225, Society for Immunotherapy of Cancer (SITC), United States (Aug. 2019).

National Cancer Institute, Colorectal Cancer, available at: http://www.cancer.gov/types/colorectal, last visited Feb. 14, 2017, 6 pages.

National Cancer Institute, "overall survival," in Dictionary of Cancer Terms, accessed at https://www.cancer.gov/publications/dictionaries/cancerterms/def/overall-survival, accessed on Aug. 9, 2024, 1 page.

National Cancer Institute, "Head and Neck Steering Committee," Cancer.gov, accessed at https://www.cancer.gov/about-nci/organization/ccct/steering-committees/nctn/head-neck, 2 pages.

National Cancer Institute, "Monotherapy," in Dictionary of Cancer Terms, accessed at https://www.cancer.gov/publications/dictionaries/cancerterms/def/monotherapy, accessed on Aug. 9, 2024, 1 page.

National Cancer Institute, "nivolumab," in NCI Drug Dictionary, accessed at https://www.cancer.gov/publications/cancer-drug/def/nivolumab, accessed on Sep. 9, 2024, 1 page.

National Comprehensive Cancer Network, "NCCN Guidelines," nccn.org, accessed at http://www.nccn.org/professionals/physician_gls/f_guidelines.asp#site, accessed on Dec. 8, 2016, 4 pages.

NCCN Guidelines (2014), available at: https://www.ncen.org/professionals/physician_gls/f_guidelines.asp, last accessed May 14, 2014, 4 pages.

NCI Drug Dictionary, "Anti-PD-1 Fusion Protein AMP-224," accessed on Dec. 1, 2016, retrieved from the Internet URL: https://www.cancer.gov/publications/dictionaries/cancer-drug?cdrid=700595, 3 pages.

NCI Drug Dictionary, "anti-PD-1 monoclonal antibody MEDI0680," cancer.gov, accessed at https://www.cancer.gov/publications/dictionaries/cancer-drug?cdrid=756047, accessed on Dec. 1, 2016, 3 pages.

NCI Drug Dictionary, "pembrolizumab," cancer.gov, accessed at https://www.cancer.gov/drugdictionary?cancer-drug?cdrid=695789, accessed on Dec. 1, 2016, 3 pages.

NCT02060188 Version 1, "A Study of Nivolumab and Nivolumab Plus Ipilimumab in Recurrent and Metastatic Colon Cancer (CheckMate 142)," accessed at (https://clinicaltrials.gov/study/NCT02060188?term=NCT02060188&rank=1&tab=history&a=1#version-content-panel), on Feb. 11, 2014, 6 pages.

Nguyen, H.P., et al., "The biology of human papillomaviruses," Curr Probl Dermatol 45:19-32, Karger Publishers, Switzerland (Mar. 2014).

Nindl, I., et al., "Distribution of 14 high risk HPV types in cervical intraepithelial neoplasia detected by a non-radioactive general primer PCR mediated enzyme immunoassay," J Clin Pathol 2(1): 17-22, BMJ, United Kingdom (Jan. 1999).

Nivolumab US Prescription Label, 1 page (Sep. 2015).

Non-Comparative, Multi-Cohort, Single Arm, Open-Label, Phase 2 Study of Nivolumab (BMS-936558) in classical Hodgkin Lymphoma (cHL) Subjects. Adisinsight: Trials, 6 pages, Jul. 10, 2014.

Office Action mailed Feb. 28, 2018, in U.S. Appl. No. 15/141,769, Yang, A., et al., filed Apr. 28, 2016, 12 pages.

Notice of Filing Date Accorded to Petition and Time for Filing Patent Owner Preliminary Response, filed in IPR2025-00603, Amgen Inc., Petitioner v. Bristol-Myers Squibb Company, Patent Owner, Apr. 10, 2025, 10 pages.

Office Action mailed Apr. 12, 2018, in U.S. Appl. No. 15/141,772, Yang, A., et al., filed Apr. 28, 2016, 13 pages.

Office Action mailed Aug. 11, 2021, in U.S. Appl. No. 16/240,316, Yang, A., filed Jan. 4, 2019, 17 pages.

Office action mailed Dec. 27, 2017, in U.S. Appl. No. 15/210,612, inventor Manekas, D. et al., filed Jul. 14, 2016, 21 pages.

Office Action mailed Dec. 6, 2017, in U.S. Appl. No. 15/141,772, Yang, A. et al., filed Apr. 28, 2016, 17 pages.

Office Action mailed Feb. 7, 2022, in U.S. Appl. No. 16/430,106, Yang, A., filed Jun. 3, 2019, 4 pages.

Office action mailed Mar. 14, 2019, in U.S. Appl. No. 15/210,612, inventor Manekas, D. et al., filed Jul. 14, 2016, 13 pages.

Office Action mailed May 27, 2021, in U.S. Appl. No. 16/430,106, Yang, A., filed Jun. 3, 2019, 29 pages.

Office Action mailed Oct. 22, 2021, in U.S. Appl. No. 16/430,106, Yang, A., filed Jun. 3, 2019, 30 pages.

Office Action mailed Oct. 3, 2018 in U.S. Appl. No. 15/141,772, Yang, A et al., filed Apr. 28, 2016, 17 pages.

(56)            References Cited

OTHER PUBLICATIONS

Olafsen, T., et al., "ImmunoPET imaging of B-Cell Lymphoma Using $^{124}$I-Anti-CD20 scFv Dimers (Diabodies)," Protein Engineering, Design & Selection 23(4):243-249, Oxford University Press, United Kingdom (Apr. 2010).

OPDIVO, FDA Approved label and prescribing information, Rev. May 2025, (BMS EX2005 filed in IPR2025-00603), 181 pages.

"OPDIVO (nivolumab) injection, for intravenous use," [package insert], Bristol-Myers Squibb: Approved by U.S. Food and Drug Administration, United States; (Aug. 2018), 32 Pages.

Zumwalt, T.J., et al., "Immunotherapy of Metastatic Colorectal Cancer: Prevailing Challenges and New Perspectives," Current Colorectal Cancer Reports 11(3):125-140, Springer, United States (Jun. 2015).

Ott, P.A., et al., "CTLA-4 and PD-1/PD-L1 Blockade: New Immunotherapeutic Modalities with Durable Clinical Benefit in Melanoma Patients," Clinical Cancer Research 19(19):5300-5309, American Association of Cancer Research, United States (Oct. 2013).

Overman M.J., et al., "479P-Nivolumab ± ipilimumab treatment (Tx) efficacy, safety, and biomarkers in patients (Pts) with metastatic colorectal cancer (mCRC) with and without High Microsatellite Instability (MSI-H): results from the CheckMate-142 study," Annals of Oncology, 27(6):149-206, Elsevier, Netherlands (Oct. 2016).

Overman, M.J., et al., "Nivolumab in Patients With DNA Mismatch Repair Deficient/microsatellite Instability High Metastatic Colorectal Cancer: Update From Checkmate 142," Journal of Clinical Oncology 35(4_Suppl):519, Meeting Abstract: 2017 Gastrointestinal Cancers Symposium, (Mar. 2017), 2 pages.

Overman, M.J., et al., "Nivolumab + ipilimumab in treatment of patients with metastatic colorectal cancer with and without high microsatellite instability: CheckMate 142 interim results.," Poster Presentation, presented at 2016 ASCO Annual Meeting, Jun. 3-7, 2016, American Society of Clinical Oncology, United States, 23 pages.

Overman, M.J., et al., "Nivolumab ± ipilimumab in treatment (tx) of patients (pts) with metastatic colorectal cancer (mCRC) with and without high microsatellite instability (MSI-H): CheckMate-142 interim results," Meeting Abstract. 2016 ASCO Annual Meeting, Journal of Clinical Oncology 34(15): Abstract 3501, American Society of Clinical Oncology, United States (May 2016).

Padlan, E.A., "X-ray crystallography of antibodies," Advances in Protein Chemistry 49:57-134, National Institute of Health, United States (1996).

Pai, S.I., "Adaptive immune resistance in HPV-associated head and neck squamous cell carcinoma," Oncoimmunology 2(5):e24065, Taylor & Francis, United Kingdom (May 2013).

Pai, S.I., "Mission impossible: how HPV-associated head and neck cancers escape a primed immune response," Oral Oncol 49:723-725, Elsevier, Netherlands (Aug. 2013).

Pan, S-D., et al., "Weight-based dosing in medication use: what should we know?" Patient Preference and Adherence 10:549-560, Dove Medical Press, United Kingdom (Apr. 2016).

Partlova, S., et al., "Distinct patterns of intratumoral immune cell infiltrates in patients with HPV-associated compared to non-virally induced head and neck squamous cell carcinoma," Oncoimmunology 4(1):e965570, Taylor & Francis, United Kingdom (Jan. 2015).

Patel, J.J., et al., "Impact of PD-L1 expression and human papillomavirus status in anti-PD1/PDL 1 immunotherapy for head and neck squamous cell carcinoma—Systematic review and meta-analysis," Head & Neck 42:774-786, Wiley, United States (Nov. 2019).

Patel, S.P., et al., "Modulation of Immune System Inhibitory Checkpoints in Colorectal Cancer," Curr Colorectal Cancer Rep 9:391-397, Springer Link, United States (Dec. 2013).

Patent Owner's Mandatory Notices Pursuant to 37 C.F.R. § 42.8, filed in IPR2025-00603, *Amgen Inc.*, Petitioner v. *Bristol-Myers Squibb Company*, Patent Owner, Mar. 21, 2025, 5 pages.

Patent Owner's Power of Attorney, filed in IPR2025-00603, *Amgen Inc.*, Petitioner v. *Bristol-Myers Squibb Company*, Patent Owner, Mar. 21, 2025, 4 pages.

Patent Owner's Request for Discretionary Denial, filed in IPR2025-00603, *Amgen Inc.*, Petitioner v. *Bristol-Myers Squibb Company*, Patent Owner, Jun. 10, 2025, 19 pages.

Pawlik. T. M., et al., "Colorectal Carcinogenesis: MSI-H Versus MSI-L," Disease Markers 20(4-5): 199-206, Hindawi Pub. Corp, United States (Oct. 2004).

PCT Request Form for filing new International Patent Application No. PCT/US2016/042297, European Patent Office, Netherlands, mailed Jul. 14, 2016, 5 pages.

Pernot, S., et al., "Colorectal Cancer and Immunity: What We Know and Perspectives," World Journal of Gastroenterology 20(14):3738-3750, Baishideng Publishing Group, United States (Apr. 2014).

Peters, M., "Colorectal Cancer, in A-Z Family Medical Encyclopedia," Sixth Edition, pp. 186, British Medical Association, United Kingdom (2014).

Petition for Inter Partes Review of U.S. Pat. No. 10,174,113, Case No. IPR2025-00602, Feb. 28, 2025, 89 pages.

Petition for Inter Partes Review Under 35 U.S.C. §§ 311-319 And 37 C.F.R. § 42.1 et seq, filed in IPR2025-00603, *Amgen Inc.*, Petitioner v. *Bristol-Myers Squibb Company*, Patent Owner, Feb. 28, 2025, 91 pages.

Petitioner's Opposition to Patent Owner's Discretionary Denial Brief, filed in IPR2025-00603, *Amgen Inc.*, Petitioner v. *Bristol-Myers Squibb Company*, Patent Owner, Jul. 10, 2025, 36 pages.

Pino, M.S., and Chung, D.C., "Microsatellite Instability' in the Management of Colorectal Cancer," Expert Review of Gastroenterology & Hepatology 5(3):385-399, Taylor & Francis, United Kingdom (Jun. 2011).

Pirog, E.C., et al., "HPV prevalence and genotypes in different histological subtypes of cervical adenocarcinoma, a worldwide analysis of 760 cases" Mod Pathol 27(12):1559-1567, Nature Publishing Group, United Kingdom (Apr. 2014).

Pollack, J.R., et al., "Microarray Analysis Reveals a Major Direct Role of DNA Copy Number Alteration in the Transcriptional Program of Human Breast Tumors," Proceedings of the National Academy of Sciences of USA 99(20):12963-12968, National Academy of Sciences, United States (Oct. 2002).

Pollack, M.H., et al., "Safety of resuming anti-PD-1 in patients with immune-related adverse events (irAEs) during combined anti-CTLA-4 and anti-PD1 in metastatic melanoma," Annals of Oncology 29(1):250-255, Elsevier, Netherlands (Jan. 2018).

Poole, R.M., "Pembrolizumab: first global approval," Drugs 74(16):1973-1981, Springer, Germany (Oct. 2014).

Postow, M.A, "Managing Immune Checkpoint-blocking Antibody Side Effects," American Society of Clinical Oncology—Educational Book 35(1):76-83, American Society of Clinical Oncology, United States (May 2015).

Poulogiannis, G., et al., "DNA Mismatch Repair Deficiency in Sporadic Colorectal Cancer and Lynch Syndrome," Histopathology 56(2):167-179, Wiley, United States (Jan. 2010).

Powell, S.F., et al., "KEYNOTE-055: A phase II trial of single agent pembrolizumab in patients (pts) with recurrent or metastatic head and neck squamous cell carcinoma (HNSCC) who have failed platinum and cetuximab," J. Clin. Oncol. (2015 ASCO Annual Meeting I Posters) 33(15S): Abstract TPS3094, May 29-Jun. 2, United States (2015).

Power of Attorney Pursuant to 37 C.F.R. § 42.10(B), filed in IPR2025-00603, *Amgen Inc.*, Petitioner v. *Bristol-Myers Squibb Company*, Patent Owner, Feb. 28, 2025, 3 pages.

Prosecution History of U.S. Pat. No. 11,332,529, filed on Nov. 30, 2018, 3093 pages.

Pugh, M.B., et al., "Stedman's Medical Dictionary," Twenty-seventh Edition pp. 382, Lippincott Williams & Wilkins, Baltimore. MD, United States (Jan. 2000).

Rahman, N., "Mainstreaming genetic testing of cancer predisposition genes," Clinical Medicine 14(4):436-439, Royal College of Physicians, United Kingdom (Aug. 2014).

(56) References Cited

OTHER PUBLICATIONS

Rajasekaran, N., et al., "Exploratory analysis of clinical and translational factors associated with the inflamed phenotype in HNSCC.," J. Clin. Oncol. (2015 ASCO Annual Meeting I Posters) 33(15S): Abstract 3031, May 29-Jun. 2, United States (2015).

Rini, B.I., et al., "Phase 1 Dose-escalation Trial of Tremelimumab Plus Sunitinib in Patients with Metastatic Renal Cell Carcinoma," Cancer 117(14):758-767, American Cancer Society, United States (Feb. 2011).

Rosenbaum, M.W., et al., "PD-L1 Expression in Colorectal Cancer Is Associated With Microsatellite Instability, BRAF Mutation, Medullary Morphology and Cytotoxic Tumor-infiltrating Lymphocytes," Modern Pathology 29(9):1104-1112, Nature Publishing Group, United States (Sep. 2016).

Schache, A., et al., "Human papillomavirus testing in head and neck squamous cell carcinoma: best practice for diagnosis," Methods Mol Biol 1180:237-255, SpringerLink, Germany (Jul. 2014).

Scott M. Lassman, Curriculum Vitae, 4 pages.

Segal, N.H., et al., "Safety and efficacy of MEDI4736, an anti-PD-L1 antibody, in patients from a squamous cell carcinoma of the head and neck (SCCHN) expansion cohort," J. Clin. Oncol. (2015 ASCO Annual Meeting) 33(15S): Abstract 3011, United States (May 2015), accessed at https://ascopubs.org/doi/10.1200/jco.2015.33.15_suppl.3011, 4 pages.

Seiwert, T., et al., "A phase 1b study of MK-3475 in patients with human papillomavirus (HPV)-associated and non-HPV-associated head and neck (H/N) cancer," J. Clin. Oncol. (ASCO Meeting Abstracts 2014) 32(15S):Abstract 6011, American Society of Clinical Oncology, United States (May 2014).

Seiwert, T., et al., "A Phase 1b Study of Pembrolizumab (MK-3475) in Patients with HPV-negative and HPV-positive Head & Neck Cancer," slide deck presented at the 2014 ASCO Annual Meeting.

Seiwert, T., et al., "Antitumor Activity of the anti-PD-1 Antibody Pembrolizumab in Biomarker-Unselected Patients with R/M Head and Neck Cancer: Preliminary Results from the Keynote-012 Expansion Cohort," slide deck presented at the 2015 ASCO Annual Meeting.

Seiwert, T.Y., et al., "Antitumor Activity and Safety of Pembrolizumab in Patients (Pts) with Advanced Squamous Cell Carcinoma of the Head and Neck (SCCHN): Preliminary Results from KEYNOTE-012 Expansion Cohort," Journal of Clinical Oncology 33(18): Abstract LBA6008, Asco Meeting Abstracts, American Society of Clinical Oncology, United States (May 29-Jun. 2, 2015).

Selby, M.J., et al., "Preclinical Development of Ipilimumab and Nivolumab Combination Immunotherapy: Mouse Tumor Models, In Vitro Functional Studies, and Cynomolgus Macaque Toxicology," PLoS One 11(9):e0161779, Public Library of Science, United States (Sep. 2016).

Sharma, P., and Allison, J.P., "The Future of Immune Checkpoint Therapy," Science 348(6230):56-61, American Association for the Advancement of Science, United States (Apr. 2015).

Siegel, R., et al., "Cancer Statistics, 2013," A Cancer Journal for Clinicians 63(1):11-30, American Cancer Society, United States (Jan. 2013).

Smyrk, T.C., et al., "Tumor-infiltrating Lymphocytes Are a Marker for Microsatellite Instability in Colorectal Carcinoma," Cancer 91(12):2417-2422, Wiley, United States (Jun. 2001).

Srivastava, R.J., et al., "Anti-PD-1 mAb pre-radiotherapy (RT) loading dose and fractionated RT induce better tumor-specific immunity and tumor shrinkage than sequential administration in an HPV+ head and neck cancer model," J Immunother Cancer 3(Suppl 2):P314, BMJ, United Kingdom (Nov. 2015).

Starr, P., "Encouraging Results for Pembrolizumab in Head and Neck Cancer," Am Health Drug Benefits 8(Spec Issue):16, Engage Healthcare Communications, Inc., United States (Aug. 2015).

Statutory Disclaimer of U.S. Pat. No. 11,332,529, dated Aug. 18, 2025, 2 pages.

Stewart, R., et al., "Identification and Characterization of MEDI4736, an Antagonistic Anti-PD-L1 Monoclonal Antibody," Cancer Immunology Research 3(9):1052-1062, American Association for Cancer Research, United States (May 2015).

Sugano, K., "Molecular genetics of hereditary nonpolyposis colorectal cancer (HNPCC)," History of Medicine 211(3):238-244, Ishiyaku Publishing Co., Ltd., Japan (2004).

Summary of Clinical Trial List, Search of: NCT02231749, version of May 25, 2016, accessed at https://clinicaltrials.gov/study/NCT02231749?term=NCT02231749&rank=1&tab=history&a=41, accessed on Dec. 21, 2023, 33 pages.

Sunshine, J. and Taube, J.M., "PD-1/PD-L1 Inhibitors," Current Opinion in Pharmacology 23:32-38, Elsevier Ltd., United Kingdom (Jun. 2015).

Swaika, A., et al., "Current state of anti-PD-L1 and anti-PD-1 agents in cancer therapy," Mol Immunol 67(2):4-17, Elsevier, Netherlands (Mar. 2015).

Swanson, M.S., et al., "Rationale for combined blockade of PD-1 and CTLA-4 in advanced head and neck squamous cell cancer—review of current data," Oral Oncol 51:12-15, Elsevier, Netherlands (Oct. 2014).

Taberno, J., et al., "Clinical activity, safety, and biomarkers of MPDL3280A, an engineered PD-L1 antibody in patients with locally advanced or metastatic CRC, gastric cancer (GC), SCCHN, or other tumors," J. Clin. Oncol. (2013 ASCO Annual Meeting I Posters) 31(15): Abstract 3622, United States (May-Jun. 2013).

Takayama, T., et al., "To what extent have genetic abnormalities in colorectal cancer been elucidated?" Molecular Gastrointestinal Medicine 6(3):245-249, Advanced Medical Company, Japan (Sep. 2009).

Zhao, X., et al., "Assessment of nivolumab benefit-risk profile of a 240-mg flat dose relative to a 3-mg/kg dosing regimen in patients with advanced tumors," Annals of Oncology: Official Journal of the European Society for Medical Oncology 28(8):2002-2008, Oxford Journals, United Kingdom (Aug. 2017).

Tarhini, A.A., and Kirkwood, J.M., "Tremelimumab (CP-675,206): A Fully Human Anticytotoxic T Lymphocyte-associated Antigen 4 Monoclonal Antibody for Treatment of Patients With Advanced Cancers," Expert Opinion on Biological Therapy 8(10):1583-1593, Taylor & Francis, United Kingdom (Oct. 2008).

Taylor, M., et al., "Phase I/II Study of Nivolumab With or Without Ipilimumab for Treatment of Recurrent Small Cell Lung Cancer (SCLC): CA209-032," Journal for ImmunoTherapy of Cancer 3(2):P376, BioMed Central Ltd, United Kingdom (Nov. 2015), 2 pages.

The ASCO Post, "ASCO 2016: Nivolumab Immunotherapy Improves Survival, Quality of Life in Metastatic or Recurrent Head and Neck Cancer,"Ascopost.com, Jun. 7, 2016, accessed at https://ascopost.com/News/41639, 4 pages.

The U.S. Generic & Biosimilar Medicines Savings Report, Sep. 2024, from the Association for Accessible Medicines, (Exhibit No. 1089 filed in IPR2025-00603), 41 pages.

Zhang, X., and Li, J., "Era of Universal Testing of Microsatellite Instability in Colorectal Cancer," World Journal of Gastrointestinal Oncology 5(2):12-19, Baishideng Publishing Group, China (Feb. 2013).

Topalian, S., et al. "Immune checkpoint blockade: a common denominator approach to cancer therapy," Cancer Cell 27:450-461, Cell Press, United States (Apr. 2015).

Topalian, S.L., et al., "Survival, Durable Tumor Remission, and Long-term Safety in Patients with Advanced Melanoma Receiving Nivolumab," Journal of Clinical Oncology 32(10):1020-1030, American Society of Clinical Oncology, United States (Mar. 2014).

Tzartos, S.J., et al., "Epitope Mapping by Antibody Competition. Methodology and Evaluation of the Validity of the Technique," Methods in Molecular Biology 66:55-66, Humana Press, United States (1996).

Ukpo, O. C., et al., "B7-H1 expression model for immune evasion in human papillomavirus-related oropharyngeal squamous cell carcinoma." Head Neck Pathol 7(2):113-121, SpringerLink, Germany (Jun. 2013).

United States Adopted Name (USAN) Drug Finder, "Pembrolizumab: Statement on a nonproprietary name adopted by the USAN Council (ZZ-165)," published Nov. 27, 2013, accessed at https://searchusan.ama-assn.org/usan/documentDownload?uri=%2Funstructured%2Fbinary%2Fusan%2Fpembrolizumab.pdf, accessed on Dec. 8, 2016, 2 pages.

(56)　　　　　References Cited

OTHER PUBLICATIONS

Urban, D., et al., "What is the best treatment for patients with human papillomavirus-positive and -negative oropharyngeal cancer?" Cancer 120:1462-1470, Wiley, United States (Feb. 2014).

U.S. National Library of Medicine, National Institutes of Health, ClinicalTrials.gov, Glossary of Common Site Terms, accessed at (https://clinicaltrials.gov/ct2/about-studies/glossary), 6 pages.

Van Eeghen, E.E., et al., "Impact of Age and Comorbidity on Survival in Colorectal Cancer," Journal of gastrointestinal Oncology 6(6):605-612, AME Publishing Group, China (Dec. 2015).

Venuti, A., et al., "HPV Detection Methods in Head and Neck Cancer" Head Neck Pathol 6:S63-S74, Humana Press, United States (Jul. 2012).

Vermorken, J.B. et al., "Optimal treatment for recurrent/metastatic head and neck cancer," Ann Oncol 21(Suppl. 7):vii252-vii261, Elsevier, Netherlands (Oct. 2010).

Vermorken, J.B., et al., "Platinum Based Chemotherapy plus Cetuximab in Head and Neck Cancer," N Engl J Med 359(11):1116-1127, Massachusetts Medical Society, United States (Sep. 2008).

Vietia, D., et al., "Human papillomavirus detection in head and neck squamous cell carcinoma," Ecancermedicalscience 8:475, Cancer Intelligence, United Kingdom (Oct. 2014).

Vilar, E., and Gruber, S.B., "Microsatellite Instability in Colorectal Cancer-the Stable Evidence," Nature Reviews. Clinical Oncology 7(3):153-162, Springer, Germany (Mar. 2010).

Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).

Ward, M.J., et al., "Tumour-infiltrating lymphocytes predict for outcome in HPV-positive oropharyngeal cancer," Br J Cancer 110(2):489-500, Nature Portfolio, Germany (Jan. 2014).

Weissman, S., et al., "Genetic Counseling Considerations in the Evaluation of Families for Lynch Syndrome—a Review," Journal of Genetic Counseling 20(1):5-19, Wiley, United States (Feb. 2011).

Wendling, P., "Pembrolizumab active in head and neck cancer, regardless of HPV status," MDEdge.com, May 3, 2015, accessed at https://www.mdedge.com/hematology-oncology/article/100061/head-neck-cancers/pembrolizumab-active-head-and-neck-cancer, 2 pages.

Wikipedia, List of Medical Abbreviations: Q, published Mar. 12, 2022, 2 pages.

Willis, C., "Common Abbreviations and Symbols, in Medical Terminology: The Language of Health Care," Second Edition, Goucher, J., eds., pp. 93. Lippincott, Williams, and Wilkins, Baltimore, MD, United States (2006).

Wolchok, J., et al., "Updated Results From a Phase Iii Trial of Nivolumab (NIVO) Combined With Ipilimumab (IPI) in Treatment-naive Patients (Pts) With Advanced Melanoma (MEL) (Checkmate 067)," Journal of Clinical Oncology 34(Suppl 15):Abstract 9505, American Society of Clinical Oncology, United States (May 2016).

Xiao, Y., and Freeman, G.J., "The Microsatellite Instable (MSI) Subset of Colorectal Cancer is a Particularly Good Candidate for Checkpoint Blockade Immunotherapy," Cancer Discovery 5(1):16-18, American Association for Cancer Research, United States (Jan. 2015).

Xiong, B., and Dong, Z., "Tumors with Mismatch-Repair Deficiency Improve the Clinical Efficacy of Anti-PD-1 Immunotherapy," Journal of Evidence-Based Medicine 15(4):228-231, Health Commission of Guangdong Province, China (2015).

Yervoy, FDA Approved label and prescribing information, Rev. May 2025, (BMS EX2004 filed in IPR2025-00603), 81 pages.

Zandberg, D.P. and Strome, S.E., "The Role of the PD-L1:PD-1 Pathway in Squamous Cell Carcinoma of the Head and Neck," Oral Oncology 50(7):627-632, Elsevier Ltd., United Kingdom (May 2014).

Zavarinos, A., "An updated overview of HPV-associated head and neck carcinomas," Oncotarget, 5(12):3956-3969, Impact Journals, United States (Jun. 2014).

* cited by examiner

FIG. 2A

FITC-10H10 binding to
anti-hPD-L1 HuMab Ab-blocked CHO/PD-L1 cells

MFI (FITC)

Blocking Antibodies

FITC-10A5 binding to
anti-hPD-L1 HuMab Ab-blocked CHO/PD-L1 cells

FITC-11E6 binding to
anti-hPD-L1 HuMab Ab-blocked CHO/PD-L1 cells

FIG. 2F

FITC-13G4 binding to
anti-hPD-L1 HuMab Ab-blocked CHO/PD-L1 cells

| Association Between Pretreatment Tumor PD-L1 Expression and Clinical Response | | | |
|---|---|---|---|
| Response Status | PD-L1-Positive no. (%) | PD-L1-Negative no. (%) | Total no. (%) |
| CR/PR | 9 (36) | 0 | 9 (21) |
| Nonresponder | 16* (64) | 17 (100) | 33 (79) |
| All Patients | 25 | 17 | 42 |

Fisher's exact test for association P=0.006.

*Two patients categorized as nonresponders at the time of data analysis are still under evaluation.

1.5 months 10 months

Pretreatment 3 months

CANCER IMMUNOTHERAPY BY DISRUPTING PD-1/PD-L1 SIGNALING

REFERENCE TO EARLIER FILED APPLICATIONS

This application is a continuation of U.S. application Ser. No. 18/662,447, filed on May 13, 2024, which is a continuation of U.S. application Ser. No. 18/052,099, filed on Nov. 2, 2022, which is a continuation of U.S. application Ser. No. 16/827,580, filed on Mar. 23, 2020, which is a continuation of U.S. application Ser. No. 16/231,211, filed on Dec. 21, 2018 (issued as U.S. Pat. No. 10,604,575 on Mar. 31, 2020), which is a division of U.S. application Ser. No. 16/006,365, filed Jun. 12, 2018 (issued as U.S. Pat. No. 10,316,090 on Jun. 11, 2019), which is a continuation of U.S. application Ser. No. 14/950,748, filed Nov. 24, 2015 (issued as U.S. Pat. No. 10,072,082 on Sep. 11, 2018), which is a division of U.S. application Ser. No. 13/892,671, filed May 13, 2013 (issued as U.S. Pat. No. 9,212,224 on Dec. 15, 2015), which claims the benefit of U.S. Provisional Application No. 61/647,442, filed May 15, 2012, and U.S. Provisional Application No. 61/790,747, filed Mar. 15, 2013, all of which are incorporated herein by reference in their entireties.

REFERENCE TO SEQUENCE LISTING SUBMITTED ELECTRONICALLY VIA EFS-WEB

The content of the electronically submitted sequence listing (Name: 3338_063000L_SequenceListing_ST26.xml, Size: 35,859 bytes; and Date of Creation: May 2, 2025) is incorporated herein by reference in its entirety.

Throughout this application, various publications are referenced in parentheses by author name and date, or by Patent No. or Patent Publication No. Full citations for these publications may be found at the end of the specification immediately preceding the claims. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

FIELD OF THE INVENTION

This invention relates to methods for immunotherapy of a cancer patient comprising administering to the patient antibodies that disrupt the PD-1/PD-L1 signaling pathway. A biomarker may be used as part of this treatment for identifying suitable patients for immunotherapy and for predicting the efficacy of anti-PD-1 treatment.

BACKGROUND OF THE INVENTION

Human cancers harbor numerous genetic and epigenetic alterations, generating neoantigens potentially recognizable by the immune system (Sjoblom et al., 2006). Although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively suppress the host immune response (Topalian et al., 2011; Mellman et al., 2011). Among these mechanisms, endogenous "immune checkpoints" that normally terminate immune responses to mitigate collateral tissue damage can be co-opted by tumors to evade immune destruction. Intensive efforts to develop specific immune checkpoint pathway inhibitors have begun to provide new immunotherapeutic approaches for treating cancer, including the development of the anti-CTLA-4 antibody (Ab), ipilimumab (YERVOY®), for the treatment of patients with advanced melanoma (Hodi et al., 2010).

Programmed Death-1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1 (Freeman et al., 2000; Latchman et al., 2001). Unlike CTLA-4, PD-1 primarily functions in peripheral tissues where activated T-cells may encounter the immunosuppressive PD-L1 (B7-H1) and PD-L2 (B7-DC) ligands expressed by tumor and/or stromal cells (Flies et al., 2011; Topalian et al., 2012a). Inhibition of the PD-1/PD-L1 interaction mediates potent antitumor activity in preclinical models (U.S. Pat. Nos. 8,008,449 and 7,943,743), and the use of Ab inhibitors of the PD-1/PD-L1 interaction for treating cancer has entered clinical trials (Brahmer et al., 2010; Flies et al., 2011; Topalian et al., 2012b; Brahmer et al., 2012).

The promise of the emerging field of personalized medicine is that advances in pharmacogenomics will increasing be used to tailor therapeutics to defined sub-populations, and ultimately, individual patients in order to enhance efficacy and minimize adverse effects. Recent successes include, for example, the development of imatinib mesylate (GLEEVEC®), a protein tyrosine kinase inhibitor that inhibits the bcr-abl tyrosine kinase, to treat Philadelphia chromosome-positive chronic myelogenous leukemia (CML); crizotinib (XALKORI®) to treat the 5% of patients with late-stage non-small cell lung cancers who express a mutant anaplastic lymphoma kinase (ALK) gene; and vemurafenib (ZELBORAF®), an inhibitor of mutated B-RAF protein (V600E-BRAF) which is expressed in around half of melanoma tumors. However, unlike the clinical development of small molecule agents that target discrete activating mutations found in select cancer populations, a particular challenge in cancer immunotherapy has been the identification of mechanism-based predictive biomarkers to enable patient selection and guide on-treatment management. Advances in validating PD-L1 expression as a biomarker for screening patients for anti-PD-1 immunotherapy are described herein.

SUMMARY OF THE INVENTION

The present disclosure provides a method for immunotherapy of a subject afflicted with cancer, which method comprises administering to the subject a composition comprising a therapeutically effective amount of an agent that reduces or suppresses signaling from an inhibitory immunoregulator. In preferred embodiments, the agent is an Ab. In other preferred embodiments, the inhibitory immunoregulator is a component of the PD-1/PD-L1 signaling pathway. In further preferred embodiments, the Ab disrupts the interaction between PD-1 and PD-L1. In certain embodiments, the Ab is an anti-PD-1 Ab of the invention or an anti-PD-L1 Ab of the invention. In preferred embodiments, the anti-PD-1 Ab of the invention is nivolumab (BMS-936558) and the anti-PD-L1 Ab of the invention is BMS-936559. In certain embodiments, the subject has been pre-treated for the cancer. In other embodiments, the cancer is an advanced, metastatic and/or refractory cancer. In preferred embodiments, the administration of the antibody or antigen-binding portion to the subject thereof induces a durable clinical response in the subject.

This disclosure also provides a method for immunotherapy of a subject afflicted with cancer, which method comprises: (a) selecting a subject that is a suitable candidate for immunotherapy, the selecting comprising (i) optionally providing a test tissue sample obtained from a patient with cancer of the tissue, the test tissue sample comprising tumor cells and tumor-infiltrating inflammatory cells, (ii) assessing the proportion of cells in the test tissue sample that express PD-L1 on the cell surface, and (iii) selecting the subject as a suitable candidate based on an assessment that the proportion of cells in the test tissue sample that express PD-L1 on the cell surface exceeds a predetermined threshold level; and (b) administering a composition comprising a therapeutically effective amount of an anti-PD-1 Ab to the selected subject.

The disclosure further provides a method for treatment of a subject afflicted with cancer, which method comprises: (a) selecting a subject that is not suitable for anti-PD-1 Ab immunotherapy, the selecting comprising (i) optionally providing a test tissue sample obtained from a patient with cancer of the tissue, the test tissue sample comprising tumor cells and tumor-infiltrating inflammatory cells; (ii) assessing the proportion of cells in the test tissue sample that express PD-L1 on the cell surface; and (iii) selecting the subject as not suitable for anti-PD-1 Ab immunotherapy based on an assessment that the proportion of cells in the test tissue sample that express PD-L1 on the cell surface is less than a predetermined threshold level; and (b) administering a standard-of-care therapeutic other than an anti-PD-1 Ab to the selected subject.

In addition, the disclosure provides a method for selecting a cancer patient for immunotherapy with an anti-PD-1 Ab, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold proportion; and (d) selecting the patient for immunotherapy based on an assessment that PD-L1 is expressed in cells of the test tissue sample.

This disclosure further provides a method for predicting the therapeutic effectiveness of an anti-PD-1 Ab for treating a cancer patient, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold value; and (d) predicting the therapeutic effectiveness of the anti-PD-1 Ab, wherein if the proportion of cells that express PD-L1 on the cell surface exceeds the threshold proportion the Ab is predicted to be effective in treating the patient, and wherein if the proportion of cells that express PD-L1 on the cell surface is below the threshold proportion the Ab is predicted to not be effective in treating the patient.

The present disclosure also provides a method for determining an immunotherapeutic regimen comprising an anti-PD-1 Ab for treating a cancer patient, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold proportion; and (d) determining an immunotherapeutic regimen comprising an anti-PD-1 Ab based on the determination that the proportion of cells that express PD-L1 on the cell surface exceeds the predetermined threshold proportion.

In certain embodiments of the methods described herein, the test tissue sample is a formalin-fixed and paraffin-embedded (FFPE) sample. In certain other embodiments, assessing the proportion of cells in the test tissue sample that express PD-L1 on the cell surface is achieved by immuno-histochemical (IHC) staining of the FFPE sample. In preferred embodiments, the mAb 28-8 is used in an automated IHC assay to bind to PD-L1 on the surface of cells in the test tissue sample. In preferred embodiments of any of the methods disclosed herein, the cancer is melanoma (MEL), renal cell carcinoma (RCC), squamous non-small cell lung cancer (NSCLC), non-squamous NSCLC, colorectal cancer (CRC), castration-resistant prostate cancer (CRPC), hepato-cellular carcinoma (HCC), squamous cell carcinoma of the head and neck, carcinomas of the esophagus, ovary, gastro-intestinal tract and breast, or a hematologic malignancy such as multiple myeloma, B-cell lymphoma, T-cell lymphoma, Hodgkin's lymphoma/primary mediastinal B-cell lymphoma, and chronic myelogenous leukemia.

This invention additionally provides a mAb or antigen-binding portion thereof that binds specifically to a cell surface-expressed human PD-L1 antigen in a FFPE tissue sample. In preferred embodiments, the mAb or antigen-binding portion thereof does not bind to a cytoplasmic PD-L1 antigen in the FFPE tissue sample. In other preferred embodiments, the monoclonal Ab (mAb) is the rabbit mAb designated 28-8, 28-1, 28-12, 29-8 or 20-12.

Other features and advantages of the instant invention will be apparent from the following detailed description and examples which should not be construed as limiting. The contents of all cited references, including scientific articles, newspaper reports, GENBANK® entries, patents and patent applications cited throughout this application are expressly incorporated herein by reference.

BRIEF DESCRIPTION OF THE FIGURES

Figure 2A:
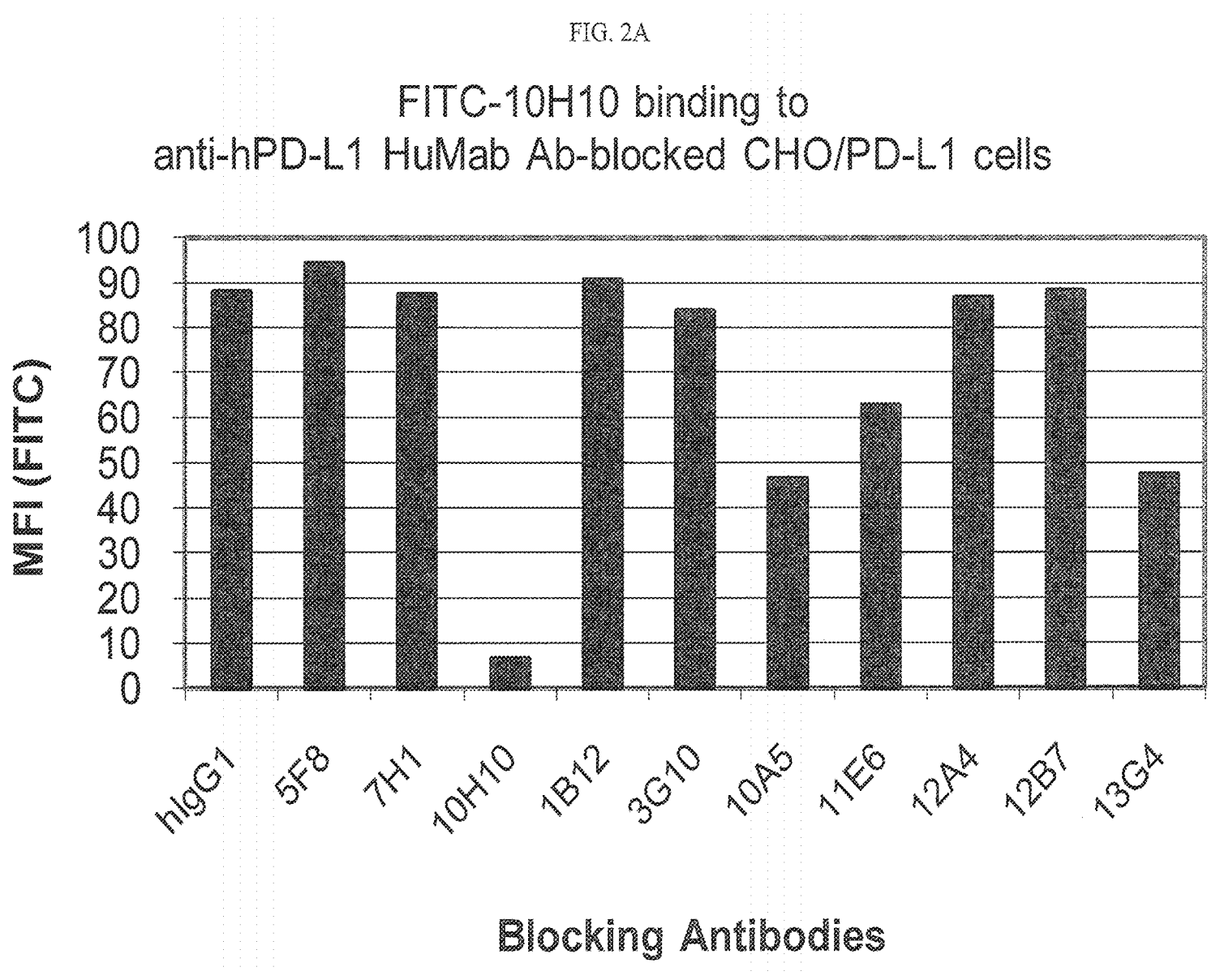
Figure 2F:
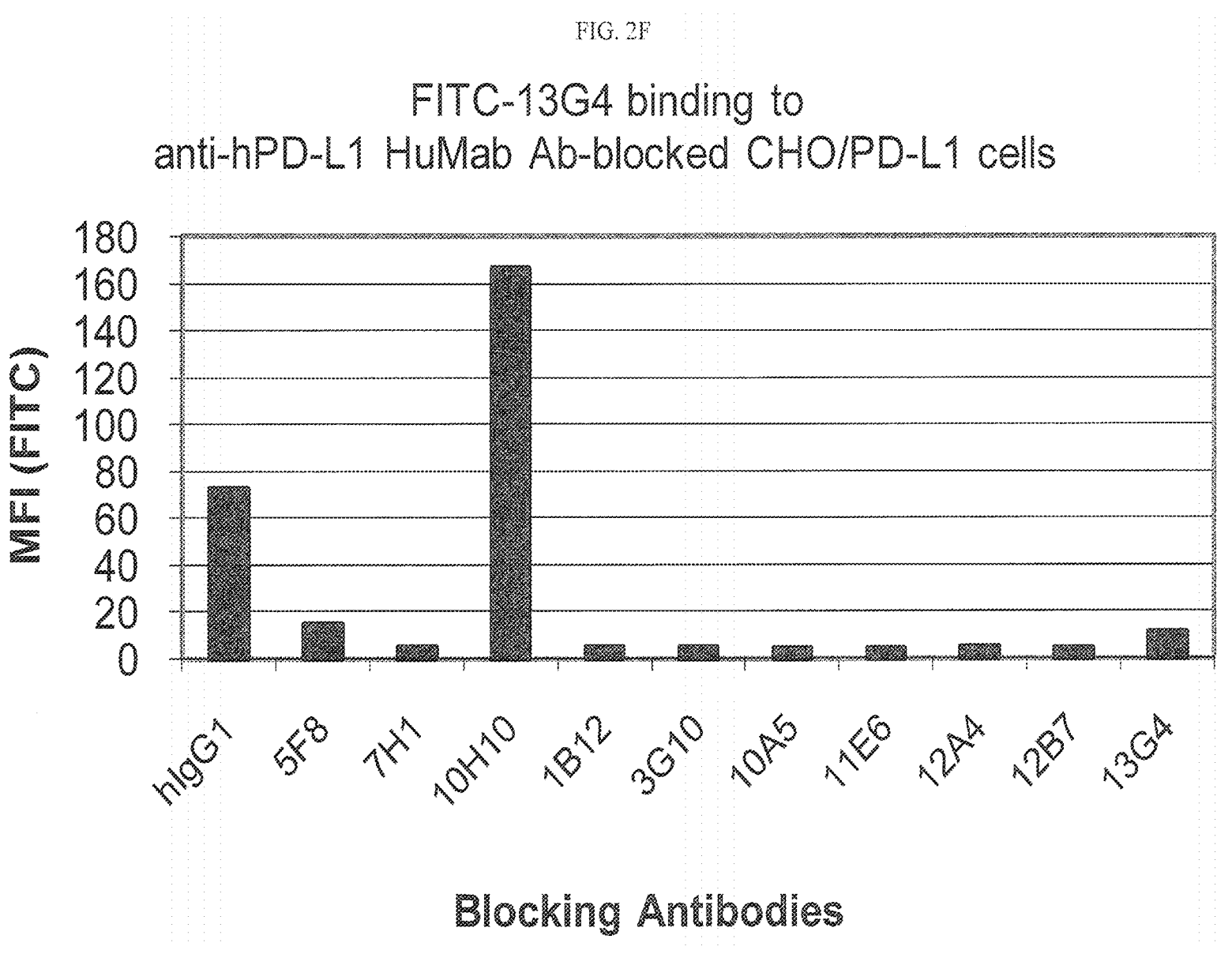

FIGS. 2A-2F. Cross-competition of FITC-conjugated human anti-hPD-L1 mAbs for binding to hPD-L1 expressed on CHO cells. A, Binding of labeled 10H10 was partially blocked by 10A5, 11E6 and 13G4 and was significantly blocked by itself; B, Binding of labeled 3G10 was significantly blocked by each of the tested anti-PD-L1 Abs except 10H10; C, Binding of labeled 10A5 was significantly blocked by each of the tested anti-PD-L1 Abs except 10H10; D, Binding of labeled 11E6 was significantly blocked by each of the tested anti-PD-L1 Abs except 10H10; and E, Binding of labeled 12A4 was significantly blocked by each of the tested anti-PD-L1 Abs except 10H10; and F, Binding of labeled 13G4 was significantly blocked by each of the tested anti-PD-L1 Abs except 10H10.

DETAILED DESCRIPTION OF THE INVENTION

Figure 1A:
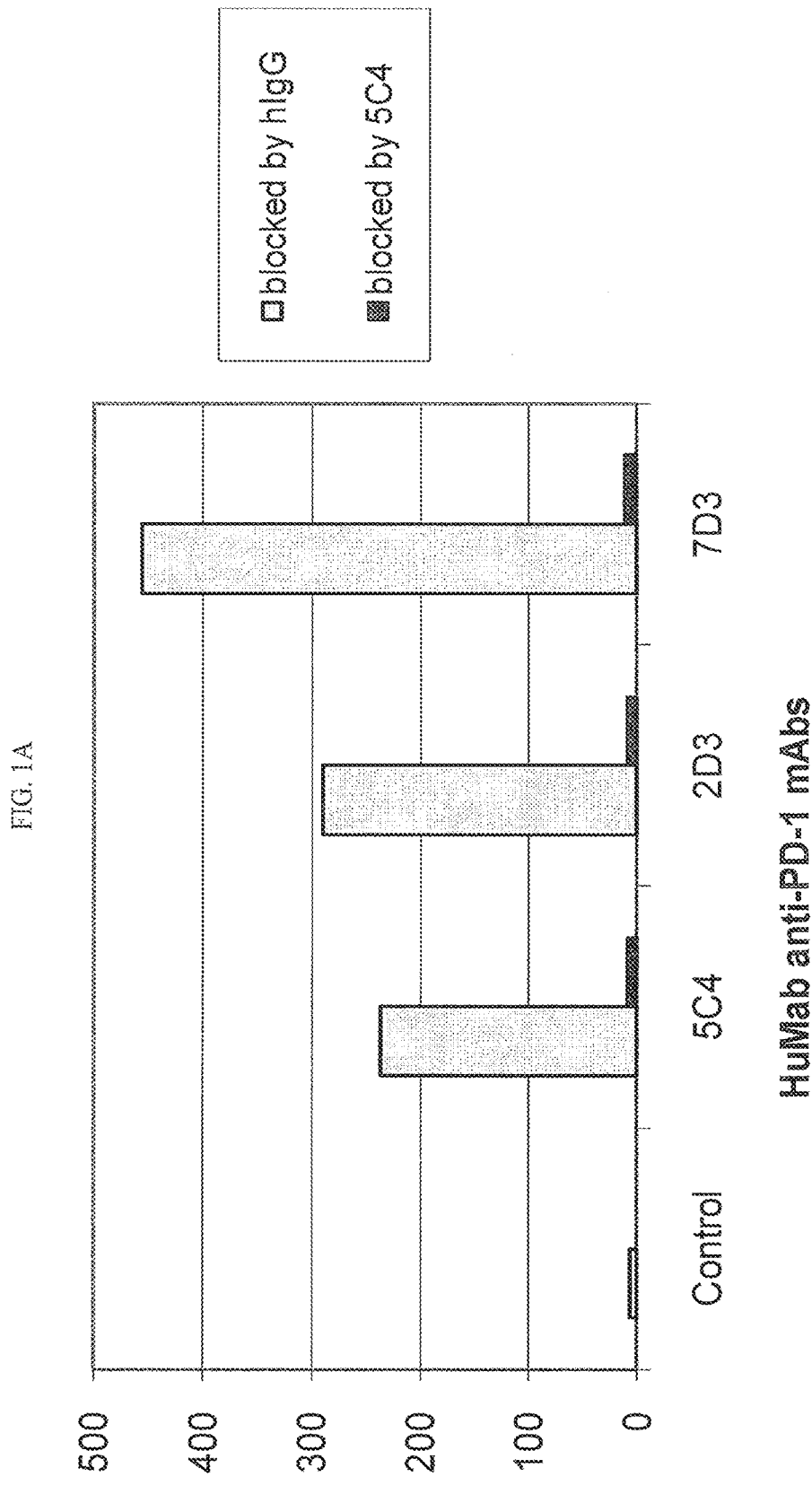
FIGS. 1A-1C. Cross-competition between 5C4 and other HuMab anti-PD-1 mAbs for binding to hPD-1 expressed on CHO cells. A, the 5C4 Fab fragment substantially blocked the binding of mAbs 5C4 itself, as well as the binding of 2D3 and 7D3; B, the 5C4 Fab fragment substantially blocked the binding of mAb 4H1; C, the 5C4 mAb substantially blocked the binding of mAb 17D8.

The present invention relates to methods for immunotherapy of a subject afflicted with diseases such as cancer or an infectious disease, which methods comprise administering to the subject a composition comprising a therapeutically effective amount of a compound or agent that potentiates an endogenous immune response, either stimulating the activation of the endogenous response or inhibiting the suppression of the endogenous response. More specifically, the disclosure provides methods for potentiating an endogenous immune response in a subject afflicted with cancer so as to thereby treat the patient, which method comprises administering to the subject a therapeutically effective amount of an Ab or an antigen-binding portion thereof that inhibits signaling from an inhibitory immunoregulator. In certain embodiments, the inhibitory immunoregulator is a component of the PD-1/PD-L1 signaling pathway. Accordingly, certain embodiments of the invention provide methods for immunotherapy of a subject afflicted with cancer, which methods comprise administering to the subject a therapeutically effective amount of an Ab or an antigen-binding portion thereof that disrupts the interaction between the PD-1 receptor and its ligand, PD-L1. In certain preferred embodiments, the Ab or antigen-binding portion thereof binds specifically to PD-1. In other preferred embodiments, the Ab or antigen-binding portion thereof binds specifically to PD-L1. In certain other embodiments, the subject is selected as suitable for immunotherapy in a method comprising measuring the surface expression of PD-L1 in a test tissue sample obtained from a patient with cancer of the tissue, for example, determining the proportion of cells in the test tissue sample that express PD-L1 on the cell surface, and selecting the patient for immunotherapy based on an assessment that PD-L1 is expressed on the surface of cells in the test tissue sample.

Terms

In order that the present disclosure may be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Preferred routes of administration for Abs of the invention include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Alternatively, an Ab of the invention can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-5}$ to $10^{-11}$ $M^{-1}$ or less. Any $K_D$ greater than about $10^{-4}$ $M^{-1}$ is generally considered to indicate nonspecific binding. As used herein, an Ab that "binds specifically" to an antigen refers to an Ab that binds to the antigen and substantially identical antigens with high affinity, which means having a $K_D$ of $10^{-7}$ M or less, preferably $10^{-8}$ M or less, even more preferably $5\times10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an Ab that binds specifically to human PD-1 may also have cross-reactivity with PD-1 antigens from certain primate species but may not cross-react with PD-1 antigens from certain rodent species or with an antigen other than PD-1, e.g., a human PD-L1 antigen.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "isolated antibody" refers to an Ab that is substantially free of other Abs having different antigenic specificities (e.g., an isolated Ab that binds specifically to PD-1 is substantially free of Abs that bind specifically to antigens other than PD-1). An isolated Ab that binds specifically to PD-1 may, however, have cross-reactivity to other antigens, such as PD-1 molecules from different species. Moreover, an isolated Ab may be substantially free of other cellular material and/or chemicals. By comparison, an "isolated" nucleic acid refers to a nucleic acid composition of matter that is markedly different, i.e., has a distinctive chemical identity, nature and utility, from nucleic acids as they exist in nature. For example, an isolated DNA, unlike native DNA, is a free-standing portion of a native DNA and not an integral part of a larger structural complex, the chromosome, found in nature. Further, an isolated DNA, unlike native genomic DNA, can typically be used in applications or methods for which native genomic DNA is unsuited, e.g., as a PCR primer or a hybridization probe for, among other things, measuring gene expression and detecting biomarker genes or mutations for diagnosing disease or assessing the efficacy of a therapeutic. An isolated nucleic acid may be purified so as to be substantially free of other cellular components or other contaminants, e.g., other cellular nucleic acids or proteins, using standard techniques well known in the art. Examples of isolated nucleic acids include fragments of genomic DNA, PCR-amplified DNA, cDNA and RNA.

The term "monoclonal antibody" ("mAb") refers to a preparation of Ab molecules of single molecular composition, i.e., Ab molecules whose primary sequences are essentially identical, and which exhibits a single binding specificity and affinity for a particular epitope. A mAb is an example of an isolated Ab. MAbs may be produced by hybridoma, recombinant, transgenic or other techniques known to those skilled in the art.

A "human" antibody (HuMAb) refers to an Ab having variable regions in which both the framework and CDR regions are derived from human germline immunoglobulin sequences. Furthermore, if the Ab contains a constant region, the constant region also is derived from human germline immunoglobulin sequences. The human Abs of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include Abs in which CDR sequences derived from the germline of another mammalian species, such as a mouse, have been grafted onto human framework sequences. The terms "human" Abs and "fully human" Abs and are used synonymously.

A "humanized" antibody refers to an Ab in which some, most or all of the amino acids outside the CDR domains of a non-human Ab are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

A "chimeric antibody" refers to an Ab in which the variable regions are derived from one species and the constant regions are derived from another species, such as an Ab in which the variable regions are derived from a mouse Ab and the constant regions are derived from a human Ab.

An "antigen-binding portion" of an Ab (also called an "antigen-binding fragment") refers to one or more fragments of an Ab that retain the ability to bind specifically to the antigen bound by the whole Ab.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

An "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer microenvironment.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

A "predetermined threshold value," relating to cell surface PD-L1 expression, refers to the proportion of cells in a test tissue sample comprising tumor cells and tumor-infiltrating inflammatory cells above which the sample is scored as being positive for cell surface PD-L1 expression. For cell surface expression assayed by IHC with the mAb 28-8, the predetermined threshold value for cells expressing PD-L1 on the cell surface ranges from at least about 0.01% to at least about 20% of the total number of cells. In preferred embodiments, the predetermined threshold value for cells expressing PD-L1 on the cell surface ranges from at least about 0.1% to at least about 10% of the total number of cells. More preferably, the predetermined threshold value is at least about 5%. Even more preferably, the predetermined threshold value is at least about 1%.

The "Programmed Death-1 (PD-1)" receptor refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GENBANK® Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GENBANK® Accession No. Q9NZQ7.

A "signal transduction pathway" or "signaling pathway" refers to the biochemical relationship between a variety of signal transduction molecules that play a role in the transmission of a signal from one portion of a cell to another portion of the cell. A "cell surface receptor" includes, for example, molecules and complexes of molecules that are located on the surface of a cell and are capable of receiving a signal and transmitting such a signal across the plasma membrane of a cell. An example of a cell surface receptor of the present invention is the PD-1 receptor, which is located on the surface of activated B cells, activated T cells and myeloid cells, and transmits a signal that results in a decrease in tumor-infiltrating lymphocytes and a decrease in T cell proliferation. An "inhibitor" of signaling refers to a compound or agent that antagonizes or reduces the initiation, reception or transmission of a signal, be that signal stimulatory or inhibitory, by any component of a signaling pathway such as a receptor or its ligand.

A "subject" includes any human or nonhuman animal. The term "nonhuman animal" includes, but is not limited to, vertebrates such as nonhuman primates, sheep, dogs, cats, rabbits, ferrets, rodents such as mice, rats and guinea pigs, avian species such as chickens, amphibians, and reptiles. In preferred embodiments, the subject is a mammal such as a nonhuman primate, sheep, dog, cat, rabbit, ferret or rodent. In more preferred embodiments, the subject is a human. The terms, "subject," "patient" and "individual" are used interchangeably herein.

A "therapeutically effective amount" or "therapeutically effective dosage" of a drug or therapeutic agent, such as an Ab of the invention, is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of the drug preferably inhibits cell growth or tumor growth by at least about 20%, more preferably by at least about 40%, even more preferably by at least about 60%, and still more preferably by at least about 80% relative to untreated subjects. In other preferred embodiments of the invention, tumor regression may be observed and continue for a period of at least about 20 days, more preferably at least about 40 days, or even more preferably at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In preferred embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

A "tumor-infiltrating inflammatory cell" is any type of cell that typically participates in an inflammatory response in a subject and which infiltrates tumor tissue. Such cells include tumor-infiltrating lymphocytes (TILs), macrophages, monocytes, eosinophils, histiocytes and dendritic cells.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Antibodies of the Invention

Abs of the present invention include a variety of Abs having structural and functional properties described herein, including high-affinity binding to PD-1 or PD-L1, respectively. These Abs may be used, for example, as therapeutic Abs to treat subjects afflicted with disease or as reagents in diagnostic assays to detect their cognate antigens. Human mAbs (HuMAbs) that bind specifically to PD-1 (e.g., bind to human PD-1 and may cross-react with PD-1 from other species, such as cynomolgus monkey) with high affinity have been disclosed in U.S. Pat. No. 8,008,449, and HuMAbs that bind specifically to PD-L1 with high affinity have been disclosed in U.S. Pat. No. 7,943,743. The Abs of the invention include, but are not limited to, all of the anti-PD-1 and anti-PD-L1 Abs disclosed in U.S. Pat. Nos. 8,008,449 and 7,943,743, respectively. Other anti-PD-1 mAbs have been described in, for example, U.S. Pat. Nos. 7,488,802 and 8,168,757, and anti-PD-L1 mAbs have been described in, for example, U.S. Pat. Nos. 7,635,757 and 8,217,149, and U.S. Publication No. 2009/0317368. To the extent these anti-PD-1 and anti-PD-L1 mAbs exhibit the structural and functional properties disclosed herein for antibodies of the invention, they too are included as antibodies of the invention.

Anti-PD-1 Antibodies of the Invention

Each of the anti-PD-1 HuMAbs disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a BIACORE® biosensor system; (b) does not substantially bind to human CD28, CTLA-4 or ICOS; (c) increases T-cell proliferation in a Mixed Lymphocyte Reaction (MLR) assay; (d) increases interferon-7 production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates Ab responses; and (j) inhibits tumor cell growth in vivo. Anti-PD-1 Abs of the present invention include mAbs that bind specifically to human PD-1 and exhibit at least one, preferably at least five, of the preceding characteristics.

U.S. Pat. No. 8,008,449 exemplifies seven anti-PD-1 HuMAbs: 17D8, 2D3, 4H1, 5C4 (also referred to herein as nivolumab or BMS-936558), 4A11, 7D3 and 5F4. Isolated DNA molecules encoding the heavy and light chain variable regions of these Abs have been sequenced, from which the amino acid sequences of the variable regions were deduced. The $V_H$ amino acid sequences of 17D8, 2D3, 4H1, 5C4, 4A11, 7D3 and 5F4 are provided herein as SEQ ID NOs. 1, 2, 3, 4, 5, 6 and 7, respectively. The $V_L$ amino acid sequences of 17D8, 2D3, 4H1, 5C4, 4A11, 7D3 and 5F4 are provided herein as SEQ ID NOs. 8, 9, 10, 11, 12, 13 and 14, respectively.

Preferred anti-PD-1 Abs of the present invention include the anti-PD-1 HuMAbs 17D8, 2D3, 4H1, 5C4, 4A11, 7D3 and 5F4. These preferred Abs bind specifically to human PD-1 and comprise: (a) a human heavy chain variable region comprising consecutively linked amino acids having the sequence set forth in SEQ ID NO: 1 and a human light chain variable region comprising consecutively linked amino acids having the sequence set forth in SEQ ID NO: 8; (b) a human heavy chain variable region comprising consecutively linked amino acids having the sequence set forth in SEQ ID NO: 2 and a human light chain variable region comprising consecutively linked amino acids having the sequence set forth in SEQ ID NO: 9; (c) a human heavy chain variable region comprising consecutively linked amino acids having the sequence set forth in SEQ ID NO: 3 and a human light chain variable region comprising consecutively linked amino acids having the sequence set forth in SEQ ID NO: 10; (d) a human heavy chain variable region comprising consecutively linked amino acids having the sequence set forth in SEQ ID NO: 4 and a human light chain variable region comprising consecutively linked amino acids having the sequence set forth in SEQ ID NO: 11; (e) a human heavy chain variable region comprising consecutively linked amino acids having the sequence set forth in SEQ ID NO: 5 and a human light chain variable region comprising consecutively linked amino acids having the sequence set forth in SEQ ID NO: 12; (f) a human heavy chain variable region comprising consecutively linked amino acids having the sequence set forth in SEQ ID NO: 6 and a human light chain variable region comprising consecutively linked amino acids having the sequence set forth in SEQ ID NO: 13; or (g) a human heavy chain variable region comprising consecutively linked amino acids having the sequence set forth in SEQ ID NO: 7 and a human light chain variable region comprising consecutively linked amino acids having the sequence set forth in SEQ ID NO: 14.

Given that each of these Abs can bind to PD-1, the $V_H$ and $V_L$ sequences can be "mixed and matched" to create other anti-PD-1 Abs of the invention. PD-1 binding of such "mixed and matched" Abs can be tested using binding assays, e.g., enzyme-linked immunosorbent assays (ELISAs), western blots, radioimmunoassays and BIACORE® analysis that are well known in the art (see, e.g., U.S. Pat. No. 8,008,449). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence. Accordingly, anti-PD-1 Abs of the invention include an isolated mAb or antigen-binding portion thereof comprising: (a) a heavy chain variable region comprising an amino acid sequence selected from the group consisting of SEQ ID NOs. 1, 2, 3, 4, 5, 6 and 7, and (b) a light chain variable region comprising an amino acid sequence selected from the group consisting of SEQ ID NOs. 8, 9, 10, 11, 12, 13 and 14, wherein the Ab specifically binds PD-1, preferably human PD-1.

The CDR domains of the above Abs have been delineated using the Kabat system, and these Abs may also be defined by combinations of their 3 heavy chain and 3 light chain CDRs (see U.S. Pat. No. 8,008,449). Since each of these Abs can bind to PD-1 and antigen-binding specificity is provided primarily by the CDR1, CDR2, and CDR3 regions, the $V_H$ CDR1, CDR2, and CDR3 sequences and $V_K$ CDR1, CDR2, and CDR3 sequences can be "mixed and matched" (i.e., CDRs from different Abs can be mixed and match, although each Ab must contain a $V_H$ CDR1, CDR2, and CDR3 and a $V_K$ CDR1, CDR2, and CDR3) to create other anti-PD-1 Abs that also constitute Abs of the invention. PD-1 binding of such "mixed and matched" Abs can be tested using the binding assays described above (e.g., ELISAs, western blots, radioimmunoassays and BIACORE® analysis).

Abs of the invention also include isolated Abs that bind specifically to PD-1 and comprise a heavy chain variable region derived from a particular germline heavy chain immunoglobulin and/or a light chain variable region derived from a particular germline light chain immunoglobulin.

Specifically, in certain embodiments, Abs of the invention include isolated Abs comprising: (a) a heavy chain variable region that comprises consecutively linked amino acids having a sequence derived from a human $V_H$ 3-33 or 4-39 germline sequence, and/or a light chain variable region that comprises consecutively linked amino acids having a sequence derived from a human $V_\kappa$ L6, or L15 germline sequence. The amino acid sequences of the $V_H$ and $V_\kappa$ regions encoded by the $V_H$ 3-33, $V_H$ 4-39, $V_\kappa$ L6 and $V_\kappa$ L15 germline genes are provided in U.S. Pat. No. 8,008,449.

As used herein, an Ab can be identified as comprising a heavy or a light chain variable region that is "derived from" a particular human germline immunoglobulin by comparing the amino acid sequence of the human Ab to the amino acid sequences encoded by human germline immunoglobulin genes, and selecting the human germline immunoglobulin sequence that is closest in sequence (i.e., greatest percentage of sequence identity) to the sequence of the human Ab. A human Ab that is "derived from" a particular human germline immunoglobulin may contain amino acid differences as compared to the germline sequence, due to, for example, naturally-occurring somatic mutations or intentional introduction of site-directed mutation. However, a selected human Ab is generally at least 90% identical in amino acids sequence to an amino acid sequence encoded by a human germline immunoglobulin gene and contains amino acid residues that identify the human Ab as being human when compared to the germline immunoglobulin amino acid sequences of other species (e.g., murine germline sequences). In certain cases, a human Ab may be at least 95%, or even at least 96%, 97%, 98%, or 99% identical in amino acid sequence to the amino acid sequence encoded by the germline immunoglobulin gene.

In certain embodiments, the sequence of a human Ab derived from a particular human germline sequence will display no more than 10 amino acid differences from the amino acid sequence encoded by the human germline immunoglobulin gene. In other embodiments, the human Ab may display no more than 5, or even no more than 4, 3, 2, or 1 amino acid differences from the amino acid sequence encoded by the germline immunoglobulin gene.

Preferred Abs of the invention also include isolated Abs or antigen-binding portions thereof comprising: (a) a heavy chain variable region that comprises consecutively linked amino acids having a sequence derived from a human $V_H$ 3-33 germline sequence, and a light chain variable region that comprises consecutively linked amino acids having a sequence derived from a human $V_\kappa$ L6 germline sequence; or (b) a heavy chain variable region that comprises consecutively linked amino acids having a sequence derived from a human $V_H$ 4-39 germline sequence, and a light chain variable region that comprises consecutively linked amino acids having a sequence derived from a human $V_\kappa$ L15 germline sequence. Examples of Abs having a $V_H$ and a $V_\kappa$ derived from $V_H$ 3-33 and $V_\kappa$ L6 germline sequences, respectively, include 17D8, 2D3, 4H1, 5C4, and 7D3. Examples of Abs having $V_H$ and $V_\kappa$ regions derived from $V_H$ 4-39 and $V_\kappa$ L15 germline sequences, respectively, include 4A11 and 5F4.

In yet other embodiments, anti-PD-1 Abs of the invention comprise heavy and light chain variable regions having amino acid sequences that are highly similar or homologous to the amino acid sequences of the preferred anti-PD-1 Abs described herein, wherein the Ab retains the functional properties of the preferred anti-PD-1 Abs of the invention. For example, Abs of the invention include mAbs comprising a heavy chain variable region and a light chain variable region, wherein the heavy chain variable region comprises consecutively linked amino acids having a sequence that is at least 80% identical to an amino acid sequence selected from the group consisting of SEQ ID NOs. 1, 2, 3, 4, 5, 6 and 7, and the light chain variable region comprises consecutively linked amino acids having a sequence that is at least 80% identical to an amino acid sequence selected from the group consisting of SEQ ID NOs. 8, 9, 10, 11, 12, 13 and 14. In other embodiments, the $V_H$ and/or $V_L$ amino acid sequences may exhibit at least 85%, 90%, 95%, 96%, 97%, 98% or 99% identity to the sequences set forth above.

As used herein, the percent sequence identity (also referred to as the percent sequence homology) between two sequences (amino acid or nucleotide sequences) is a function of the number of identical positions shared by the sequences relative to the length of the sequences compared (i.e., % identity=number of identical positions/total number of positions being compared×100), taking into account the number of any gaps, and the length of each such gap, introduced to maximize the degree of sequence identity between the two sequences. The comparison of sequences and determination of percent identity between two sequences can be accomplished using mathematical algorithms that are well know to those of ordinary skill in the art (see, e.g., U.S. Pat. No. 8,008,449).

Antibodies having very similar amino acid sequences are likely to have essentially the same functional properties where the sequence differences are conservative modifications. As used herein, "conservative sequence modifications" refer to amino acid modifications that do not significantly affect the binding characteristics of the Ab containing the amino acid sequence. Such conservative modifications include amino acid substitutions, additions and deletions. Conservative amino acid substitutions are substitutions in which the amino acid residue is replaced with an amino acid residue having a similar side chain. Thus, for example, one or more amino acid residues within the CDR regions of an Ab of the invention can be replaced with other amino acid residues from the same side chain family and the altered Ab can be tested for retained function using functional assays that are well known in the art. Accordingly, certain embodiments of the anti-PD-1 Abs of the invention comprise heavy and light chain variable regions each comprising CDR1, CDR2 and CDR3 domains, wherein one or more of these CDR domains comprise consecutively linked amino acids having sequences that are the same as the CDR sequences of the preferred anti-PD-1 Abs described herein (e.g., 17D8, 2D3, 4H1, 5C4, 4A11, 7D3 or 5F4), or conservative modifications thereof, and wherein the Abs retain the desired functional properties of the preferred anti-PD-1 Abs of the invention.

Further, it is well known in the art that the heavy chain CDR3 is the primary determinant of binding specificity and affinity of an Ab, and that multiple Abs can predictably be generated having the same binding characteristics based on a common CDR3 sequence (see, e.g., Klimka et al., 2000; Beiboer et al., 2000; Rader et al., 1998; Barbas et al., 1994; Barbas et al., 1995; Ditzel et al., 1996; Berezov et al., 2001; Igarashi et al., 1995; Bourgeois et al., 1998; Levi et al., 1993; Polymenis et al., 1994; and Xu et al., 2000). The foregoing publications demonstrate that, in general, once the heavy chain CDR3 sequence of a given Ab is defined, variability in the other five CDR sequences will not greatly affect the binding specificity of that Ab. Thus, Abs of the invention comprising 6 CDRs can be defined by specifying the sequence of the heavy chain CDR3 domain.

Anti-PD-1 Abs of the invention also include isolated Abs that bind specifically to human PD-1 and cross-compete for binding to human PD-1 with any of HuMAbs 17D8, 2D3, 4H1, 5C4, 4A11, 7D3 and 5F4. Thus, anti-PD-1 Abs of the invention include isolated Abs or antigen-binding portions thereof that cross-compete for binding to PD-1 with a reference Ab or a reference antigen-binding portion thereof comprising: (a) a human heavy chain variable region comprising consecutively linked amino acids having the sequence set forth in SEQ ID NO: 1 and a human light chain variable region comprising consecutively linked amino acids having the sequence set forth in SEQ ID NO: 8; (b) a human heavy chain variable region comprising consecutively linked amino acids having the sequence set forth in SEQ ID NO: 2 and a human light chain variable region comprising consecutively linked amino acids having the sequence set forth in SEQ ID NO: 9; (c) a human heavy chain variable region comprising consecutively linked amino acids having the sequence set forth in SEQ ID NO: 3 and a human light chain variable region comprising consecutively linked amino acids having the sequence set forth in SEQ ID NO: 10; (d) a human heavy chain variable region comprising consecutively linked amino acids having the sequence set forth in SEQ ID NO: 4 and a human light chain variable region comprising consecutively linked amino acids having the sequence set forth in SEQ ID NO: 11; (e) a human heavy chain variable region comprising consecutively linked amino acids having the sequence set forth in SEQ ID NO: 5 and a human light chain variable region comprising consecutively linked amino acids having the sequence set forth in SEQ ID NO: 12; (f) a human heavy chain variable region comprising consecutively linked amino acids having the sequence set forth in SEQ ID NO: 6 and a human light chain variable region comprising consecutively linked amino acids having the sequence set forth in SEQ ID NO: 13; or (g) a human heavy chain variable region comprising consecutively linked amino acids having the sequence set forth in SEQ ID NO: 7 and a human light chain variable region comprising consecutively linked amino acids having the sequence set forth in SEO ID NO: 14.

Figure 1B:
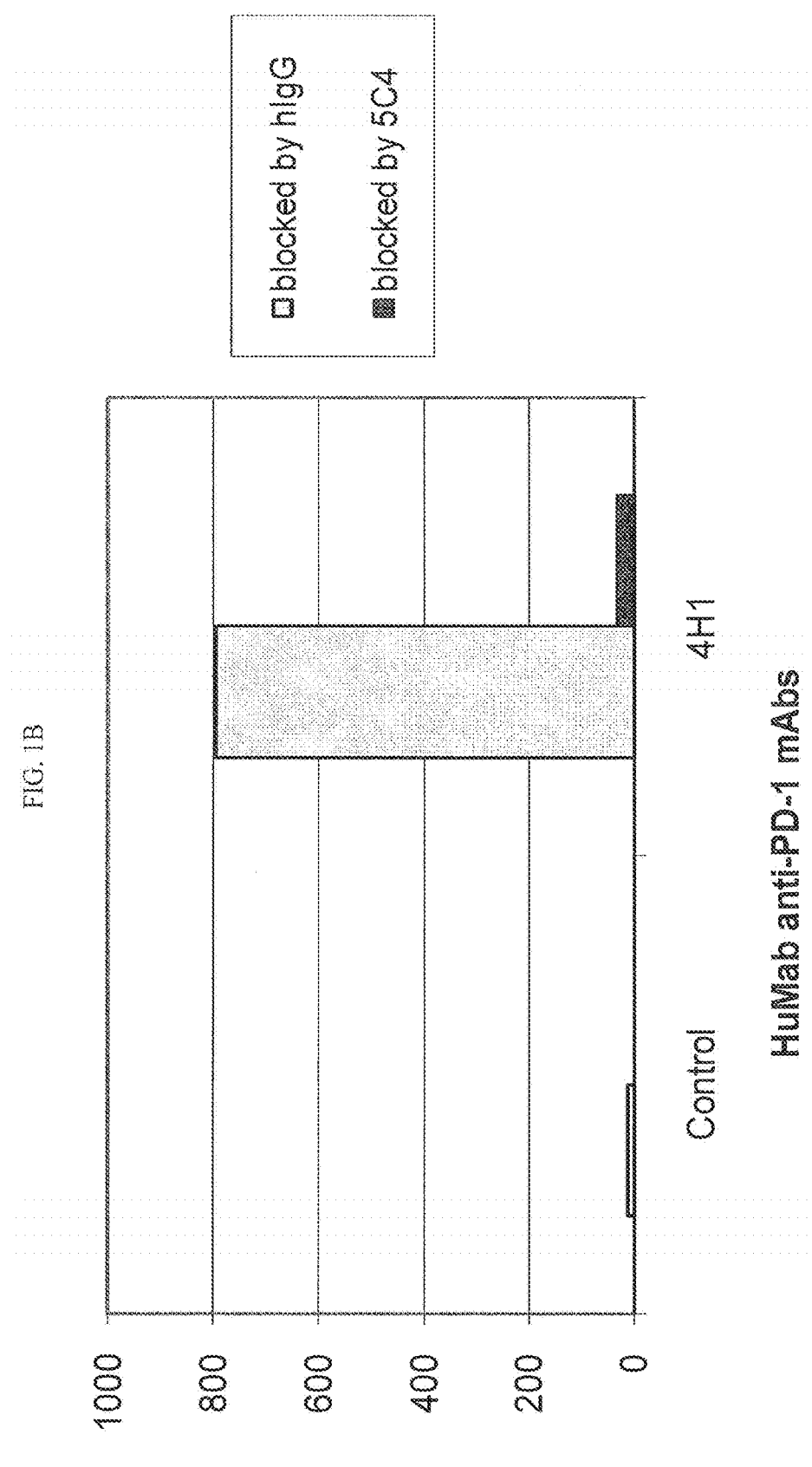
Figure 1C:
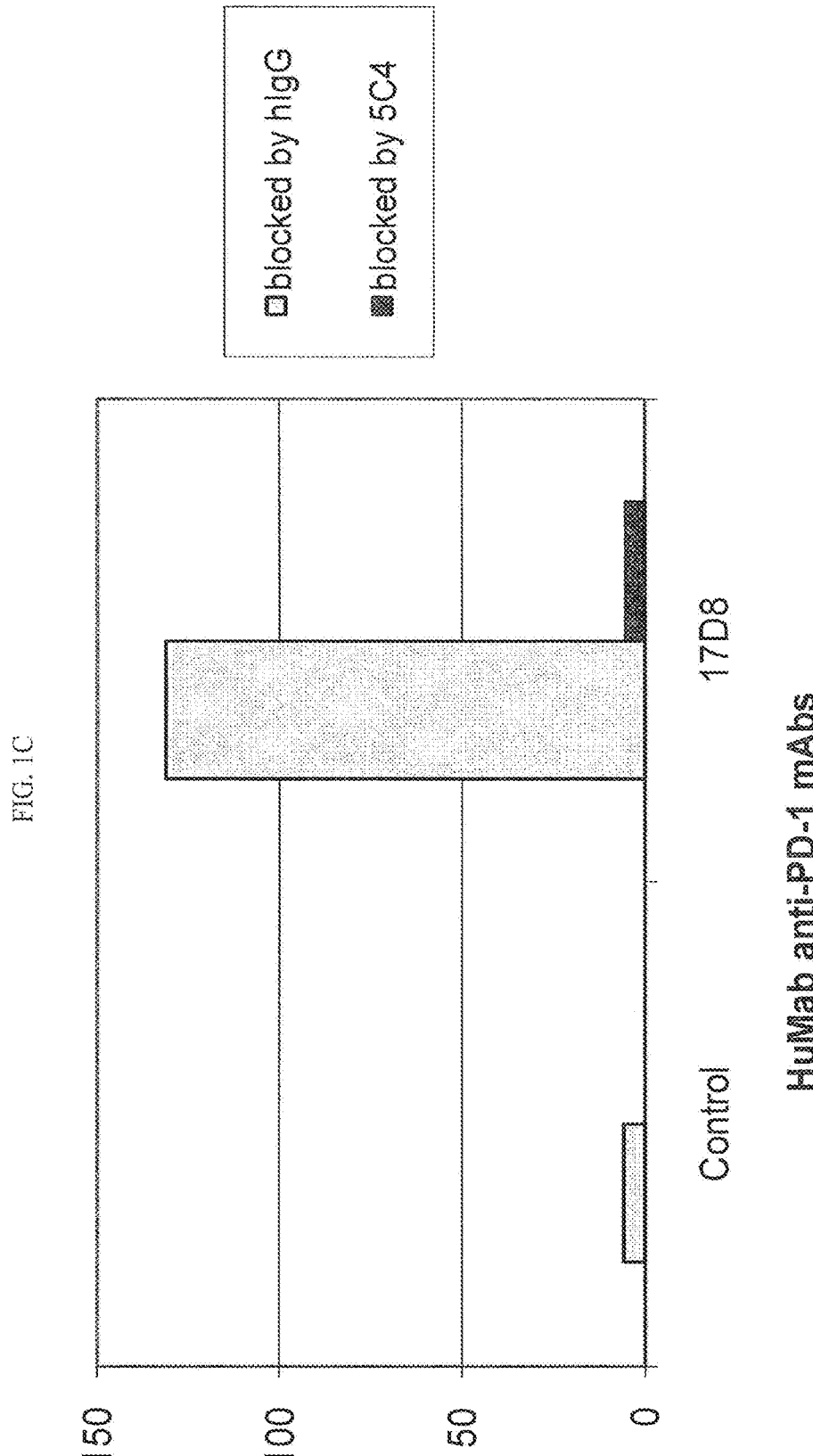
Figure 2B:
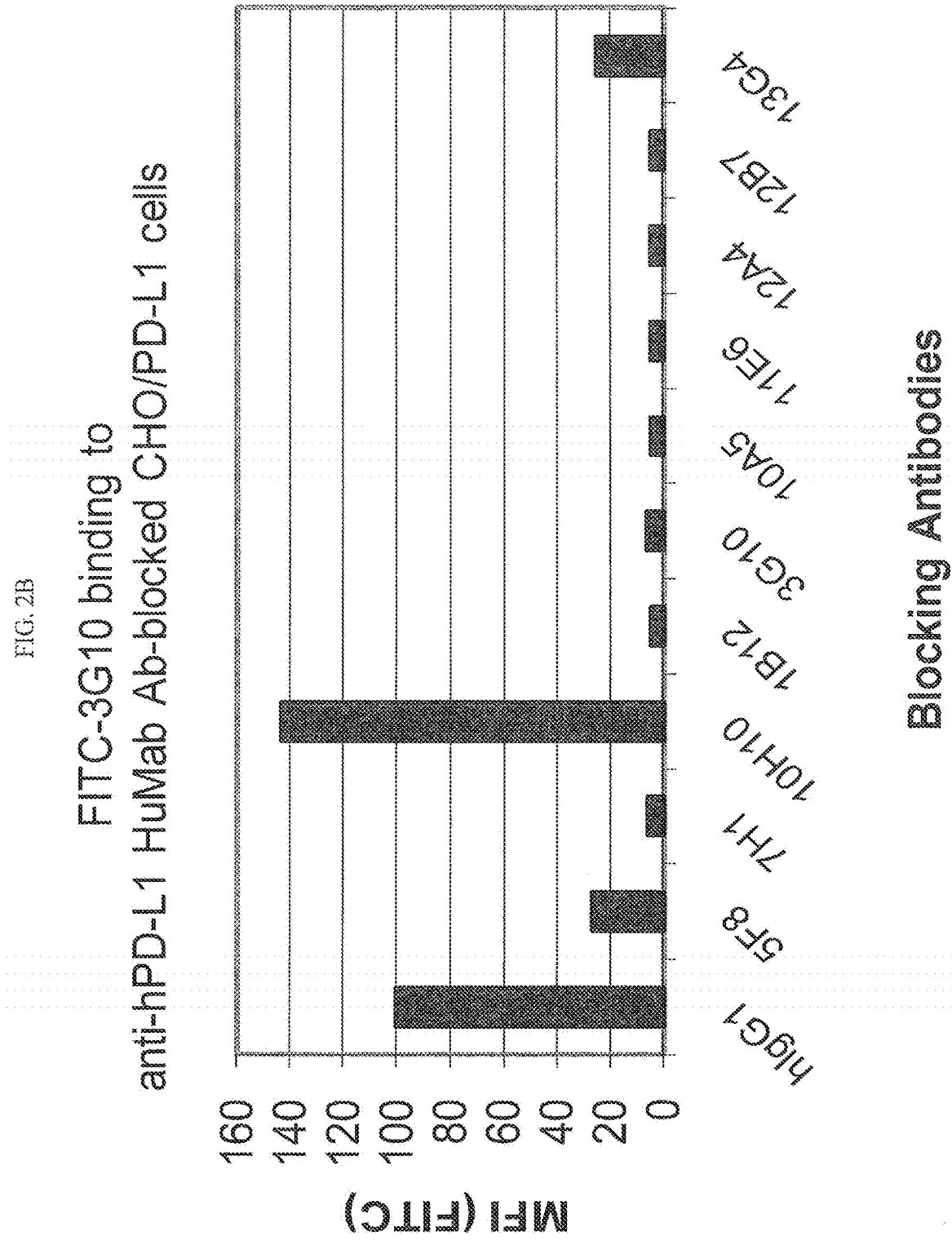
Figure 2C:
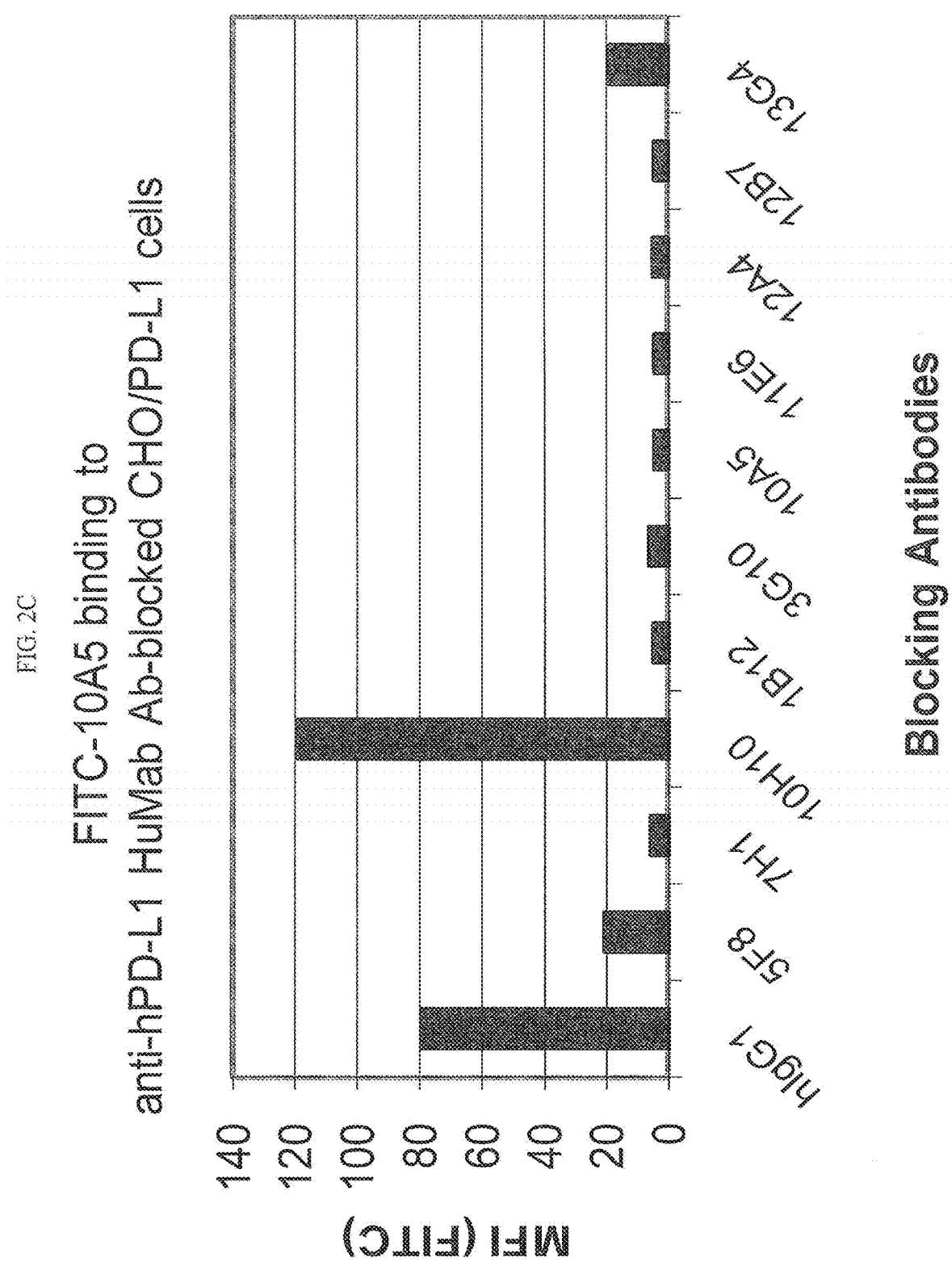
Figure 2D:
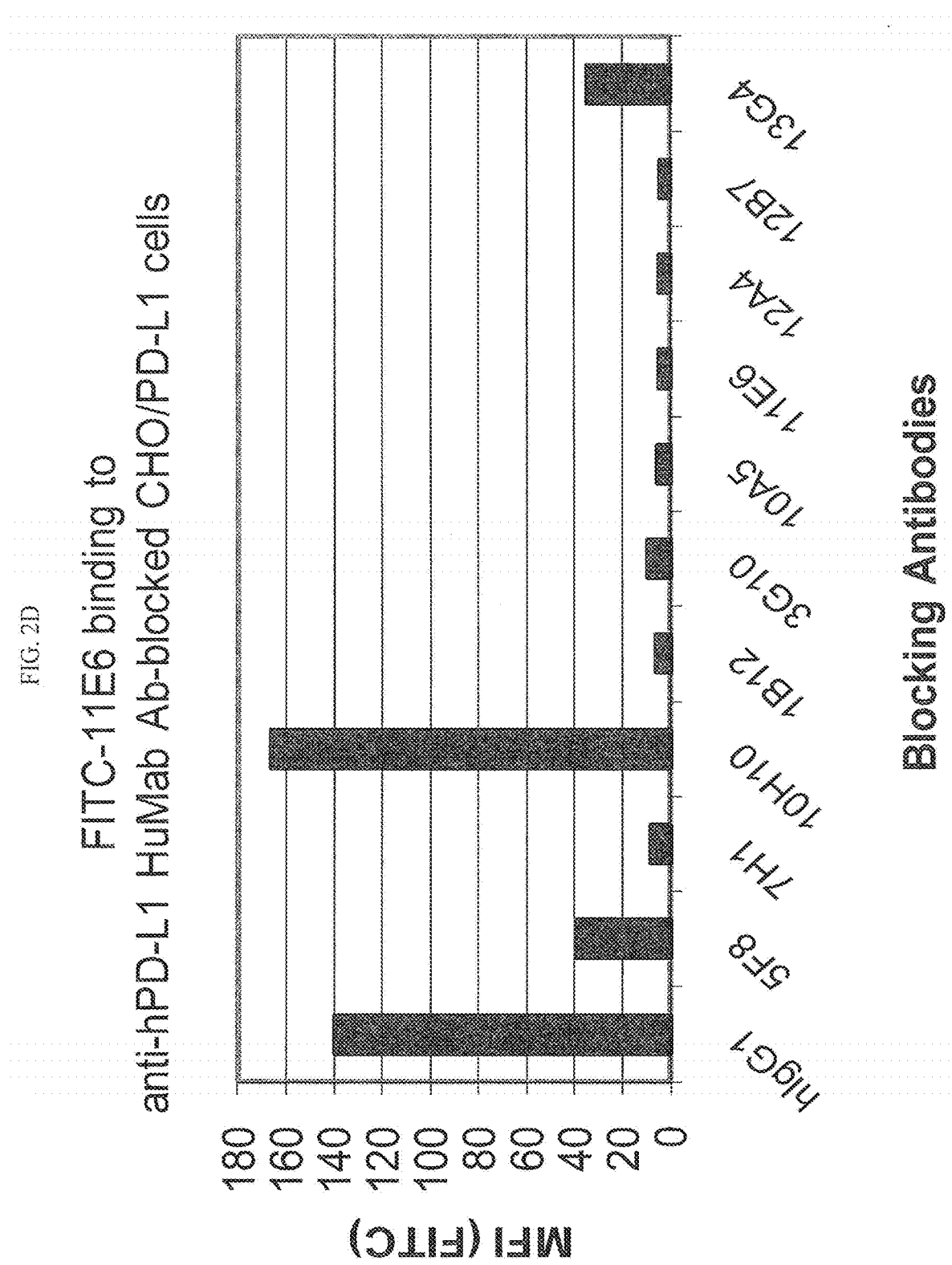
Figure 2E:
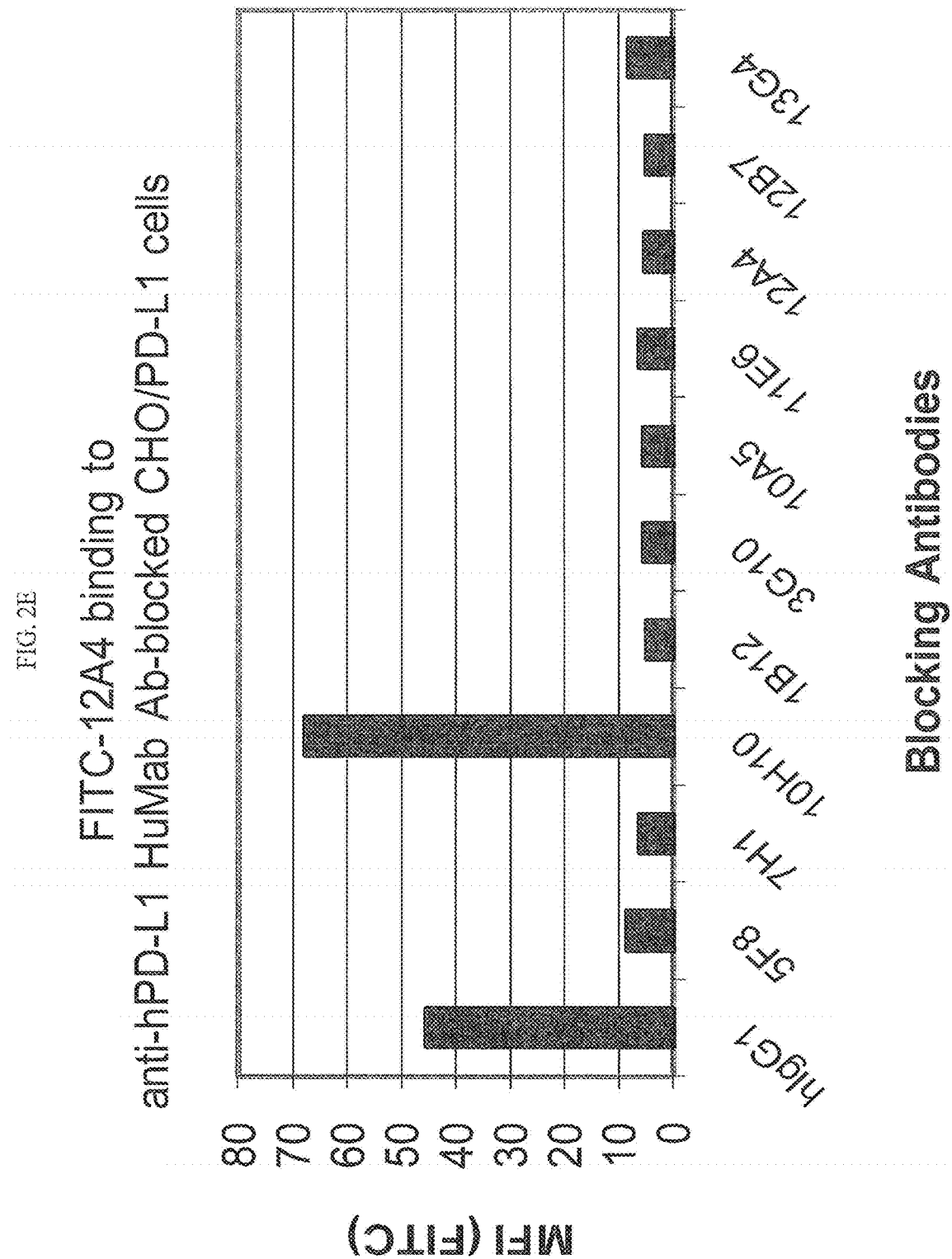

The ability of Abs to cross-compete for binding to an antigen indicates that these Abs bind to the same epitope region (i.e., the same or an overlapping epitope) of the antigen and sterically hinder the binding of other cross-competing Abs to that particular epitope region. Thus, the ability of a test Ab to competitively inhibit the binding of, for example, 17D8, 2D3, 4H1, 5C4, 4A11, 7D3 or 5F4, to human PD-1 demonstrates that the test Ab binds to the same epitope region of human PD-1 as 17D8, 2D3, 4H1, 5C4, 4A11, 7D3 or 5F4, respectively. All isolated Abs that bind to the same epitope region of human PD-1 as does HuMAb 17D8, 2D3, 4H1, 5C4, 4A11, 7D3 or 5F4 are included among the Abs of the invention. These cross-competing Abs are expected to have very similar functional properties by virtue of their binding to the same epitope region of PD-1. For example, cross-competing anti-PD-1 mAbs 5C4, 2D3, 7D3, 4H1 and 17D8 have been shown to have similar functional properties (see U.S. Pat. No. 8,008,449 at Examples 3-7). The higher the degree of cross-competition, the more similar will the functional properties be. Further, cross-competing Abs can be readily identified based on their ability to cross-compete with 17D8, 2D3, 4H1, 5C4, 4A11, 7D3 or 5F4 in standard PD-1 binding assays. For example, BIACORE® analysis, ELISA assays or flow cytometry may be used to demonstrate cross-competition with the Abs of the invention (see, e.g., Examples 1 and 2). In preferred embodiments, the Abs that cross-compete for binding to human PD-1 with, or bind to the same epitope region of human PD-1 as, 17D8, 2D3, 4H1, 5C4, 4A11, 7D3 or 5F4 are mAbs, preferably chimeric Abs, or more preferably humanized or human Abs. Such human mAbs can be prepared and isolated as described in U.S. Pat. No. 8,008,449. Data provided in Example 1 show that 5C4 or a Fab fragment thereof cross-competes with each of 2D3, 7D3, 4H1 or 17D8 for binding to hPD-1 expressed on the surface of a cell, indicating that all five anti-PD-1 mAbs bind to the same epitope region of hPD-1 (FIGS. 1A-1C).

An anti-PD-1 Ab of the invention further can be prepared using an Ab having one or more of the $V_H$ and/or $V_L$ sequences disclosed herein as starting material to engineer a modified Ab, which modified Ab may have altered properties from the starting Ab. An Ab can be engineered by modifying one or more residues within one or both variable regions (i.e., $V_H$ and/or $V_L$), for example within one or more CDR regions and/or within one or more framework regions. Additionally or alternatively, an Ab can be engineered by modifying residues within the constant region(s), for example, to alter the effector function(s) of the Ab. Specific modifications to Abs include CDR grafting, site-specific mutation of amino acid residues within the $V_H$ and/or $V_\kappa$ CDR1, CDR2 and/or CDR3 regions to thereby improve one or more binding properties (e.g., affinity) of the Ab, site-specific mutation of amino acid residues within the $V_H$ and/or $V_\kappa$ framework regions to decrease the immunogenicity of the Ab, modifications within the Fc region, typically to alter one or more functional properties of the Ab, such as serum half-life, complement fixation, Fc receptor binding, and/or antigen-dependent cellular cytotoxicity, and chemical modification such as pegylation or alteration in glycosylation patterns to increase or decrease the biological (e.g., serum) half life of the Ab. Specific examples of such modifications and methods of engineering Abs are described in detail in U.S. Pat. No. 8,008,449. Anti-PD-1 Abs of the invention include all such engineered Abs that bind specifically to human PD-1 and are obtained by modification of any of the above-described anti-PD-1 Abs.

Anti-PD-1 Abs of the invention also include antigen-binding portions of the above Abs. It has been amply demonstrated that the antigen-binding function of an Ab can be performed by fragments of a full-length Ab. Examples of binding fragments encompassed within the term "antigen-binding portion" of an Ab include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an Ab.

These fragments, obtained initially through proteolysis with enzymes such as papain and pepsin, have been subsequently engineered into monovalent and multivalent antigen-binding fragments. For example, although the two domains of the Fv fragment, $V_L$ and $V_H$, are coded for by separate genes, they can be joined, using recombinant methods, by a synthetic linker peptide that enables them to be made as a single protein chain in which the $V_L$ and $V_H$ regions pair to form monovalent molecules known as single chain variable fragments (scFv). Divalent or bivalent scFvs (di-scFvs or bi-scFvs) can be engineered by linking two scFvs in within a single peptide chain known as a tandem scFv which contains two $V_H$ and two $V_L$ regions. ScFv dimers and higher multimers can also be created using linker peptides of fewer than 10 amino acids that are too short for the two variable regions to fold together, which forces the scFvs to dimerize and produce diabodies or form other multimers. Diabodies have been shown to bind to their cognate antigen with much higher affinity than the corresponding scFvs, having dissociation constants up to 40-fold lower than the $K_D$ values for the scFvs. Very short linkers (≤3 amino acids) lead to the formation of trivalent triabodies or tetravalent tetrabodies that exhibit even higher affinities for to their antigens than diabodies. Other variants include minibodies, which are scFv-$C_{H3}$ dimers, and larger scFv-Fc fragments (scFv-$C_{H2}$-$C_{H3}$ dimers), and even an isolated CDR may exhibit antigen-binding function. These Ab fragments are engineered using conventional recombinant techniques known to those of skill in the art, and the fragments are screened for utility in the same manner as are intact Abs. All of the above proteolytic and engineered fragments of Abs and related variants (see Hollinger et al., 2005; Olafsen et al., 2010, for further details) are intended to be encompassed within the term "antigen-binding portion" of an Ab.

Anti-PD-L1 Antibodies of the Invention

Each of the anti-PD-L1 HuMAbs disclosed in U.S. Pat. No. 7,943,743 has been demonstrated to exhibit one or more of the following characteristics (a) binds to human PD-L1 with a $K_D$ of $1\times10^{-7}$ M or less; (b) increases T-cell proliferation in a Mixed Lymphocyte Reaction (MLR) assay; (c) increase interferon-7 production in an MLR assay; (d) increase IL-2 secretion in an MLR assay; (e) stimulates Ab responses; (f) inhibits the binding of PD-L1 to PD-1; and (g) reverses the suppressive effect of T regulatory cells on T cell effector cells and/or dendritic cells. Anti-PD-L1 Abs of the present invention include mAbs that bind specifically to human PD-L1 and exhibit at least one, preferably at least four, of the preceding characteristics.

U.S. Pat. No. 7,943,743 exemplifies ten anti-PD-1 HuMAbs: 3G10, 12A4 (also referred to herein as BMS-936559), 10A5, 5F8, 10H10, 1B12, 7H1, 11E6, 12B7, and 13G4. Isolated DNA molecules encoding the heavy and light chain variable regions of these Abs have been sequenced, from which the amino acid sequences of the variable regions were deduced. The $V_H$ amino acid sequences of 3G10, 12A4, 10A5, 5F8, 10H10, 1B12, 7H1, 11E6, 12B7, and 13G4 are shown in SEQ ID NOs. 15, 16, 17, 18, 19, 20, 21, 22, 23 and 24, respectively, whereas their $V_L$ amino acid sequences are shown in SEQ ID NOs. 25, 26, 27, 28, 29, 30, 31, 32, 33 and 34, respectively.

Preferred anti-PD-L1 Abs of the present invention include the anti-PD-L1 HuMAbs 3G10, 12A4, 10A5, 5F8, 10H10, 1B12, 7H1, 11E6, 12B7, and 13G4. These preferred Abs bind specifically to human PD-L1 and comprise: (a) a human heavy chain variable region comprising consecutively linked amino acids having the sequence set forth in SEQ ID NO: 15 and a human light chain variable region comprising consecutively linked amino acids having the sequence set forth in SEQ ID NO: 25; (b) a human heavy chain variable region comprising consecutively linked amino acids having the sequence set forth in SEQ ID NO: 16 and a human light chain variable region comprising consecutively linked amino acids having the sequence set forth in SEQ ID NO: 26; (c) a human heavy chain variable region comprising consecutively linked amino acids having the sequence set forth in SEQ ID NO: 17 and a human light chain variable region comprising consecutively linked amino acids having the sequence set forth in SEQ ID NO: 27; (d) a human heavy chain variable region comprising consecutively linked amino acids having the sequence set forth in SEQ ID NO: 18 and a human light chain variable region comprising consecutively linked amino acids having the sequence set forth in SEQ ID NO: 28; (e) a human heavy chain variable region comprising consecutively linked amino acids having the sequence set forth in SEQ ID NO: 19 and a human light chain variable region comprising consecutively linked amino acids having the sequence set forth in SEQ ID NO: 29; (f) a human heavy chain variable region comprising consecutively linked amino acids having the sequence set forth in SEQ ID NO: 20 and a human light chain variable region comprising consecutively linked amino acids having the sequence set forth in SEQ ID NO: 30; (g) a human heavy chain variable region comprising consecutively linked amino acids having the sequence set forth in SEQ ID NO: 21 and a human light chain variable region comprising consecutively linked amino acids having the sequence set forth in SEQ ID NO: 31; (h) a human heavy chain variable region comprising consecutively linked amino acids having the sequence set forth in SEQ ID NO: 22 and a human light chain variable region comprising consecutively linked amino acids having the sequence set forth in SEQ ID NO: 32; (i) a human heavy chain variable region comprising consecutively linked amino acids having the sequence set forth in SEQ ID NO: 23 and a human light chain variable region comprising consecutively linked amino acids having the sequence set forth in SEO ID NO: 33; or (j) a human heavy chain variable region comprising consecutively linked amino acids having the sequence set forth in SEQ ID NO: 24 and a human light chain variable region comprising consecutively linked amino acids having the sequence set forth in SEQ ID NO: 34.

Given that each of these Abs can bind to PD-L1, the $V_H$ and $V_L$ sequences can be "mixed and matched" to create other anti-PD-L1 Abs of the invention. PD-L1 binding of such "mixed and matched" Abs can be tested using binding assays e.g., ELISAs, western blots, radioimmunoassays and BIACORE® analysis that are well known in the art (see, e.g., U.S. Pat. No. 7,943,743). Preferably, when $V_H$ and $V_L$ chains are mixed and matched, a $V_H$ sequence from a particular $V_H$/$V_L$ pairing is replaced with a structurally similar $V_H$ sequence. Likewise, preferably a $V_L$ sequence from a particular $V_H$/$N_L$ pairing is replaced with a structurally similar $V_L$ sequence. Accordingly, Abs of the invention also include a mAb, or antigen binding portion thereof, comprising a heavy chain variable region comprising consecutively linked amino acids having the sequence set forth in any of SEQ ID NOs. 15, 16, 17, 18, 19, 20, 21, 22, 23 or 24, and a light chain variable region comprising consecutively linked amino acids having the sequence set forth in any of SEQ ID NOs. 25, 26, 27, 28, 29, 30, 31, 32, 33 or 34, wherein the Ab binds specifically to PD-L1, preferably human PD-L1.

The CDR domains of the above anti-PD-L1 HuMAbs have been delineated using the Kabat system, and these Abs may also be defined by combinations of their 3 heavy chain and 3 light chain CDRs (see U.S. Pat. No. 7,943,743). Since each of these Abs can bind to PD-L1 and antigen-binding specificity is provided primarily by the CDR1, CDR2, and CDR3 regions, the $V_H$ CDR1, CDR2, and CDR3 sequences and $V_κ$ CDR1, CDR2, and CDR3 sequences can be "mixed and matched" (i.e., CDRs from different Abs can be mixed and match, although each Ab must contain a $V_H$ CDR1, CDR2, and CDR3 and a $V_κ$ CDR1, CDR2, and CDR3) to create other anti-PD-1 Abs that also constitute Abs of the invention. PD-L1 binding of such "mixed and matched" Abs can be tested using, for example, ELISAs, western blots, radioimmunoassays and BIACORE® analysis.

Antibodies of the invention also include Abs that bind specifically to PD-L1 and comprise a heavy chain variable region derived from a particular germline heavy chain immunoglobulin and/or a light chain variable region derived from a particular germline light chain immunoglobulin. Specifically, in certain embodiments, Abs of the invention include Abs comprising: (a) a heavy chain variable region that comprises consecutively linked amino acids having a sequence derived from a human $V_H$ 1-18, 1-69, 1-3 or 3-9 germline sequence, and/or a light chain variable region that comprises consecutively linked amino acids having a sequence derived from a human $V_\kappa$ L6, L15, A27 or L18 germline sequence. The amino acid sequences of the $V_H$ and $V_\kappa$ regions encoded by the $V_H$ 1-18, $V_H$ 1-3, $V_H$ 1-69, $V_H$ 3-9, $V_\kappa$ L6, $V_\kappa$ L15 and $V_\kappa$ A27 germline genes are provided in U.S. Pat. No. 7,943,743.

Preferred Abs of the invention include isolated Abs or antigen-binding portions thereof comprising: (a) a heavy chain variable region that comprises consecutively linked amino acids having a sequence derived from a human $V_H$ 1-18 germline sequence, and a light chain variable region that comprises consecutively linked amino acids having a sequence derived from a human $V_\kappa$ L6 germline sequence; (b) a heavy chain variable region that comprises consecutively linked amino acids having a sequence derived from a human $V_H$ 1-69 germline sequence, and a light chain variable region that comprises consecutively linked amino acids having a sequence derived from a human $V_\kappa$ L6 germline sequence; (c) a heavy chain variable region that comprises consecutively linked amino acids having a sequence derived from a human $V_H$ 1-3 germline sequence, and a light chain variable region that comprises consecutively linked amino acids having a sequence derived from a human $V_\kappa$ L15 germline sequence; (d) a heavy chain variable region that comprises consecutively linked amino acids having a sequence derived from a human $V_H$ 1-69 germline sequence, and a light chain variable region that comprises consecutively linked amino acids having a sequence derived from a human $V_\kappa$ A27 germline sequence; (e) a heavy chain variable region that comprises consecutively linked amino acids having a sequence derived from a human $V_H$ 3-9 germline sequence, and a light chain variable region that comprises consecutively linked amino acids having a sequence derived from a human $V_\kappa$ L15 germline sequence; or (f) a heavy chain variable region that comprises consecutively linked amino acids having a sequence derived from a human $V_H$ 3-9 germline sequence, and a light chain variable region that comprises consecutively linked amino acids having a sequence derived from a human $V_\kappa$ L18 germline sequence.

An example of an Ab having a $V_H$ and a $V_\kappa$ derived from $V_H$ 1-18 and $V_\kappa$ L6 germline sequences, respectively, is 3G10. Examples of Abs having $V_H$ and $V_\kappa$ regions derived from $V_H$ 1-69 and $V_\kappa$ L6 germline sequences, respectively, include 12A4, 1B12, 7H1 and 12B7. An example of an Ab having a $V_H$ and a $V_\kappa$ derived from $V_H$ 1-3 and $V_\kappa$ L15 germline sequences, respectively, is 10A5. Examples of Abs having $V_H$ and $V_\kappa$ regions derived from $V_H$ 1-69 and $V_\kappa$ A27 germline sequences, respectively, include 5F8, 11E6 and 11E6a. An example of an Ab having a $V_H$ and a $V_K$ derived from $V_H$ 3-9 and $V_\kappa$ L15 germline sequences, respectively, is 10H10. An example of an Ab having a $V_H$ and a $V_\kappa$ derived from $V_H$ 1-3 and $V_\kappa$ L15 germline sequences, respectively, is 10A5. An example of an Ab having a $V_H$ and a $V_\kappa$ derived from $V_H$ 3-9 and $V_\kappa$ L18 germline sequences, respectively, is 13G4.

In certain embodiments, anti-PD-L1 Abs of the invention comprise heavy and light chain variable regions having amino acid sequences that are highly similar or homologous to the amino acid sequences of the preferred anti-PD-L1 Abs described herein, wherein the Ab retains the functional properties of the aforementioned anti-PD-L1 Abs of the invention. For example, Abs of the invention include mAbs comprising a heavy chain variable region and a light chain variable region, wherein the heavy chain variable region comprises consecutively linked amino acids having a sequence that is at least 80% identical to an amino acid sequence selected from the group consisting of SEQ ID NOs. 15, 16, 17, 18, 19, 20, 21, 22, 23, and 24, and the light chain variable region comprises consecutively linked amino acids having a sequence that is at least 80% identical to an amino acid sequence selected from the group consisting of SEQ ID NOs. 25, 26, 27, 28, 29, 30, 31, 32, 33, and 34. In other embodiments, the $V_H$ and/or $V_L$ amino acid sequences may exhibit at least 85%, 90%, 95%, 96%, 97%, 98% or 99% identity to the sequences set forth above.

Certain embodiments of the anti-PD-L1 Abs of the invention comprise heavy and light chain variable regions each comprising CDR1, CDR2 and CDR3 domains, wherein one or more of these CDR domains comprise consecutively linked amino acids having sequences that are the same as the CDR sequences of the preferred anti-PD-L1 Abs described herein (e.g., 3G10, 12A4, 10A5, 5F8, 10H10, 1B12, 7H1, 11E6, 12B7 and 13G4), or conservative modifications thereof, and wherein the Abs retain the desired functional properties of the preferred anti-PD-L1 Abs of the invention.

On the basis of the evidence that the heavy chain CDR3 is the primary determinant of binding specificity and affinity of an Ab, it is generally true that once the heavy chain CDR3 sequence of a given Ab is defined, variability in the other five CDR sequences does not greatly affect the binding specificity of that Ab. Accordingly, anti-PD-L1 Abs of the invention include isolated Abs comprising 6 CDRs, wherein the Abs are defined by specifying the sequence of the heavy chain CDR3 domain.

Anti-PD-L1 Abs of the invention also include isolated Abs that bind specifically to human PD-L1 and cross-compete for binding to human PD-L1 with any of HuMAbs 3G10, 12A4, 10A5, 5F8, 10H10, 1B12, 7H1, 11E6, 12B7 and 13G4. Thus, anti-PD-L1 Abs of the invention include isolated Abs or antigen-binding portions thereof that cross-compete for binding to PD-L1 with a reference Ab or a reference antigen-binding portion thereof comprising: (a) a human heavy chain variable region comprising consecutively linked amino acids having the sequence set forth in SEQ ID NO: 15 and a human light chain variable region comprising consecutively linked amino acids having the sequence set forth in SEQ ID NO: 25; (b) a human heavy chain variable region comprising consecutively linked amino acids having the sequence set forth in SEQ ID NO: 16 and a human light chain variable region comprising consecutively linked amino acids having the sequence set forth in SEQ ID NO: 26; (c) a human heavy chain variable region comprising consecutively linked amino acids having the sequence set forth in SEQ ID NO: 17 and a human light chain variable region comprising consecutively linked amino acids having the sequence set forth in SEQ ID NO: 27; (d) a human heavy chain variable region comprising consecutively linked amino acids having the sequence set forth in SEQ ID NO: 18 and a human light chain variable region comprising consecutively linked amino acids having the sequence set forth in SEQ ID NO: 28; (e) a human heavy chain variable region comprising consecutively linked amino acids having the sequence set forth in SEQ ID NO: 19 and a human light chain variable region comprising consecutively linked amino acids having the sequence set forth in SEQ ID NO: 29; (f) a human heavy chain variable region comprising consecutively linked amino acids having the sequence set forth in SEQ ID NO: 20 and a human light chain variable region comprising consecutively linked amino acids having the sequence set forth in SEQ ID NO: 30; (g) a human heavy chain variable region comprising consecutively linked amino acids having the sequence set forth in SEQ ID NO: 21 and a human light chain variable region comprising consecutively linked amino acids having the sequence set forth in SEQ ID NO: 31; (h) a human heavy chain variable region comprising consecutively linked amino acids having the sequence set forth in SEQ ID NO: 22 and a human light chain variable region comprising consecutively linked amino acids having the sequence set forth in SEQ ID NO: 32; (i) a human heavy chain variable region comprising consecutively linked amino acids having the sequence set forth in SEQ ID NO: 23 and a human light chain variable region comprising consecutively linked amino acids having the sequence set forth in SEQ ID NO: 33; or (j) a human heavy chain variable region comprising consecutively linked amino acids having the sequence set forth in SEQ ID NO: 24 and a human light chain variable region comprising consecutively linked amino acids having the sequence set forth in SEQ ID NO: 34.

The ability of an Ab to cross-compete with any of 3G10, 12A4, 10A5, 5F8, 10H10, 1B12, 7H1, 11E6, 12B7 and 13G4 for binding to human PD-L1 demonstrates that such Ab binds to the same epitope region of each of 3G10, 12A4, 10A5, 5F8, 10H10, 1B12, 7H1, 11E6, 12B7 and 13G4, respectively. All isolated Abs that bind to the same epitope region of human PD-L1 as does HuMAb 3G10, 12A4, 10A5, 5F8, 10H10, 1B12, 7H1, 11E6, 12B7 or 13G4 are included among the Abs of the invention. These cross-competing Abs are expected to have very similar functional properties by virtue of their binding to the same epitope region of PD-L1. For example, cross-competing anti-PD-L1 mAbs 3G10, 1B12, 13G4, 12A4 (BMS-936559), 10A5, 12B7, 11E6 and 5F8 have been shown to have similar functional properties (see U.S. Pat. No. 7,943,743 at Examples 3-11), whereas mAb 10H10, which binds to a different epitope region, behaves differently (U.S. Pat. No. 7,943,743 at Example 11). The higher the degree of cross-competition, the more similar will the functional properties be. Further, cross-competing Abs can be identified in standard PD-L1 binding assays, e.g., BIACORE® analysis, ELISA assays or flow cytometry, that are well known to persons skilled in the art. In preferred embodiments, the Abs that cross-compete for binding to human PD-1 with, or bind to the same epitope region of human PD-L1 as, 3G10, 12A4, 10A5, 5F8, 10H10, 1B12, 7H1, 11E6, 12B7 or 13G4 are mAbs, preferably chimeric Abs, or more preferably humanized or human Abs. Such human mAbs can be prepared and isolated as described in U.S. Pat. No. 7,943,743.

Data provided in Example 2 show that each of the anti-PD-L1 HuMAbs 5F8, 7H1, 1B12, 3G10, 10A5, 11E6, 12A4, 12B7 and 13G4, i.e., all of the HuMAbs tested except 10H10, substantially blocked binding of mAbs 3G10, 10A5, 11E6, 12A4 and 13G4 to Chinese Hamster Ovary (CHO) cells expressing PD-L1 cells. HuMAb 10H10 substantially blocked the binding only of itself to CHO/PD-L1 cells. These data show that 3G10, 10A5, 11E6, 12A4 and 13G4 cross-compete with all of the HuMAbs tested, except for 10H10, for binding to the same epitope region of human PD-L1 (FIGS. 2A-F).

Data provided in Example 3 show that the binding of HuMAb 12A4 to ES-2 ovarian carcinoma cells expressing PD-L1 cells was substantially blocked by 12A4 itself and by 1B12 and 12B7, and was moderately to significantly blocked by mAbs 5F8, 10A5, 13G4 and 3G10, but was not blocked by mAb 10H10. These data, largely consistent with the data in Example 2, show that 12A4 itself, and 2 other HuMabs, 12B7 and 1B12, substantially cross-compete with 12A4 for binding to the same epitope region, possibly the same epitope, of human PD-L1; 5F8, 10A5, 13G4 and 3G10, exhibit a significant but lower level of cross-competition with 12A4, suggesting that these mAbs may bind to epitopes that overlap the 12A4 epitope; whereas 10H10 does not cross-compete at all with 12A4 (FIG. 3), suggesting that this mAb binds to a different epitope region from 12A4.

Anti-PD-L1 Abs of the invention also include Abs engineered starting from Abs having one or more of the $V_H$ and/or $V_L$ sequences disclosed herein, which engineered Abs may have altered properties from the starting Abs. An anti-PD-L1 Ab can be engineered by a variety of modifications as described above for the engineering of modified anti-PD-1 Abs of the invention.

Anti-PD-L1 Abs of the invention also include isolated Abs selected for their ability to bind to PD-L1 in formalin-fixed, paraffin-embedded (FFPE) tissue specimens. The use of FFPE samples is essential for the long-term follow-up analysis of the correlation between PD-L1 expression in tumors and disease prognosis or progression. Yet, studies on measuring PD-L1 expression have often been conducted on frozen specimens because of the difficulty in isolating anti-human PD-L1 Abs that can be used to stain PD-L1 in FFPE specimens by IHC in general (Hamanishi et al., 2007) and, in particular, Abs that bind specifically to membranous PD-L1 in these tissues. The use of different Abs to stain PD-L1 in frozen versus FFPE tissues, and the ability of certain Abs to distinguish membranous and/or cytoplasmic forms of PD-L1, may account for some of the disparate data reported in the literature correlating PD-L1 expression with disease prognosis (Hamanishi et al., 2007; Gadiot et al., 2011). This disclosure provides several rabbit mAbs that bind with high affinity specifically to membranous human PD-L1 in FFPE tissue samples comprising tumor cells and tumor-infiltrating inflammatory cells.

Rabbit and mouse anti-hPD-L1 mAbs were produced as described in the Examples. Out of almost 200 rabbit Ab multiclones and purified mouse subclones screened, only ten rabbit multiclone Abs were found to specifically detect the membranous form of PD-L1, and the top five multiclones (designated Nos. 13, 20, 28, 29 and 49) were subsequently subcloned. The clone that produced the most robust detection specifically of membranous PD-L1, rabbit clone 28-8, was selected for the IHC assays. The sequences of the variable regions of mAb 28-8 are set forth in SEQ ID NOs. 35 and 36, respectively. Rabbit clones 28-1, 28-12, 29-8 and 20-12 were the next best mAbs in terms of robust detection of membranous PD-L1 in FFPE tissues.

Anti-PD-L1 Abs of the invention also include antigen-binding portions of the above Abs, including Fab, F(ab')₂ Fd, Fv, and scFv, di-scFv or bi-scFv, and scFv-Fc fragments, diabodies, triabodies, tetrabodies, and isolated CDRs (see Hollinger et al., 2005; Olafsen et al., 2010, for further details).

Nucleic Acid Molecules Encoding Antibodies of the Invention

Another aspect of the present disclosure pertains to isolated nucleic acid molecules that encode any of the Abs of the invention. These nucleic acids may be present in whole cells, in a cell lysate, or in a partially purified or substantially pure form. A nucleic acid of the invention can be, for example, DNA or RNA, and may or may not contain intronic sequences. In a preferred embodiment, the nucleic acid is a cDNA.

Nucleic acids of the invention can be obtained using standard molecular biology techniques. For Abs expressed by hybridomas (e.g., hybridomas prepared from transgenic mice carrying human immunoglobulin genes as described further below), cDNAs encoding the light and heavy chains of the Ab made by the hybridoma can be obtained by standard PCR amplification or cDNA cloning techniques. Nucleic acids encoding Abs obtained from an immunoglobulin gene library (e.g., using phage display techniques) can be recovered from the library.

Preferred nucleic acids molecules of the invention are those encoding the $V_H$ and $V_\kappa$ sequences of the anti-PD-1 HuMAbs, 17D8, 2D3, 4H1, 5C4, 4A11, 7D3 and 5F4 (disclosed in U.S. Pat. No. 8,008,449), and those encoding the $V_H$ and $V_\kappa$ sequences of the anti-PD-L1 HuMAbs, 3G10, 12A4, 10A5, 5F8, 10H10, 1B12, 7H1, 11E6, 12B7, and 13G4 (disclosed in U.S. Pat. No. 7,943,743). An isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$), the sequences of which are known in the art and can be obtained by standard PCR amplification. The heavy chain constant region can be an IgG1, IgG2, IgG3, IgG4, IgA, IgE, IgM or IgD constant region, but is preferably an IgG1 or IgG4 constant region. Similarly, an isolated DNA encoding the $V_L$ region can be converted to a full-length light chain gene by operatively linking the $V_L$-encoding DNA to another DNA molecule encoding the light chain constant region ($C_L$), the sequence of which is known in the art and can be obtained by standard PCR amplification. The light chain constant region can be a kappa or lambda constant region, but most preferably is a kappa constant region.

Pharmaceutical Compositions

Antibodies of the present invention may be constituted in a composition, e.g., a pharmaceutical composition, containing one Ab or a combination of Abs, or an antigen-binding portion(s) thereof, and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and nonaqueous carriers, and/or adjuvants such as preservatives, wetting agents, emulsifying agents and dispersing agents.

Dosage regimens are adjusted to provide the optimum desired response, e.g., a therapeutic response or minimal adverse effects. For administration of an anti-PD-1 or anti-PD-L1 Ab, the dosage ranges from about 0.0001 to about 100 mg/kg, usually from about 0.001 to about 20 mg/kg, and more usually from about 0.01 to about 10 mg/kg, of the subject's body weight. Preferably, the dosage is within the range of 0.1-10 mg/kg body weight. For example, dosages can be 0.1, 0.3, 1, 3, 5 or 10 mg/kg body weight, and more preferably, 0.3, 1, 3, or 10 mg/kg body weight. The dosing schedule is typically designed to achieve exposures that result in sustained receptor occupancy (RO) based on typical pharmacokinetic properties of an Ab. An exemplary treatment regime entails administration once per week, once every two weeks, once every three weeks, once every four weeks, once a month, once every 3 months or once every three to 6 months. The dosage and scheduling may change during a course of treatment. For example, dosing schedule may comprise administering the Ab: (i) every two weeks in 6-week cycles; (ii) every four weeks for six dosages, then every three months; (iii) every three weeks; (iv) 3-10 mg/kg body weight once followed by 1 mg/kg body weight every 2-3 weeks. Considering that an IgG4 Ab typically has a half-life of 2-3 weeks, a preferred dosage regimen for an anti-PD-1 or anti-PD-L1 Ab of the invention comprises 0.3-10 mg/kg body weight, preferably 3-10 mg/kg body weight, more preferably 3 mg/kg body weight via intravenous administration, with the Ab being given every 14 days in up to 6-week or 12-week cycles until complete response or confirmed progressive disease.

In some methods, two or more mAbs with different binding specificities are administered simultaneously, in which case the dosage of each Ab administered falls within the ranges indicated. Antibody is usually administered on multiple occasions. Intervals between single dosages can be, for example, weekly, every 2 weeks, every 3 weeks, monthly, every three months or yearly. Intervals can also be irregular as indicated by measuring blood levels of Ab to the target antigen in the patient. In some methods, dosage is adjusted to achieve a plasma Ab concentration of about 1-1000 μg/ml and in some methods about 25-300 μg/ml.

Alternatively, the Ab can be administered as a sustained release formulation, in which case less frequent administration is required. Dosage and frequency vary depending on the half-life of the Ab in the patient. In general, human Abs show the longest half-life, followed by humanized Abs, chimeric Abs, and nonhuman Abs. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Uses and Methods of the Invention

The Abs, Ab compositions, nucleic acids and methods of the present invention have numerous in vitro and in vivo utilities including, for example, methods to determine and quantify the expression of PD-1 or PD-L1 comprising binding of the Abs to the target polypeptides or measuring the amount of nucleic acid encoding these polypeptides, and a method for immunotherapy of a subject afflicted with a disease comprising administering to the subject a composition comprising a therapeutically effective amount of a therapeutic agent that inhibits signaling from an inhibitory immunoregulator. In preferred embodiments of the latter method, the inhibitory immunoregulator is a component of the PD-1/PD-L1 signaling pathway, and the therapeutic agent disrupts signaling of this pathway. More preferably, the therapeutic agent is an Ab that interferes with the interaction between PD-1 and PD-L1. In certain preferred embodiments of this method, the Ab binds specifically to PD-1 and blocks the interaction of PD-1 with PD-L1 and/or PD-L2. In other preferred embodiments, the therapeutic agent is an Ab that binds specifically to PD-L1 and blocks the interaction of PD-L1 with PD-1 and/or B7-1 (CD80). Thus, the disclosure provides methods for potentiating an immune response in a subject comprising administering an anti-PD-1 and/or an anti-PD-L1 Ab in order to disrupt the interaction between PD-1 and PD-L1, and methods of treating diseases mediated by such a potentiation of the immune response. When Abs to PD-1 and PD-L1 are administered together, the two can be administered sequentially in either order or simultaneously. In certain aspects, this disclosure provides methods of modifying an immune response in a subject comprising administering to the subject an anti-PD-1 and/or an anti-PD-L1 Ab of the invention, or antigen-binding portion thereof, such that the immune response in the subject is modified. Preferably, the immune response is potentiated, enhanced, stimulated or up-regulated. In preferred embodiments, the Abs of the present invention are human Abs.

Preferred subjects include human patients in need of enhancement of an immune response. The immunotherapeutic methods disclosed herein are particularly suitable for treating human patients having a disorder that can be treated by potentiating a T-cell mediated immune response. In certain embodiments, the methods are employed for treatment of subjects afflicted with a disease caused by an infectious agent. In preferred embodiments, the methods are employed for treatment of subjects afflicted with, or at risk of being afflicted with, a cancer.

Cancer Immunotherapy

Blockade of PD-1/PD-L1 interaction has been shown to potentiate immune responses in vitro (U.S. Pat. Nos. 8,008, 449 and 7,943,743; Fife et al., 2009) and mediate preclinical antitumor activity (Dong et al., 2002; Iwai et al., 2002). However, the molecular interactions potentially blocked by these two Abs are not identical: anti-PD-1 Abs of the invention disrupt PD-1/PD-L1 and potentially PD-1/PD-L2 interactions; in contrast, whereas anti-PD-L1 Abs of the invention also disrupt PD-1/PD-L1 interactions, they do not block PD-1/PD-L2 interactions but instead may disrupt the PD-1-independent PD-L1/CD80 interaction, which has also been shown to down-modulate T-cell responses in vitro and in vivo (Park et al., 2010; Paterson et al., 2011; Yang et al., 2011; Butte et al., 2007; Butte et al., 2008). Thus, it is possible that among these varied ligand-receptor pairings, different interactions may dominate in different cancer types, contributing to dissimilar activity profiles for the two Abs.

Disruption of the PD-1/PD-L1 interaction by antagonistic Abs can enhance the immune response to cancerous cells in a patient. PD-L1 is not expressed in normal human cells, but is abundant in a variety of human cancers (Dong et al., 2002). The interaction between PD-1 and PD-L1 impairs T cell responses as manifested by a decrease in tumor-infiltrating lymphocytes (TILs) and a decrease in T-cell receptor mediated proliferation, resulting in T cell anergy, exhaustion or apoptosis, and immune evasion by the cancerous cells (Zou et al., 2008; Blank et al., 2005; Konishi et al., 2004; Dong et al., 2003; Iwai et al., 2002). Immune suppression can be reversed by inhibiting the local interaction between PD-L1 and PD-1 using an anti-PD-1 and/or an anti-PD-L1 Ab. These Abs may be used alone or in combination to inhibit the growth of cancerous tumors. In addition, either or both of these Abs may be used in conjunction with other immunogenic agents including cytokines, standard cancer chemotherapies, vaccines, radiation, surgery, or other Abs.

Immunotherapy of Cancer Patients Using an Anti-PD-1 Antibody

This disclosure provides a method for immunotherapy of a subject afflicted with cancer, which method comprises administering to the subject a composition comprising a therapeutically effective amount of an Ab or an antigen-binding portion thereof that disrupts the interaction of PD-1 with PD-L1 and/or PD-L2. The disclosure also provides a method of inhibiting growth of tumor cells in a subject, comprising administering to the subject an Ab or an antigen-binding portion thereof that disrupts the interaction of PD-1 with PD-L1 and/or PD-L2 in an amount effective to inhibit growth of the tumor cells. In preferred embodiments, the subject is a human. In other preferred embodiments, the Ab or antigen-binding portion thereof is an anti-PD-1 Ab of the invention or an antigen-binding portion thereof. In certain embodiments, the Ab or antigen-binding portion thereof is of an IgG1 or IgG4 isotype. In certain embodiments, the Ab or antigen-binding portion thereof is a mAb or an antigen-binding portion thereof. In certain other embodiments, the Ab or antigen-binding portion thereof is a chimeric, humanized or human Ab or an antigen-binding portion thereof. In preferred embodiments for treating human subjects, the Ab or antigen-binding portion thereof is a human Ab or an antigen-binding portion thereof.

The clinical trials described in the Examples employed the anti-PD-1 HuMAb, nivolumab (designated 5C4 in U.S. Pat. No. 8,008,449), to treat cancer. While 5C4 was selected as the lead Ab for entering the clinic, it is notable that several anti-PD-1 Abs of the invention share with 5C4 functional properties that are important to the therapeutic activity of 5C4, including high affinity binding specifically to human PD-1, increasing T-cell proliferation, IL-2 secretion and interferon-7 production in an MLR assay, inhibiting the binding of PD-L1 and/or PD-L2 to PD-1, and inhibiting tumor cell growth in vivo. Moreover, certain of the anti-PD-1 Abs of the invention, 17D8, 2D3, 4H1 and 7D3 are structurally related to 5C4 in comprising $V_H$ and $V_\kappa$ regions that have sequences derived from $V_H$ 3-33 and $V_\kappa$ L6 germline sequences, respectively. In addition, 5C4, 2D3, 7D3, 4H1 and 17D8 all cross-compete for binding to the same epitope region of hPD-1 (Example 1). Thus, the preclinical characterization of nivolumab and other anti-PD-1 HuMabs indicate that the methods of treating cancer provided herein may be performed using different Abs selected from the broad genus of anti-PD-1 Abs of the invention.

Accordingly, certain embodiments of the immunotherapy methods disclosed herein comprise administering to a patient an anti-PD-1 Ab or antigen-binding portion thereof comprising: (a) a heavy chain variable region that comprises consecutively linked amino acids having a sequence derived from a human $V_H$ 3-33 germline sequence, and a light chain variable region that comprises consecutively linked amino acids having a sequence derived from a human $V_\kappa$ L6 germline sequence, or (b) a heavy chain variable region that comprises consecutively linked amino acids having a sequence derived from a human $V_H$ 4-39 germline sequence, and a light chain variable region that comprises consecutively linked amino acids having a sequence derived from a human $V_\kappa$ L15 germline sequence.

In certain other embodiments, the Ab or antigen-binding portion thereof that is administered to the patient cross-competes for binding to PD-1 with a reference Ab or a reference antigen-binding portion thereof comprising: (a) a human heavy chain variable region comprising consecutively linked amino acids having the sequence set forth in SEQ ID NO: 1 and a human light chain variable region comprising consecutively linked amino acids having the sequence set forth in SEQ ID NO: 8; (b) a human heavy chain variable region comprising consecutively linked amino acids having the sequence set forth in SEQ ID NO: 2 and a human light chain variable region comprising consecutively linked amino acids having the sequence set forth in SEQ ID NO: 9; (c) a human heavy chain variable region comprising consecutively linked amino acids having the sequence set forth in SEQ ID NO: 3 and a human light chain variable region comprising consecutively linked amino acids having the sequence set forth in SEQ ID NO: 10; (d) a human heavy chain variable region comprising consecutively linked amino acids having the sequence set forth in SEQ ID NO: 4 and a human light chain variable region comprising consecutively linked amino acids having the sequence set forth in SEQ ID NO: 11; (e) a human heavy chain variable region comprising consecutively linked amino acids having the sequence set forth in SEQ ID NO: 5 and a human light chain variable region comprising consecutively linked amino acids having the sequence set forth in SEQ ID NO: 12; (f) a human heavy chain variable region comprising consecutively linked amino acids having the sequence set forth in SEQ ID NO: 6 and a human light chain variable region comprising consecutively linked amino acids having the sequence set forth in SEQ ID NO: 13; or (g) a human heavy chain variable region comprising consecutively linked amino acids having the sequence set forth in SEQ ID NO: 7 and a human light chain variable region comprising consecutively linked amino acids having the sequence set forth in SEO ID NO: 14. In preferred embodiments, the Ab or antigen-binding portion thereof cross-competes for binding to PD-1 with nivolumab.

In certain preferred embodiments of the immunotherapy methods disclosed herein, the anti-PD-1 Ab or antigen-binding portion thereof administered to the patient comprises: (a) a human heavy chain variable region comprising consecutively linked amino acids having the sequence set forth in SEQ ID NO: 1 and a human light chain variable region comprising consecutively linked amino acids having the sequence set forth in SEQ ID NO: 8; (b) a human heavy chain variable region comprising consecutively linked amino acids having the sequence set forth in SEQ ID NO: 2 and a human light chain variable region comprising consecutively linked amino acids having the sequence set forth in SEQ ID NO: 9; (c) a human heavy chain variable region comprising consecutively linked amino acids having the sequence set forth in SEQ ID NO: 3 and a human light chain variable region comprising consecutively linked amino acids having the sequence set forth in SEQ ID NO: 10; (d) a human heavy chain variable region comprising consecutively linked amino acids having the sequence set forth in SEQ ID NO: 4 and a human light chain variable region comprising consecutively linked amino acids having the sequence set forth in SEQ ID NO: 11; (e) a human heavy chain variable region comprising consecutively linked amino acids having the sequence set forth in SEQ ID NO: 5 and a human light chain variable region comprising consecutively linked amino acids having the sequence set forth in SEQ ID NO: 12; (f) a human heavy chain variable region comprising consecutively linked amino acids having the sequence set forth in SEQ ID NO: 6 and a human light chain variable region comprising consecutively linked amino acids having the sequence set forth in SEQ ID NO: 13; or (g) a human heavy chain variable region comprising consecutively linked amino acids having the sequence set forth in SEQ ID NO: 7 and a human light chain variable region comprising consecutively linked amino acids having the sequence set forth in SEO ID NO: 14. In more preferred embodiments, the anti-PD-1 Ab or antigen-binding portion comprises a human heavy chain variable region comprising consecutively linked amino acids having the sequence set forth in SEQ ID NO: 4 and a human light chain variable region comprising consecutively linked amino acids having the sequence set forth in SEQ ID NO: 11. In yet more preferred embodiments, the anti-PD-1 Ab is nivolumab.

In the clinical trials of anti-PD-1 immunotherapy described in the Examples below, intriguing ORs with durable clinical responses, even in heavily pretreated patients, were observed across multiple tumor types including a substantial proportion of NSCLC, MEL, and RCC patients and in various sites of metastasis including liver, lung, lymph nodes, and bone. See, also, Topalian et al. (2012b). MEL and RCC are considered to be immunogenic neoplasms, having previously been demonstrated to be responsive to cancer immunotherapy, e.g., IL-2 (McDermott et al., 2006) and/or anti-CTLA-4 Ab (Hodi et al., 2010). In contrast, NSCLC has been considered "non-immunogenic" and poorly responsive to immune-based therapies (Holt et al., 2011). Thus, the results with NSCLC are particularly striking, unexpected and surprising. In NSCLC patients, based on data analyzed up to February 2012, 14 ORs were observed at BMS-936558 doses of 1, 3, or 10 mg/kg with response rates of 6%, 32%, and 18%, respectively. ORs were observed across NSCLC histologies: 6 responders of 18 squamous (33%), 7 of 56 nonsquamous (13%), and 1 of 2 unknown. This level of activity seen with anti-PD-1 in NSCLC patients with significant prior therapy (47% with 3 lines of previous therapy) and across histologies is unique, particularly in the squamous histology patients (cf. Gridelli et al., 2008; Miller, 2006), and provides a very favorable benefit/risk dynamic regarding efficacy and safety compared to existing standard-of-care.

Durability of Clinical Responses to Anti-PD-1 in Heavily-Pretreated Cancer Patients The durability of ORs across multiple cancer types in patients treated with the anti-PD-1 Ab is particularly notable. The objective response rate (ORR) in heavily pretreated NSCLC patients receiving anti-PD-1 Ab, including patients with squamous histology, is particularly surprising and unexpected, as standard salvage therapies historically show modest benefit in these patients (Scagliotti et al., 2011). As measured by standard RECIST in this study, ORs were long-lasting, with response durations≥1 year in 20 of 31 responders in the data analyzed up to February 2012. In addition, patterns of tumor regression consistent with immune-related patterns of response were observed.

These findings have established the PD-1 pathway as a new therapeutic focus in oncology (Pardoll, 2012; Topalian et al., 2012c; McDermott et al., 2013). In the current study, in which 47% of patients had progressive disease following 3 or more prior systemic regimens, preliminary analysis has been conducted up to March 2013. This updated analysis has supported and reinforced the data obtained and conclusions reached from the earlier February 2012 analyses. Thus, conventional ORs were documented in patients with NSCLC (16%), MEL (31%) and RCC (29%), and prolonged disease stabilization in others (9%, 6%, and 27%, respectively) across all doses tested (see Example 7, Table 2). Additionally, 13 patients (4%) manifested unconventional, "immune-related" response patterns as previously described with anti-CTLA-4 therapy, several of which were sustained (Sharma et al., 2011). The updated analyses again underscored the durability of survival in nivolumab-treated patients, which has not been observed with chemotherapy or small molecule inhibitors to date, but has been observed in patients with advanced melanoma receiving ipilimumab, another immune checkpoint blocking agent (Hodi et al., 2010).

Of particular importance, the objective tumor regression and disease stabilization induced by nivolumab in heavily-pretreated patients with advanced NSCLC, MEL, and RCC translate to survival outcomes that compare very favorably with historical data for these patient populations treated with conventional chemotherapy and/or tyrosine-kinase inhibitor (TKI) treatments. In NSCLC, nivolumab induced median overall survivals of 9.6 and 9.2 months in patients with squamous and non-squamous histologies, respectively. Landmark survival rates of 43% (1-year), 32% (2-year) and 24% (3-year) were achieved (see Example 7, Table 2). This high level of efficacy is especially impressive since 55% of these patients had received 3 or more prior therapies. Historically, 2L chemotherapeutics for lung cancer (i.e., docetaxel and pemetrexed) have achieved a median overall survival of 7.5-8.3 months (Shepherd et al., 2000; Hanna et al., 2004). In a 2/3-L population, erlotinib-treated patients had a median survival of 6.7 months, versus 4.7 months in placebo-treated patients (Shepherd et al., 2005). No therapy is currently approved for use in lung cancer beyond the 3L setting, and minimal data exist to benchmark survival in this patient population.

In nivolumab-treated MEL patients, overall survival (OS) of 16.8 months was achieved, with landmark survival rates of 61% (1-year), 44% (2-year) and 40% (3-year) (see Example 7, Table 2). Survival outcomes in pretreated melanoma patients supported the recent PDA approvals of ipilimumab and vemurafenib. In patients with at least one prior treatment for metastatic disease, ipilimumab increased median OS from 6.4 to 10.1 months, compared to a gp100 peptide vaccine (Hodi et al., 2010). In phase 2 trials of ipilimumab in previously treated patients, landmark 2-year survival rates ranged from 24.2-32.8% (Lebbe et al., 2012). Median OS in previously treated MEL patients enrolled on a large phase 2 of vemurafenib was 15.9 months (Sosman et al., 2012).

In nivolumab-treated patients with RCC, among whom 44% received 3 or more prior therapies and 74% received prior anti-angiogenic therapy, the median OS has not been achieved and exceeds 22 months. Landmark survival rates of 70% (1-year), 52% (2-year) and 52% (3-year) were achieved (see Example 7, Table 2). In a recent Phase 3 trial enrolling kidney cancer patients whose disease progressed following anti-angiogenic therapy, everolimus was compared with placebo: median OS was 14.8 versus 14.4 months, respectively (Motzer et al., 2008; Motzer et al., 2008). A recent Phase 3 trial comparing sorafenib to temsirolimus in a sunitinib-refractory kidney cancer population yielded median OS of 16.6 and 12.3 months, respectively (Hutson et al., 2012). Thus, treatment of a heavily-pretreated patient population with nivolumab has yielded a considerably longer median OS (>22 months) than treatment of a less refractory population with standard-of-care therapies. Controlled Phase 3 trials with prospective survival endpoints are underway in NSCLC, MEL and RCC (NCT01673867, NCT01721772, NCT01642004, NCT01668784, and NCT01721746 (see Clinical Trials Website). The results from these trials are expected to further demonstrate the high efficacy of, and durability of responses to, nivolumab in these cancers compared standard-of-care therapies.

The data disclosed herein demonstrating the high efficacy, durability and broad applicability of anti-PD-1 immunotherapy for treating cancer has led to nivolumab being tested for additional types of cancer. For example, on the basis that increased PD-L1 expression has been reported with various hematologic malignancies and may prevent the host immune response from exerting a beneficial impact on the malignant cells, a trial to confirm the ability of nivolumab to mediate antitumor activity in patients with hematologic malignancies (multiple myeloma, B-cell lymphoma, T-cell lymphoma, Hodgkin's lymphoma/primary mediastinal B-cell lymphoma, and chronic myelogenous leukemia) has been initiated (NCT01592370). Nivolumab is also being tested as a monotherapy in advanced hepatocellular carcinoma (NCT01658878).

In summary, the results of anti-PD-1 immunotherapy disclosed herein are remarkable in at least the following three respects. First, anti-PD-1 has been shown to be highly efficacious compared to historical data for patients on standard-of-care treatments for cancer. Notably, this efficacy has been demonstrated in patient in heavily pretreated populations in which about half of the patients had progressive disease following 3 or more prior systemic regimens. Such patients, afflicted with advanced, metastatic and/or refractory cancers, are notoriously difficult to treat. Accordingly, this disclosure provides methods for immunotherapy of a patient afflicted with an advanced, metastatic and/or refractory cancer, which method comprises administering to the patient a therapeutically effective amount of an Ab or an antigen-binding portion thereof that disrupts the interaction of PD-1 with PD-L1 and/or PD-L2. In certain embodiments of any of the therapeutic methods disclosed herein, the subject has been pre-treated for the cancer; for example, the subject had undergone at least one, two, or three prior lines of therapy for cancer.

Second, the present therapeutic methods have been shown to be applicable to a broad genus of different cancers. Based on the surprising discovery that even a "non-immunogenic" cancer such as NSCLC (Holt et al., 2011) and hard-to-treat cancers such as ovarian and gastric cancers (as well as other cancers tested, including MEL, RCC, and CRC) are amendable to treatment with anti-PD-1 and/or anti-PD-L1 (see Examples 7 and 14), this disclosure provides methods for immunotherapy of a patient afflicted with any cancer.

Third, treatment with an anti-PD-1 or anti-PD-L1 Ab has been shown to produce strikingly durable clinical activity in cancer patients. Accordingly, this disclosure provides immunotherapeutic methods of inducing a durable clinical response in a cancer patient comprising administering to the patient a therapeutically effective amount of an Ab or an antigen-binding portion thereof that disrupts the interaction of PD-1 with PD-L1 and/or PD-L2. In preferred embodiments of any of the therapeutic methods described herein, the clinical response is a durable response.

As used herein, a "durable" response is a therapeutic or clinical response that exceeds the anticipated median OS rate in a patient population. The anticipated median OS rate varies with different cancer and different patient populations. In certain embodiments, a durable response exceeds the anticipated median OS rate in the relevant patient population by at least 10%, preferably by at least 20%, more preferably by at least 30%, and even more preferably by at least 50%. A major benefit of immunotherapeutic approaches based on PD-1 pathway blockade may be the functional restoration of exhausted T cells with long-term generation of memory T cells that may maintain antitumor immune surveillance and inhibit tumor growth for prolonged periods extending to many years, even in the absence of continued therapy (Kim et al., 2010). Indeed, long-term follow-up studies on patients following cessation of nivolumab therapy have confirmed that a patient with CRC experienced a complete response which was ongoing after 3 years; a patient with RCC experienced a partial response lasting 3 years off therapy, which converted to a complete response that was ongoing at 12 months; and a patient with melanoma achieved a partial response that was stable for 16 months off therapy, and recurrent disease was successfully treated with reinduction anti-PD-1 therapy (Lipson et al., 2013).

Combination Therapy Including Anti-PD-1 Abs

While monotherapy with anti-PD-1 and anti-PD-L1 Abs has been shown herein to significantly increase the survival of patients with lung cancer, melanoma, kidney cancer, and potentially other malignancies, preclinical evidence indicates that synergistic treatment combinations based on PD-1 pathway blockade could have even more potent effects. Clinical evaluation of nivolumab combined with ipilimumab (anti-CTLA-4), whose mechanism of action is similar yet distinct from nivolumab's (Mellman et al., 2011; Topalian et al., 2012c), is ongoing (Wolchok et al., 2013), as are studies of nivolumab in combination with melanoma vaccines (NCT01176461, NCT01176474; Weber et al., 2013), and BMS-986015, an anti-KIR Ab (NCT01714739).

Anti-PD-1 Abs can be combined with an immunogenic agent, for example a preparation of cancerous cells, purified tumor antigens (including recombinant proteins, peptides, and carbohydrate molecules), antigen-presenting cells such as dendritic cells bearing tumor-associated antigens, and/or cells transfected with genes encoding immune stimulating cytokines (He et al., 2004). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. PD-1 blockade may also be effectively combined with standard cancer treatments, including chemotherapeutic regimes, radiation, surgery, hormone deprivation and angiogenesis inhibitors, as well as another immunotherapeutic Ab (e.g., an anti-PD-L1, anti-CTLA-4 and/or anti-LAG-3 Ab).

Immune-Related Clinical Responses

It has become evident that conventional response criteria may not adequately assess the activity of immunotherapeutic agents because progressive disease (by initial radiographic evaluation) does not necessarily reflect therapeutic failure. For example, treatment with the anti-CTLA-4 Ab, ipilimumab, has been shown to produce four distinct response patterns, all of which were associated with favorable survival: (a) shrinkage in baseline lesions, without new lesions; (b) durable stable disease (in some patients followed by a slow, steady decline in total tumor burden); (c) response after an increase in total tumor burden; and (d) response in the presence of new lesions. Accordingly, to properly evaluate immunotherapeutic agents, long-term effects on the target disease must also be captured. In this regard, systematic immune-related response criteria (irRC) that make allowances for an early increase in tumor burden and/or the appearance of new lesions, and which seek to enhance the characterization of immune-related response patterns, have been proposed (Wolchok et al., 2009). While the full impact of these unconventional response patterns remains to be defined in randomized trials of nivolumab with survival endpoints, the present observations are reminiscent of findings with ipilimumab in which a significant extension of OS was observed in treated patients (Hodi et al., 2010; Robert et al., 2011).

The overall risk/benefit profile of anti-PD-1 immunotherapy is also favorable, with a low incidence of more severe drug-related adverse events (AEs; >grade 3), the specific events observed to date being consistent with other immunotherapeutic agents. This suggests that anti-PD-1 immunotherapy can be delivered in an outpatient setting with minimal supportive care.

Broad Spectrum of Cancers Treatable by Anti-PD-1 Immunotherapy

The clinical data presented herein demonstrate that immunotherapy based on PD-1 blockade is not limited to only "immunogenic" tumor types, such as MEL and RCC, but extends to tumor types not generally considered to be immune-responsive, including NSCLC. The unexpected successes with treatment-refractory metastatic NSCLC underscore the possibility that any neoplasm can be "immunogenic" in the context of proper immune modulation, and suggest that PD-1 blockade as an immunotherapeutic approach is broadly applicable across a very diverse range of tumor types. Cancers that may be treated using the anti-PD-1 Abs of the invention also include cancers typically responsive to immunotherapy. Non-limiting examples of preferred cancers for treatment include NSCLC, MEL, RCC, CRC, CRPC, HCC, squamous cell carcinoma of the head and neck, carcinomas of the esophagus, ovary, gastrointestinal tract and breast, and a hematologic malignancy. Although NSCLC is not generally considered responsive to immunotherapy, data disclosed herein unexpectedly demonstrate that both squamous and non-squamous NSCLC are responsive to treatment with an anti-PD-1 Ab. Additionally, the disclosure provides for the treatment of refractory or recurrent malignancies whose growth may be inhibited using an anti-PD-1 Ab of the invention.

Examples of other cancers that may be treated using an anti-PD-1 Ab in the methods of the present invention, based on the indications of very broad applicability of anti-PD-1 immunotherapy provided herein, include liver cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present invention is also applicable to treatment of metastatic cancers.

Medical Uses of Anti-PD-1 Abs

One aspect of this invention is the use of any anti-PD-1 Ab or antigen-binding portion thereof of the invention for the preparation of a medicament for inhibiting signaling from the PD-1/PD-L1 pathway so as to thereby potentiate an endogenous immune response in a subject afflicted with cancer. Another aspect is the use of any anti-PD-1 Ab or an antigen-binding portion thereof of the invention for the preparation of a medicament for immunotherapy of a subject afflicted with cancer comprising disrupting the interaction between PD-1 and PD-L1. These uses for the preparation of medicaments are broadly applicable to the full range of cancers disclosed herein. In preferred embodiments of these uses, the cancers include squamous NSCLC, non-squamous NSCLC, MEL, RCC, CRC, CRPC, HCC, squamous cell carcinoma of the head and neck, and carcinomas of the esophagus, ovary, gastrointestinal tract and breast, and a hematologic malignancy. This disclosure also provides medical uses of any anti-PD-1 Ab or antigen-binding portion thereof of the invention corresponding to all the embodiments of the methods of treatment employing an anti-PD-1 Ab described herein.

The disclosure also provides an anti-PD-1 Ab or an antigen-binding portion thereof of the invention for use in potentiating an endogenous immune response in a subject afflicted with cancer by inhibiting signaling from the PD-1/PD-L1 pathway. The disclosure further provides an anti-PD-1 Ab or an antigen-binding portion thereof of the invention for use in immunotherapy of a subject afflicted with cancer comprising disrupting the interaction between PD-1 and PD-L1. These Abs may be used in potentiating an endogenous immune response against, or in immunotherapy of, the full range of cancers disclosed herein. In preferred embodiments, the cancers include squamous NSCLC, non-squamous NSCLC, MEL, RCC, CRC, CRPC, HCC, squamous cell carcinoma of the head and neck, and carcinomas of the esophagus, ovary, gastrointestinal tract and breast, and a hematologic malignancy.

Immunotherapy of Cancer Patients Using an Anti-PD-L1 Antibody

PD-L1 is the primary PD-1 ligand up-regulated within solid tumors, where it can inhibit cytokine production and the cytolytic activity of PD-1-positive, tumor-infiltrating CD4$^+$ and CD8$^+$ T-cells, respectively (Dong et al., 2002; Hino et al., 2010; Taube et al., 2012). These properties make PD-L1 a promising target for cancer immunotherapy. The clinical trials of anti-PD-L1 immunotherapy described in the Examples demonstrate for the first time that mAb blockade of the immune inhibitory ligand, PD-L1, produces both durable tumor regression and prolonged (≥24 weeks) disease stabilization in patients with metastatic NSCLC, MEL, RCC and OV, including those with extensive prior therapy. The human anti-PD-L1 HuMAb, BMS-936559, had a favorable safety profile overall at doses up to and including 10 mg/kg, as is evident from the low (9%) incidence of grade 3-4 drug-related AEs. These findings are consistent with the mild autoimmune phenotype seen in PD-L1$^{-/-}$ mice (Dong et al., 2004) and the more severe hyperproliferation seen in CTLA-4$^{-/-}$ mice relative to PD-1$^{-/-}$ mice (Phan et al., 2003; Tivol et al., 1995; Nishimura et al., 1999). Most of the toxicities associated with anti-PD-L1 administration in patients were immune-related, suggesting on-target effects. The spectrum and frequency of adverse events of special interest (AEOSIs) is somewhat different between anti-PD-L1 and anti-CTLA-4, emphasizing the distinct biology of these pathways (Ribas et al., 2005). Infusion reactions were observed with BMS-936559, although they were mild in most patients. Severe colitis, a drug-related AE observed in ipilimumab-treated patients (Beck et al., 2006), was infrequently noted with anti-PD-L1.

As noted above for anti-PD-1 immunotherapy, another important feature of anti-PD-L1 therapy is the durability of responses across multiple tumor types. This is particularly notable considering the advanced disease and prior treatment of patients on the current study. Although not compared directly, this durability appears greater than that observed with most chemotherapies and kinase inhibitors used in these diseases.

Because peripheral blood T-cells express PD-L1, it is possible to assess in vivo RO by BMS-963559 as a pharmacodynamic measure. Median RO was 65.8%, 66.2%, and 72.4% for the doses tested. Whereas these studies provide a direct assessment and evidence of target engagement in patients treated with BMS-936559, relationships between RO in peripheral blood and the tumor microenvironment remain poorly understood.

Based on the clinical data disclosed herein, this disclosure provides a method for immunotherapy of a subject afflicted with cancer, which method comprises administering to the subject a composition comprising a therapeutically effective amount of an anti-PD-L1 Ab of the invention or an antigen-binding portion thereof. The disclosure also provides a method of inhibiting growth of tumor cells in a subject, comprising administering to the subject an anti-PD-L1 Ab of the invention or an antigen-binding portion thereof. In preferred embodiments, the subject is a human. In certain embodiments, the Ab or antigen-binding portion thereof is of an IgG1 or IgG4 isotype. In certain embodiments, the Ab or antigen-binding portion thereof is a mAb or an antigen-binding portion thereof. In certain other embodiments, the Ab or antigen-binding portion thereof is a chimeric, humanized or human Ab or an antigen-binding portion thereof. In preferred embodiments for treating human subjects, the Ab or antigen-binding portion thereof is a human Ab or an antigen-binding portion thereof.

Clinical trials described in the Examples employed the anti-PD-L1 HuMAb BMS-936559 to treat cancer. While BMS-936559 (designated HuMAb 12A4 in U.S. Pat. No. 7,943,743) was selected as the lead anti-PD-L1 Ab for entering the clinic, it is notable that several anti-PD-L1 Abs of the invention share with 12A4 functional properties that are important to the therapeutic activity of 12A4, including high affinity binding specifically to human PD-L1, increasing T-cell proliferation, IL-2 secretion and interferon-7 production in an MLR assay, inhibiting the binding of PD-L1 to PD-1, and reversing the suppressive effect of T regulatory cells on T cell effector cells and/or dendritic cells. Moreover, certain of the anti-PD-L1 Abs of the invention, namely 1B12, 7H1 and 12B7 are structurally related to 12A4 in comprising $V_H$ and $V_κ$ regions that have sequences derived from $V_H$ 1-69 and $V_κ$ L6 germline sequences, respectively.

In addition, at least 12B7, 3G10, 1B12 and 13G4 cross-compete with 12A4 for binding to the same epitope region of hPD-L1, whereas 5F8 and 10A5 may bind to the same or an overlapping epitope region as 12A4 (Examples 2 and 3). Thus, the preclinical characterization of 12A4 and other anti-PD-L1 HuMabs indicate that the methods of treating cancer provided herein may be performed using any of the broad genus of anti-PD-L1 Abs of the invention.

Accordingly, this disclosure provides immunotherapy methods comprising administering to a patient an anti-PD-L1 Ab or antigen-binding portion thereof comprising (a) a heavy chain variable region that comprises consecutively linked amino acids having a sequence derived from a human $V_H$1-18 germline sequence, and a light chain variable region that comprises consecutively linked amino acids having a sequence derived from a human $V_\kappa$ L6 germline sequence; (b) a heavy chain variable region that comprises consecutively linked amino acids having a sequence derived from a human $V_H$1-69 germline sequence, and a light chain variable region that comprises consecutively linked amino acids having a sequence derived from a human $V_\kappa$ L6 germline sequence; (c) a heavy chain variable region that comprises consecutively linked amino acids having a sequence derived from a human $V_H$ 1-3 germline sequence, and a light chain variable region that comprises consecutively linked amino acids having a sequence derived from a human $V_\kappa$ L15 germline sequence; (d) a heavy chain variable region that comprises consecutively linked amino acids having a sequence derived from a human $V_H$ 1-69 germline sequence, and a light chain variable region that comprises consecutively linked amino acids having a sequence derived from a human $V_\kappa$ A27 germline sequence; (e) a heavy chain variable region that comprises consecutively linked amino acids having a sequence derived from a human $V_H$ 3-9 germline sequence, and a light chain variable region that comprises consecutively linked amino acids having a sequence derived from a human $V_\kappa$ L15 germline sequence; or (f) a heavy chain variable region that comprises consecutively linked amino acids having a sequence derived from a human $V_H$ 3-9 germline sequence, and a light chain variable region that comprises consecutively linked amino acids having a sequence derived from a human $V_\kappa$ L18 germline sequence.

In certain other embodiments, the anti-PD-L1 Ab or antigen-binding portion thereof administered to the patient cross-competes for binding to PD-L1 with a reference Ab or a reference antigen-binding portion thereof comprising: (a) a human heavy chain variable region comprising consecutively linked amino acids having the sequence set forth in SEQ ID NO: 15 and a human light chain variable region comprising consecutively linked amino acids having the sequence set forth in SEQ ID NO: 25; (b) a human heavy chain variable region comprising consecutively linked amino acids having the sequence set forth in SEQ ID NO: 16 and a human light chain variable region comprising consecutively linked amino acids having the sequence set forth in SEQ ID NO: 26; (c) a human heavy chain variable region comprising consecutively linked amino acids having the sequence set forth in SEQ ID NO: 17 and a human light chain variable region comprising consecutively linked amino acids having the sequence set forth in SEQ ID NO: 27; (d) a human heavy chain variable region comprising consecutively linked amino acids having the sequence set forth in SEQ ID NO: 18 and a human light chain variable region comprising consecutively linked amino acids having the sequence set forth in SEQ ID NO: 28; (e) a human heavy chain variable region comprising consecutively linked amino acids having the sequence set forth in SEQ ID NO: 19 and a human light chain variable region comprising consecutively linked amino acids having the sequence set forth in SEQ ID NO: 29; (f) a human heavy chain variable region comprising consecutively linked amino acids having the sequence set forth in SEQ ID NO: 20 and a human light chain variable region comprising consecutively linked amino acids having the sequence set forth in SEQ ID NO: 30; (g) a human heavy chain variable region comprising consecutively linked amino acids having the sequence set forth in SEQ ID NO: 21 and a human light chain variable region comprising consecutively linked amino acids having the sequence set forth in SEO ID NO: 31; (h) a human heavy chain variable region comprising consecutively linked amino acids having the sequence set forth in SEQ ID NO: 22 and a human light chain variable region comprising consecutively linked amino acids having the sequence set forth in SEQ ID NO: 32; (i) a human heavy chain variable region comprising consecutively linked amino acids having the sequence set forth in SEQ ID NO: 23 and a human light chain variable region comprising consecutively linked amino acids having the sequence set forth in SEO ID NO: 33; or (j) a human heavy chain variable region comprising consecutively linked amino acids having the sequence set forth in SEQ ID NO: 24 and a human light chain variable region comprising consecutively linked amino acids having the sequence set forth in SEQ ID NO: 34. In preferred embodiments, the Ab or antigen-binding portion thereof cross-competes for binding to PD-1 with a reference Ab or reference antigen-binding portion thereof comprising a human heavy chain variable region comprising consecutively linked amino acids having the sequence set forth in SEQ ID NO: 16 and a human light chain variable region comprising consecutively linked amino acids having the sequence set forth in SEQ ID NO: 26.

In certain preferred embodiments of the immunotherapy methods disclosed herein, the anti-PD-L1 Ab or antigen-binding portion thereof administered to the subject comprises: (a) a human heavy chain variable region comprising consecutively linked amino acids having the sequence set forth in SEQ ID NO: 15 and a human light chain variable region comprising consecutively linked amino acids having the sequence set forth in SEQ ID NO: 25; (b) a human heavy chain variable region comprising consecutively linked amino acids having the sequence set forth in SEQ ID NO: 16 and a human light chain variable region comprising consecutively linked amino acids having the sequence set forth in SEQ ID NO: 26; (c) a human heavy chain variable region comprising consecutively linked amino acids having the sequence set forth in SEQ ID NO: 17 and a human light chain variable region comprising consecutively linked amino acids having the sequence set forth in SEQ ID NO: 27; (d) a human heavy chain variable region comprising consecutively linked amino acids having the sequence set forth in SEQ ID NO: 18 and a human light chain variable region comprising consecutively linked amino acids having the sequence set forth in SEQ ID NO: 28; (e) a human heavy chain variable region comprising consecutively linked amino acids having the sequence set forth in SEQ ID NO: 19 and a human light chain variable region comprising consecutively linked amino acids having the sequence set forth in SEQ ID NO: 29; (f) a human heavy chain variable region comprising consecutively linked amino acids having the sequence set forth in SEQ ID NO: 20 and a human light chain variable region comprising consecutively linked amino acids having the sequence set forth in SEQ ID NO: 30; (g) a human heavy chain variable region comprising consecutively linked amino acids having the sequence set forth in SEQ ID NO: 21 and a human light chain variable region comprising consecutively linked amino acids having the sequence set forth in SEO ID NO: 31; (h) a human heavy chain variable region comprising consecutively linked amino acids having the sequence set forth in SEQ ID NO: 22 and a human light chain variable region comprising consecutively linked amino acids having the sequence set forth in SEQ ID NO: 32; (i) a human heavy chain variable region comprising consecutively linked amino acids having the sequence set forth in SEQ ID NO: 23 and a human light chain variable region comprising consecutively linked amino acids having the sequence set forth in SEO ID NO: 33; or (j) a human heavy chain variable region comprising consecutively linked amino acids having the sequence set forth in SEQ ID NO: 24 and a human light chain variable region comprising consecutively linked amino acids having the sequence set forth in SEQ ID NO: 34. In more preferred embodiments, the anti-PD-L1 Ab or antigen-binding portion comprises a human heavy chain variable region comprising consecutively linked amino acids having the sequence set forth in SEQ ID NO: 16 and a human light chain variable region comprising consecutively linked amino acids having the sequence set forth in SEQ ID NO: 26.

Broad Spectrum of Cancers Treatable by Anti-PD-L1 Immunotherapy

The clinical activity of anti-PD-L1 in patients with advanced NSCLC, similar to the activity of anti-PD-1 in these patients, was surprising and unexpected since NSCLC has been considered to be poorly responsive to immune-based therapies (Holt and Disis, 2008; Holt et al., 2011). The present clinical data obtained with BMS-936559, an anti-PD-L1 Ab of the invention, substantiate and extend the evidence obtained using the anti-PD-1 Ab that immunotherapy based on PD-1 blockade is not applicable only to "immunogenic" tumor types, such as MEL and RCC, but is also effective with a broad range of cancers, including treatment-refractory metastatic NSCLC, that are generally not considered to be immune-responsive. Preferred cancers that may be treated using the anti-PD-L1 Abs of the invention include MEL (e.g., metastatic malignant melanoma), RCC, squamous NSCLC, non-squamous NSCLC, CRC, ovarian cancer (OV), gastric cancer (GC), breast cancer (BC), pancreatic carcinoma (PC) and carcinoma of the esophagus. Additionally, the invention includes refractory or recurrent malignancies whose growth may be inhibited using the anti-PD-L1 Abs of the invention.

Examples of other cancers that may be treated using an anti-PD-L1 Ab in the methods of the invention, based on the indications of very broad applicability of anti-PD-L1 immunotherapy provided herein, include bone cancer, skin cancer, cancer of the head or neck, breast cancer, lung cancer, cutaneous or intraocular malignant melanoma, renal cancer, uterine cancer, castration-resistant prostate cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, carcinomas of the ovary, gastrointestinal tract and breast, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, multiple myeloma, environmentally induced cancers including those induced by asbestos, metastatic cancers, and any combinations of said cancers. The present invention is also applicable to treatment of metastatic cancers.

Combination Therapy with Anti-PD-L1 Abs

Optionally, Abs to PD-L1 can be combined with an immunogenic agent, for example a preparation of cancerous cells, purified tumor antigens (including recombinant proteins, peptides, and carbohydrate molecules), antigen-presenting cells such as dendritic cells bearing tumor-associated antigens, and cells transfected with genes encoding immune stimulating cytokines (He et al., 2004). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. PD-1 blockade may also be effectively combined with standard cancer treatments, including chemotherapeutic regimes, radiation, surgery, hormone deprivation and angiogenesis inhibitors, as well as another immunotherapeutic Ab (e.g., an anti-PD-1, anti-CTLA-4 or anti-LAG-3 Ab).

Uses of Anti-PD-L1 Abs

This disclosure provides the use of any anti-PD-L1 Ab or antigen-binding portion thereof of the invention for the preparation of a medicament for inhibiting signaling from the PD-1/PD-L1 pathway so as to thereby potentiate an endogenous immune response in a subject afflicted with cancer. The disclosure also provides the use of any anti-PD-L1 Ab or antigen-binding portion thereof of the invention for the preparation of a medicament for immunotherapy of a subject afflicted with cancer comprising disrupting the interaction between PD-1 and PD-L1. The disclosure provides medical uses of any anti-PD-L1 Ab or antigen-binding portion thereof of the invention corresponding to all the embodiments of the methods of treatment employing an anti-PD-L1 Ab described herein.

This disclosure also provides an anti-PD-L1 Ab or an antigen-binding portion thereof of the invention for use in potentiating an endogenous immune response in a subject afflicted with cancer by inhibiting signaling from the PD-1/PD-L1 pathway. The disclosure further provides an anti-PD-L1 Ab or an antigen-binding portion thereof of the invention for use in immunotherapy of a subject afflicted with cancer comprising disrupting the interaction between PD-1 and PD-L1. These Abs may be used in potentiating an endogenous immune response against, or in immunotherapy of, the full range of cancers disclosed herein. In preferred embodiments, the cancers include MEL (e.g., metastatic malignant MEL), RCC, squamous NSCLC, non-squamous NSCLC, CRC, ovarian cancer (OV), gastric cancer (GC), breast cancer (BC), pancreatic carcinoma (PC) and carcinoma of the esophagus.

Validation of Cancer Immunotherapy by Immune Checkpoint Blockade

A major implication of the clinical activity of immune checkpoint blockade is that significant endogenous immune responses to tumor antigens are generated and these responses may be harnessed therapeutically to mediate clinical tumor regression upon checkpoint inhibition. In fact, there is evidence that inhibitory ligands such as PD-L1 are induced in response to immune attack, a mechanism termed adaptive resistance (Gajewski et al., 2010; Taube et al., 2012). This potential mechanism of immune resistance by tumors suggests that PD-1/PD-L1-directed therapy might synergize with other treatments that enhance endogenous antitumor immunity. Follow-up studies have verified that patients continue to demonstrate tumor control after cessation of PD-1/PD-L1 pathway blockade (Lipson et al., 2013). Such tumor control may reflect a persistent antitumor immune response and the generation of effective immunologic memory to enable sustained control of tumor growth.

The data disclosed herein on the clinical testing of Abs that block the immunoregulatory receptor, PD-1, and also of Abs that block one of its cognate ligands, PD-L1, are unprecedented. These data constitute the largest clinical experience to date with PD-1 pathway-directed cancer immunotherapy, and the first report specifically describing the safety, tolerability, and initial clinical activity of an anti-PD-L1-directed agent. These findings show that both anti-PD-1 and anti-PD-L1 have favorable overall safety profiles and provide clear evidence of clinical activity across diverse cancers, including NSCLC, a tumor not historically considered responsive to immunotherapy, as well as tumors known to respond to immunotherapy, including MEL, RCC and OV. Thus, these data strongly validate the PD-1/PD-L1 pathway as an important target for therapeutic intervention in cancer.

The remarkable similarities observed between the patterns of clinical activity obtained with the anti-PD-1 and anti-PD-L1 mAbs, and among the tumor types analyzed to date, validate the general importance of the PD-1/PD-L1 signaling pathway in tumor immune resistance and as a target for therapeutic intervention. Although the molecular interactions blocked by these two Abs are not identical, it has been clearly demonstrated herein that, irrespective of mechanistic details, both anti-PD-1 and anti-PD-L1 Abs of the invention are effective in treating patients afflicted with a wide variety of cancers, including "immunogenic" cancers such as MEL and RCC as well as treatment-refractory metastatic NSCLC, a tumor that is generally not considered to be immune-responsive. In certain embodiments of the invention, either or both of these Abs can be administered in combination with another therapeutic agent such as a cytokine.

Infectious Diseases

Other methods of the invention are used to treat patients that have been exposed to particular toxins or pathogens. For example, another aspect of the disclosure provides a method of treating an infectious disease in a subject comprising administering to the subject an anti-PD1 or an anti-PD-L1 Ab, or antigen-binding portion thereof, of the invention such that the subject is treated for the infectious disease. Preferably, the Ab is a human anti-human PD-1 or PD-L1 Ab (such as any of the human Abs described herein). Alternatively, the Ab is a chimeric or humanized Ab.

Similar to its application to tumors as discussed above, Ab-mediated PD-1 or PD-L1 blockade can be used alone, or as an adjuvant, in combination with vaccines, to potentiate an immune response to pathogens, toxins, and/or self-antigens. Examples of pathogens for which this therapeutic approach may be particularly useful include pathogens for which there is currently no effective vaccine, or pathogens for which conventional vaccines are less than completely effective. These include, but are not limited to HIV, Hepatitis (A, B, and C), Influenza, Herpes, Giardia, Malaria, *Leishmania, Staphylococcus aureus, Pseudomonas aeruginosa*. PD-1 and/or PD-L1 blockade is particularly useful against established infections by agents such as HIV that present altered antigens over the course of an infection. Novel epitopes on these antigens are recognized as foreign at the time of anti-human PD-1 or PD-L1 administration, thus provoking a strong T cell response that is not dampened by negative signals through the PD-1/PD-L1 pathway.

In the above methods, PD-1 or PD-L1 blockade can be combined with other forms of immunotherapy such as cytokine treatment (e.g., administration of interferons, GM-CSF, G-CSF or IL-2).

Kits

Also within the scope of the present invention are kits, including pharmaceutical kits, comprising an anti-PD-1 and/or an anti-PD-L1 Ab of the invention for therapeutic uses, and diagnostic kits comprising an anti-PD-L1 Ab of the invention for assaying membranous PD-L1 expression as a biomarker for screening patients for immunotherapy or for predicting the efficacy of an immunotherapeutic agent. Kits typically include a label indicating the intended use of the contents of the kit and instructions for use. The term label includes any writing, or recorded material supplied on or with the kit, or which otherwise accompanies the kit. In certain embodiments of a pharmaceutical kit, the anti-PD-1 and/or anti-PD-L1 Abs may be co-packaged with other therapeutic agents in unit dosage form. In certain embodiments of a diagnostic kit, the anti-PD-L1 Ab may be co-packaged with other reagents for performing an assay to detect and/or quantify PD-L1 expression.

In certain preferred embodiments, the pharmaceutical kit comprises the anti-human PD-1 HuMAb, nivolumab. In other preferred embodiments, the pharmaceutical kit comprises the anti-human PD-L1 HuMAb, BMS-936559. In certain preferred embodiments, the diagnostic kit comprises the rabbit anti-human PD-L1 mAb, 28-8, comprising the $V_H$ and $V_\kappa$ regions whose amino acid sequences are set forth in SEQ ID NOs. 35 and 36, respectively. In other preferred embodiments, the diagnostic kit comprises the murine anti-human PD-L1 mAb, 5H1 (Dong et al., 2002).

Pd-L1 Biomarker for Predicting Anti-Pd-1 Efficacy

A particular challenge in cancer immunotherapy has been the identification of mechanism-based predictive biomarkers to enable patient selection and guide on-treatment management. Data disclosed in the Examples below indicate that cell surface PD-L1 expression in tumors is a useful molecular marker for predicting the efficacy of, and selecting patients for, anti-PD-1 immunotherapy.

There are conflicting reports in the literature about the clinical implications of PD-L1 being expressed in tumors. Several studies have concluded that PD-L1 expression in tumors correlates with a poor prognosis for the patient. See, e.g., Hino et al., 2010 (MEL); Hamanishi et al., 2007 (OV); Thompson et al., 2006 (RCC). These findings may be rationalized on the basis that the interaction of PD-L1 on tumor cells and PD-1 on T cells helps abrogate immune responses directed against the tumor, resulting in immune evasion from tumor-specific T cells. However, in contrast to the foregoing studies, Gadiot et al., 2011 and Taube et al., 2012 have recently reported that PD-L1 expression in melanoma tumors correlates with a trend toward better survival. These seemingly contradictory data may reflect the relatively small numbers of patients analyzed, different histologic subtypes studied, or different methodologies used, e.g., the use of different Abs to stain PD-L1, the use of frozen versus paraffin-embedded material for IHC, and the detection of membranous and/or cytoplasmic staining of PD-L1. Taube et al., 2012 note that PD-L1 is a type I transmembrane molecule, and hypothesize that while the cytoplasmic presence of PD-L1 may represent intracellular stores of this polypeptide that may be deployed to the cell surface upon appropriate stimulation, it is cell surface PD-L1 expression of that is biologically relevant as a potential biomarker for predicting clinical response to PD-1 blockade. See, also, Brahmer et al., 2010, which describes preliminary evidence, obtained on a small sample size of only 9 patients, of a correlation between membranous PD-L1 expression and anti-PD-1 efficacy. The data described in the Examples below on the use of membranous PD-L1 expression as a biomarker for anti-PD-1 efficacy, which was obtained from analysis of a much larger sample, substantiate the hypothesis that PD-L1 expression may be used as a biomarker for predicting anti-PD-1 clinical response and for screening patients to identify suitable candidates for immunotherapy with an anti-PD-1 Ab or other inhibitors of inhibitory immunoregulators.

Specifically, membranous PD-L1 expression was assayed using an automated IHC protocol and a rabbit anti-hPD-L1 Ab. Strikingly, in the initial set of data analyzed (see Example 8), no patients with cell surface PD-L1-negative tumors (MEL, NSCLC, CRC, RCC and CRPC) experienced an OR following treatment with the anti-PD-1 Ab, nivolumab. In contrast, cell surface expression of PD-L1 on tumor cells in pretreatment biopsies may be associated with an increased rate of OR among patients treated with nivolumab. While tumor cell expression of PD-L1 may be driven by constitutive oncogenic pathways, it may also reflect "adaptive immune resistance" in response to an endogenous antitumor immune response, part of a host inflammatory response, which may remain in check unless unleashed by blockade of the PD-1/PD-L1 pathway (Taube et al., 2012). This emerging concept of adaptive immune resistance in cancer immunology suggests that inhibitory ligands such as PD-L1 are induced in response to immune attack (Gajewski et al., 2010; Taube et al., 2012). A major implication of the clinical activity of immune checkpoint blockade as described herein is that significant endogenous immune responses to tumor antigens are generated and these responses may be harnessed therapeutically to mediate clinical tumor regression upon checkpoint inhibition. This potential mechanism of immune resistance by tumors suggests that PD-1/PD-L1-directed therapy might synergize with other treatments that enhance endogenous antitumor immunity. It also suggests that cell surface expression of PD-L1 in tumors and/or inflammatory cells in the tumor microenvironment may be a marker not just for treatment of cancer patients with an anti-PD-1 Ab, but also for treatment with an anti-PD-L1 Ab as well as treatments targeting inhibitory immunoregulatory pathways other than the PD-1/PD-L1 pathway.

Assaying Cell-Surface PD-L1 Expression by Automated IHC

As described in the Examples, an automated IHC method was developed for assaying the expression of PD-L1 on the surface of cells in FFPE tissue specimens. The disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a mAb that specifically binds to human PD-L1, under conditions that allow for formation of a complex between the Ab or portion thereof and human PD-L1. Preferably, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary Ab; incubating with a post-primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1 tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently and the scores are subsequently consolidated. In certain other embodiments, the identification of positive and negative cells is scored using appropriate software.

A histoscore is used as a more quantitative measure of the IHC data. The histoscore is calculated as follows:

$$\text{Histoscore} = [(\% \ \text{tumor} \times 1(\text{low intensity})) + (\% \ \text{tumor} \times 2(\text{medium intensity})) + (\% \ \text{tumor} \times 3(\text{high intensity})]$$

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., 2012).

Cancer Immunotherapy with Anti-PD-1 Comprising a Patient Selection Step

This disclosure also provides a method for immunotherapy of a subject afflicted with cancer, which method comprises: (a) selecting a subject that is a suitable candidate for immunotherapy, the selecting comprising (i) optionally providing a test tissue sample obtained from a patient with cancer of the tissue, the test tissue sample comprising tumor cells and tumor-infiltrating inflammatory cells, (ii) assessing the proportion of cells in the test tissue sample that express PD-L1 on the cell surface, and (iii) selecting the subject as a suitable candidate based on an assessment that the proportion of cells in the test tissue sample that express PD-L1 on the cell surface exceeds a predetermined threshold level; and (b) administering to the selected subject a composition comprising a therapeutically effective amount of an agent that inhibits signaling from an inhibitory immunoregulator.

There is evidence that membranous PD-L1 expression is a surrogate for an endogenous antitumor immune response that is part of a host inflammatory response (Gajewski et al., 2010; Taube et al., 2012). Accordingly, cell surface expression of PD-L1 in tumors and/or tumor-infiltrating inflammatory cells is a marker not just for selecting cancer patients who would benefit from treatment with an anti-PD-1 Ab, but also for treatment with an anti-PD-L1 Ab as well as treatments targeting inhibitory immunoregulatory pathways other than the PD-1/PD-L1 pathway. For example, cell surface expression of PD-L1 in tumors and/or tumor-infiltrating inflammatory cells may be used as a marker for identifying or selecting suitable cancer patients who would benefit from immunotherapy with agents, including Abs, that target, and disrupt or inhibit signaling from, inhibitory immunoregulators such as PD-L1, Cytotoxic T-Lymphocyte Antigen-4 (CTLA-4), B and T Lymphocyte Attenuator (BTLA), T cell Immunoglobulin and Mucin domain-3 (TIM-3), Lymphocyte Activation Gene-3 (LAG-3), Killer cell Lectin-like Receptor G1 (KLRG-1), Natural Killer Cell Receptor 2B4 (CD244), and CD160 (Baitsch et al., 2012). In certain preferred embodiments, the inhibitory immunoregulator is a component of the PD-1/PD-L1 signaling pathway. In other preferred embodiments, the inhibitory immunoregulator is an anti-PD-1 Ab of the invention. In yet other preferred embodiments, the inhibitory immunoregulator is an anti-PD-L1 Ab of the invention.

Although many of the immunotherapy methods below comprising assaying PD-L1 expression, i.e., employing a PD-L1 expression biomarker, are described as comprising the selection of a patient that is, or is not, suitable for anti-PD-1 immunotherapy or as comprising the administration of an anti-PD-1 Ab for immunotherapeutic purposes, it should be understood that these methods apply generally to the selection of a patient that is, or is not, suitable for immunotherapy with, or to the administration of an inhibitor of an inhibitory immunoregulator or a component or ligand thereof. Further, in any the methods comprising the measurement of PD-L1 expression in a test tissue sample, it should be understood that the step comprising the provision of a test tissue sample obtained from a patient is an optional step. That is, in certain embodiments the method includes this step, and in other embodiments, this step is not included in the method. It should also be understood that in certain preferred embodiments the "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other medical practitioner for use in selecting a suitable candidate for immunotherapy and/or administering an immunotherapeutic agent to the patient. In certain embodiments, the steps that provide the intermediate result may be performed by a medical practitioner or someone acting under the direction of a medical practitioner. In other embodiment, these steps are performed by an independent person or laboratory.

The disclosure further provides a method for treatment of a subject afflicted with cancer, which method comprises: (a) selecting a subject that is not suitable for treatment with an agent that inhibits an inhibitory immunoregulator, e.g., anti-PD-1 Ab immunotherapy, the selecting comprising (i) optionally providing a test tissue sample obtained from a patient with cancer of the tissue, the test tissue sample comprising tumor cells and tumor-infiltrating inflammatory cells; (ii) assessing the proportion of cells in the test tissue sample that express PD-L1 on the surface of the cells; and (iii) selecting the subject as not suitable for immunotherapy with an inhibitor of an inhibitory immunoregulator, e.g., an anti-PD-1 Ab, based on an assessment that the proportion of cells in the test tissue sample that express PD-L1 on the cell surface is less than a predetermined threshold level; and (b) administering a standard-of-care therapeutic other than an inhibitor of an inhibitory immunoregulator, e.g., an anti-PD-1 Ab, to the selected subject.

Measurement of PD-L1 Expression

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In preferred embodiments, PD-L1 expression is assayed by IHC. Flow cytometry may be particularly suitable for assaying PD-L1 expression in cells of hematologic tumors. In preferred embodiments of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis et al., 2010). Ab specificity, coupled with the sensitivity and resolution of PET, makes immunoPET imaging particularly attractive for monitoring and assaying expression of antigens in tissue samples (McCabe et al., 2010; Olafsen et al., 2010). In certain embodiments of any of the present methods, PD-L1 expression is assayed by immunoPET imaging.

In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In certain preferred embodiments, the presence of PD-L1 polypeptide is determined by IHC assay. In further embodiments, the IHC assay is performed using an automated process. In further embodiments, the IHC assay is performed using an anti-PD-L1 mAb to bind to the PD-L1 polypeptide.

Abs that Bind Specifically to Cell-Surface-Expressed PD-L1 in FFPE Tissues

An Ab may bind to an antigen in fresh tissues but completely fail to recognize the antigen in an FFPE tissue sample. This phenomenon, well known in the art, is thought to be due primarily to intra- and inter-molecular cross-linking of polypeptides induced by formalin fixation, which alters the epitope recognized by the Ab (Sompuram et al., 2006). In addition, several factors known to influence staining in FFPE tissue, including variable time to fixation, inadequate fixation period, differences in fixative used, tissue processing, Ab clone and dilution, antigen retrieval, detection system, and interpretation of results using different threshold points are important variables that can affect tissue antigenicity and IHC measurements (Bordeaux et al., 2010). In particular, a lack of anti-human PD-L1 Abs that stain PD-L1 in FFPE specimens has been noted in the art (Hamanishi et al., 2007). Thus, the contradictory results reported by different groups on the implications of PD-L1 expression for prognosis of a tumor may, in part, reflect the differential abilities of anti-PD-L1 Abs used to detect PD-L1 polypeptide in FFPE tissue samples. Indeed, our analysis of five commercially available anti-hPD-L1 Abs shows that these Abs failed to distinguish FFPE cells expressing PD-L1 from cells that did not express PD-L1 (see Example 9, Table 6). Accordingly, in order to detect hPD-L1 on the surface of cells using an IHC assay on FFPE tissues, there is a need for anti-hPD-L1 Abs that bind specifically to cell surface-expressed PD-L1 in FFPE tissue samples.

This disclosure provides a mAb or an antigen-binding portion thereof that binds specifically to a cell surface-expressed PD-L1 antigen in a FFPE tissue sample. In preferred embodiments, the mAb or antigen-binding portion thereof does not bind to a cytoplasmic PD-L1 polypeptide in the FFPE tissue sample or exhibits a very low level of background binding. In certain other embodiments, the presence or absence of binding specifically to a cell surface-expressed or a cytoplasmic PD-L1 polypeptide is detected by immunohistochemical staining. In certain preferred aspects of the invention, the mAb or antigen-binding portion is a rabbit Ab or a portion thereof. In other preferred embodiments, the mAb is the rabbit mAb designated 28-8, 28-1, 28-12, 29-8 or 20-12. In more preferred embodiments, the mAb is the rabbit mAb designated 28-8 or an antigen-binding portion thereof. In further embodiments, the mAb is an Ab comprising a heavy chain variable region ($V_H$)

comprising consecutively linked amino acids having the sequence set forth in SEQ ID NO: 35 and a light chain variable region ($V_\kappa$) comprising consecutively linked amino acids having the sequence set forth in SEQ ID NO: 36. In other embodiments, the mAb comprises the CDR1, CDR2 and CDR3 domains in a $V_H$ having the sequence set forth in SEQ ID NO: 35, and the CDR1, CDR2 and CDR3 domains in a $V_\kappa$ having the sequence set forth in SEQ ID NO: 36.

It is known in the art that rabbit Abs have certain advantages over murine Abs. For example, rabbit Abs generally exhibit more diverse epitope recognition, improved immune response to small-size epitopes, and higher specificity and affinity compared to murine Abs (see, e.g., Fischer et al., 2008; Cheang et al., 2006; Rossi et al., 2005). For example, the rabbit's lower immune dominance and larger B-cell repertoire results in greater epitope recognition compared to murine Abs. Further, the high specificity and novel epitope recognition of rabbit antibodies translates to success with recognition of post-translational modifications (Epitomics, 2013). In addition, many protein targets relevant to signal transduction and disease are highly conserved between mice, rats and humans, and can therefore be recognized as self-antigens by a mouse or rat host, making them less immunogenic. This problem is avoided by generating Abs in rabbits. In addition, in applications in which two antigen-specific Abs are required, it is more convenient to have the Abs come from two different species. Thus, for example, it is easier to multiplex a rabbit Ab such as 28-8 with other Abs (likely to be murine Abs since the best immune marking Abs are murine Abs) that can mark immune cells that also express PD-L1 (e.g., macrophages and lymphocytes). Thus, rabbit anti-hPD-L1 mAbs, e.g., 28-8, are particularly suited to IHC assays for detecting surface-expressed PD-L1 in FFPE tissue samples and have distinct advantages over murine Abs, such as 5H1.

As described in Example 9, a large number (185) of antibody multiclones from both rabbit and mouse immunizations were screened, and only ten rabbit Ab, but no mouse Ab, multiclones specifically detected the membranous form of hPD-L1. After further extensive screening by multiple rounds of IHC, 15 purified rabbit subclones were selected based on their specificity and intensity of staining (see Table 4). Following further characterization of the antibodies to determine their binding affinity and cross-competition by surface plasmon resonance, as well as screening by IHC on FFPE tissues, mAb 28-8 was selected as the Ab with the best combination of binding to membranous PDF-L1 with high affinity and specificity, and low background staining.

In certain aspects of this invention, the mAb or antigen-binding portion cross-competes with mouse mAb 5H1 for binding to PD-L1, which indicates that these antibodies bind to the same epitope region of PD-L1. In certain other aspects, the mAb or antigen-binding portion thereof does not cross-compete with mouse mAb 5H1 for binding to PD-L1, indicating that they do not bind to the same epitope region of PD-L1.

The disclosure also provides nucleic acids encoding all of the rabbit anti-hPD-L1 Abs or portions thereof disclosed herein.

Immunotherapeutic Methods Comprising Measurement of Cell Surface PD-L1 Expression The availability of rabbit Abs that bind with high affinity specifically to membranous PD-L1 in FFPE tissue specimens facilitates methods comprising a step of detecting PD-L1 polypeptide on the surface of cells in FFPE tissue samples. Accordingly, this disclosure also provides a method for immunotherapy of a subject afflicted with cancer, which method comprises: (a) selecting a subject that is a suitable candidate for immunotherapy, the selecting comprising: (i) optionally providing a FFPE test tissue sample obtained from a patient with cancer of the tissue, the test tissue sample comprising tumor cells and tumor-infiltrating inflammatory cells; (ii) assessing the proportion of cells in the test tissue sample that express PD-L1 on the cell surface by IHC using a rabbit anti-human PD-L1 Ab, e.g., mAb 28-8, to bind to the PD-L1; and (iii) selecting the subject as a suitable candidate based on an assessment that the proportion of cells in the test tissue sample that express PD-L1 on the cell surface exceeds a predetermined threshold level; and (b) administering a composition comprising a therapeutically effective amount of an anti-PD-1 Ab to the selected subject.

In certain embodiments of methods employing IHC to assay PD-L1 expression in FFPE tissues, an automated IHC assay is used. The automated IHC process is performed on an autostainer and comprises: (a) de-paraffinizing the FFPE sample with xylene and rehydrating the sample; (b) retrieving the antigen using a decloaking chamber; (c) blocking nonspecifc protein binding sites by incubation with a Protein Block; (d) incubating the sample with a primary anti-PD-L1 Ab; (e) adding a polymeric horseradish peroxidase (HRP)-conjugated secondary Ab; (f) detecting the bound secondary Ab comprising staining with a 3,3'-diaminobenzidine (DAB) chromogen; and/or (g) counterstaining with hematoxylin. This automated IHC process has been optimized by minimization of the number of steps, optimization of incubation times, and selection of primary Abs, blocking and detection reagents that produce strong specific staining with a low level of background staining. In preferred embodiments of this automated IHC assay, the primary anti-PD-L1 Ab is rabbit mAb 28-8 or murine mAb 5H1. In certain embodiments of this invention, this IHC assay, and any other IHC assay described herein to measure PD-L1 expression, may be used as part of a method of immunotherapy. In other embodiments, any of the IHC methods described herein is used independently of any therapeutic process requiring the administration of a therapeutic, i.e., solely as a diagnostic method to assay PD-L1 expression.

In certain embodiments any of the immunotherapy methods described herein, the Ab administered to the selected subject is any anti-PD-1 or anti-PD-L1 Ab or antigen-binding portion thereof of the invention. In certain preferred embodiments, the subject is a human. In other preferred embodiments, the Ab is a human Ab or antigen-binding portion thereof. In more preferred embodiments, the anti-PD-1 Ab is nivolumab and the anti-PD-L1 Ab is BMS-936559. In certain other embodiments, the anti-PD-1 Ab is an Ab or antigen-binding portion thereof that cross-competes with nivolumab for binding to PD-1, and the anti-PD-L1 Ab is an Ab or antigen-binding portion thereof that cross-competes with BMS-936559 for binding to PD-L1. In certain preferred embodiments, the cancer to be treated is selected from the group consisting MEL, RCC, squamous NSCLC, non-squamous NSCLC, CRC, castration-resistant prostate cancer CRPC, HCC, squamous cell carcinoma of the head and neck, carcinomas of the esophagus, ovary, gastrointestinal tract and breast, and a hematological malignancy.

In certain embodiments of the disclosed methods, the predetermined threshold is based on a proportion of (a) tumor cells, (b) tumor-infiltrating inflammatory cells, (c) particular tumor-infiltrating inflammatory cells, e.g., TILs or macrophages, or (d) a combination of tumor cells and tumor-infiltrating inflammatory cells, in a test tissue sample that expresses PD-L1 on the cell surface. In certain embodiments, the predetermined threshold is at least 0.001% of tumor cells expressing membranous PD-L1 as determined by IHC. In other embodiments, the predetermined threshold is at least 0.01%, preferably at least 0.1%, more preferably at least 1% of tumor cells expressing membranous PD-L1, as determined by IHC. In certain embodiments, the predetermined threshold is at least 5% of tumor cells expressing membranous PD-L1 as determined by IHC. In certain embodiments, the predetermined threshold is at least 0.01%, at least 0.1%, at least 1%, or at least 5% of tumor cells expressing membranous PD-L1 as determined by IHC, and/or a single tumor-infiltrating inflammatory cell expressing membranous PD-L1 as determined by IHC. In certain other embodiments, the predetermined threshold is at least 0.01%, at least 0.1%, at least 1%, or at least 5% of a tumor-infiltrating inflammatory cell expressing membranous PD-L1 as determined by IHC. In certain other embodiments, the predetermined threshold is at least 0.01%, at least 0.1%, at least 1%, or at least 5% of a tumor-infiltrating lymphocyte expressing membranous PD-L1 as determined by IHC. In certain other embodiments, the predetermined threshold is at least 0.01%, at least 0.1%, at least 1%, or at least 5% of a tumor-infiltrating macrophage expressing membranous PD-L1 as determined by IHC. In yet other embodiments, the predetermined threshold is at least a single tumor cell or a single tumor-infiltrating inflammatory cell expressing membranous PD-L1 as determined by IHC. Preferably, PD-L1 expression is assayed by automated IHC using mAb 28-8 or 5H1 as the primary Ab.

This disclosure also provides a method for treatment of a subject afflicted with cancer, which method comprises: (a) screening a plurality of subjects to identify a subject that is not a suitable candidate for immunotherapy comprising the administration of an anti-PD-1 Ab to the subject, the screening comprising: (i) optionally providing test tissue samples from the plurality of subjects, the test tissue samples comprising tumor cells and tumor-infiltrating inflammatory cells; (ii) assessing the proportion of cells in the test tissue samples that express PD-L1 on the surface of the cells; and (iii) selecting the subject as a candidate that is not suitable for anti-PD-1 Ab immunotherapy based on an assessment that the proportion of cells that express PD-L1 on the surface of cells in the subject's test tissue sample is below a predetermined threshold level; and (b) administering a standard-of-care therapeutic other than an anti-PD-1 Ab to the selected subject.

This disclosure also provides a method for immunotherapy of a subject afflicted with cancer, which method comprises: (a) screening a plurality of subjects to identify a subject that is a suitable candidate for immunotherapy, the screening comprising: (i) optionally providing test tissue samples from the plurality of subjects, the test tissue samples comprising tumor cells and tumor-infiltrating inflammatory cells; (ii) assessing the proportion of cells in the test tissue samples that express PD-L1 on the surface of the cells; and (iii) selecting the subject as a candidate that is suitable for anti-PD-1 Ab immunotherapy based on an assessment that the proportion of cells in the test tissue sample that express PD-L1 on the cell surface exceeds a predetermined threshold level; and (b) administering a composition comprising a therapeutically effective amount of an anti-PD-1 Ab to the selected subject.

This disclosure further provides a method for treatment of a subject afflicted with cancer, which method comprises: (a) screening a plurality of subjects to identify a subject that is a suitable candidate for the treatment, the screening comprising: (i) optionally providing test tissue samples from the plurality of subjects, the test tissue samples comprising tumor cells and tumor-infiltrating inflammatory cells; (ii) assessing the proportion of cells in the test tissue samples that express PD-L1 on the surface of the cells, wherein the subject is identified as a suitable candidate for anti-PD-1 Ab immunotherapy if the proportion of cells in the tissue sample that express PD-L1 on the cell surface exceeds a predetermined threshold level, and the subject is identified as a candidate that is not a suitable candidate for anti-PD-1 Ab immunotherapy if the proportion of cells in the tissue sample that express PD-L1 on the cell surface is below a predetermined threshold level; and (b) administering a composition comprising a therapeutically effective amount of an anti-PD-1 Ab to the subject identified as a suitable candidate for anti-PD-1 Ab immunotherapy, or (c) administering a standard-of-care therapeutic other than an anti-PD-1 Ab to the subject identified as not a suitable candidate for anti-PD-1 Ab immunotherapy.

One aspect of this invention is a method for immunotherapy of a subject afflicted with cancer, which method comprises: (a) optionally providing a test tissue sample obtained from a patient with cancer of the tissue, the test tissue sample comprising tumor cells and tumor-infiltrating inflammatory cells; (b) determining that a proportion of cells in the test tissue sample express PD-L1 above a predetermined threshold level on the cell surface; and (c) based on that determination administering a composition comprising a therapeutically effective amount of an anti-PD-1 Ab to the subject. Another aspect of the invention is a method for treatment of a subject afflicted with cancer, which method comprises: (a) optionally providing a test tissue sample obtained from a patient with cancer of the tissue, the test tissue sample comprising tumor cells and tumor-infiltrating inflammatory cells; (b) determining that the proportion of cells in the test tissue sample that express PD-L1 on the cell surface is below a predetermined threshold level; and (c) based on that determination administering a standard-of-care therapeutic other than an anti-PD-1 Ab to the subject.

Yet another aspect of the invention is a method for immunotherapy of a subject afflicted with cancer, which method comprises: (a) optionally providing a test tissue sample obtained from a patient with cancer of the tissue, the test tissue sample comprising tumor cells and tumor-infiltrating inflammatory cells; (b) determining that cells in the test tissue sample express PD-L1 on the cell surface; (c) selecting an anti-PD-1 Ab as a treatment for the subject based on the recognition that an anti-PD-1 Ab is effective in patients whose test tissue sample contains a proportion of cells above a predetermined threshold level that express PD-L1 on the cell surface; and (d) administering a composition comprising a therapeutically effective amount of an anti-PD-1 Ab to the subject. In a further aspect, the disclosure provides a method for treatment of a subject afflicted with cancer, which method comprises: (a) optionally providing a test tissue sample obtained from a patient with cancer of the tissue, the test tissue sample comprising tumor cells and tumor-infiltrating inflammatory cells; (b) determining that cells in the test tissue sample do not express PD-L1 on the cell surface; (c) selecting a standard-of-care therapeutic other than an anti-PD-1 Ab as a treatment for the subject based on the recognition that an anti-PD-1 Ab is ineffective in patients whose test tissue sample contains a proportion of cells that express PD-L1 on the cell surface is below a predetermined threshold level; and (d) administering the standard-of-care therapeutic to the subject.

This disclosure also provides a method of selecting an immunotherapy for a subject afflicted with cancer, which method comprises: (a) assaying cells of a test tissue sample comprising tumor cells and tumor-infiltrating inflammatory cells to assess the proportion of cells in the test tissue sample that express PD-L1; and (b) based on an assessment that the proportion of cells that express membranous PD-L1 is above a predetermined threshold level, selecting an immunotherapy comprising a therapeutically effective amount of an anti-PD-1 Ab for the subject. The disclosure further provides a method of selecting a treatment for a subject afflicted with cancer, which method comprises: (a) assaying cells of a test tissue sample comprising tumor cells and tumor-infiltrating inflammatory cells to assess the proportion of cells in the test tissue sample that express PD-L1; and (b) based on an assessment that the proportion of cells that express membranous PD-L1 is below a predetermined threshold level, selecting a standard-of-care treatment other than an anti-PD-1 Ab for the subject.

In addition, the disclosure provides a method for treatment of a subject afflicted with cancer, which method comprises administering to the subject a composition comprising a therapeutically effective amount of an anti-PD-1 Ab, the subject having been selected on the basis that the proportion of cells in a test tissue sample from the subject that express PD-L1 is determined to exceed a predetermined threshold level, wherein the test tissue sample comprises tumor cells and tumor-infiltrating inflammatory cells. This disclosure also provides a method for treatment of a subject afflicted with cancer, which method comprises administering to the subject a standard-of-care treatment other than an anti-PD-1 Ab, the subject having been selected on the basis that the proportion of cells in a test tissue sample from the subject that express PD-L1 is determined to be below a predetermined threshold level, wherein the test tissue sample comprises tumor cells and tumor-infiltrating inflammatory cells.

This disclosure further provides a method for selecting a cancer patient for immunotherapy with an anti-PD-1 Ab, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold proportion; and (d) selecting the patient for immunotherapy based on an assessment that the proportion of cells in the test tissue sample that express surface PD-L1 is above the predetermined threshold level. In any of the methods described herein comprising a step for assessing PD-L1 expression, the test tissue sample may be a FFPE tissue sample.

In addition, in any method where an immunotherapy is selected or administered based on an assessment that the proportion of cells in a test tissue sample from the subject expresses PD-L1 at a level above a predetermined threshold level, it follows that a complementary method of treatment may be performed wherein a standard-of-care treatment other than the immunotherapy is selected or administered based on an assessment that the proportion of cells in a test tissue sample from the subject expresses PD-L1 at a level below the predetermined threshold level.

This disclosure further provides a method for predicting the therapeutic effectiveness of an anti-PD-1 Ab for treating a cancer patient, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold value; and (d) predicting the therapeutic effectiveness of the anti-PD-1 Ab, wherein if the proportion of cells that express PD-L1 on the cell surface exceeds the threshold proportion the Ab is predicted to be effective in treating the patient, and wherein if the proportion of cells that express PD-L1 on the cell surface is below the threshold proportion the Ab is predicted to not be effective in treating the patient.

This disclosure also provides a method for determining an immunotherapeutic regimen comprising an anti-PD-1 Ab for treating a cancer patient, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold proportion; and (d) determining an immunotherapeutic regimen comprising an anti-PD-1 Ab based on the determination that the proportion of cells that express PD-L1 on the cell surface exceeds the predetermined threshold proportion.

Standard-of-Care Therapeutics

Several of the methods of treatment described herein comprise the administration of a standard-of-care therapeutic to a patient. As used herein, a "standard-of-care therapeutic" is a treatment process, including a drug or combination of drugs, radiation therapy, surgery or other medical intervention that is recognized by medical practitioners as appropriate, accepted, and/or widely used for a certain type of patient, disease or clinical circumstance. Standard-of-care therapeutics for treating different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2013). By way of example, standard-of-care treatments for MEL, RCC and NSCLC are summarized below.

Melanoma

For in situ or early-stage MEL, surgical treatment is the primary treatment. Where surgical excision is not feasible for in situ melanoma due to comorbidity or cosmetically sensitive tumor location, topical imiquimod and radiotherapy are emerging as treatments, especially for lentigo maligna. Chemotherapeutic agents for treating MEL include dacarbazine, temozolomide, imatinib for melanoma with c-KIT mutation, high-dose interleukin-2, and paclitaxel with or without carboplatin. However, these treatments have modest success, with response rates below 20% in first-line (1L) and second-line (2L) settings.

There is no consensus on the best treatments for metastatic melanoma, though a variety of treatments including excision to clear margins, intralesional injections, laser ablation, radiation and biochemotherapy (combination of chemotherapy and biological agents such as interferon-alpha and IL-2) are being investigated. The therapeutic landscape for metastatic melanoma has recently seen dramatic improvements with the development of novel drugs such as vemurafenib and ipilimumab. Vemurafenib specifically inhibits signaling by a mutated intracellular kinase, BRAF, that is present in about 50% of patients with metastatic melanoma (Flaherty et al., 2010). Ipilimumab is a HuMAb that inhibits the immune checkpoint receptor, CTLA-4, and thereby stimulates a T cell immune response (Hodi et al., 2010). Besides these two agents, no other agent has demonstrated an OS benefit in a Phase 3 randomized study. Dacarbazine is approved by the FDA and the EMA for treatment of metastatic MEL with a reported objective response rate of 5% to 20% and a median OS of 6.4 months, but these responses are short-lived. Other drugs such as temozolomide and fotemustine have not resulted in significant improvement in survival when compared to dacarbazine. IL-2 has also been approved by the FDA for the treatment of metastatic MEL as it is associated with a 15 to 20% response rate including 4-6% complete responses which can be durable, but it is associated with significant toxicities including hypotension, cardiac arrhythmias, and pulmonary edema. Further details on standard-of-care treatments for melanoma are provided by Garbe et al., 2012. Despite the recent approval of ipilimumab and vemurafenib for advanced MEL, there is still a large unmet need for patients who have progressed on anti-CTLA-4 therapy and a BRAF inhibitor (depending on BRAF status) or patients with previously untreated, unresectable or metastatic BRAF wild-type MEL. The 5-year survival rate for late-stage MEL is currently only 15%.

Renal Cell Carcinoma

For clinically localized RCC (Stage IA and IB), surgical resection, including radical nephrectomy and nephron-sparing surgery, is an effective therapy. Partial nephrectomy is generally not suitable for patients with locally advanced tumors (Stage II and III), in which case radical nephrectomy is preferred. Patients with Stage IV disease may also benefit from surgery, and cytoreductive nephrectomy before systemic therapy is recommended for patients with a potentially surgically resectable primary and multiple resectable metastases.

Until recently, the cytokines IL-2 and IFNα were the only active systemic treatments for advanced or metastatic RCC. However, due to each of these agent's limited clinical benefit and substantial toxicity profile, newer targeted agents have largely replaced cytokines in the treatment of advanced or metastatic renal cell carcinoma. The recognition of the importance of hypoxia inducible factor alpha (HIFa) signaling in the pathogenesis of clear-cell RCC has led to widespread study of two classes of targeted therapies, anti-angiogenic agents and mammalian target of rapamycin (mTOR) inhibitors (Mulders, 2009). Targeting of angiogenesis is rational because constitutive HIFa activation leads to the upregulation or activation of several proteins including vascular endothelial growth factor (VEGF), which can subsequently lead to tumor proliferation and neovasculature formation. Targeting of the mTOR pathway is important because activation of the upstream PI3K/Akt/mTOR signaling pathway is one method by which constitutive HIFa activation or upregulation occurs (Mulders, 2009). Agents that target angiogenesis include VEGF-receptor (VEGFr) TKIs (e.g., sorafenib, sunitinib, pazopanib, axitinib, and tivozanib) and VEGF-binding mAbs (e.g., bevacizumab), while agents that target the mTOR pathway include the mTOR inhibitors (e.g., everolimus and temsirolimus). However, most patients develop resistance, and overall survival (OS) improvement has only been shown in one Phase 3 trial in poor-risk patients. Everolimus demonstrated a 3-month improvement in median progression-free survival (PFS) versus placebo, with no OS improvement (Motzer et al., 2008). Among the five approved anti-angiogenic agents (sorafenib, sunitinib, bevacizumab, pazopanib, and axitinib)

and two approved mTOR inhibitors (temsirolimus, everolimus), only everolimus is approved specifically for use after the failure of treatment with anti-angiogenic therapy. In the US, everolimus is indicated for the treatment of advanced RCC after failure of treatment with sunitinib or sorafenib, whereas in the EU, everolimus is more broadly indicated for patients with advanced RCC, whose disease has progressed on or after treatment with VEGF-targeted therapy.

Non-Small Cell Lung Cancer

NSCLC is the leading cause of cancer death worldwide, exceeding breast, colon and prostate cancer combined. The majority of subjects (approximately 78%) are diagnosed with advanced/recurrent or metastatic disease. NSCLC therapies have incrementally improved OS, but benefit has reached a plateau (median OS for late stage patients is just 1 year). Progression after 1 L therapy occurred in nearly all of these subjects and the 5-year survival rate is only 3.6% in the refractory setting.

There is a particular unmet need among patients who have squamous cell NSCLC (representing up to 25% of all NSCLC) as there are few treatment options after 1 L therapy. Surgery, radiation therapy (RT) and chemotherapy are the three modalities commonly used to treat NSCLC patients. As a class, NSCLCs are relatively insensitive to chemotherapy, compared to small cell carcinoma. In general, for patients with Stage I or II disease, surgery provides the best chance for cure, with chemotherapy increasingly being used both pre-operatively and post-operatively. RT can also be used as adjuvant therapy for patients with resectable NSCLC, the primary local treatment, or as palliative therapy for patients with incurable NSCLC.

Patients with Stage IV disease who have a good performance status (PS) benefit from chemotherapy. Many drugs, including platinum agents (e.g., cisplatin, carboplatin), taxanes agents (e.g., paclitaxel, albumin-bound paclitaxel, docetaxel) vinorelbine, vinblastine, etoposide, pemetrexed and gemcitabine are useful for Stage IV NSCLC. Combinations using many of these drugs produce 1-year survival rates of 30% to 40% and are superior to single agents. Specific targeted therapies have also been developed for the treatment of advanced lung cancer. For example, bevacizumab (AVASTIN®) is a mAb that blocks vascular endothelial growth factor A (VEGF-A). Erlotinib (TARCEVA®) is a small-molecule TKI of epidermal growth factor receptor (EGFR). Crizotinib (XALKORI®) is a small-molecule TKI that targets ALK and MET, and is used to treat NSCLC in patients carrying the mutated ALK fusion gene. Cetuximab (ERBITUX®) is a mAb that targets EGFR.

Squamous cell carcinoma (SCC) represents one quarter of NSCLC cases and has limited treatment options. Currently, second-line treatment for SCC remains an area of unmet need. Single-agent chemotherapy is standard of care following progression with platinum-based doublet chemotherapy (Pt-doublet), resulting in median OS of approximately 7 months. Docetaxel remains the benchmark treatment in this line of therapy although erlotinib may also used with less frequency. Pemetrexed has also been shown to produce clinically equivalent efficacy outcomes but with significantly fewer side effects compared with docetaxel in the 2L treatment of patients with advanced NSCLC (Hanna et al., 2004). No therapy is currently approved for use in lung cancer beyond the 3L setting. Pemetrexed and bevacizumab are not approved in SCC, and molecularly targeted therapies have limited application.

The present invention is further illustrated by the following examples which should not be construed as further limiting. The contents of all figures and all references, patents and published patent applications cited throughout this application are expressly incorporated herein by reference.

Example 1

Cross-Competition Between Anti-PD-1 HuMAbs for Binding to CHO Cells Expressing Human PD-1

Chinese Hamster Ovary (CHO) cells transfected to express human PD-1 (CHO/PD-1 cells) were incubated with 10 µg/ml of Fab fragment of the anti-PD-1 HuMAb 5C4 or human IgG1 (hIgG1) isotype control Ab for 30 minutes at 4° C. before addition of anti-PD-1 HuMAbs 2D3, 7D3 or 4H1 at a concentration of 0.2 µg/ml. Binding of 4H1, 2D3 or 7D3 to CHO/PD-1 cells were detected by fluorescein isothiocyanate (FITC)-conjugated goat anti-hIgG, Fe-gamma specific Ab. In the case of cross-competition assay with 5C4 and 17D8, CHO/PD-1 cells were incubated with the whole molecule of 5C4 before addition of FITC-labeled 17D8. Binding of 2D3, 7D3, 4H1 or 17D8 to the CHO/PD-1 cells was measured by flow cytometric analysis using a FACS® calibur flow cytometer (Becton Dickinson, San Jose, CA).

The results are depicted in FIG. 1. The data show that the 5C4 Fab fragment substantially blocked the binding of mAbs 5C4 itself, as well as the binding of 2D3, 7D3 (FIG. 1A) and 4H1 (FIG. 1B), while the 5C4 whole mAb substantially blocked the binding of 17D8 (FIG. 1C) to CHO/PD-1 cells as measured by mean fluorescent intensity (MFI) of staining.

Example 2

Cross-Competition Between Anti-PD-L1 HuMAbs for Binding to CHO Cells Expressing Human PD-L1

CHO cells transfected to express hPD-L1 (CHO/PD-L1 cells) were incubated with 10 µg/ml of each of ten unconjugated human anti-PD-L1 mAbs (5F8, 7H1, 10H10, 1B12, 3G10, 10A5, 11E6, 12A4, 12B7, and 13G4) or human IgG1 (hIgG1) isotype control Ab for 20 min at 4° C. FITC-conjugated 10H10 (A), 3G10 (B), 10A5 (C), 11E6 (D), 12A4 (E) or 13G4 (F) was added to the cells to a final concentration of 0.09 µg/ml (B, D), 0.27 µg/ml (A, C), 0.91 µg/ml (F), or 2.73 µg/ml (E) for an additional 20 min at 4° C. without prior washout of unbound, unconjugated Ab. Different quantities of the various FITC-conjugated HuMAbs were used due to differences in binding efficiency following labeling, and the optimal amounts of these FITC-conjugated HuMAbs were previously determined by dose-titration analysis of binding to CHO/PD-L1 cells. Binding of FITC-conjugated 10H10, 3G10, 10A5, 11E6, 12A4 or 13G4 to the CHO/PD-L1 cells was measured by flow cytometry.

The results are depicted in FIG. 2. Binding of labeled 10H10 was partially blocked by 10A5, 11E6 and 13G4, but was substantially blocked only by itself (FIG. 2A). Conversely, 10H10 substantially blocked the binding only of itself to CHO/PD-L1 cells. Each of anti-PD-L1 HuMAbs 5F8, 7H1, 1B12, 3G10, 10A5, 11E6, 12A4, 12B7 and 13G4 substantially blocked binding of labeled mAbs 3G10 (FIG. 2B), 10A5 (FIG. 2C), 11E6 (FIG. 2D), 12A4 (FIG. 2E) and 13G4 (FIG. 2F) to CHO/PD-L1 cells as measured by MFI, though mAbs 5F8 and 13G4 generally blocked binding of the labeled mAbs to a slightly lesser extent.

Example 3

Cross-Competition Between Anti-PD-L1 mAbs for Binding to Ovarian Carcinoma Cells Expressing Human PD-L1

Figure 3:
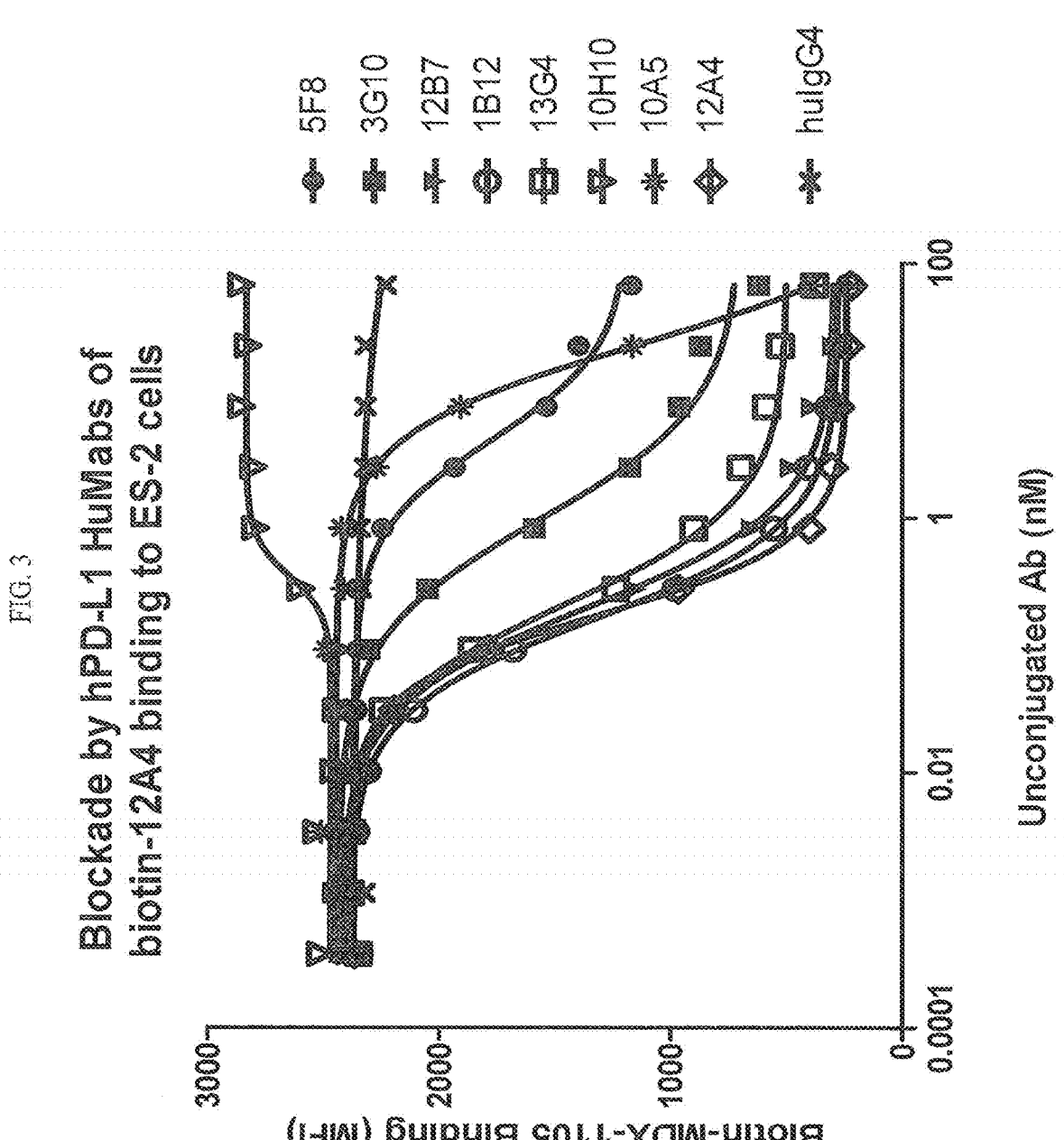
FIG. 3. Cross-competitive inhibition of binding of biotinylated mAb 12A4 to ES-2 cells by human anti-hPD-L1 mAbs. Fluorescence of bound biotin-12A4 is plotted against the concentration of unlabeled hPD-L1 HuMabs.

Anti-PD-L1 HuMAbs 5F8, 12B7, 3G10, 1B12, 13G4, 10H10, 10A5 and 12A4, and a human IgG1 (huIgG1) isotype control Ab were serially diluted from 10 μg/ml and incubated with hPD-L1-expressing ES-2 ovarian carcinoma cells for 20 minutes at 4° C. Without washing, biotinylated-12A4 Ab was added to a final concentration of 0.4 μg/ml for an additional 20 minutes at 4° C. After washing, bound biotin-12A4 was detected using fluorescent streptavidin-PE secondary reagent and measured by flow cytometry. FIG. 3 shows the fluorescence of bound biotin-12A4 plotted against the concentration of unlabeled hPD-L1 HuMAbs. Binding of biotin-12A4 to ES-2 cells was substantially blocked by 12A4 itself and by 1B12 and 12B7, and was moderately to significantly blocked by mAbs 5F8, 10A5, 13G4 and 3G10, but was not blocked by mAb 10H10.

Example 4

Design of Phase I Clinical Study of Anti-PD-1 Antibody

A Phase I study was conducted to assess the safety, antitumor activity, and pharmacokinetics of an anti-PD-1 in patients with selected advanced solid tumors. The human anti-PD-1 mAb, BMS-936558 (also referred to herein as nivolumab, and in U.S. Pat. No. 8,008,449 as 5C4), was administered as an intravenous infusion every 2 weeks of each 8-week treatment cycle. Patients continued treatment for up to 2 years (12 cycles), unless they experienced complete remission, unacceptable toxicity, disease progression, or withdrew consent. In patients who were otherwise clinically stable, study treatment was continued beyond apparent initial disease progression until further progression was noted as recommended by proposed immune response criteria (Wolchok et al., 2009). Patients with stable disease (SD) or an ongoing objective response (OR: complete [CR] or partial response [PR]) at the end of treatment were followed for 1 year and were offered retreatment for 1 additional year in the event of progression.

Dose Escalation

Patients with advanced melanoma (MEL), non-small cell lung (NSCLC), renal cell carcinoma (RCC), castration-resistant prostate (CRPC) and colorectal cancer (CRC) were eligible to enroll. Cohorts of 3-6 patients per dose level were enrolled sequentially at 1.0, 3.0, and 10.0 mg/kg. Dose escalation proceeded when a minimum of 3 patients had completed the safety evaluation period (56 days) at the given dose level, with dose-limiting toxicity in less than one-third of patients. Intra-patient dose escalation was not permitted.

Cohort Expansion

A maximum tolerated dose (MTD) was not reached. Initially, 5 expansion cohorts of approximately 16 patients each were enrolled at 10 mg/kg for MEL, NSCLC, RCC, CRPC and CRC. Based on initial signals of activity, additional expansion cohorts of approximately 16 patients each were enrolled for MEL (at 1.0 and 3.0 mg/kg, followed by cohorts randomized to 0.1, 0.3, or 1.0 mg/kg), NSCLC (squamous or nonsquamous histology cohorts randomized to 1, 3, or 10 mg/kg), and RCC (at 1.0 mg/kg).

Patients

Eligible patients had documented advanced solid tumors; age>18 years; life expectancy>12 weeks; Eastern Cooperative Oncology Group performance status of ≤2; measurable disease by Response Evaluation Criteria in Solid Tumors (RECIST), v1.0 with modification (see Topalian et al., 2012b); adequate hematologic, hepatic, and renal function; and received 1-5 prior systemic treatment regimens. Patients with stable treated brain metastases were enrolled. Exclusion criteria included a history of chronic autoimmune disease, prior therapy with T-cell modulating Abs (e.g., anti-CTLA-4), conditions requiring immunosuppressive medications, and chronic infections (HIV, hepatitis B or C).

A total of 296 patients with advanced solid tumors including MEL (n=104), NSCLC (n=122), RCC (n=34), CRPC (n=17), and CRC (n=19) were treated with BMS-936558 for 40 months up to February 2012. By March 2013, 304 patients including patients with non-small cell lung cancer (n=127), melanoma (n=107), RCC (n=34), CRPC (n=17), and CRC (n=19) had been treated with BMS-936558 from October 2008 through March 2012, all with a minimum of one year and up to about 4.4 years of observation. Two patients did not receive a full cycle of treatment and were not considered response-evaluable. The majority of patients were heavily pretreated, with 47% having received at least 3 prior regimens. Notable prior therapies included immunotherapy (64%) and B-RAF inhibitor (8%) in MEL patients; platinum-based chemotherapy (94%) and tyrosine kinase inhibitors (TKIs, 34%) in NSCLC patients; and nephrectomy (94%), immunotherapy (59%), and anti-angiogenic therapy (74%) in RCC patients. Baseline characteristics of the total treated population (N=296) were similar to those of the efficacy population (response evaluable patients, N=236). Details on the patient pre-treatments are provided in Topalian et al., 2012b.

Statistical Analysis

All patients (N=304) treated as of the date of analysis (March 2013) were used for summaries of baseline characteristics and AEs. Pharmacokinetic and molecular-marker populations consisted of treated patients with available data as of the date of analysis. The efficacy population consisted of response-evaluable patients commencing treatment at least 8 months before the date of analysis. Tumor measurements were collected after each treatment cycle (4 doses) by investigators. Individual best objective responses based on the tumor measurements were assessed by the sponsor per modified RECIST v1.0. Objective response was confirmed by at least one sequential tumor assessment. Objective response and stable disease rates were estimated with confidence intervals using the Clopper-Pearson method. Time-to-event endpoints including progression-free survival, overall survival, survival rates, and duration of response, were estimated using the Kaplan-Meier method. AEs were coded using Medical Dictionary for Regulatory Activities (MedDRA), version 14.1. AEs of special interest (AEOSIs), with potential immune-related etiologies, defined as adverse events that require more frequent monitoring and/or unique intervention, were identified using a pre-defined list of MeDRA terms. Individual best ORs were derived from investigator-reported data per modified RECIST v1.0. OR was confirmed by at least one sequential tumor assessment and OR rate (ORR={[CR+PR]÷n}×100) was calculated.

Example 5

Safety Evaluations on Patients Treated with Anti-PD-1 Antibody

Safety evaluations, including clinical examination and laboratory assessments, were conducted in all treated patients at baseline and regular intervals up to 100 days following last administration of drug. The severity of AEs was graded based on the NCI Common Terminology Criteria for Adverse Events (NCI CTCAE), v3.0. Computed tomography (CT) or magnetic resonance imaging was performed for tumor assessment at baseline and following each treatment cycle.

A MTD was not defined across the doses of BMS-936558 tested on this study. A relative BMS-936558 dose intensity of 90% or higher was achieved in 87% of patients (see Topalian et al., 2012b, for details). AEs were coded using Medical Dictionary for Regulatory Activities (MedDRA), version 14.1. AEOSIs were identified using a pre-defined list of MeDRA terms. Fifteen of 296 (5%) patients discontinued treatment due to BMS-936558-related AEs. As of the date of analysis, 62 (21%) patients had died, with disease progression being the most common cause of death (Topalian et al., 2012b).

The most common adverse events, regardless of causality included fatigue, decreased appetite, diarrhea, nausea, cough, dyspnea, constipation, vomiting, rash, pyrexia and pruritus (Topalian et al., 2012b). Common BMS-936558-related AEs included fatigue, rash, diarrhea, decreased appetite, and nausea. The majority of the events were low grade, with grade 3-4 drug-related AEs observed in 41 of 296 (14%) patients. Drug-related serious AEs occurred in 32 of 296 (11%) patients (Topalian et al., 2012b). The spectrum, frequency, and severity of BMS-936558-related AEs were generally similar across the dose levels tested. Drug-related AEOSIs, with potential immune-related etiologies, included pneumonitis, vitiligo, colitis, hepatitis, hypophysitis, and thyroiditis among others. Hepatic or gastrointestinal AEOSIs were managed with treatment interruption and, as necessary, with administration of corticosteroids. Among patients treated to-date, these AEs (in 13 patients with diarrhea; 11 patients with hepatic AEs) were reversible in all cases. Endocrine AEOSIs were managed with replacement therapy. At the discretion of the treating physician, patients successfully reinitiated treatment with BMS-936558. Drug-related pneumonitis occurred in 9 of 296 (3%) patients. Grade 3-4 pneumonitis developed in 3 patients (1%). No clear relationship between the occurrence of pneumonitis and tumor type, dose level, or the number of doses received was noted. Early grade pneumonitis was generally reversible with treatment discontinuation and corticosteroid administration. In 3 patients with pneumonitis, infliximab and/or mycophenolate were utilized for additional immunosuppression; however, given the small number of patients and variable outcomes, the effectiveness of this treatment is unclear. There were 3 (1%) drug-related deaths due to pneumonitis (2 NSCLC patients, 1 CRC).

Example 6

Pharmacokinetics/Pharmacodynamics Analyses on Anti-PD-1 Antibody

For pharmacokinetic (PK) analyses, serial blood samples were collected and serum concentrations of BMS-936558 were quantified using by ELISA. For pharmacodynamic (PD) analysis, peripheral blood mononuclear cells were isolated from patients at baseline and following cycle 1 to estimate PD-1 receptor occupancy (RO) by BMS-936558 on circulating CD3+ T-cells via flow cytometry (Brahmer et al., 2010).

The maximum concentration of BMS-936558 was observed at a median $T_{max}$ of 1-4 hours after the start of infusion. The PK of BMS-936558 was linear with a dose proportional increase in $C_{max}$ and $AUC_{(0-14\ d)}$ in the dose range of 0.1-10 mg/kg (n=35). BMS-936558 PD was assessed by PD-1 RO on circulating T-cells. PBMCs from 65 MEL patients treated with one cycle of BMS-936558 at 0.1-10 mg/kg biweekly demonstrated median occupancy of PD-1 molecules on circulating $CD3^+$ T-cells by BMS-936558 ranging from 64%-70% (see Topalian et al., 2012b, for details).

Example 7

Antitumor Efficacy Exhibited by Anti-PD-1 Antibody

Figure 4:
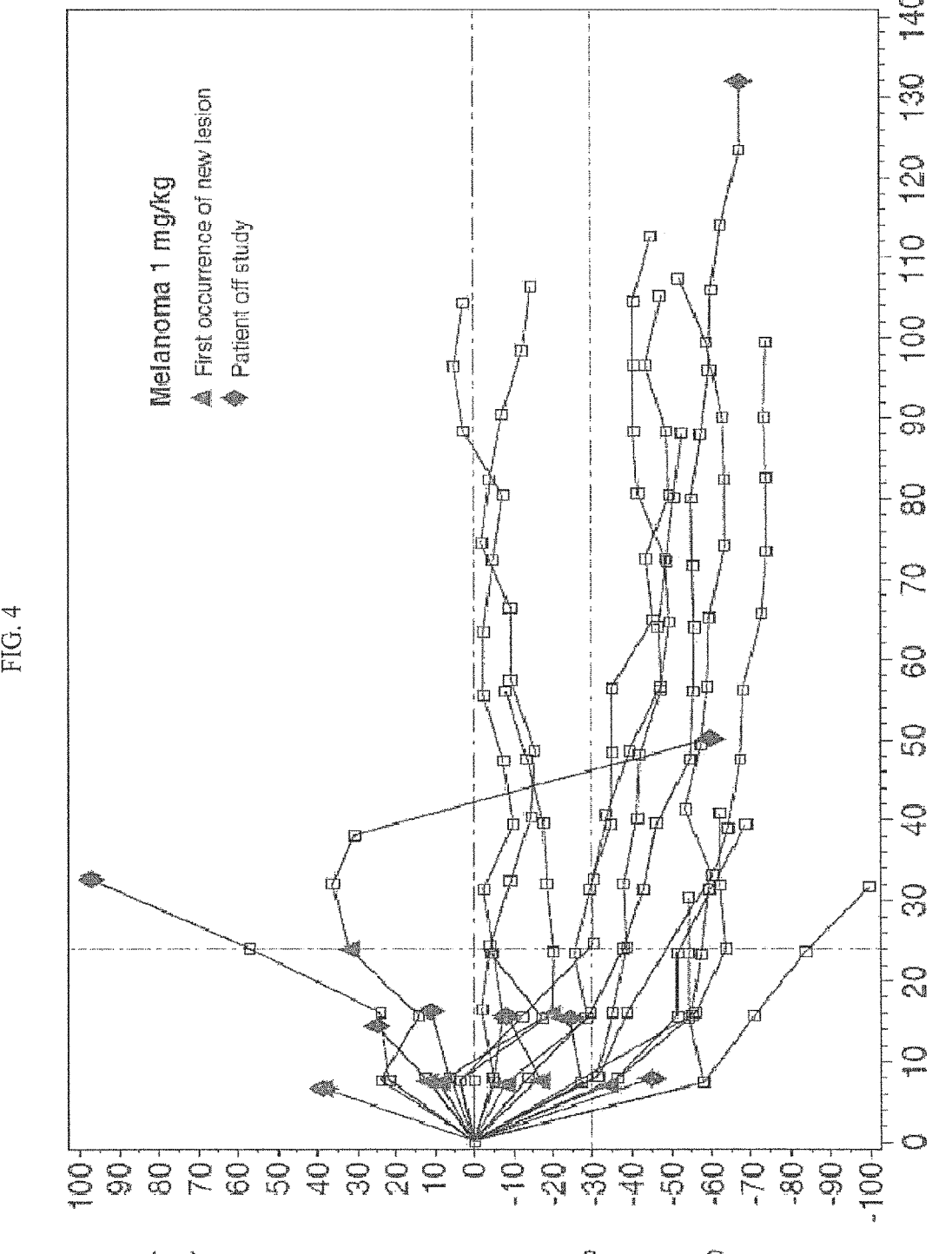
FIG. 4. Spider plot showing activity of anti-PD-1 mAb in patients with treatment-refractory melanoma (MEL). A representative plot of changes in tumor burden over time demonstrates the time course of change in the sum of the longest diameters of target lesions, compared with baseline, in 27 MEL patients treated with 5C4 at a dose of 1.0 mg/kg. In the majority of patients who achieved an objective response (OR), responses were durable and evident by the end of cycle 3 (6 months) of treatment (vertical dashed line). Tumor regressions followed conventional as well as "immune-related" patterns of response, such as prolonged reduction in tumor burden in the presence of new lesions.
Figure 5:
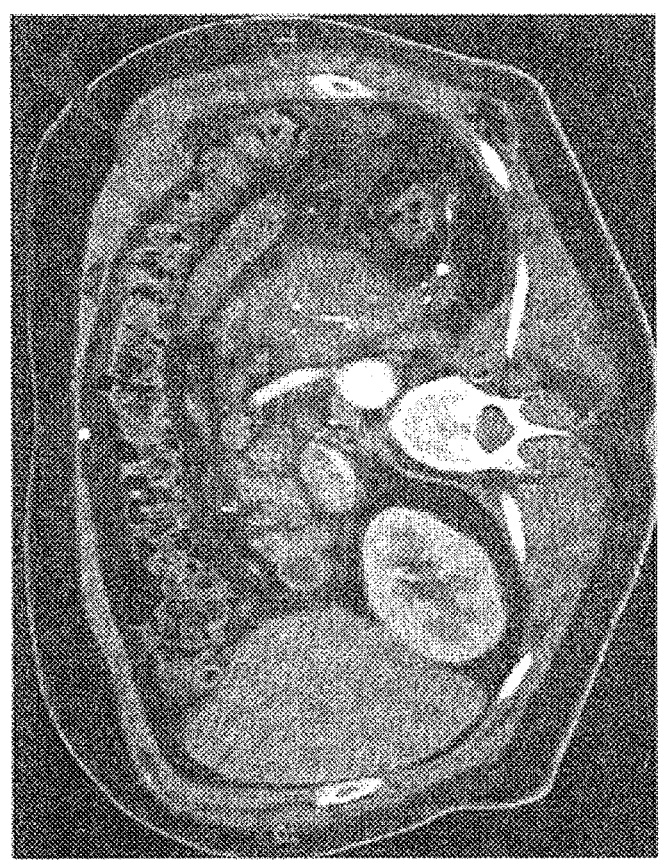
FIG. 5. Activity of anti-PD-1 mAb in patient with metastatic RCC. Partial regression of metastatic RCC in a 57-year-old patient treated with 5C4 at 1 mg/kg is illustrated. This patient had previously undergone radical surgery and had developed progressive disease after receiving sunitinib, temsirolimus, sorafenib, and pazopanib. Arrows show regression of recurrent tumor in the operative field.
Figure 5:
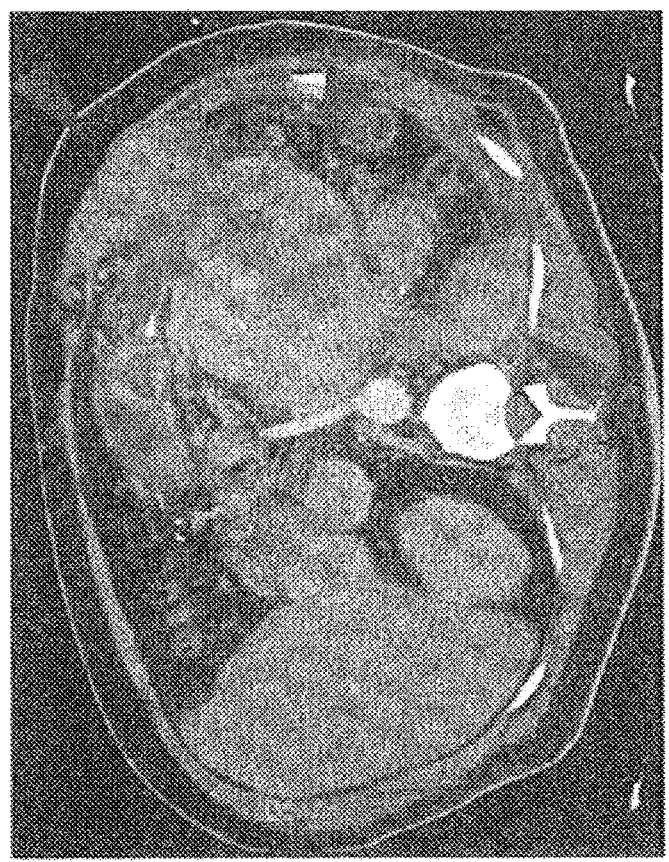
Figure 6:
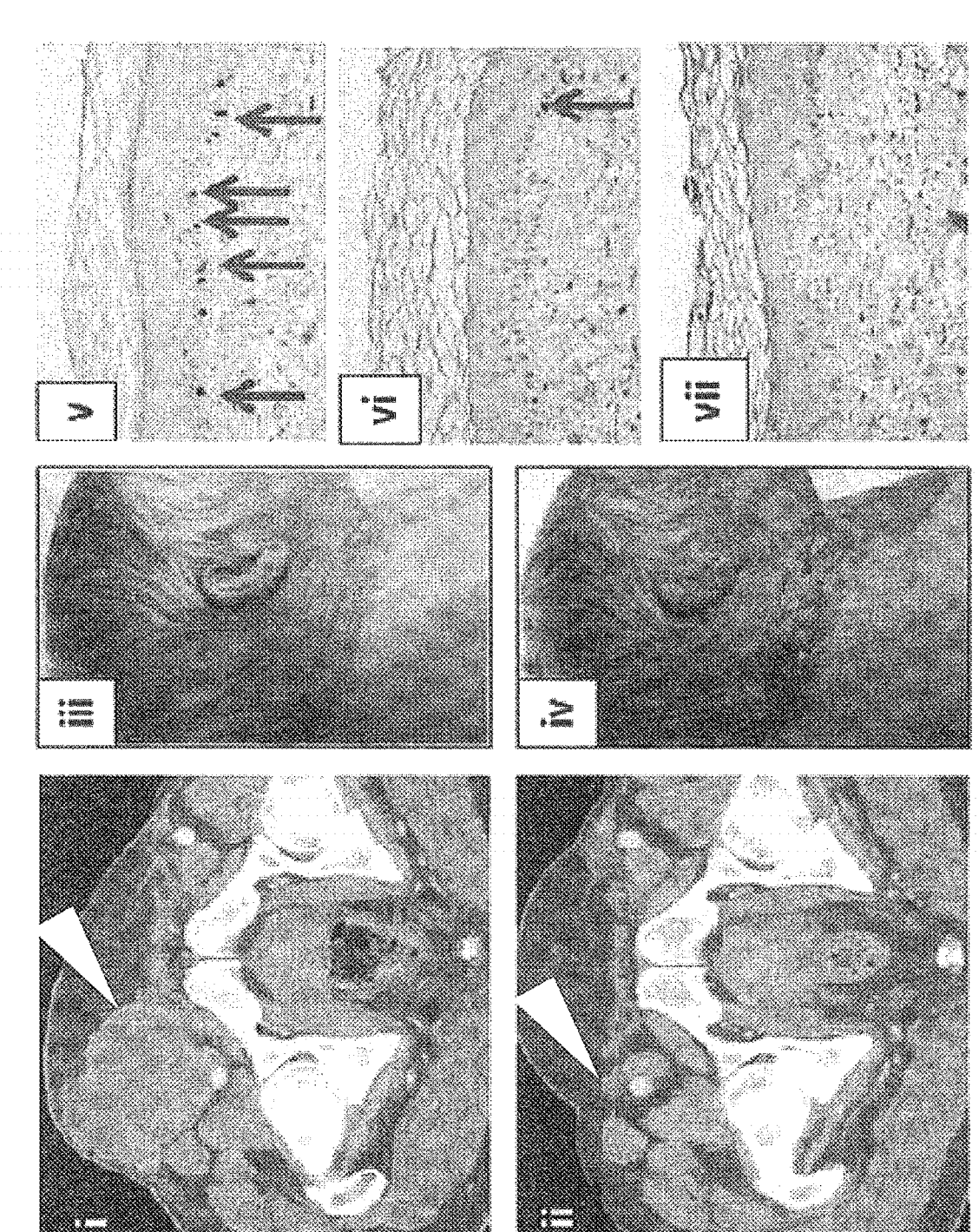
FIG. 6. Activity of anti-PD-1 mAb in patient with metastatic MEL. A complete response of metastatic MEL is illustrated in a 62-year-old patient treated with 5C4 at 3 mg/kg, associated with vitiligo. (i) Pretreatment CT scan, inguinal lymph node metastasis (arrow); (ii) after 13 months of treatment. Numerous metastases in the subcutaneous tissue and retroperitoneum also regressed completely (not shown). Vitiligo developed after 6 months of treatment; photos taken at 9 months under visible light (iii) and ultraviolet light (iv). Skin biopsies with immunohistochemistry for microphthalmia-associated transcription factor (MITF) show melanocytes (arrows) at the epidermal-dermal junction in normal skin (v), and scarce (vi) or absent (vii) melanocytes in skin partially or fully affected by vitiligo.
Figure 7:
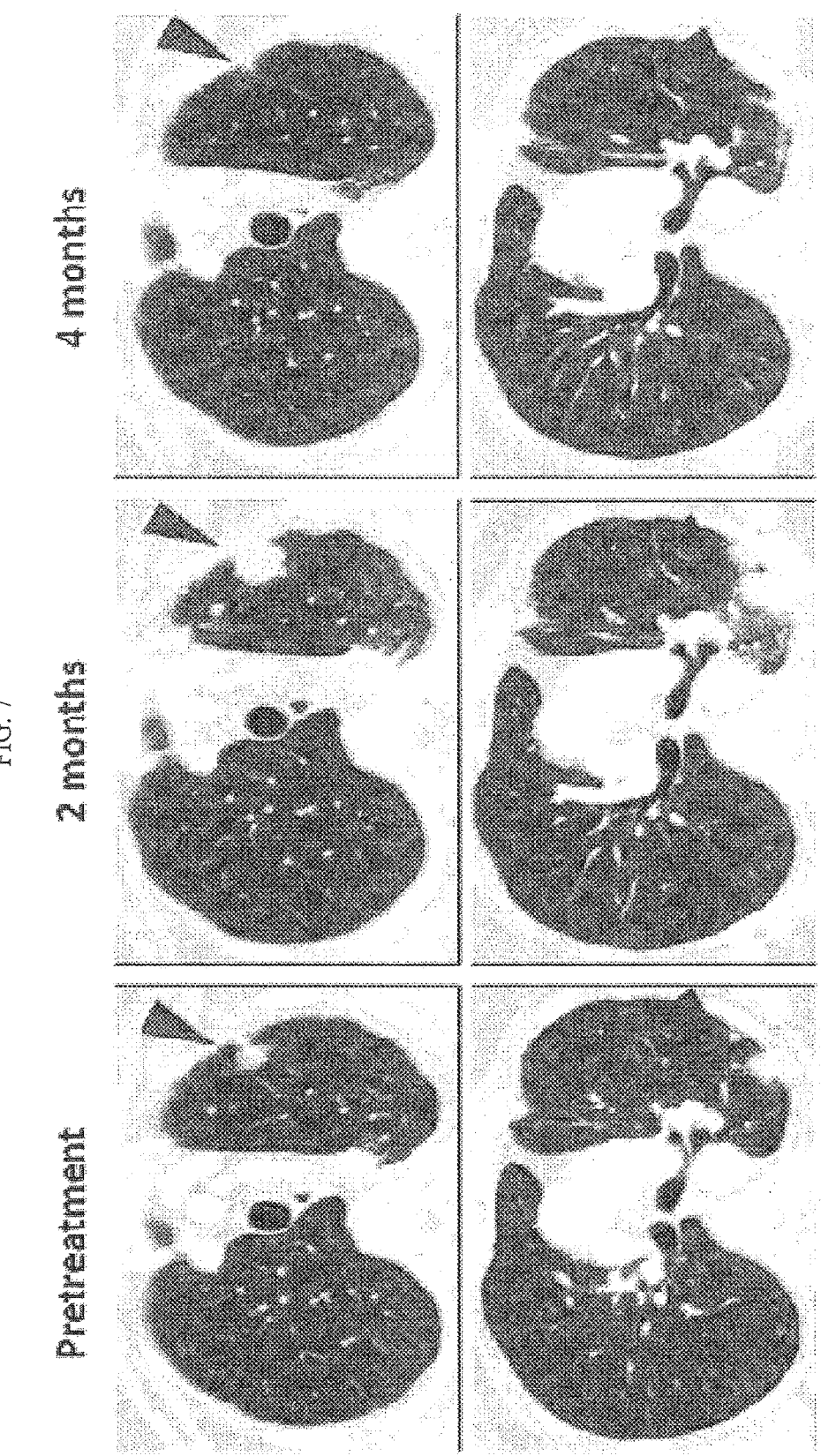
FIG. 7. Activity of anti-PD-1 mAb in patient with metastatic NSCLC. A partial response is illustrated in a patient with metastatic NSCLC (nonsquamous histology) treated with 5C4 at 10 mg/kg. Arrows show initial progression in pulmonary lesions followed by regression ("immune-related" pattern of response).

Analysis of data obtained since February 2012 is ongoing; thus, unless otherwise noted, the data presented below were obtained as of February 2012. Clinical antitumor activity was observed at all BMS-936558 doses tested. ORs (confirmed CR or PR) were observed in a substantial portion of patients with NSCLC, MEL, and RCC (Tables 1-3; FIG. 4), and in various sites of metastatic disease including liver, lung, lymph nodes, and bone (FIGS. 5-7 and not shown). Tumor regressions followed conventional as well as "immune-related" patterns of response, such as prolonged reduction in tumor burden in the presence of new lesions. Individual best overall responses were derived from investigator-reported data according to modified RECIST v1.0. OR was confirmed by at least one sequential tumor assessment. At the time of data analysis, 2 patients with NSCLC who were treated with 10 mg/kg had unconfirmed responses, and 8 additional patients (with MEL, NSCLC, or RCC) had a persistent reduction in baseline target lesions in the presence of new lesions, (i.e., an "immune-related" response pattern). None of these patients was categorized as a responder for the purpose of calculating OR rates. Antitumor responses and/or prolonged disease stabilization were observed in patients irrespective of prior therapies received (see summary of progression free interval for patients with OR and SD in Supplementary Appendix 4 of Topalian et al., 2012b).

In NSCLC patients, 14 ORs were observed at BMS-936558 doses of 1, 3, or 10 mg/kg with response rates of 6%, 32%, and 18%, respectively. ORs were observed across NSCLC histologies: 6 responders of 18 squamous (33%), 7 responders of 56 nonsquamous (13%), and 1 of 2 unknown. All 14 patients with ORs started treatment≥24 weeks before data analysis, and of these, 8 had response duration≥24 weeks (Table 1). Stable disease (SD) lasting ≥24 weeks was observed in 5 (7%) NSCLC patients, all with nonsquamous histology. Among MEL patients, 26 ORs were observed at doses ranging from 0.1-10 mg/kg, with response rates ranging from 19%-41% per dose level. At the 3 mg/kg dose level, ORs were noted in 7 of 17 (41%) patients. Of 26 MEL patients who achieved an OR, 17 started treatment≥1 year before data analysis, and of these, 13 patients had an OR duration (1 yr. The remaining 8 patients with OR were on study (1 year and 6 had responses ranging from 1.9-5.6 months. SD lasting ≥24 weeks was observed in 6 (6%) patients. In RCC patients, ORs occurred in 4 of 17 (24%) patients treated with a BMS-936558 dose of 1 mg/kg and 5 of 16 (371) patients treated with 10 mg/kg. Among 8 RCC patients with OR who started treatment≥1 year prior to data analysis, 5 (631) had OR duration 1 yr. SD lasting 24 weeks was observed in an additional 9 (27%) patients.

TABLE 1

Clinical Activity of BMS-936558 in the Efficacy Population* (N = 236)[†]

| Tumor Type | Dose (mg/kg) | n | ORR[‡] No. Patients (%) [95% CI][†] | SD ≥24 wk No. Patients (%) [95% CI] | PFSR[§] at 24 wk (%) [95% CI] |
|---|---|---|---|---|---|
| MEL | 0.1 | 14 | 4 (29) [8-58] | 1 (7) [0.2-34] | 40 [13-66] |
| | 1.0 | 27 | 8 (30) [14-50] | 3 (11) [2-29] | 45 [26-65] |
| | 3.0 | 17 | 7 (41) [18-67] | 1 (6) [0.1-29] | 55 [30-80] |
| | 10.0 | 20 | 4 (20) [6-44] | 0 | 30 [9-51] |
| ALL MEL | | 94 | 26 (28) [19-38] | 6 (6) [2-13] | 41 [30-51] |
| NSCLC** | | | | | |
| All | 1 | 18 | 1 (6) [0.1-27] | 1 (6) [0.1-27] | 16 [0-34] |
| Squamous | 1 | 5 | 0 | 0 | 0 |
| Nonsquamous | 1 | 12 | 0 | 1 (8) [0.2-39] | 14 [0-37] |
| Unknown | 1 | 1 | 1 (100) [3-100] | 0 | 1 |
| All | 3 | 19 | 6 (32) [13-57] | 2 (11) [1-33] | 41 [18-64] |
| Squamous | 3 | 6 | 3 (50) [12-88] | 0 | 50 [10-90] |
| Nonsquamous | 3 | 13 | 3 (23) [5-54] | 2 (15) [2-45] | 37 [10-64] |
| All | 10 | 39 | 7 (18) [8-34] | 2 (5) [0.6-17] | 24 [11-38] |
| Squamous | 10 | 7 | 3 (43) [10-82] | 0 | 43 [6-80] |
| Nonsquamous | 10 | 31 | 4 (13) [4-30] | 2 (7) [0.8-21] | 21 [6-36] |
| Unknown | 10 | 1 | 0 | 0 | 0 |
| ALL NSCLC | | 76 | 14 (18) [11-29] | 5 (7) [2-15] | 26 [16-36] |
| All Squamous | | 18 | 6 (33) [13-59] | 0 | 33 [12-55] |
| All Nonsquamous | | 56 | 7 (13) [5-24] | 5 (9) [3-20] | 22 [11-34] |
| RCC | 1 | 17 | 4 (24) [7-50] | 4 (24) [7-50] | 47 [23-71] |
| | 10 | 16 | 5 (31) [11-59][‡] | 5 (31) [11-59][¶] | 67 [43-91] |
| ALL RCC | | 33 | 9 (27) [13-46] | 9 (27) [13-46] | 56 [39-73 |

*The efficacy population consists of response-evaluable patients whose treatment was initiated at least 8 months before data analysis in February 2012, and had measurable disease at baseline and one of the following: at least 1 on-treatment scan or clinical evidence of disease progression or death.
[†]CR denotes complete response, MEL melanoma, NSCLC non-small cell lung cancer, ORR objective response rate, PFSR progression-free survival rate, PR partial response, RCC renal cell cancer, SD stable disease, n number of patients.
[‡]Objective response rates ({[CR + PR] ÷ n} × 100) have been calculated based on confirmed responses with confidence intervals calculated using the Clopper-Pearson method. Individual patient responses were adjudicated per RECIST v1.0 with modification (see Topalian et al., 2012b).
[§]Progression-free survival rate was the proportion of patients who did not progress and were alive at 24 weeks calculated by the Kaplan-Meier methodology with confidence intervals using the Greenwood method.
[¶]One CR.
**One NSCLC patient who was treated at the 3 mg/kg dose level had an initial evaluation of progressive disease, subsequently had a PR, and was classified as a responder.

TABLE 2

Clinical Activity of BMS-936558 in the Efficacy Population*

| Tumor Type | ORR[a] No. of patients/total no. of patients (%) [95% CI] | SD ≥24 wk No. of patients/total no. of patients (%) [95% CI] | Median Overall Survival (95% CI) | Overall Survival Rate (95% CI); patients at risk, n 1 y | 2 y | 3 y |
|---|---|---|---|---|---|---|
| NSCLC | 20/122 (16.4) [10.3, 24.2] | 11/122 (9.0) [4.6, 15.6] | NA | 43 (33-53); 24 | 32 (18-47); 4 | 24 (7-41); 1 |
| Squamous | 9/48 (18.8) [8.9, 32.6] | NA | NA | NA | NA | NA |
| Non-sq. | 11/73 (15.1) [7.8, 25.4] | NA | NA | NA | NA | NA |
| MEL | 33/106 (31.1) [22.5, 40.9] | 6/106 (5.7) [2.1, 11.9] | 16.8 (12.5, NR) | 61 (52-71); 50 | 44 (33-56); 24 | 40 (29-52); 1 |
| RCC | 10/34 (29.4) [15.1, 47.5] | 9/34 (26.5) [12.9, 44.4] | NR (13.6, NR) | 70 (55-86); 22 | 52 (32-72); 7 | 52 (32-72); 1 |

*The efficacy population consists of response-evaluable patients up to March 2013
[a]Objective response rate was calculated as {[CR + PR] ÷ n} × 100.
NR——not reached
NA——not available from Jul. 3, 2012 data cut. The percentage of patients with stable disease for ≥36 weeks or ≥48 weeks [95% CI], median duration of response (months) and median progression-free survival (95% CI) were N/A.

60

The following results are drawn from preliminary analyses of BMS-936558 clinical efficacy data as of March 2013. Sustained survival, as reflected by median overall survival and 1- and 2-year landmark overall survival rates, was noted in each of the responding patient populations (Table 2). Median overall survivals of 9.6 months for lung cancer, 16.8 months for melanoma, and greater than 22 months for kidney cancer, were observed. Thirteen patients with melanoma, lung or kidney cancer were characterized as having unconventional response patterns that did not meet RECIST criteria (e.g., persistent reduction in target lesions in the presence of new lesions or following initial progression) (Wolchok et al, 2009).

TABLE 3

Duration of Objective Responses to BMS-936558*

| Tumor Type | Dose (mg/kg) | No. of Patients with OR | Duration of Response (months)[†] |
|---|---|---|---|
| MEL | 0.1 | 4 | 7.5+, 5.6+, 5.6, 5.6 |
| | 0.3 | 3 | 3.8+, 2.1+, 1.9+ |
| | 1 | 8 | 24.9+, 22.9, 20.3+, 19.3+, 18.4+, 7.6+, 5.6+, 5.3+ |
| | 3 | 7 | 22.4+, 18.3+, 15.2+, 12.9, 11.1, 9.3, 9.2+ |
| | 10 | 4 | 24.6+, 23.9+, 18.0+, 17.0 |
| NSCLC[§] | 1 | 1 | 9.2+ |
| | 3 | 6 | 30.8+, 7.6+, 5.5+, 3.7+, 1.9+, NA[‡] |
| | 10 | 7 | 14.8+, 7.6+, 7.3+, 6.7, 4.2, 3.7+, 3.7 |
| RCC | 1 | 4 | 17.5+, 9.2+, 9.2, 5.6+ |
| | 10 | 5 | 22.3+. 21.7+, 12.9, 12.0, 8.4 |

*MEL denotes melanoma, NA not applicable, NSCLC non-small cell lung cancer, RCC renal cell cancer.
[†]Time from first response to time of documented progression, death, or for censored data, time to last tumor assessment.
[‡]One patient was treated beyond an initial evaluation of progressive disease and subsequently had a PR; this patient was classified as a responder for the purposes of calculating response rates by RECIST v1.0 but was not eligible for calculation of duration of response.

Example 8

Measurement of Membranous PD-L1 Expression by Standard IHC Assay

IHC staining of PD-L1 was performed on pretreatment formalin-fixed paraffin-embedded (FFPE) tumor specimens using the murine anti-human PD-L1 mAb 5H1 (Dong et al., 2002) in a standard IHC protocol (Taube et al., 2012; Supp. Materials). Briefly, 5 μm-FFPE sections mounted on glass slides were deparaffinized in xylene and antigen retrieval was performed using a Tris-EDTA buffer, pH 9.0 at 120° C. for 10 min in a Decloaking Chamber (Biocare Medical). Endogenous peroxidase, biotin and proteins were blocked (CAS system K1500, Dako; Avidin/biotin Blocking Kit, SP-2001, Vector Laboratories; Serotec Block ACE). The primary 5H1 Ab was applied at a concentration of 2 μg/ml and allowed to incubate at 4° C. for 20 h. Secondary Ab (biotinylated anti-mouse IgG1, 553441 BD) was applied at a concentration of 1 μg/ml for 30 min at room temperature (RT). The signal was then developed with amplification according to the manufacturer's protocol (CAS system K1500, Dako). Sections were counterstained with hematoxylin, dehydrated in ethanol and cleared in xylene, and a coverslip was applied.

The percentage of tumor cells exhibiting cell surface staining for PD-L1 was scored by two independent pathologists who were blinded to treatment outcomes. PD-L1 positivity was defined per specimen by a 5% expression threshold (Taube et al., 2012; Thompson et al., 2006), and in cases with multiple specimens, if any specimen met this criterion. A Fisher's exact test was applied to assess the association between PD-L1 expression and OR, noting, however, that this analysis was based in part on optional biopsies from a non-random subset of the population and testing of a statistical hypothesis was not pre-specified.

Figure 8A:
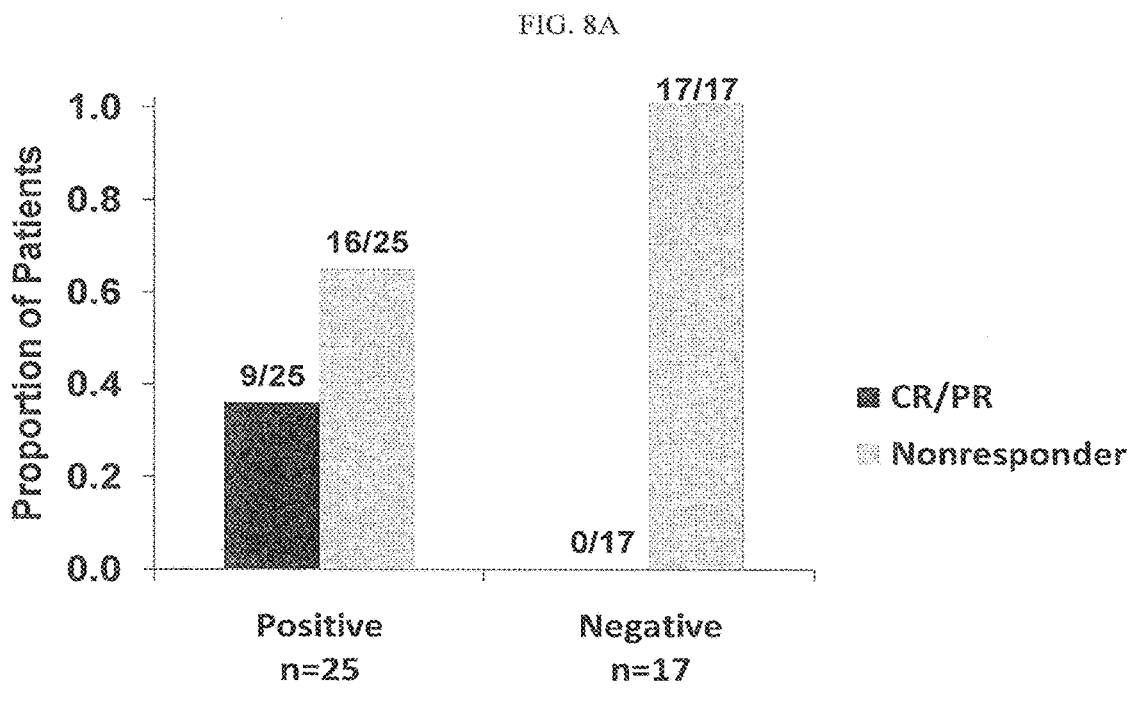
FIGS. 8A and 8B. Correlation between tumor PD-L1 expression and anti-PD-1 clinical response. Pretreatment tumor cell surface expression of PD-L1, as determined by IHC on formalin-fixed paraffin-embedded specimens, correlates with OR to PD-1 blockade. Forty-two subjects with advanced cancers including melanoma, non-small cell lung cancer, colorectal cancer, renal cell cancer, and castration-resistant prostate cancer (n=18, 10, 7, 5, and 2, respectively) were studied. A, There was a significant correlation of tumor cell surface PD-L1 expression with objective clinical response. No patients with PD-L1 negative tumors experienced an OR. B, Examples of IHC analysis with the anti-PD-L1 mAb 5H1 are shown in a melanoma lymph node metastasis (top), a renal cell cancer nephrectomy specimen (middle), and a lung adenocarcinoma brain metastasis (bottom). All 400× original magnification. Arrows indicate one of many tumor cells in each specimen with surface membrane staining for PD-L1. Asterisk indicates a normal glomerulus in the nephrectomy specimen, which is negative for PD-L1 staining.
Figure 8B:
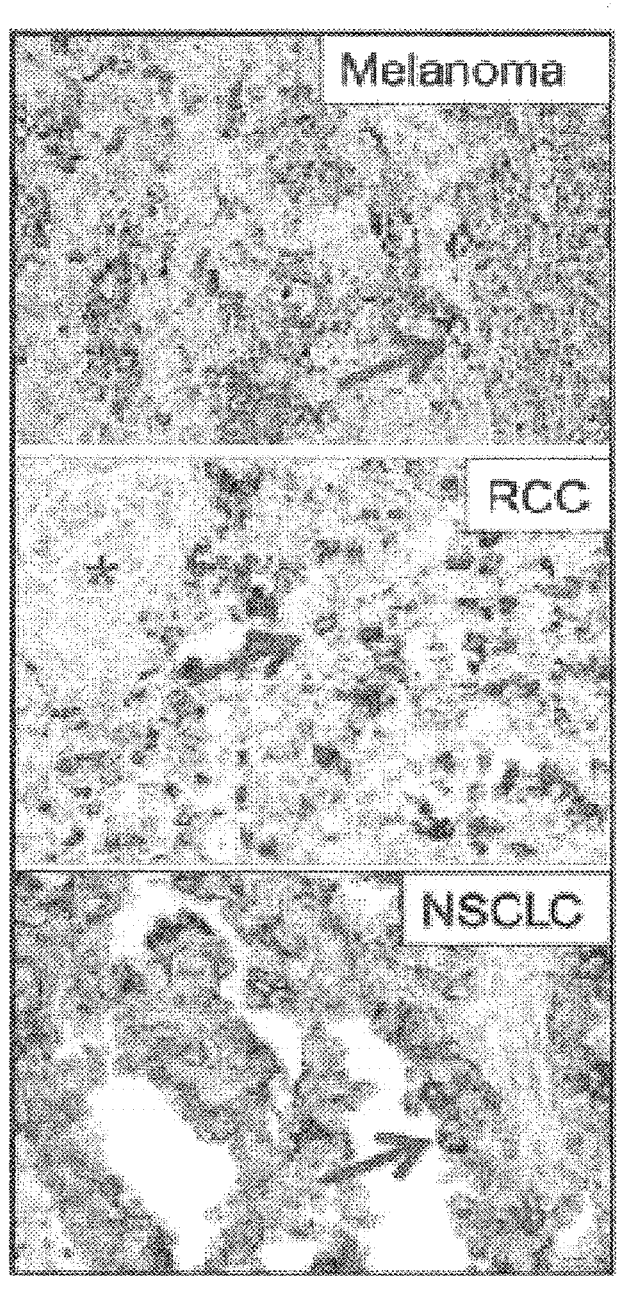

Sixty-one pretreatment tumor specimens from 42 patients (18 MEL, 10 NSCLC, 7 CRC, 5 RCC, and 2 CRPC) were analyzed for tumor cell surface PD-L1 expression (FIG. 8). Biopsy specimens from 25 of 42 patients were positive for PD-L1 expression by IHC. A Fisher's exact test was applied to assess the association between PD-L1 expression and OR in a post-hoc analysis. Among the 42 surface-PD-L1$^+$ patients, 9 (36%) achieved an OR. Importantly, among 17 patients with PD-L1$^-$ tumors, none achieved an OR. Thus, in a subset of patients cell surface expression of PD-L1 on tumor cells in pretreatment biopsies is associated with an increased rate of OR among patients treated with BMS-936558, while no patients with documented PD-L1-negative tumors experienced an OR. These data indicate that tumor PD-L1 expression is a molecular marker that can enable patient selection for anti-PD-1 immunotherapy.

Example 9

Isolation of Rabbit mAbs that Detect Membranous hPD-L1 Antigen in FFPE Tissues

Rabbit Abs against human PD-L1 polypeptide were prepared by Epitomics, Inc. (Burlingame, CA) by immunization of rabbits using a recombinant human PD-L1 fusion protein. Antiserum titers were evaluated using standard direct ELISA with the hPD-L1 antigen and cell ELISA using transfected cells overexpressing hPD-L1. These Abs were also screened for their ability to bind to PD-L1 by IHC assay of FFPE tissue sections. The rabbit with the highest Ab titer was selected for splenectomy. Lymphocytes isolated from the spleen were fused to myeloma cells in 40×96-well plates, and screened by ELISA against the immunizing PD-L1 antigen and by cell ELISA against cells overexpressing hPD-L1. Positive clones were expanded into 24-well plates, and confirmatory screens were conducted by direct ELISA and cell ELISA. The supernatants (sups) of clones that were specific to the screening antigen were re-screened by IHC.

A set of mouse anti-hPD-L1 mAbs were also produced by immunization of mice using a protocol similar to that described above for the rabbit mAbs.

Out of a total of 185 multiclones from both rabbit and mouse immunizations screened, only ten rabbit multiclone Abs specifically detected the membranous form of hPD-L1. None of the purified mouse subclones were found to specifically detect cell surface hPD-L1. Sixty subclones from the top five rabbit multiclones (designated Nos. 13, 20, 28, 29 and 49, each comprising 12 subclones) were screened initially by IHC on FFPE low density tissue microarrays (TMAs), followed by confirmation and specificity verification in narrowed 25 subclones. Rabbit IgG was used as a negative isotype control, and mAb 5H1 (Dong et al., 2002) was used as the positive control. Specificity was further verified by antigen preabsorption assay. Through two rounds of IHC, the following 15 purified subclones were selected as the most promising Abs in terms of specificity and intensity of staining: 13-1, 13-3, 13-7, 13-8; 20-5, 20-7, 20-12, 20-6; 28-1, 28-8, 28-12; 49-5, 49-7, 49-9; and 29-8. Immunoreactivity data on these selected Abs are summarized in Table 4.

Additional assays were performed to further characterize the purified Ab clones, including determining binding affinity and cross-competition among the Abs (to identify overlapping versus different epitope regions) by surface plasmon resonance. All the Abs exhibited high binding affinity ($K_D < 10^{-9}$ M). These 15 purified clones were also re-screened by IHC on FFPE low density TMA or regular sections against various cell and tissue types known to be positive or negative for cell surface expression of PD-L1. Rabbit IgG was used as the isotype control, and mAb 5H1 was used as the positive control. At high concentration (10 μg/ml), clones 28-x and 49-x displayed low to moderate levels of background staining in tissues, while clones 13-x exhibited no background staining, which suggests that the 13-x clones have a wider dynamic range. The 20-x clones displayed various degree of background staining which was primarily cytoplasmic and diffuse. The clone with most robust detection specifically of membranous PD-L1, rabbit clone 28-8 ($K_D$=100 pM, as determined by SPR), was selected as the lead Ab for subsequent IHC assays. MAbs 28-1, 28-12, 20-12 and 29-8 had $K_D$ values of 130 pM, 94 pM, 160 pM and 1200 pM, respectively. The sequences of the $V_H$ and regions of mAb 28-8 are set forth in SEQ ID NOs. 35 and 36, respectively. The 28-8 Ab was shown to recognize a different epitope from mouse mAb 5H1, based on SPR analysis. Clones 28-1, 28-12, 29-8 and 20-12 were the next best Abs in terms of robust detection of membranous PD-L1 in FFPE tissues. Although mAb 13-1 had the best specificity in terms of detection of membranous PD-L1, the maximal detection level was lower than that of the other lead Abs. Western blotting was also performed with plus/minus antigen competition to verify the specificity of the top selected Abs for PD-L1.

TABLE 4

Immunoreactivity of Rabbit Anti-hPD-L1 mAbs

| Antibody Name | Specific Staining | | Non-Specific staining Background |
| | Pos. vs Neg. Staining on PD-L1 Cells* | Intensity Range on Tissues[†] (Very High, High, Medium, Low) | Staining on Tissues (High, Medium, Low) |
| --- | --- | --- | --- |
| 13-1 | Pos | Low to Very High | None |
| 13-3 | Pos | Low to High | None |
| 13-7 | Pos | Low to High | None |
| 13-8 | Pos | Low to High | None |
| 20-5 | Pos | Low to Very High | High |
| 20-6 | Pos | Low to High | Medium |
| 20-7 | Pos | Low to High | Medium |
| 20-12 | Pos | Low to High | Medium |
| 28-1 | Pos | Low to Very High | None |
| 28-8 | Pos | Medium to Very High | None |
| 28-10 | Pos | Medium to Very High | Low |
| 28-12 | Pos | Low to Very High | None |
| 49-5 | Pos | Low to High | None |
| 49-7 | Pos | Low to High | Low |
| 49-9 | Pos | Low to High | None |
| 5H1 | Pos | High to Very High | None |
| Rb IgG | Neg | Neg | None |

*PD-L1 stably transfected CHO cells vs. CHO-S control;

[†]PD-L1 positive tissues included placenta and one non-small cell lung cancer; Detection up to "very high" expression suggests better sensitivity at detecting membranous PD-L1.

Figure 9:
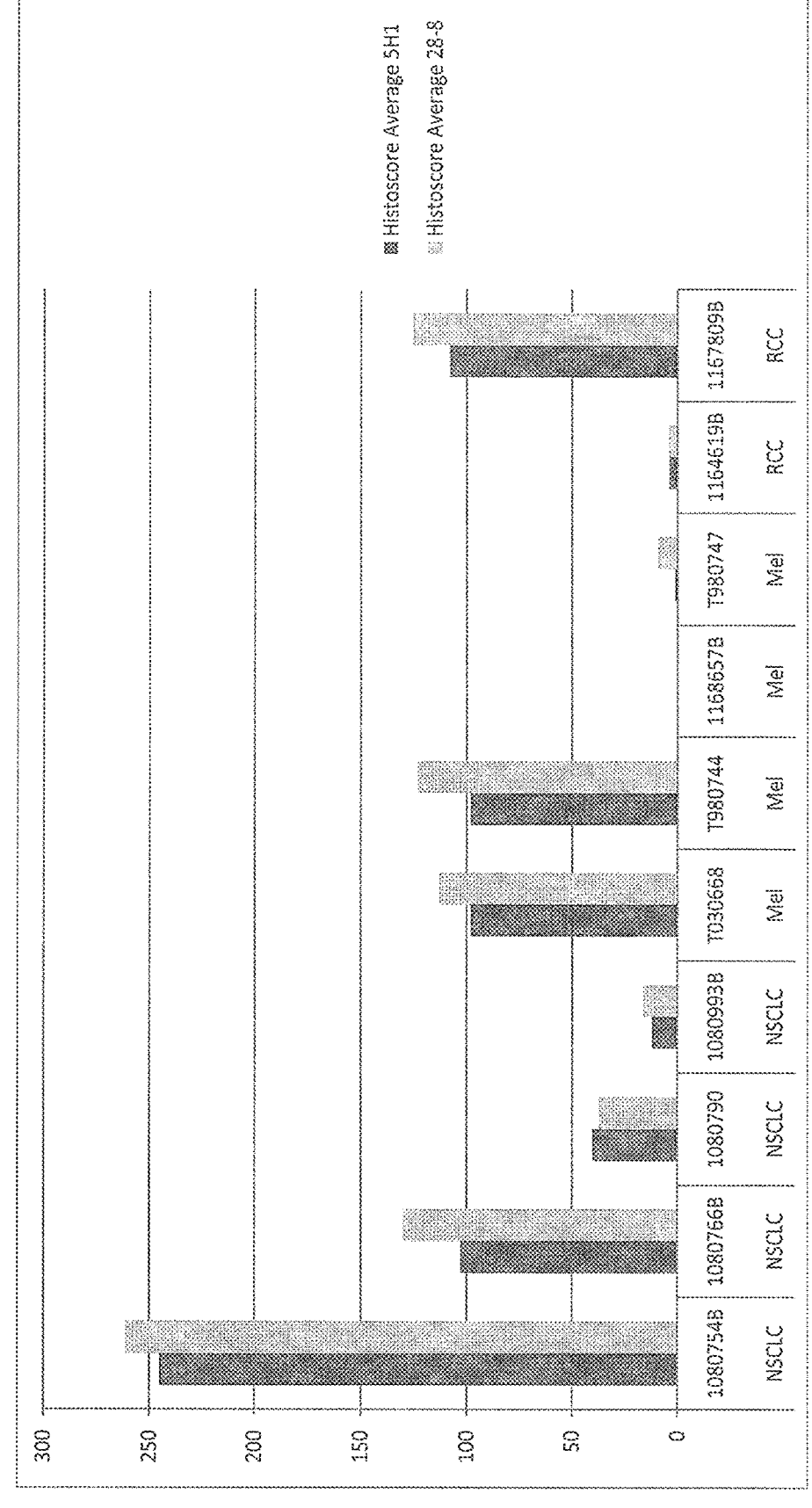
FIG. 9. Graphical comparison of the binding of mAbs 28-8 and 5H1 to PD-L1 antigen in tumor tissues by histoscore analysis. The rabbit mAb 28-8 showed higher histoscores in 7 out of 10 samples tested.
Figure 10A:
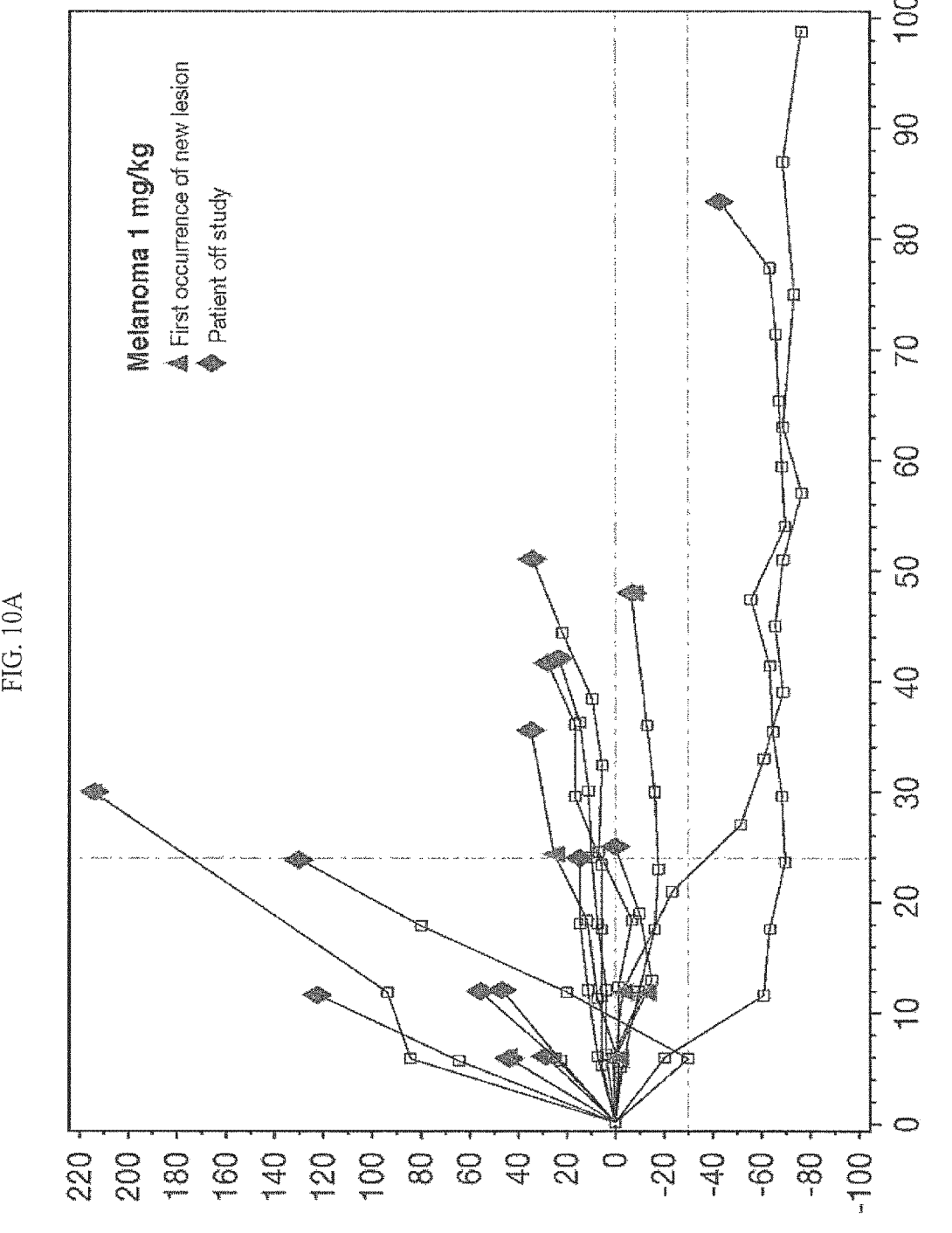
FIGS. 10A-10D. Spider plot showing activity of anti-PD-L1 mAb in patients with treatment-refractory MEL and NSCLC. Representative plots demonstrate the time course of target lesion tumor burden over time in patients with MEL treated with BMS-936559 at doses of 1 (A), 3 (B), 10 mg/kg (C) and in patients with NSCLC treated at 10 mg/kg (D). In the majority of patients who achieved ORs, responses were durable and were evident by the end of cycle 2 (3 months) of treatment, irrespective of dose or tumor type. Tumor regressions followed conventional as well as "immune-related" patterns of response.
Figure 10B:
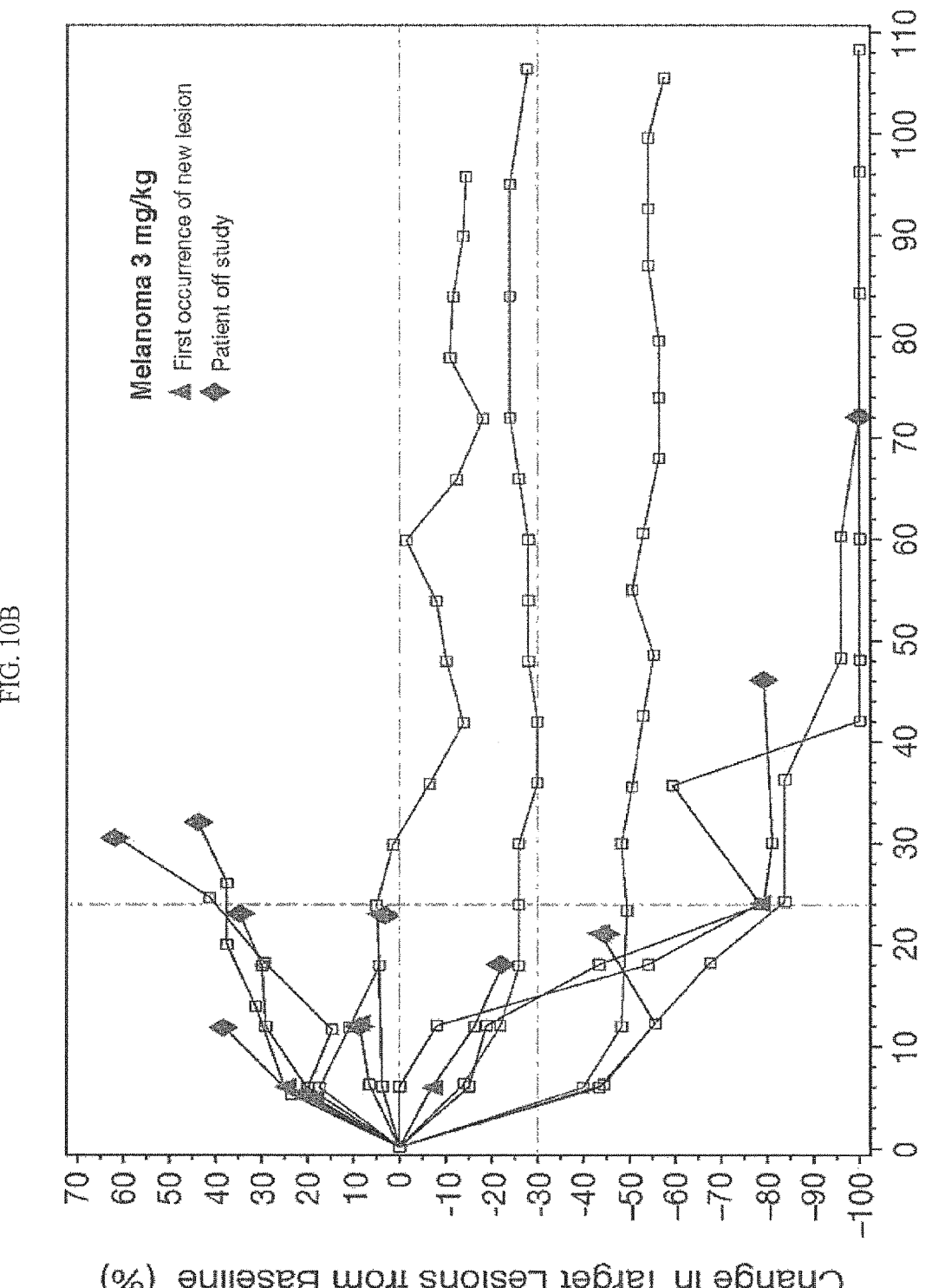
Figure 10C:
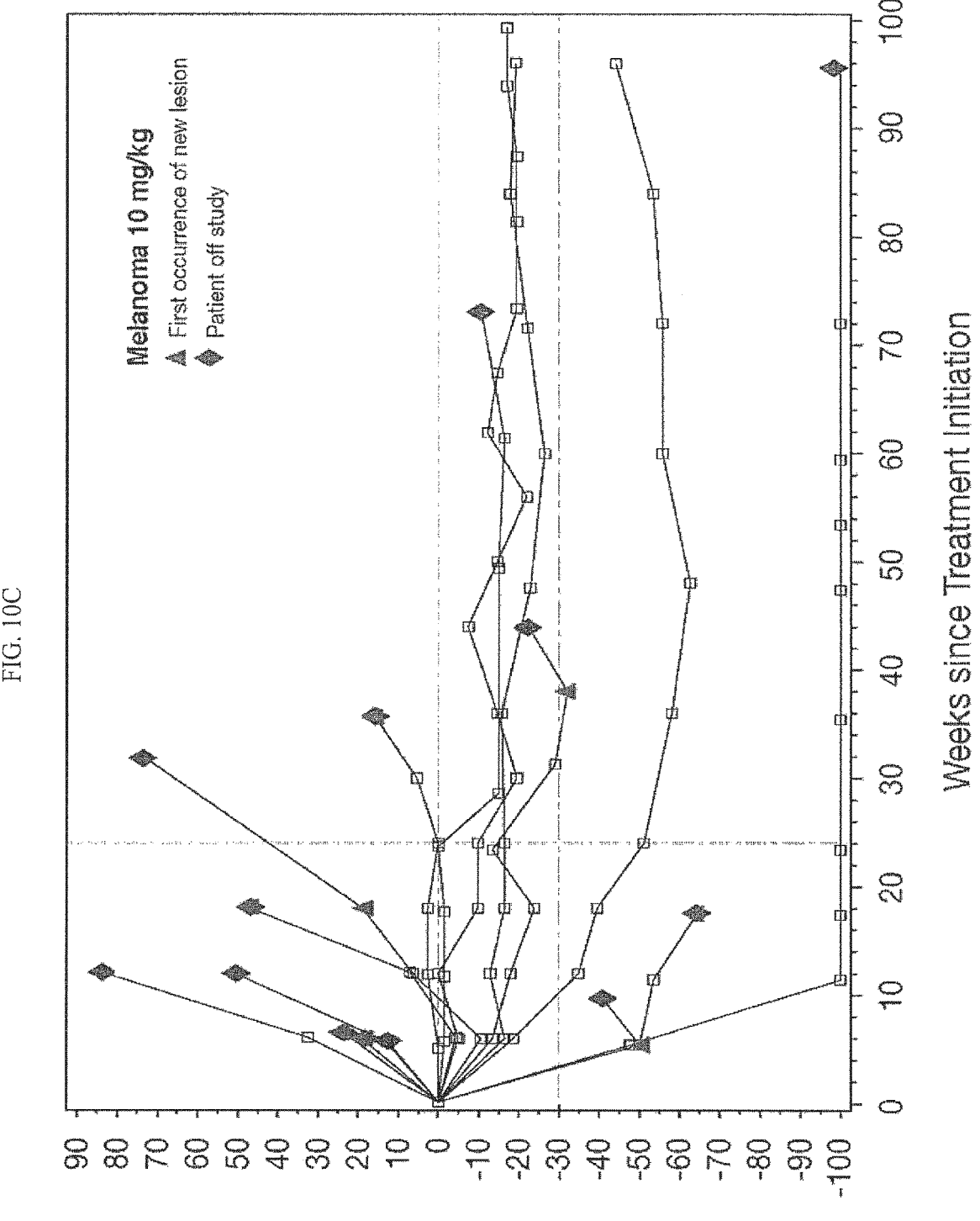
Figure 10D:
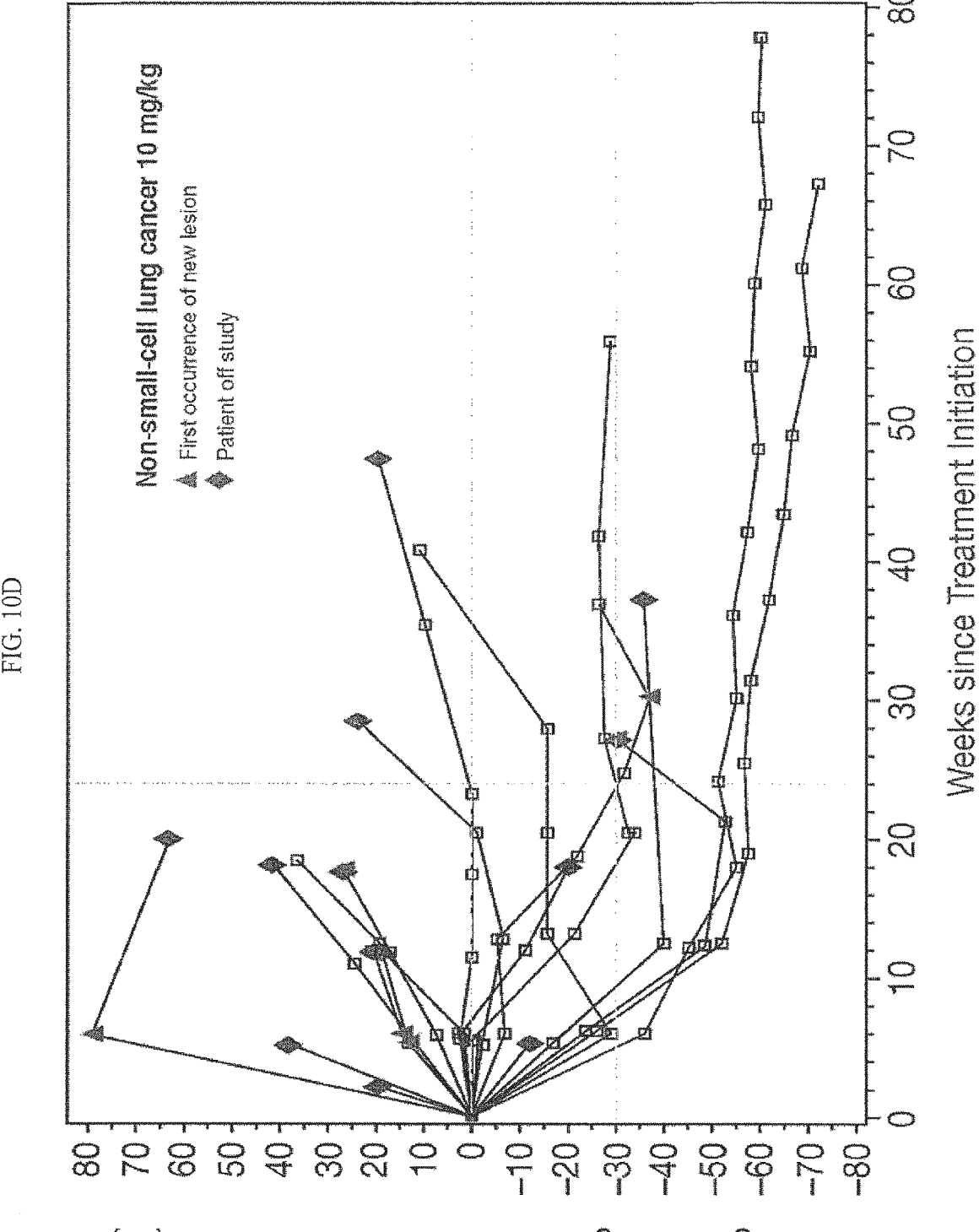
Figure 11:
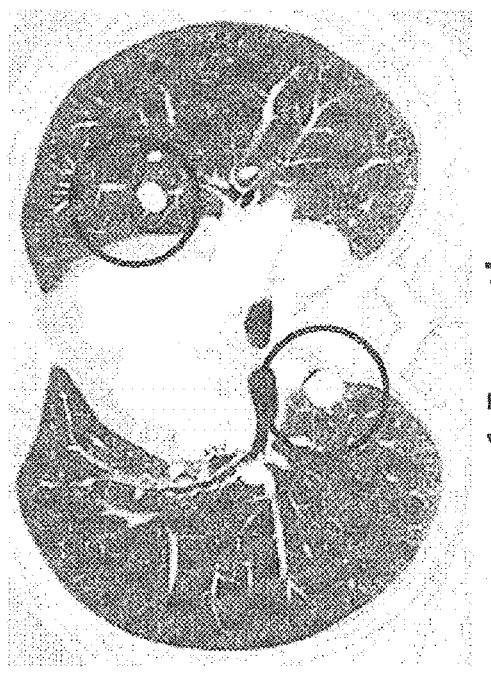
FIG. 11. Complete response in a patient with melanoma treated with BMS-936559 at 3 mg/kg. Circles indicate an initial increase in the size of pulmonary nodules at 6 weeks and 3 months followed by complete regression at 10 months ("immune-related" pattern of response).
Figure 11:
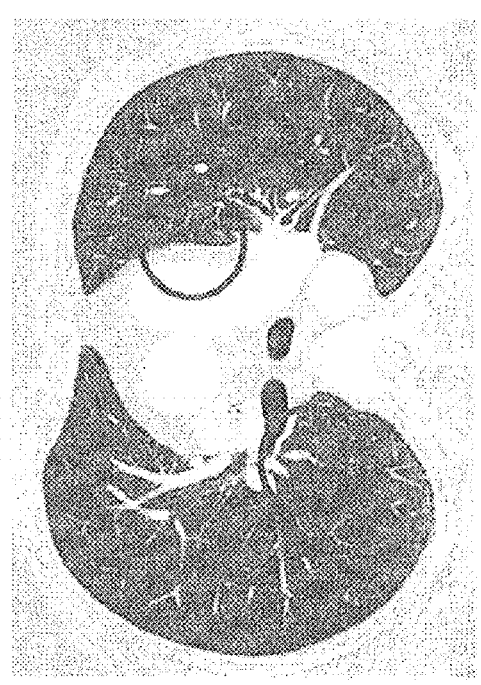
Figure 11:
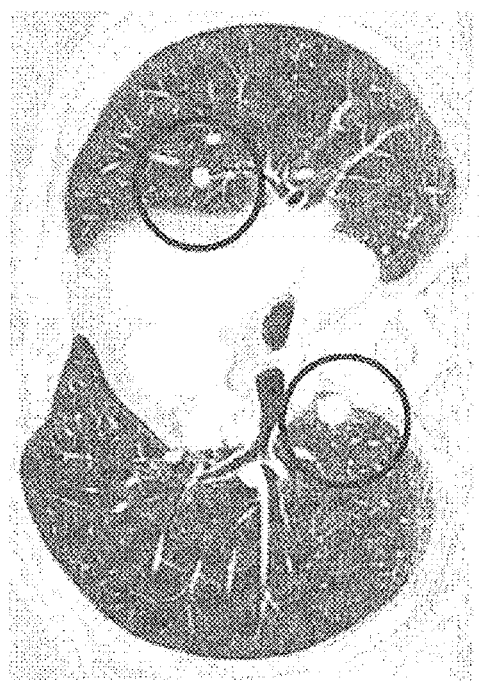
Figure 11:
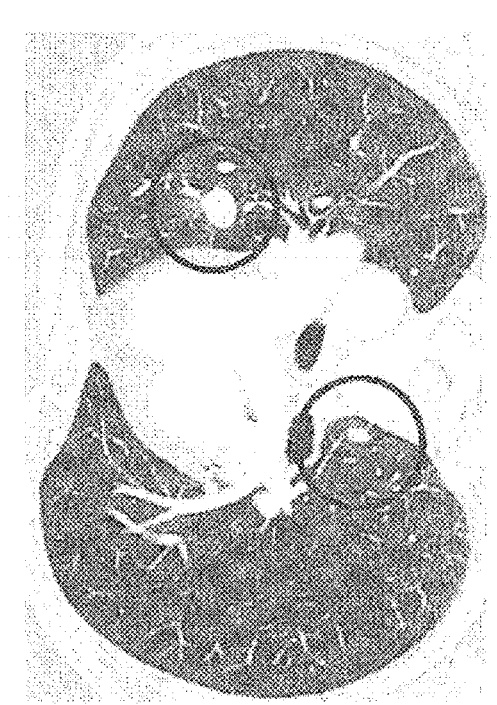
Figure 12:
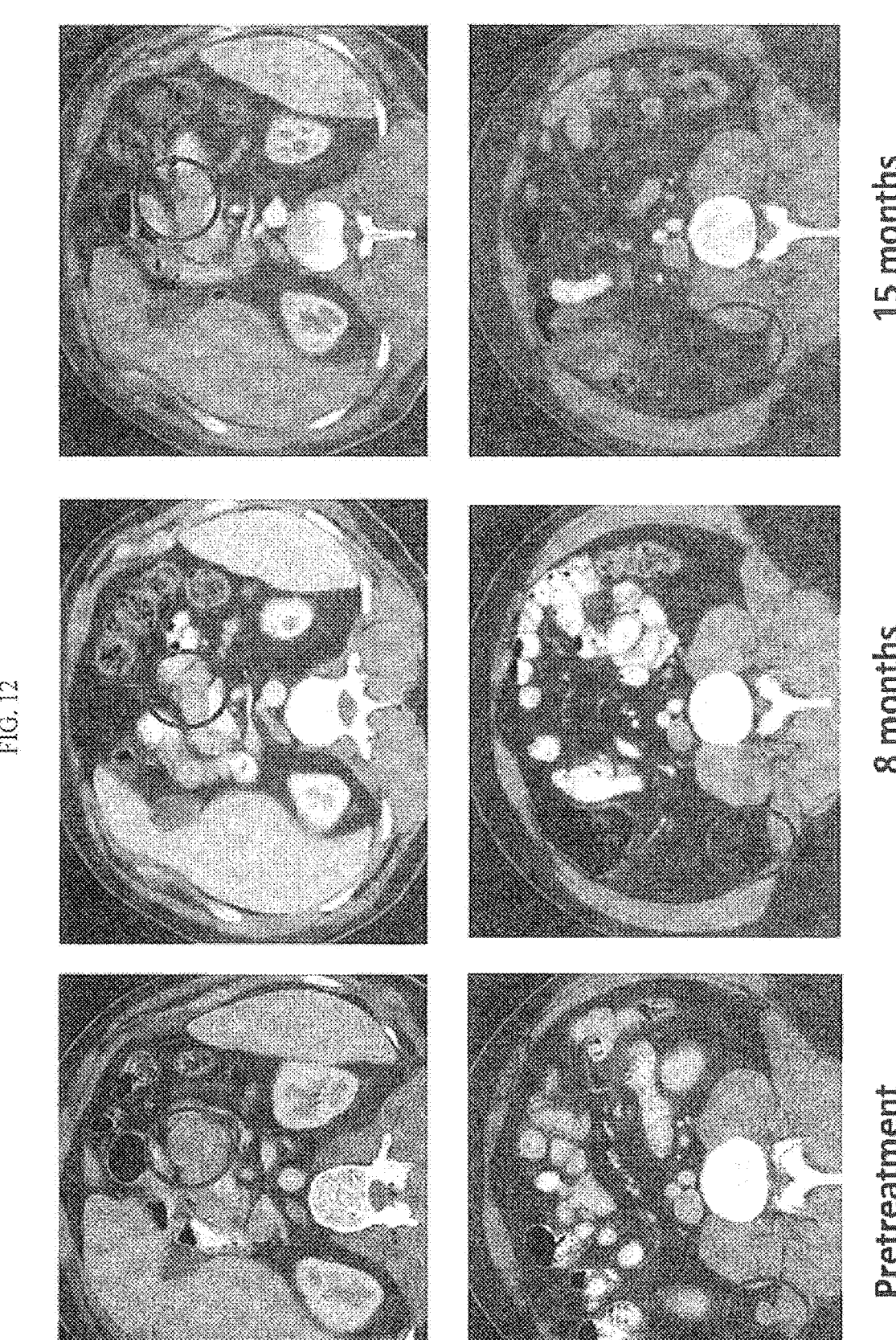
FIG. 12. Complete response in a patient with melanoma treated with BMS-936559 at 1 mg/kg. This patient developed an isolated brain metastasis 3 months after initiation of treatment that was successfully treated with stereotactic radiosurgery. A partial response in abdominal disease (circled) was noted at 8 months, with no evidence of disease at 15 months.
Figure 13:
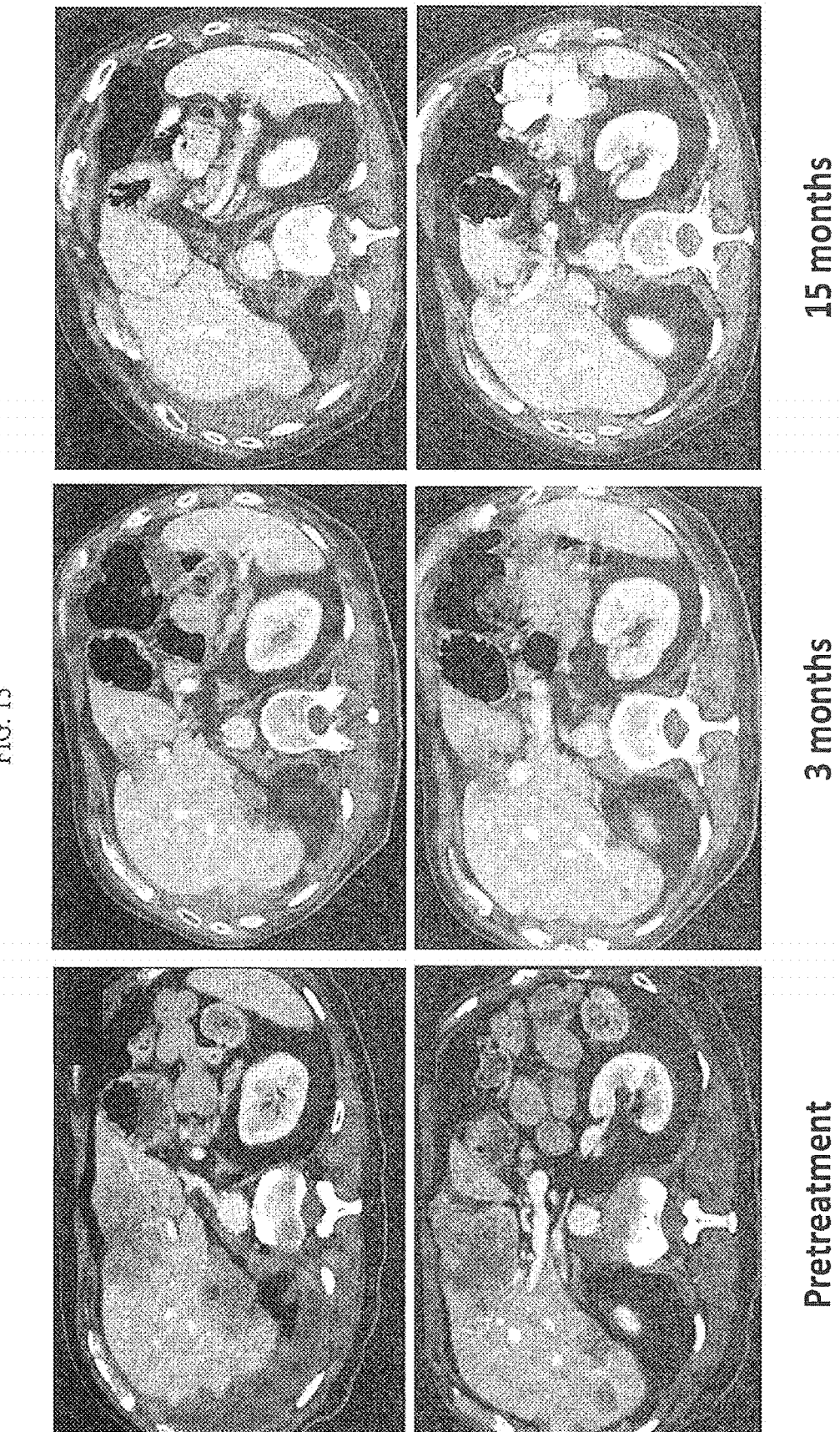
FIG. 13. Partial response in a patient with NSCLC (nonsquamous histology) treated with BMS-936559 at 10 mg/kg. Note the response in disease in right lung pleura and liver.

The binding of mAbs 5H1 and 28-8 to membranous PD-L1 in FFPE test tissue samples comprising tumor cells and tumor-infiltrating inflammatory cells from different types of tumors was compared. Membranous PD-L1 expression was evaluated using the histoscore method performed by 2 independent pathologists. Four NSCLC, 2 MEL, and 2 RCC tumors were stained with 28-8 at 2 mg/ml and 5H1 at 5 mg/ml. The data are tabulated in Table 5, and shown graphically in FIG. 9. The rabbit mAb 28-8 showed better detection (higher histoscores) for 7 out of 10 samples using 2.5-fold less Ab, and in only one sample was the histoscore for 5H1 slightly higher than for mAb 28-8.

TABLE 5

Comparison of mAbs 28-8 and 5H1 by histoscore analysis

| Tissue | Sample I.D. | Histoscore Average (5H1) | Histoscore Average (28-8) |
| --- | --- | --- | --- |
| NSCLC | 1080754B | 245 | 261 |
| NSCLC | 1080766B | 103 | 130 |
| NSCLC | 1080790 | 40 | 37 |
| NSCLC | 1080993B | 12 | 16 |
| Mel | T030668 | 98 | 113 |
| Mel | T980744 | 98 | 123 |
| Mel | 1168657B | 0 | 0 |
| Mel | T980747 | 1 | 9 |
| RCC | 1164619B | 4 | 4 |
| RCC | 1167809B | 108 | 125 |

Taube et al., 2012 demonstrated by flow cytometry on cultured cells that mAb 5H1 bound to the cell surface, and the specificity of binding to PD-L1 was confirmed using a PD-L1 fusion protein to competitively block binding of the 5H1 mAb to tissue sections. These authors also compared 5H1 with a rabbit polyclonal anti-hPD-L1 Ab, 4059, previously described by Gadiot et al., 2011, and found that whereas 5H1 showed a cell surface staining pattern on FFPE samples, Ab 4059 demonstrated diffuse cytoplasmic staining. Further, when 5H1 was compared to Ab 4059 by western blot analysis, Ab 4059 bound to multiple proteins in lysates of melanoma cells in addition to a 50 kDa protein corresponding to the expected mass of glycosylated PD-L1, in contrast to 5H1 which specifically detected the 50 kDa band of glycosylated PD-L1 (Taube et al., 2012).

In the present study, an automated IHC assay (see Example 10) was used to evaluate the binding of several commercially available anti-PD-L1 Abs and 5H1 (Dong et al., 2002) to FFPE tissue samples containing various cells expressing PD-L1. The results, summarized in Table 6, show that none of the commercially available Abs tested specifically recognized membranous PD-L1 expression in human tissues known to express PD-L1, or to clearly distinguish CHO cells expressing PD-L1 versus the untransfected parent CHO cells that did not express PD-L1. The inability of the polyclonal Ab (pAb) 4059 to bind specifically recognized membranous PD-L1 is consistent with the findings of Taube et al., 2012. The binding of 28-8 was similar to that of 5H1 in this assay, though histoscore analysis suggests that 28-8 performs better than 5H1.

TABLE 6

Binding of mAbs to FFPE Samples Containing PD-L1-expressing cells

| Source | Antibody Types | Clone No. (mAb)/ Catalog No. (pAb) | Pos. vs. Neg. Staining on PD-L1 Cells* | Human Positive Tissues[†] |
| --- | --- | --- | --- | --- |
| MBL | mAb | 27A2 | Failed | Failed |
| BioLegend | mAb | 29E.2A3 | Failed | Failed |
| eBiosciences | mAb | M1H1 | No Staining | No staining |
| Collaborator | mAb | 5H1 | Passed | Passed |
| ProSci | pAb | 4059 | Failed | Failed |
| LifeSpan BioSciences | pAb | LS-B480/0604 | Failed | Failed |

*PD-L1 stably transfected CHO cells vs. parent CHO-S negative control;

[†]PD-L1 positive tissues included tonsil and/or thymus; mAb, mouse mAb; pAb, rabbit polyclonal Ab.

Example 10

Development of Automated IHC Protocol for Assessing PD-L1 Expression

An automated IHC protocol was developed to assay PD-L1 expression in FFPE specimens. Tissue sections (4 μm) were mounted on slides, deparaffinized in an autostainer (Leica) by soaking twice for 5 min in xylene, and re-hydrated through soaking twice for 2 min each time in 100% EtOH, twice in 95% (v/v) EtOH, once in 70% (v/v) EtOH, and once in de-ionized water (dH₂O). Antigen retrieval was performed using a decloaking chamber (Biocare Medical Decloaking Chamber Plus) and Dako pH 6 buffer, heated to 110° C. (P1) for 10 min, then moved to the next step (P2 FAN ON at 98° C.; FAN OFF at 90° C.). The slides were cooled at room temperature (RT) for 15 min and rinsed with water for about 1 min.

Reagents were set up on an autostainer (BIOGENEX® i6000), using a pap pen to define the tissue area. The IHC assay, run using the autostainer in research mode, comprised the following steps: neutralizing endogenous peroxidase using the Peroxidase Block (Leica) for 10 min, followed by rinsing 3 times with IHC wash buffer (Dako); applying Protein Block (Leica) to the slides, and incubating for 10 min at RT, followed by washing 3 times with wash buffer; applying the primary Ab to the slides (2 μg/ml) and incubating for 1 h at RT, followed by washing 6 times with wash buffer; adding Post Primary Block (NovoLink Kit) to the slides and incubating for 30 min, followed by washing 6 times with wash buffer; adding NovoLink Polymer (Novo-Link Kit) to the slides and incubating for 30 min, followed by washing 6 times with wash buffer; adding the DAB chromogen substrates (NovoLink Kit) and developing for 3 min, followed by rinsing 5 times with dH₂O at RT; coun-terstaining with hematoxylin (NovoLink Kit) for 1 min at RT, followed by washing 3 times with dH₂O for 5 times at RT. The primary Ab was selected from the rabbit anti-PD-L1 Abs shown in Table 4; mAb 28-8 was the preferred Ab. As a negative control, rabbit IgG (Dako) was used. The tissue sections were dehydrated using a Leica autostainer by washing once for 2 min in 70% EtOH, twice for 2 min in 95% EtOH, and three times for 2 min in 70% EtOH, then cleared by washing three times for 5 min in xylene. The sections were permanently mounted with permount to the slide, covered with a coverslip, and transferred to a chemical hood to dry.

Example 11

Design of Phase I Clinical Study on Anti-PD-L1 Antibody

Study Design

A Phase I study was conducted to assess the safety and tolerability of BMS-936559 (also referred to herein and in U.S. Pat. No. 7,943,743 as 12A4) in patients with selected advanced solid tumors. Secondary objectives included initial assessment of the antitumor activity of BMS-936559 and pharmacokinetic evaluation. Pharmacodynamic measures were included under exploratory objectives. Patients were treated in 6-week cycles of BMS-936559 administered as a 60-minute intravenous infusion every 2 weeks on days 1, 15, and 29 of each cycle. Patients continued treatment for up to 16 cycles unless they experienced unacceptable toxicity, disease progression, or withdrew consent. In some patients who were clinically stable, treatment beyond initial disease progression was permitted until further progression was confirmed.

Dose Escalation

Patients with advanced NSCLC, MEL, CRC, RCC, ovar-ian (OV), gastric (GC), breast (BC), and pancreatic (PC) carcinoma were eligible to enroll. Using an accelerated titration design, safety was assessed at doses of 0.3, 1, 3, and 10 mg/kg. One patient was enrolled in each successive cohort until there was a ≥grade 2 drug-related AE during cycle 1. Two additional patients were then enrolled at that dose level and the study was transitioned to a standard 3+3 design. Intra-patient dose escalation or de-escalation was not permitted. The maximum tolerated dose (MTD) was defined as the highest dose where less than one-third of patients had a dose-limiting toxicity.

Cohort Expansion

Initially, 5 expansion cohorts (n=16/cohort) were enrolled at 10 mg/kg for patients with NSCLC, MEL, RCC, OV, and CRC. Based on initial signals of activity, additional expan-sion cohorts (up to n=16/cohort) were enrolled for MEL (at 1.0 and 3.0 mg/kg), NSCLC (squamous or nonsquamous histology cohorts randomized to 1, 3, or 10 mg/kg), and at 10 mg/kg for PC, BC, and GC.

Patients

Patients were required to have documented advanced NSCLC, MEL, RCC, OV, CRC, PC, GC, or BC, and have failed at least one prior tumor-appropriate therapy for advanced/metastatic disease (except for PC or GC patients who could be treatment-naïve). Other inclusion criteria included age≥18 years, life expectancy≥12 weeks, Eastern Cooperative Oncology Group performance status of ≤2, measurable disease as defined by RECIST v1.0, and adequate hematologic, hepatic, and renal function. Patients with treated brain metastases were allowed, if stable for at least 8 weeks. Major exclusion criteria included a history of autoimmune disease or other diseases requiring systemic steroids or immunosuppressive medication, prior therapy with T cell-modulating Abs (including anti-PD-1, anti-PD-L1 and anti-CTLA-4), history of HIV, or active hepatitis B or C.

In this ongoing study, 207 patients with NSCLC (n=75), MEL (n=55), CRC (n=18), RCC (n=17), OV (n=17), PC (n=14), GC (n=7), or BC (n=4) were treated with BMS-936559 during a 34-month period and are included in the safety data. Efficacy was characterized in 160 response-evaluable patients. The baseline demographic characteristics of the total and response-evaluable patient populations were very similar (Brahmer et al., 2012). Among treated patients, 86% had received prior chemotherapy and 28% immuno-logic or biological therapy. Prior therapies by tumor type included immunotherapy (56%) and B-RAF inhibitor (9%) in patients with MEL; platinum-based chemotherapy (95%) and tyrosine kinase inhibitors (TKI; 41%) in patients with NSCLC; and nephrectomy (94%), anti-angiogenic therapy (82%), and immunotherapy (41%) in patients with RCC (see Brahmer et al., 2012) for more details on patient pre-treatments).

Statistical Analysis

All 207 patients commencing treatment as of the date of analysis were used for summaries of baseline characteristics and AEs. The efficacy population consisted of 160 response-evaluable patients who initiated treatment at least 7 months before the date of analysis. AEs were coded using MedDRA v14.1. Individual best overall responses were derived from radiographic scan measurements according to modified RECIST v1.0. ORs were confirmed by at least one sequen-tial tumor assessment. Additional details regarding statistical methods are provided in Brahmer et al., 2012.

Example 12

Safety Evaluations on Patients Treated with Anti-PD-L1 Antibody

Safety evaluations (clinical examination and laboratory assessments) were conducted on all treated patients at baseline and regular intervals (weekly during cycle 1 and biweekly thereafter). AE severity was graded based on the NCI CTCAE, v3.0. Disease assessment via computed tomography (CT) scans or magnetic resonance imaging was performed at baseline and prior to each treatment cycle.

A MTD was not reached up to the highest tested dose of 10 mg/kg of BMS-936559. The median duration of therapy was 12 weeks (range 2.0-111.1 weeks). A relative dose intensity of ≥90% was achieved in 86% of patients. Twelve of 207 patients (6%) discontinued treatment due to a BMS-936559-related AE (see Brahmer et al., 2012, for details).

AEs regardless of causality (any grade) were reported in 188 of 207 patients. Investigator-assessed BMS-936559-related AEs were noted in 126 of 207 (61%) patients. The most common drug-related AEs were fatigue, infusion reactions, diarrhea, arthralgia, rash, nausea, pruritus, and headache. Most events were low grade with BMS-936559-related grade 3-4 events noted in 19 of 207 (9%) patients (Brahmer et al., 2012). The spectrum, frequency, and severity of BMS-936559-related AEs were similar across the dose levels, with the exception of infusion reactions. Drug-related AEOSIs, with potential immune-related etiologies, were observed in 81 of 207 (39%) of the patients and included rash, hypothyroidism, hepatitis, and single cases each of sarcoidosis, endophthalmitis, diabetes mellitus, and myasthenia gravis (Brahmer et al., 2012). These AEs were predominantly grade 1-2 and generally reversible with treatment interruption or discontinuation. Notably, 9 patients were treated with corticosteroids for the management of AEs. AEs improved or resolved in all patients. Furthermore, 4 of these 9 patients maintained disease control despite treatment with corticosteroids. Endocrine AEs were managed with replacement therapy and patients reinitiated treatment with BMS-936559 at the discretion of the treating physician. Infusion reactions were observed in 21 of 207 (10%) patients, predominantly at 10 mg/kg. They were grade 1-2 with the exception of one grade 3 event at 10 mg/kg. Infusion reactions were generally rapidly reversible with antihistamines and antipyretics and, in some cases, corticosteroids. A prophylactic regimen with antihistamines and antipyretics was implemented during the study. Patients with grade 1-2 infusion reactions were able to continue treatment with BMS-936559 with prophylactic antihistamines and antipyretics and at a reduced infusion rate. BMS-936559-related serious AEs occurred in 11 of 207 (5%) patients. As of the data analysis date, 45 patients (22%) had died (Brahmer et al., 2012); no drug-related deaths were observed.

Example 13

Pharmacokinetics/Pharmacodynamics Analyses on Anti-PD-L1 Antibody

For PK analyses, serial blood samples were collected and serum concentrations of BMS-936559 were quantified by ELISA. Peripheral blood mononuclear cells were isolated from patients at baseline and following one treatment cycle to assay PD-L1 RO by BMS-936559 on circulating CD3-positive T-cells via flow cytometry (Brahmer et al., 2010).

Serum concentrations of BMS-936559 increased in a dose-dependent manner from 1-10 mg/kg (n=131). Geometric mean area under the curve (0-14 days) for the 1, 3, and 10 mg/kg dose levels were 2210, 7750, and 36620 μg/mL·hr (coefficient of variation [CV]34-59%), respectively; geometric mean peak concentrations at these dose levels were 27, 83, and 272 μg/mL (CV 30-34%), respectively, after the first dose. The half-life of BMS-936559 was estimated from population pharmacokinetic data as approximately 15 days. PD-L1 RO on CD3-positive peripheral blood lymphocytes was assessed in 29 MEL patients at the end of 1 cycle of treatment, at BMS-936559 doses from 1-10 mg/kg. Median RO exceeded 65% for all groups (Brahmer et al., 2012).

Example 14

Antitumor Efficacy Exhibited by Anti-PD-L1 Antibody

One-hundred and sixty patients out of the 207 treated were evaluable for response and included those with NSCLC, MEL, CRC, RCC, OV, and PC, but not patients with GC or BC. Clinical activity was observed at all doses≥1 mg/kg (Brahmer et al., 2012). ORs (confirmed complete [CR] or partial [PR] responses) were observed in patients with MEL, NSCLC, RCC, and OV (Table 7), as illustrated by representative spider plots and CT scans (FIGS. 10-13), and many ORs were also durable (Table 8). Four additional patients had a persistent reduction in target lesions in the presence of new lesions, consistent with an "immune-related" pattern of response; however, for the purpose of calculating response rates, they were not categorized as responders. Antitumor responses and/or prolonged stable disease (SD) were observed in patients with a variety of prior therapies received. ORs were observed even in patients with an extensive burden of metastatic disease.

In patients with MEL, there were 9 ORs across the 1, 3, and 10 mg/kg dose levels, with response rates of 6%, 29%, and 19%, respectively. Three MEL patients achieved a CR. All 9 MEL patients who experienced an OR started treatment≥1 year prior to data analysis; of these 5 had a response duration 1 year. Additionally 14 MEL patients (27%) had SD lasting 24 weeks. In patients with NSCLC, there were 5 ORs amongst the 3 and 10 mg/kg dose levels, with response rates of 8% and 16%, respectively. There were ORs in patients with non-squamous (n=4) or squamous histology (n=1). All 5 NSCLC responders started treatment≥24 weeks prior to data analysis; of these, 3 had responses lasting ≥24 weeks. Six additional NSCLC patients had SD lasting ≥24 weeks. There was 1 PR out of 17 patients with OV (60 response rate) and 3 patients (18) with SD lasting ≥24 weeks, all at the 10 mg/kg dose. In patients with RCC, there were ORs in 2 of 17 (123) patients treated at 10 mg/kg with responses lasting 4 and 18 months, respectively. Seven additional RCC patients had SD lasting ≥24 weeks.

TABLE 7

| Tumor Type | Dose (mg/kg) | n | ORR§ No. of patients (%) [95% CI] | SD ≥24 wk No. of patients (%) [95% CI] | PFSR** at 24 wk (%) [95% CI] |
|---|---|---|---|---|---|
| MEL | 0.3 | 1 | 0 [0-98] | 0 [0-98] | N/A |
| | 1 | 18 | 1 (6) [0.1-27] | 6 (33) [13-59] | 39 [16-61] |
| | 3 | 17 | 5 (29)† [10-56] | 3 (18) [4-43] | 47 [21-72] |
| | 10 | 16 | 3 (19)†† [4-46] | 5 (31) [11-59] | 44 [19-68] |
| ALL MEL | | 52 | 9 (17) (8-30) | 14 (27) [16-41] | 42 [28-56] |
| NSCLC§ | 1 | 11 | 0 [0-29] | 0 [0-29] | N/A |
| Squamous | 1 | 1 | 0 [0-98] | 0 [0-98] | N/A |
| Non-Squamous | 1 | 10 | 0 [0-31] | 0 [0-31] | N/A |
| | 3 | 13 | 1 (8) [0.2-36] | 1 (8) [0.2-36] | 34 [7-60] |
| Squamous | 3 | 4 | 0 [0-60] | 1 (25) [0.6-81] | 50 [1-99] |
| Non-Squamous | 3 | 9 | 1 (11) [0.3-48] | 0 [0-34] | 25 [0-55] |
| | 10 | 25 | 4 (16) [5-36] | 5 (20) [7-41] | 46 [25-67] |
| Squamous | 10 | 8 | 1 (13) [0.3-53] | 2 (25) [3-65] | 47 [10-83] |
| Non-Squamous | 10 | 17 | 3 (18) [4-43] | 3 (18) [4-43] | 46 [20-72] |
| ALL NCSLC | | 49 | 5 (10) [3-22] | 6 (12) [5-25] | 31 [17-45] |
| ALL Squamous | | 13 | 1 (8) [0.2-36] | 3 (23.1) [5-54] | 43 [15-71] |
| ALL Non-Squamous | | 36 | 4 (11) [3-26] | 3 (8) [2-23] | 26 [10-42] |
| OV | 3 | 1 | 0 [0-98] | 0 [0-98] | N/A |
| | 10 | 16 | 1 (6) [0.2-30] | 3 (19) [4-46] | 25 [4-46] |
| ALL OV | | 17 | 1 (6) [0.1-29] | 3 (18) [4-43] | 22 [2-43] |
| RCC | 10 | 17 | 2 (12) [2-36] | 7 (41) [18-67] | 53 [29-77] |

CI denotes Confidence intervals, MEL melanoma, RCC renal cell carcinoma, NSCLC non-small cell lung cancer, OV ovarian cancer, RCC renal cell carcinoma, N/A not applicable, ORR objective response rate (complete response + partial response), SD stable disease, and PFSR progression-free survival rate.
*Efficacy population consists of response-evaluable patients who initiated treatment at least 7 months prior to the date of analysis and had measurable disease at a baseline tumor assessment and at least one of the following: an on-study tumor assessment, clinical progression, or death.
†Includes two CRs.
††Includes one CR.
§Objective response rates ({[CR + PR] ÷ n} × 100) are based on confirmed responses only, with confidence intervals calculated using the Clopper-Pearson method.
**Progression-free survival rate was the proportion of patients who did not progress, and were alive at 24 weeks, calculated by the Kaplan-Meier methodology, with confidence intervals using the Greenwood method Individual patient responses were adjudicated per RECIST v1.0 with modification (see study protocol in Brahmer et al. (2012) *N. Engl. J. Med.* (submitted) for additional information).

TABLE 8

Duration of Objective Responses to BMS-936559*

| Tumor Type | Dose (mg/kg) | No. of Patients with OR | Duration of Response (months)† |
|---|---|---|---|
| MEL | 1 | 1 | 6.9 |
| | 3 | 5 | 23.5+, 22.9+, 16.2+, 4.1+, 3.5 |
| | 10 | 4 | 24.6+, 23.9+, 18.0+, 17.0 |
| NSCLC | 1 | 0 | 9.2+ |
| | 3 | 1 | 2.3+ |
| | 10 | 4 | 16.6+, 12.6+, 9.8, 3.5 |
| RCC | 10 | 2 | 17, 4 |
| OV | 10 | 1 | 1.3+ |

*MEL denotes melanoma, NSCLC non-small cell lung cancer, RCC renal cell cancer, OV ovarian cancer.
†Time from first response to time of documented progression, death, or for censored data Denoted by +), time to last tumor assessment.

Sequence Listing Summary

Sequence Listing Summary

| SEQ ID NO: | Description |
|---|---|
| 1 | $V_H$ amino acid sequence of 17D8 |
| 2 | $V_H$ amino acid sequence of 2D3 |
| 3 | $V_H$ amino acid sequence of 4H1 |
| 4 | $V_H$ amino acid sequence of 5C4 |
| 5 | $V_H$ amino acid sequence of 4A11 |
| 6 | $V_H$ amino acid sequence of 7D3 |

-continued

Sequence Listing Summary

| SEQ ID NO: | Description |
|---|---|
| 7 | $V_H$ amino acid sequence of 5F4 |
| 8 | $V_L$ amino acid sequence of 17D8 |
| 9 | $V_L$ amino acid sequence of 2D3 |
| 10 | $V_L$ amino acid sequence of 4H1 |
| 11 | $V_L$ amino acid sequence of 5C4 |
| 12 | $V_L$ amino acid sequence of 4A11 |
| 13 | $V_L$ amino acid sequence of 7D3 |
| 14 | $V_L$ amino acid sequence of 5F4 |
| 15 | $V_H$ amino acid sequence of 3G10 |
| 16 | $V_H$ amino acid sequence of 12A4 |
| 17 | $V_H$ amino acid sequence of 10A5 |
| 18 | $V_H$ amino acid sequence of 5F8 |
| 19 | $V_H$ amino acid sequence of 10H10 |
| 20 | $V_H$ amino acid sequence of 1B12 |
| 21 | $V_H$ amino acid sequence of 7H1 |
| 22 | $V_H$ amino acid sequence of 11E6 |
| 23 | $V_H$ amino acid sequence of 12B7 |
| 24 | $V_H$ amino acid sequence of 13G4 |
| 25 | $V_L$ amino acid sequence of 3G10 |
| 26 | $V_L$ amino acid sequence of 12A4 |
| 27 | $V_L$ amino acid sequence of 10A5 |
| 28 | $V_L$ amino acid sequence of 5F8 |
| 29 | $V_L$ amino acid sequence of 10H10 |
| 30 | $V_L$ amino acid sequence of 1B12 |
| 31 | $V_L$ amino acid sequence of 7H1 |
| 32 | $V_L$ amino acid sequence of 11E6 |
| 33 | $V_L$ amino acid sequence of 12B7 |
| 34 | $V_L$ amino acid sequence of 13G4 |
| 35 | $V_H$ amino acid sequence of 28-8 |
| 36 | $V_L$ amino acid sequence of 28-8 |

REFERENCES

Baitsch et al. (2012) *PloS One* 7(2):e30852.
Barbas et al. (1994) *J Am Chem Soc* 116:2161-62.
Barbas et al. (1995) *Proc Natl Acad Sci USA* 92:2529-33.
Beck et al. (2006) *J Clin Oncol* 24:2283-89.
Beiboer et al. (2000) *J Mol Biol* 296:833-49.
Berezov et al. (2001) *BIA journal* 8:Scientific Review 8.
Blank et al. (2005) *Cancer Immunol Immunother* 54:307-14.
Bordeaux et al. (2010) *BioTechniques* 48:197-209.
Bourgeois et al. (1998) *J Virol* 72:807-10.
Brahmer et al. (2010) *J Clin Oncol* 28:3167-75.
Brahmer et al. (2012) *N Engl J Med* 366:2455-65.
Butte et al. (2007) *Immunity* 27:111-22.
Butte et al. (2008) *Mol Immunol* 45:3567-72.
Cheang et al. (2006) *J Clin Oncol* 24:5637-44.
Condeelis et al. (2010) *Cold Spring Harb Perspect Biol* 2010; 2:a003848.
Clinical Trials Website, http://www.clinicaltrials.gov, last accessed Mar. 14, 2013.
McDermott et al. (2013), submitted.
Ditzel et al. (1996) *J Immunol* 157:739-49.
Dong et al. (2002) *Nat Med* 8:793-800.
Dong et al. (2003) *J Mol Med* 81:281-87.
Dong et al. (2004) *Immunity* 20:327-36.
Epitomics (2013) http://www.epitomics.com/services/7point.php#, last accessed Mar. 14, 2013.
Fife et al. (2009) *Nat Immunol* 10:1185-92.
Fischer et al. (2008) *PloS One* 3(12):e4069.
Flaherty et al. (2010) *N Engl J Med* 363:809-19.
Flies et al. (2011) *Yale J Biol Med* 84:409-21.
Gadiot et al. (2011) *Cancer* 117:2192-201.
Garbe et al. (2012) *Eur J Cancer* 48:2375-90.
Gridelli et al. (2008) *J Thorac Oncol* 3:430-40.
Freeman et al. (2000) *J Exp Med* 192:1027-34.
Gajewski et al. (2010) *Cancer J* 16:399-403.
Hamanishi et al. (2007) *Proc Natl Acad Sci USA* 104:3360-65.
Hanna et al. (2004) *J Clin Oncol* 22:1589-97.
He et al. (2004) *J Immunol* 173:4919-28.
Hino et al. (2010) *Cancer* 116:1757-66.
Hodi et al. (2010) *N Engl J Med* 363:711-23.
Hollinger et al. (2005) *Nature Biotech* 23(9):1126-36.
Holt et al. (2011) *Therapy* 8:43-54.
Hutson et al. (2012) *Ann Oncol* 23 (Suppl. 9): ixe14, Abstr LBA22 PR.
Igarashi et al. (1995) *J Biochem* (Tokyo) 117:452-7.
Iwai et al. (2002) *Proc Natl Acad Sci USA* 99:12293-97.
Kim et al. (2010) *Curr Opin Immunol* 22:223-30.
Klimka et al. (2000) *Br J Cancer* 83(2):252-60.
Konishi et al. (2004) *Clin. Cancer Res.* 10:5094-100.
Latchman et al. (2001) *Nat Immunol* 2:261-8.
Lebbe et al. (2012) *Ann Oncol* 23 (Suppl 9):ix363, Abstr 116PD.
Levi et al. (1993) *Proc Natl Acad Sci USA* 90:4374-78.

Lipson et al. (2013) *Clin Cancer Res* 19:462-68.
McCabe et al. (2010) *Cancer Biother Radiopharm* 25(3): 253-61.
McDermott et al. (2006) *Semin Oncol* 33:583-87.
Mellman et al. (2011) *Nature* 480:480-489.
Miller (2006) *Semin Oncol* 33:S25-S31.
Motzer et al. (2008) *Lancet* 372:449-56.
Motzer et al. (2010) *Cancer* 116:4256-65.
Mulders (2009) *BJUInt* 104:1585-89.
NCCN GUIDELINES® (2013) http://www.ncen.org/pr-cofessionals/physician_gls/f_guidelines.asp#site, last accessed Mar. 14, 2013.
Nishimura et al. (1999) *Immunity* 11:141-51.
Olafsen et al. (2010) *Semin Nucl Med* 40(3):167-81.
Pardoll (2012) *Nat Rev Cancer* 12:252-64.
Park et al. (2010) *Blood* 116:1291-98.
Paterson et al. (2011) *J Immunol* 187:1097-105.
Phan et al. (2003) *Proc Natl Acad Sci USA* 100:8372-77.
Polymenis et al. (1994) *J Immunol* 152:5218-29.
Rader et al. (1998) *Proc Natl Acad Sci USA* 95:8910-15.
Ribas et al. (2005) *J Clin Oncol* 23:8968-77.
Robert et al. (2011) *N Engl J Med* 364:2517-26.
Rossi et al. (2005) *Am J Clin Pathol* 124:295-302.
Scagliotti et al. (2011) *J Thorac Oncol* 6:64-70.
Sharma et al. (2011) *Nat Rev Cancer* 11:805-12.
Shepherd et al. (2000) *J Clin Oncol* 18:2095-103.
Shepherd et al. (2005) *N Engl J Med* 353:123-32.
Sjoblom et al. (2006) *Science* 314:268-74.
Sosman et al. (2012) *N Engl J Med* 366:707-14.
Sompuram et al. (2006) *Am J Clin Pathol* 125:82-90.
Taube et al. (2012) *Sci Transl Med* 4:127ra37.
Thompson et al. (2006) *Cancer Res* 66:3381-85.
Tivol et al. (1995) *Immunity* 3:541-47.
Topalian et al. (2011) *J Clin Oncol* 29:4828-36.
Topalian et al. (2012a) *Curr Opin Immunol* 24:1-6.
Topalian et al. (2012b) *N Engl J Med* 366:2443-54.
Topalian et al. (2012c) *Curr Opin Immunol* 24:207-12.
U.S. Pat. No. 7,488,802, issued Feb. 10, 2009 to Collins et al.
U.S. Pat. No. 7,635,757, issued Dec. 22, 2009 to Freeman et al.
U.S. Pat. No. 7,943,743, issued May 17, 2011 to Korman et al.
U.S. Pat. No. 8,008,449, issued Aug. 30, 2011 to Korman et al.
U.S. Pat. No. 8,168,757, issued May 1, 2012 to Finnefrock et al.
U.S. Pat. No. 8,217,149, issued Jul. 10, 2012 to Irving et al.
U.S. Publication No. 2009/0317368, published Dec. 24, 2009 by Chen et al.
Weber et al. (2013), submitted to *N Engl J Med*.
Wolchok et al. (2009) *Clin Cancer Res* 15:7412-20.
Wolchok et al. (2013), submitted to N Engl *J Med*.
Xu and Davis (2000) *Immunity* 13: 37-45.
Yang et al. (2011) *J Immunol* 187:1113-19.
Zou et al. (2008) *Nat Rev Immunol* 8:467-77.

---

What is claimed is:

1. A method of treating a renal cell carcinoma in a human subject in need thereof, comprising administering to the subject 3 mg/kg of nivolumab and 1 mg/kg of ipilimumab every 3 weeks for 4 cycles, followed by subsequently administering the nivolumab alone.

2. The method of claim 1, wherein the renal cell carcinoma is advanced.

3. The method of claim 1, further comprising administering to the subject an anti-cancer agent.

4. The method of claim 3, wherein the anti-cancer agent comprises a chemotherapy.

5. The method of claim 2, further comprising administering to the subject an anti-cancer agent.

6. The method of claim 5, wherein the anti-cancer agent comprises a chemotherapy.

* * * * *

```
                    SEQUENCE LISTING

Sequence total quantity: 36
SEQ ID NO: 1            moltype = AA  length = 113
FEATURE                 Location/Qualifiers
source                  1..113
                        mol_type = protein
                        organism = Homo sapiens
SEQUENCE: 1
QVQLVESGGD VVQPGGSLRL SCAASGVAFS NYGMHWVRQA PGKGLEWVAV IWYDGSNKYY  60
```

```
ADSVKGRFTI SRDNSKNMLY LQMNSLRAED TAMYYCARND DYWGQGTLVT VSS           113

SEQ ID NO: 2                moltype = AA   length = 113
FEATURE                     Location/Qualifiers
source                      1..113
                            mol_type = protein
                            organism = Homo sapiens
SEQUENCE: 2
QVQLVESGGD VVQPGRSLRL SCAASGLTFT NYGFHWVRQA PGKGLEWVAV IWYDGSKKYY     60
ADSVKGRFTI SRDNSKNTLY LQMNNLRAED TAVYYCATGD DYWGQGTLVT VSS           113

SEQ ID NO: 3                moltype = AA   length = 113
FEATURE                     Location/Qualifiers
source                      1..113
                            mol_type = protein
                            organism = Homo sapiens
SEQUENCE: 3
QVYLVESGGG VVQPGRSLRL SCAASGFTFS NYGMHWVRQA PGKGLEWVAL IWYDGSNKYY     60
ADSVKGRFTI SRDNSKNTLY LQMTSLRVED TAVYYCASNV DHWGQGTLVT VSS           113

SEQ ID NO: 4                moltype = AA   length = 113
FEATURE                     Location/Qualifiers
source                      1..113
                            mol_type = protein
                            organism = Homo sapiens
SEQUENCE: 4
QVQLVESGGG VVQPGRSLRL DCKASGITFS NSGMHWVRQA PGKGLEWVAV IWYDGSKRYY     60
ADSVKGRFTI SRDNSKNTLF LQMNSLRAED TAVYYCATND DYWGQGTLVT VSS           113

SEQ ID NO: 5                moltype = AA   length = 121
FEATURE                     Location/Qualifiers
source                      1..121
                            mol_type = protein
                            organism = Homo sapiens
SEQUENCE: 5
QLQLQESGPG LVKPSETLSL TCTVSGGSLS RSSFFWGWIR QPPGKGLEWI GSIYYSGSTY     60
YNPSLKSRVT ISVDTSKNQF SLKLSSVTAA DTAVYYCVRD YDILTGDEDY WGQGTLVTVS    120
S                                                                   121

SEQ ID NO: 6                moltype = AA   length = 113
FEATURE                     Location/Qualifiers
source                      1..113
                            mol_type = protein
                            organism = Homo sapiens
SEQUENCE: 6
QVQLVESGGG VVQPGRSLRL SCTTSGITFS SYGFHWVRQA PGKGLEWVAV IWYDGSKKYY     60
ADSVKGRFTL SRDDSKNTLY LQMNSLRAED TAVYYCVTGD DYWGQGTLVT VSS           113

SEQ ID NO: 7                moltype = AA   length = 121
FEATURE                     Location/Qualifiers
source                      1..121
                            mol_type = protein
                            organism = Homo sapiens
SEQUENCE: 7
QLQLQESGPG LVKPSETLSL TCSVSGGSLS RSSYFWGWIR QPPGKGLEWI ASIFYSGETY     60
FNPSLKSRVT ISVDTSRNQF SLKLSSVTAA DTAVYYCARD YDILTGDEDY WGQGTLVTVS    120
S                                                                   121

SEQ ID NO: 8                moltype = AA   length = 107
FEATURE                     Location/Qualifiers
source                      1..107
                            mol_type = protein
                            organism = Homo sapiens
SEQUENCE: 8
EIVLTQSPAT LSLSPGERAT LSCRASQSVS SYLAWYQQKP GQAPRLIIYD ASNRATGIPA     60
RFSGSGSGTD FTLTISSLEP EDFAVYYCQQ RSNWPLTFGG GTKVEIK                 107

SEQ ID NO: 9                moltype = AA   length = 107
FEATURE                     Location/Qualifiers
source                      1..107
                            mol_type = protein
                            organism = Homo sapiens
SEQUENCE: 9
EIVLTQSPAT LSLSPGERAT LSCRASQSVS SYLAWYQQKP GQAPRLLIYD TSNRATGIPA     60
RFSGSGSGTD FTLTISSLEP EDFAVYYCQQ RSNWPLTFGG GTKVEIK                 107

SEQ ID NO: 10               moltype = AA   length = 107
FEATURE                     Location/Qualifiers
source                      1..107
```

-continued

```
                          mol_type = protein
                          organism = Homo sapiens
SEQUENCE: 10
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 11             moltype = AA   length = 107
FEATURE                   Location/Qualifiers
source                    1..107
                          mol_type = protein
                          organism = Homo sapiens
SEQUENCE: 11
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 12             moltype = AA   length = 107
FEATURE                   Location/Qualifiers
source                    1..107
                          mol_type = protein
                          organism = Homo sapiens
SEQUENCE: 12
DIQMTQSPSS LSASVGDRVS ITCRASQGIS SWLAWYQQKP EKAPKSLIYA ASNLRSGVPS  60
RFSGSGSGTD FTLTISSLQP EDFATYYCQQ YYSYPRTFGQ GTKVEIK                107

SEQ ID NO: 13             moltype = AA   length = 107
FEATURE                   Location/Qualifiers
source                    1..107
                          mol_type = protein
                          organism = Homo sapiens
SEQUENCE: 13
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPLTFGG GTKVEIK                107

SEQ ID NO: 14             moltype = AA   length = 107
FEATURE                   Location/Qualifiers
source                    1..107
                          mol_type = protein
                          organism = Homo sapiens
SEQUENCE: 14
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YYSYPRTFGQ GTKVEIK                107

SEQ ID NO: 15             moltype = AA   length = 117
FEATURE                   Location/Qualifiers
source                    1..117
                          mol_type = protein
                          organism = Homo sapiens
SEQUENCE: 15
QVQLVQSGAE VKKPGASVKV SCKASGYTFT DYGFSWVRQA PGQGLEWMGW ITAYNGNTNY  60
AQKLQGRVTM TTDTSTSTVY MELRSLRSDD TAVYYCARDY FYGMDVWGQG TTVTVSS     117

SEQ ID NO: 16             moltype = AA   length = 123
FEATURE                   Location/Qualifiers
source                    1..123
                          mol_type = protein
                          organism = Homo sapiens
SEQUENCE: 16
QVQLVQSGAE VKKPGSSVKV SCKTSGDTFS TYAISWVRQA PGQGLEWMGG IIPIFGKAHY  60
AQKFQGRVTI TADESTSTAY MELSSLRSED TAVYFCARKF HFVSGSPFGM DVWGQGTTVT  120
VSS                                                                123

SEQ ID NO: 17             moltype = AA   length = 118
FEATURE                   Location/Qualifiers
source                    1..118
                          mol_type = protein
                          organism = Homo sapiens
SEQUENCE: 17
QVQLVQSGAE VKKPGASVKV SCKASGYTFT SYDVHWVRQA PGQRLEWMGW LHADTGITKF  60
SQKFQGRVTI TRDTSASTAY MELSSLRSED TAVYYCARER IQLWFDYWGQ GTLVTVSS    118

SEQ ID NO: 18             moltype = AA   length = 120
FEATURE                   Location/Qualifiers
source                    1..120
                          mol_type = protein
                          organism = Homo sapiens
SEQUENCE: 18
QVQLVQSGAE VKKPGSSVKV SCKVSGGIFS TYAINWVRQA PGQGLEWMGG IIPIFGTANH  60
AQKFQGRVTI TADESTSTAY MELSSLRSED TAVYYCARDQ GIAAALFDYW GQGTLVTVSS  120
```

```
SEQ ID NO: 19              moltype = AA  length = 113
FEATURE                    Location/Qualifiers
source                     1..113
                           mol_type = protein
                           organism = Homo sapiens
SEQUENCE: 19
EVQLVESGGG LVQPGRSLRL SCAVSGFTFD DYVVHWVRQA PGKGLEWVSG ISGNSGNIGY  60
ADSVKGRFTI SRDNAKNSLY LQMNSLRAED TALYYCAVPF DYWGQGTLVT VSS         113

SEQ ID NO: 20              moltype = AA  length = 123
FEATURE                    Location/Qualifiers
source                     1..123
                           mol_type = protein
                           organism = Homo sapiens
SEQUENCE: 20
QVQLVQSGAE VKKPGSSVKV SCKTSGDTFS SYAISWVRQA PGQGLEWMGG IIPIFGRAHY  60
AQKFQGRVTI TADESTSTAY MELSSLRSED TAVYFCARKF HFVSGSPFGM DVWGQGTTVT  120
VSS                                                                123

SEQ ID NO: 21              moltype = AA  length = 123
FEATURE                    Location/Qualifiers
source                     1..123
                           mol_type = protein
                           organism = Homo sapiens
SEQUENCE: 21
QVQLVQSGAE VKKPGSSVKV SCKTSGGTFS SYAISWVRQA PGQGLEWMGG IIPIFGKAHY  60
AQKFQGRVTI TADESTTTAY MELSSLRSED TAVYYCARKY DYVSGSPFGM DVWGQGTTVT  120
VSS                                                                123

SEQ ID NO: 22              moltype = AA  length = 121
FEATURE                    Location/Qualifiers
source                     1..121
                           mol_type = protein
                           organism = Homo sapiens
SEQUENCE: 22
QVQLVQSGAE VKKPGSSVKV SCKASGGTFS SYAINWVRQA PGQGLEWMGG IIPIFGSANY  60
AQKFQDRVTI TADESTSAAY MELSSLRSED TAVYYCARDS SGWSRYYMDV WGQGTTVTVS  120
S                                                                  121

SEQ ID NO: 23              moltype = AA  length = 123
FEATURE                    Location/Qualifiers
source                     1..123
                           mol_type = protein
                           organism = Homo sapiens
SEQUENCE: 23
QVQLVQSGAE VKEPGSSVKV SCKASGGTFN SYAISWVRQA PGQGLEWMGG IIPLFGIAHY  60
AQKFQGRVTI TADESTNTAY MDLSSLRSED TAVYYCARKY SYVSGSPFGM DVWGQGTTVT  120
VSS                                                                123

SEQ ID NO: 24              moltype = AA  length = 121
FEATURE                    Location/Qualifiers
source                     1..121
                           mol_type = protein
                           organism = Homo sapiens
SEQUENCE: 24
EVQLVESGGG LVQPGRSLRL SCAASGITFD DYGMHWVRQA PGKGLEWVSG ISWNRGRIEY  60
ADSVKGRFTI SRDNAKNSLY LQMNSLRAED TALYYCAKGR FRYFDWFLDY WGQGTLVTVS  120
S                                                                  121

SEQ ID NO: 25              moltype = AA  length = 107
FEATURE                    Location/Qualifiers
source                     1..107
                           mol_type = protein
                           organism = Homo sapiens
SEQUENCE: 25
EIVLTQSPAT LSLSPGERAT LSCRASQSVS SYLVWYQQKP GQAPRLLIYD ASNRATGIPA  60
RFSGSGSGTD FTLTISSLEP EDFAVYYCQQ RSNWPRTFGQ GTKVEIK              107

SEQ ID NO: 26              moltype = AA  length = 106
FEATURE                    Location/Qualifiers
source                     1..106
                           mol_type = protein
                           organism = Homo sapiens
SEQUENCE: 26
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK               106

SEQ ID NO: 27              moltype = AA  length = 107
FEATURE                    Location/Qualifiers
```

-continued

```
source                    1..107
                          mol_type = protein
                          organism = Homo sapiens
SEQUENCE: 27
DIQMTQSPSS LSASVGDRVT ITCRASQGIS SWLAWYQQKP EKAPKSLIYA ASSLQSGVPS   60
RFSGSGSGTD FTLTISSLQP EDFATYYCQQ YNSYPYTFGQ GTKLEIK                 107

SEQ ID NO: 28            moltype = AA   length = 108
FEATURE                  Location/Qualifiers
source                    1..108
                          mol_type = protein
                          organism = Homo sapiens
SEQUENCE: 28
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPWTFG QGTKVEIK                108

SEQ ID NO: 29            moltype = AA   length = 107
FEATURE                  Location/Qualifiers
source                    1..107
                          mol_type = protein
                          organism = Homo sapiens
SEQUENCE: 29
DIQMTQSPSS LSASVGDRVT ITCRASQGIS SWLAWYQQKP EKAPKSLIYA ASSLQSGVPS   60
RFSGSGSGTD FTLTISSLQP EDFATYYCQQ YNSYPYTFGQ GTKLEIK                 107

SEQ ID NO: 30            moltype = AA   length = 106
FEATURE                  Location/Qualifiers
source                    1..106
                          mol_type = protein
                          organism = Homo sapiens
SEQUENCE: 30
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPTFGQG TKVEIK                  106

SEQ ID NO: 31            moltype = AA   length = 106
FEATURE                  Location/Qualifiers
source                    1..106
                          mol_type = protein
                          organism = Homo sapiens
SEQUENCE: 31
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPTFGQG TKVEIK                  106

SEQ ID NO: 32            moltype = AA   length = 106
FEATURE                  Location/Qualifiers
source                    1..106
                          mol_type = protein
                          organism = Homo sapiens
SEQUENCE: 32
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPFGGG TKVEIK                  106

SEQ ID NO: 33            moltype = AA   length = 106
FEATURE                  Location/Qualifiers
source                    1..106
                          mol_type = protein
                          organism = Homo sapiens
SEQUENCE: 33
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPTFGQG TRLEIK                  106

SEQ ID NO: 34            moltype = AA   length = 107
FEATURE                  Location/Qualifiers
source                    1..107
                          mol_type = protein
                          organism = Homo sapiens
SEQUENCE: 34
AIQLTQSPSS LSASVGDRVT ITCRASQGIS SALAWYQQKP GKAPKLLIYD ASSLESGVPS   60
RFSGSGSGTD FTLTISSLQP EDFATYYCQQ FNSYPFTFGP GTKVDIK                 107

SEQ ID NO: 35            moltype = AA   length = 141
FEATURE                  Location/Qualifiers
source                    1..141
                          mol_type = protein
                          organism = Oryctolagus cuniculus
SEQUENCE: 35
METGLRWLLL VAVLKGVQCL SVEESGGRLV TPGTPLTLTC TASGFTITNY HMFWVRQAPG   60
KGLEWIGVIT SSGIGSSSTT YYATWAKGRF TISKTSTTVN LRITSPTTED TATYFCARDY  120
FTNTYYALDI WGPGTLVTVS S                                            141
```

-continued

```
SEQ ID NO: 36        moltype = AA  length = 116
FEATURE              Location/Qualifiers
source               1..116
                     mol_type = protein
                     organism = Oryctolagus cuniculus
SEQUENCE: 36
MDTRAPTQLL GLLLLWLPGA RCALVMTQTP SSTSTAVGGT VTIKCQASQS ISVYLAWYQQ  60
KPGQPPKLLI YSASTLASGV PSRFKGSRSG TEYTLTISGV QREDAATYYC LGSAGS       116
```